US012662539B2

(12) United States Patent　　(10) Patent No.: US 12,662,539 B2
Gelfman et al.　　　　　　　　　(45) Date of Patent: *Jun. 23, 2026

(54) MODULATION OF ENDOPLASMIC RETICULUM AMINOPEPTIDASE 2 (ERAP2)-MEDIATED IMMUNE RESPONSE

(71) Applicant: Regeneron Pharmaceuticals, Inc., Tarrytown, NY (US)

(72) Inventors: Sahar Gelfman, Tarrytown, NY (US); Ann Ligocki, Tarrytown, NY (US); Giovanni Coppola, Tarrytown, NY (US); Aris Baras, Tarrytown, NY (US); Arden Moscati, Tarrytown, NY (US); Eli A. Stahl, Tarrytown, NY (US); Jack A. Kosmicki, Tarrytown, NY (US); Manuel Allen Revez Ferreira, Tarrytown, NY (US); Carmelo Romano, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 840 days.

This patent is subject to a terminal disclaimer.

(21) Appl. No.: 17/384,601

(22) Filed: Jul. 23, 2021

(65) Prior Publication Data

US 2023/0059929 A1　　Feb. 23, 2023

Related U.S. Application Data

(60) Provisional application No. 63/056,562, filed on Jul. 25, 2020, provisional application No. 63/171,672, filed on Apr. 7, 2021.

(51) Int. Cl.
| | |
|---|---|
| *A61K 31/00* | (2006.01) |
| *A61K 31/713* | (2006.01) |
| *A61K 38/08* | (2019.01) |
| *A61K 45/06* | (2006.01) |
| *C07K 16/28* | (2006.01) |
| *C12N 15/113* | (2010.01) |

(52) U.S. Cl.
CPC ........ *C07K 16/2833* (2013.01); *A61K 31/713* (2013.01); *A61K 38/08* (2013.01); *A61K 45/06* (2013.01); *C12N 15/113* (2013.01); *C12N 2310/11* (2013.01); *C12N 2310/14* (2013.01); *C12N 2310/531* (2013.01); *C12N 2320/30* (2013.01)

(58) Field of Classification Search
CPC .. C07K 16/2833; A61K 31/713; A61K 38/08; A61K 45/06; C12N 15/113; C12N 2310/11; C12N 2310/14; C12N 2310/531; C12N 2320/30
See application file for complete search history.

(56) References Cited

U.S. PATENT DOCUMENTS

| | | | |
|---|---|---|---|
| 8,969,254 | B2 | 3/2015 | Reinherz et al. |
| 9,617,596 | B2 | 4/2017 | Comabella et al. |
| 9,907,833 | B2 | 3/2018 | Conrad |
| 10,047,396 | B2 | 8/2018 | Sharp et al. |
| 10,166,210 | B2 | 1/2019 | Pogue-Geile et al. |
| 10,385,398 | B2 | 8/2019 | Hakonarson et al. |
| 10,407,725 | B2 | 9/2019 | Hakonarson et al. |
| 10,927,412 | B2 | 2/2021 | Giudice et al. |
| 2003/0228314 | A1 | 12/2003 | Shastri et al. |
| 2012/0015904 | A1 | 1/2012 | Sharp et al. |
| 2015/0141273 | A1 | 5/2015 | Bosch et al. |
| 2016/0145687 | A1 | 5/2016 | Kallionpaa et al. |
| 2017/0199196 | A1 | 7/2017 | Bosch et al. |
| 2019/0076391 | A1 | 3/2019 | Pogue-Geile et al. |
| 2019/0136322 | A1 | 5/2019 | Kallionpaa et al. |
| 2019/0241633 | A1 | 8/2019 | Fotin-Mleczek et al. |
| 2019/0375842 | A1 | 12/2019 | Drake |
| 2020/0080152 | A1 | 3/2020 | Hakonarson et al. |
| 2021/0002296 | A1 | 1/2021 | Mainolfi et al. |
| 2021/0147799 | A1 | 5/2021 | Zhang et al. |

FOREIGN PATENT DOCUMENTS

| | | |
|---|---|---|
| WO | 2012047294 | 4/2012 |
| WO | 2013152001 | 10/2013 |
| WO | 2014171800 | 10/2014 |
| WO | 2017208001 | 12/2017 |
| WO | 202111376 | 6/2021 |
| WO | 2021113805 | 6/2021 |
| WO | 2022026336 | 2/2022 |

OTHER PUBLICATIONS

Babaie et al, Molecule Immunology 121: 7-19, Epub Mar. 2, 2020, IDS # 5, filed on Dec. 21, 2021 (Year: 2020).*
Kato et al (J Immunology 143: 3371-3378, 1989 (Year: 1989).*
Lopes de Castro et al (mole Immunology 77:193-204, 2016 (Year: 2016).*
Gelfman et al (IOVS 62 (14):3 2021) (Year: 2021).*
Castro-Santos et al., "ERAPI and HLA-C interaction in inflammatory bowel disease in the Spanish population", Innate Immunity, 2017, 23(5), pp. 476-481.
Chiaroni-Clarke et al., "Independent confirmation of juvenile idiopathic arthritis genetic risk loci previously identified by immunochip array analysis", Pediatric Rheumatology, 2014, 12(53), pp. 1-4.
Deddouche-Grass et al., "Discovery and Optimization of a Series of Benzofuran Selective ERAP1 Inhibitors: Biochemical and In Silico Studies", ACS Med Chem Lett, 2021, 12, pp. 1137-1142.

(Continued)

*Primary Examiner* — Lei Yao
(74) *Attorney, Agent, or Firm* — Armstrong Teasdale LLP

(57) ABSTRACT

The present disclosure provides methods of treating subjects having an immune disorder by administering a therapeutically effective amount of an Endoplasmic Reticulum Aminopeptidase 2 (ERAP2) inhibitor to the subject, and optionally an Endoplasmic Reticulum Aminopeptidase 1 (ERAP1) agonist or inhibitor and/or an HLA-Aw19 inhibitor, and also provides methods of identifying subjects having an increased risk for developing an MHC-I-opathy.

6 Claims, 15 Drawing Sheets

Specification includes a Sequence Listing.

(56) References Cited

OTHER PUBLICATIONS

Franke et al., "Genome-wide meta-analysis increases to 71 the number of confirmed Crohn's disease susceptibility loci", Nature Genetics, 2010, 42(12), pp. 1118-1126.

Liddle et al., "Targeting the Regulatory Site of ER Aminopeptidase 1 Leads to the Discovery of a Natural Product Modulator of Antigen Presentation", J Med Chem, 2020, 63(6), pp. 3348-3358.

Weglarz-Tomczak et al., "Discovery of potent and selective inhibitors of human aminopeptidases ERAP1 and ERAP2 by screening libraries of phosphorus-containing amino acid and dipeptide analogues", Bioorganic and Medicinal Chemistry Letters, 2016, 26, pp. 4122-4126.

Zervoudi et al., "Rationally designed inhibitor targeting antigentrimming aminopeptidases enhances antigen presentation and cytotoxic T-cell responses", PNAS, 2013, 110(49), pp. 19890-19895.

Van Hout et al., "Exome sequencing and characterization of 49,960 individuals in the UK Biobank", Nature, 2020, 586(7831), pp. 749-756.

Reid et al., "Launching genomics into the cloud: deployment of Mercury, a next generation sequence analysis pipeline", BMC Bioinformatics, 2014, 15(30), pp. 1-11.

Bai et al., "Inference of high resolution HLA types using genome-wide RNA or DNA sequencing reads", BMC Genomics, 2014, 15(325), pp. 1-16.

Robinson et al., "The IPD-IMGT/HLA Database—New developments in reporting HLA variation", Hum Immunol, 2016, 77(3), pp. 233-237.

Jia et al., "Imputing Amino Acid Polymorphisms in Human Leukocyte Antigens", PLOS One, 2013, 8(6), pp. e64683.

Rich et al., "The Type 1 Diabetes Genetics Consortium", Ann NY Acad Sci, 2006, 1079, pp. 1-8.

Delaneau et al., "Accurate, scalable and integrative haplotype estimation", Nature Communications, 2019, 10(5436), pp. 1-10.

Das et al., "Next-generation genotype imputation service and methods", Nat Genet, 2016, 48(10), pp. 1284-1287.

Mbatchou et al., "Computationally efficient whole genome regression for quantitative and binary traits", BioRxiv, 2020, pp. 1-88.

Zhou et al., "Efficiently controlling for case-control imbalance and sample relatedness in large-scale genetic association studies", Nature Genetics, 2018, 50, pp. 1335-1341.

Purcell et al., "PLINK: a tool set for whole-genome association and population-based linkage analyses", Am J Hum Genet, 2007, 81(3), pp. 559-575.

Kuiper et al., "A genome-wide association study identifies a functional ERAP2 haplotype associated with birdshot chorioretinopathy", Hum Mol Genet, 2014, 23(22), pp. 6081-6087.

Kuiper et al., "Functionally distinct ERAP1 and ERAP2 are a hallmark of HLA-A29-(Birdshot) Uveitis", Hum Mol Genet, 2018, 27(24), pp. 4333-4343.

Paladini et al., "An allelic variant in the intergenic region between ERAP1 and ERAP2 correlates with an inverse expression of the two genes", Scientific Reports, 2018, 8(10398), pp. 1-10.

Andres et al., "Balancing Selection Maintains a Form of ERAP2 that Undergoes Nonsense-Mediated Decay and Affects Antigen Presentation", PLOS Genetics, 2010, 6(10), pp. e1001157.

Coulombe-Huntington et al., "Fine-Scale Variation and Genetic Determinants of Alternative Splicing across Individuals", PLOS Genetics, 2009, 5(12), pp. e1000766.

Sanz-Bravo et al., "Allele-specific Alterations in the Peptidome Underlie the Joint Association of HLA-A*29:02 and Endoplasmic Reticulum Aminopeptidase 2 (ERAP2) with Birdshot Chorioretinopathy", Mol Cell Proteomics, 2018, 17 (8), pp. 1564-1577.

Yao et al., "Influence of ERAP1 and ERAP2 gene polymorphisms on disease susceptibility in different populations", Human Immunology, 2019, 80(5), pp. 325-334.

Evans et al., "Interaction between ERAP1 and HLA-B27 in ankylosing spondylitis implicates peptide handling in the mechanism for HLA-B27 in disease susceptibility", Nat Genet, 2011, 43(8), pp. 761-767.

Wisniewski et al., "The association of ERAP1 and ERAP2 single nucleotide polymorphisms and their haplotypes with psoriasis vulgaris is dependent on the presence or absence of the HLA-C*06:02 allele and age at disease onset", Hum Immunol, 2018, 79(2), pp. 109-116.

Strange et al., "A genome-wide association study identifies new psoriasis susceptibility loci and an interaction between HLA-C and ERAP1", Nat Genet, 2010, 42(11), pp. 985-990.

Takeuchi et al., "A single endoplasmic reticulum aminopeptidase-1 protein allotype is a strong risk factor for Behçet's disease in HLA-B*51 carriers", Ann Rheum Dis, 2016, 75(12), pp. 2208-2211.

Sanz-Bravo et al., "Ranking the Contribution of Ankylosing Spondylitis-associated Endoplasmic Reticulum Aminopeptidase 1 (ERAP1) Polymorphisms to Shaping the HLA-B*27 Peptidome*", Mol Cell Proteomics, 2018, 17(7), pp. 1308-1323.

Guasp et al., "The Behçet's disease-associated variant of the aminopeptidase ERAP1 shapes a low-affinity HLA-B*51 peptidome by differential subpeptidome processing", J Biol Chem, 2017, 292(23), pp. 9680-9689.

Mckenzie et al., "Taxonomic hierarchy of HLA class I allele sequences", Genes and Immunity, 1999, 1, pp. 120-129.

Maben et al., "Discovery of Selective Inhibitors of Endoplasmic Reticulum Aminopeptidase 1", J Med Chem, 2020, 63, pp. 103-121.

Lopez De Castro, "How ERAP1 and ERAP2 Shape the Peptidomes of Disease-Associated MHC-I Proteins", Front Immunol, 2018, 9(2463), pp. 1-17.

Worth et al., "Novel Therapeutic Targets in Axial Spondyloarthritis", Curr Treat Options in Rheum, 2018, 4, pp. 174-182.

Chen et al., "Silencing or inhibition of endoplasmic reticulum aminopeptidase 1 (ERAP1) suppresses free heavy chain expression and Th17 responses in ankylosing spondylitis", Ann Rheum Dis, 2016, 75, pp. 916-923.

Non-Final Office Action dated Apr. 2, 2024 in related U.S. Appl. No. 17/714,717.

Notice of Allowance dated Mar. 26, 2025 in related U.S. Appl. No. 17/714,717.

Notice of Allowance dated Apr. 24, 2025 in related U.S. Appl. No. 17/714,717.

Freitas-Neto et al., "Birdshot retinochoroidopathy review", Arq Bras Oftalmol, 2015, 78(1), pp. 56-61.

Ferenchak et al., "Antisense Oligonucleotide Therapy for Ophthalmic Conditions", Seminars in Ophthalmology, 2021, 36(5-6), pp. 452-457.

Hu et al., "Modulation of Gene Expression in the Eye with Antisense Oligonucleotides", Nucleic Acid Therapeutics, 2023, 33(6), pp. 339-347.

Garanto, "Antisense RNA Design, Delivery, and Analysis", Methods in Molecular Biology 2434, 2021, Chapter 22, pp. 321-332.

Vazquez-Dominguez et al., "Efficacy, biodistribution and safety comparison of chemically modified antisense oligonucleotides in the retina", Nucleic Acids Research, 2024, 52, pp. 10447-10463.

Advisory Action dated Oct. 16, 2024 in related U.S. Appl. No. 17/714,717.

Georgiadis et al. "Inhibitiors of ER Aminopeptidase 1 and 2: From Design to Clinical Application", Current Medicinal Chemistry, 2019, 26(15), pp. 2715-2729.

De Castro et al., "Molecular and pathogenic effects of endoplasmic reticulum aminopeptidases ERAP1 and ERAP2 in MHC-I-associated inflammatory disorders: Towards a unifying view", Molecular Immunology, 2016, 77, pp. 193-204.

Agrawal et al., "Genetic associations and functional characterization of M1 aminopeptidases and immune-mediated diseases", Genes and Immunity, 2014, 15(8), pp. 521-527.

Dimopoulou et al., "Variant in ERAP1 promoter region is associated with low expression in a patient with a Behcet-like MHC-I-opathy", Journal of Human Genetics, 2019, 65(3), pp. 325-335.

Babaie et al., "The roles of ERAP1 and ERAP2 in autoimmunity and cancer immunity: New insights and perspective", Molecular Immunology, 2020, 121, pp. 7-19.

(56) References Cited

OTHER PUBLICATIONS

Kuo et al., "Endoplasmic reticulum aminopeptidase 2 involvement in metastasis of oral cavity squamous cell carcinoma discovered by proteome profiling of primary cancer cells", Oncotarget, 2017, 8(37), pp. 61698-61708.

Final Office Action dated Aug. 2, 2024 in related U.S. Appl. No. 17/714,717.

Bousquet et al., "Birdshot Chorioretinopathy: A Review", Journal of Clinical Medicine, 2022, 11(4772), pp. 1-17.

Venema et al., "ERAP2 Increases the Abundance of a Peptide Submotif Highly Selective for the Birdshot Associated HLA-A29", Front Immunol, 2021, 12(634441), pp. 1-15.

* cited by examiner

| Second HLA-A Allele | UParis (A29 EUR Carriers) | | | | GHS cohort #1 (A29 EUR) | | | GHS cohort #2 (A29 EUR) | | | UKB (A29 EUR) | | |
|---|---|---|---|---|---|---|---|---|---|---|---|---|---|
| | Cases n=286 | Ctrls n=108 | OR (LCI-UCI) | p-val | Carriers n=4014 | OR (LCI-UCI) | p-val | Carriers n=2829 | OR (LCI-UCI) | p-val | Carriers n=38,543 | OR (LCI-UCI) | p-val |
| Aw19 co-susceptible (29,30,31,33) | 41 | 4 | 4.44 (1.55-17.53) | 2.20E-03 | 247 | 2.63 (1.80-3.78) | 1.29E-06 | 184 | 2.69 (1.81-3.92) | 1.07E-06 | 2416 | 2.51 (1.75-3.52) | 9.62E-07 |
| A3002 | 13 | 1 | 5.19 (0.76-222.84) | 0.12 | 45 | 4.31 (2.11-8.26) | 6.15E-05 | 20 | 6.60 (2.98-14.13) | 3.03E-06 | 396 | 4.60 (2.39-8.09) | 1.25E-05 |
| A3301 | 9 | 0 | Inf (0.77-Inf) | 0.07 | 39 | 3.40 (1.43-7.23) | 3.20E-03 | 32 | 2.80 (1.16-6.09) | 0.01 | 255 | 4.89 (2.19-9.56) | 1.63E-04 |
| A0301 | 26 | 15 | 0.63 (0.31-1.35) | 0.20 | 592 | 0.59 (0.38-0.90) | 0.01 | 380 | 0.63 (0.40-0.97) | 0.03 | 5497 | 0.60 (0.38-0.90) | 0.01 |
| A0101 | 71 | 17 | 1.81 (0.99-3.48) | 0.04 | 662 | 1.73 (1.29-2.31) | 2.67E-04 | 448 | 1.74 (1.28-2.33) | 3.21E-04 | 7411 | 1.39 (1.05-1.83) | 0.02 |
| A3201 | 3 | 4 | 0.28 (0.04-1.70) | 0.18 | 152 | 0.38 (0.06-0.80) | 0.01 | 105 | 0.37 (0.05-0.82) | 0.02 | 1323 | 0.30 (0.06-0.80) | 0.02 |
| A0201 | 64 | 24 | 1.03 (0.59-1.85) | 1.00 | 1085 | 0.80 (0.59-1.08) | 0.14 | 756 | 0.78 (0.57-1.04) | 0.09 | 10680 | 0.75 (0.56-1.00) | 0.05 |
| A2902 | 10 | 1 | 3.95 (0.55-173.12) | 0.30 | 48 | 3.07 (1.37-6.24) | 3.65E-03 | 37 | 2.70 (1.18-5.61) | 9.43E-03 | 750 | 1.83 (0.86-3.43) | 0.08 |
| A2601 | 8 | 3 | 1.03 (0.24-6.13) | 1.00 | 115 | 1.00 (0.42-2.07) | 1.00 | 91 | 0.85 (0.35-1.78) | 0.86 | 834 | 1.30 (0.55-2.62) | 0.41 |
| A2501 | 3 | 2 | 0.57 (0.06-6.96) | 0.62 | 101 | 0.42 (0.08-1.28) | 0.16 | 47 | 0.62 (0.12-1.94) | 0.62 | 673 | 0.60 (0.12-1.77) | 0.50 |
| A2402 | 23 | 11 | 0.79 (0.35-1.86) | 0.55 | 356 | 0.92 (0.57-1.44) | 0.83 | 249 | 0.89 (0.55-1.40) | 0.74 | 2801 | 1.12 (0.69-1.72) | 0.57 |
| A3101 | 9 | 2 | 1.75 (0.35-16.95) | 0.73 | 115 | 1.13 (0.50-2.26) | 0.71 | 75 | 1.18 (0.51-2.39) | 0.57 | 1015 | 1.20 (0.54-2.33) | 0.58 |
| A1101 | 14 | 10 | 0.52 (0.21-1.34) | 0.16 | 255 | 0.78 (0.41-1.36) | 0.44 | 177 | 0.76 (0.40-1.33) | 0.44 | 2278 | 0.82 (0.44-1.40) | 0.61 |
| A2301 | 6 | 2 | 1.16 (0.20-11.91) | 1.00 | 94 | 0.92 (0.33-2.10) | 1.00 | 61 | 0.96 (0.34-2.24) | 1.00 | 672 | 1.21 (0.44-2.68) | 0.65 |
| A6801 | 9 | 8 | 0.42 (0.14-1.27) | 0.09 | 128 | 1.01 (0.45-2.01) | 0.86 | 100 | 0.87 (0.38-1.76) | 0.87 | 1142 | 1.07 (0.48-2.06) | 0.86 |
| A19 all (29,30,31,32,33) | 44 | 8 | 2.07 (0.92-4.64) | 0.08 | 399 | 1.49 (1.02-2.18) | 0.04 | 269 | 1.58 (1.07-2.34) | 0.02 | 3739 | 1.51 (1.04-2.18) | 0.03 |

Figure 1

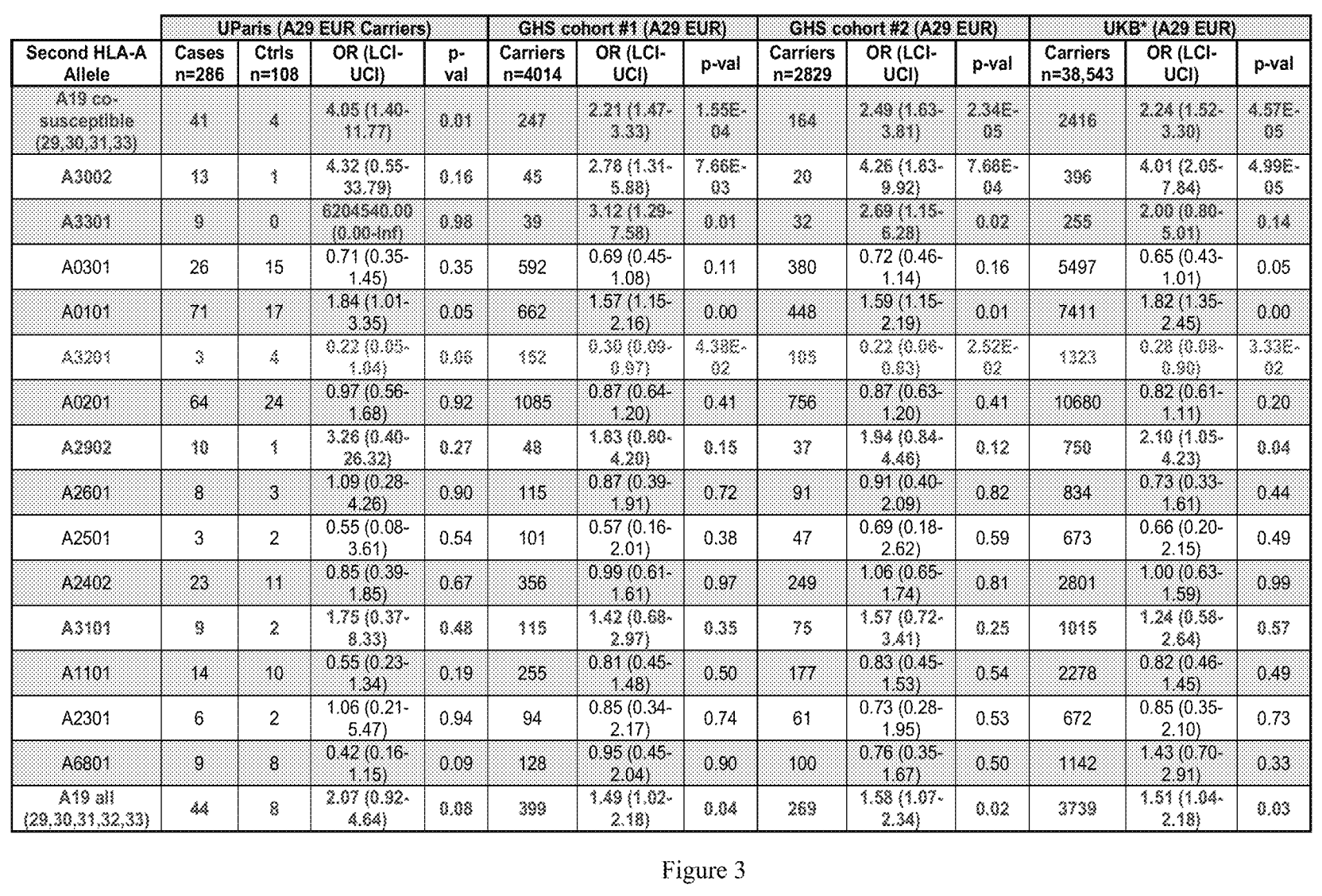

| Second HLA-A Allele | UParis (A29:EUR Carriers) | | | | GHS cohort #1 (A29:EUR) | | | GHS cohort #2 (A29:EUR) | | | UKB* (A29:EUR) | | |
|---|---|---|---|---|---|---|---|---|---|---|---|---|---|
| | Cases n=286 | Ctrls n=108 | OR (LCI-UCI) | p-val | Carriers n=4014 | OR (LCI-UCI) | p-val | Carriers n=2829 | OR (LCI-UCI) | p-val | Carriers n=38,543 | OR (LCI-UCI) | p-val |
| A19 co-susceptible (29,30,31,33) | 41 | 4 | 4.05 (1.40-11.77) | 0.01 | 247 | 2.21 (1.47-3.33) | 1.55E-04 | 164 | 2.49 (1.63-3.81) | 2.34E-05 | 2416 | 2.24 (1.52-3.30) | 4.57E-05 |
| A3002 | 13 | 1 | 4.32 (0.55-33.79) | 0.16 | 45 | 2.78 (1.31-5.88) | 7.66E-03 | 20 | 4.26 (1.83-9.92) | 7.68E-04 | 396 | 4.01 (2.05-7.84) | 4.99E-05 |
| A3301 | 9 | 0 | 8204548.00 (0.00-Inf) | 0.98 | 39 | 3.12 (1.29-7.58) | 0.01 | 32 | 2.69 (1.15-6.28) | 0.02 | 255 | 2.00 (0.80-5.01) | 0.14 |
| A0301 | 26 | 15 | 0.71 (0.35-1.45) | 0.35 | 592 | 0.69 (0.45-1.08) | 0.11 | 380 | 0.72 (0.46-1.14) | 0.16 | 5497 | 0.65 (0.43-1.01) | 0.05 |
| A0101 | 71 | 17 | 1.84 (1.01-3.35) | 0.05 | 662 | 1.57 (1.15-2.16) | 0.00 | 448 | 1.59 (1.15-2.19) | 0.01 | 7411 | 1.82 (1.35-2.45) | 0.00 |
| A3201 | 3 | 4 | 0.22 (0.05-1.04) | 0.06 | 152 | 0.30 (0.09-0.97) | 4.39E-02 | 105 | 0.22 (0.06-0.83) | 2.52E-02 | 1323 | 0.28 (0.09-0.90) | 3.33E-02 |
| A0201 | 64 | 24 | 0.97 (0.56-1.68) | 0.92 | 1085 | 0.87 (0.64-1.20) | 0.41 | 756 | 0.87 (0.63-1.20) | 0.41 | 10680 | 0.82 (0.61-1.11) | 0.20 |
| A2902 | 10 | 1 | 3.26 (0.40-26.32) | 0.27 | 48 | 1.63 (0.60-4.20) | 0.15 | 37 | 1.94 (0.84-4.46) | 0.12 | 750 | 2.10 (1.05-4.23) | 0.04 |
| A2601 | 8 | 3 | 1.09 (0.28-4.26) | 0.90 | 115 | 0.87 (0.39-1.91) | 0.72 | 91 | 0.91 (0.40-2.09) | 0.82 | 834 | 0.73 (0.33-1.61) | 0.44 |
| A2501 | 3 | 2 | 0.55 (0.08-3.61) | 0.54 | 101 | 0.57 (0.16-2.01) | 0.38 | 47 | 0.69 (0.18-2.62) | 0.59 | 673 | 0.66 (0.20-2.15) | 0.49 |
| A2402 | 23 | 11 | 0.85 (0.39-1.85) | 0.67 | 356 | 0.99 (0.61-1.61) | 0.97 | 249 | 1.06 (0.65-1.74) | 0.81 | 2801 | 1.00 (0.63-1.59) | 0.99 |
| A3101 | 9 | 2 | 1.75 (0.37-8.33) | 0.48 | 115 | 1.42 (0.68-2.97) | 0.35 | 75 | 1.57 (0.72-3.41) | 0.25 | 1015 | 1.24 (0.58-2.64) | 0.57 |
| A1101 | 14 | 10 | 0.55 (0.23-1.34) | 0.19 | 255 | 0.81 (0.45-1.48) | 0.50 | 177 | 0.83 (0.45-1.53) | 0.54 | 2278 | 0.82 (0.46-1.45) | 0.49 |
| A2301 | 6 | 2 | 1.06 (0.21-5.47) | 0.94 | 94 | 0.85 (0.34-2.17) | 0.74 | 61 | 0.73 (0.28-1.95) | 0.53 | 672 | 0.85 (0.35-2.10) | 0.73 |
| A6801 | 9 | 8 | 0.42 (0.16-1.15) | 0.09 | 128 | 0.95 (0.45-2.04) | 0.90 | 100 | 0.76 (0.35-1.67) | 0.50 | 1142 | 1.43 (0.70-2.91) | 0.33 |
| A19 all (29,30,31,32,33) | 44 | 8 | 2.07 (0.92-4.64) | 0.08 | 399 | 1.49 (1.02-2.18) | 0.04 | 269 | 1.58 (1.07-2.34) | 0.02 | 3739 | 1.51 (1.04-2.18) | 0.03 |

Figure 3

| ERAP1 | | | | | | | | | UParis | | | |
|---|---|---|---|---|---|---|---|---|---|---|---|---|
| rs27773968 5:96803892 G:A | rs3734016 5:96803761 C:T | rs26618 5:96795133 T:C | rs27895 5:96793840 C:T | rs2287987 5:96793827 T:C | rs30187 5:96788627 T:C | rs10050860 5:96786506 C:T | rs17482078 5:96783162 C:G | rs27044 5:96783148 C:G | F cases | F controls | OR | P |
| Function | | | | | | | | | | | | |
| I12T | E36K | I276M | G346D | M349V | K528R | D575N | R725Q | Q730E | | | | |
| Hap 1 T | E | I | G | M | K | D | R | Q | 0.17 | 0.35 | 0.41 | 6.7E-6 |
| Hap 2 T | E | I | G | M | K | D | R | Q | | | | |
| Hap 3 T | E | I | G | M | K | D | R | E | | | | |
| Hap 5 T | E | I | D | M | R | D | R | E | | | | |
| Hap 6 T | E | I | G | M | R | D | R | E | 0.55 | 0.48 | 1.32 | 0.11 |
| Hap 7 T | K | I | G | M | R | D | R | E | | | | |
| Hap 8 T | E | M | G | M | R | D | R | E | | | | |
| Hap 10 T | E | I | G | V | R | N | Q | E | 0.28 | 0.17 | 1.78 | 8.0E-3 |

Figure 4

| Gene | Variant | Variant type | Study | OR (LCI-UCI) | p-value | Hom OR | Case MAF | Control MAF | Meta OR (LCI-UCI) | Meta p-value |
|------|---------|--------------|-------|--------------|---------|--------|----------|-------------|-------------------|--------------|
| ERAP2-LNPEP | rs10044354 5:96984791:C:T | Intronic | Kuiper et al. | 2.3 (1.69-3.61) | 1.21E-06 | | 0.63 | 0.42 | 1.95 (1.55-2.44) | 6.20E-09 |
| | | | UParis | 1.55 (1.13-2.11) | 5.80E-03 | 2.6 (1.3-5.15) | 0.52 | 0.41 | | |
| | LD between rs10044354 (ERAP2-LNPEP) and rs27432 (ERAP1): D' = 0.79 R2 = 0.18 | | | | | | | | | |
| ERAP1 | rs27432 5:96783569:A:G* | Intronic | Kuiper et al. | 2.26 (2.05-2.47) | 7.20E-05 | | 0.85 | 0.71 | 2.46 (1.85-3.26) | 4.07E-10 |
| | | | UParis | 2.58 (1.78-3.76) | 6.60E-07 | 4.77 (1.98-11.51) | 0.83 | 0.65 | | |

Figure 5

| Gene | Variant | Variant type | Study | OR (LCI-UCI) | p-value | Hom OR | Case MAF | Control MAF | Meta OR (LCI-UCI) | Meta p-value |
|---|---|---|---|---|---|---|---|---|---|---|
| ERAP2 | rs2248374 5:96900192:A:G | Splice region | Kuiper et al. | 0.44 (0.31-0.63) | 6.60E-06 | | 0.33 | 0.53 | 0.56 (0.45-0.70) | 2.39E-07 |
| | | | UParis | 0.68 (0.5-0.92) | 1.40E-02 | 0.45 (0.23-0.87) | 0.43 | 0.53 | | |

Figure 6

| Aw19 | ERAP2-rs10044354 | case_n | contr_n | case_F | controlF | OR | OR CI_low | OR CI_high | P |
|---|---|---|---|---|---|---|---|---|---|
| A29/- | CC | 46 | 1296 | 0.167 | 0.319 | 1.000 | NA | NA | NA |
| A29/- | CT | 132 | 1842 | 0.478 | 0.453 | 2.019 | 1.421 | 2.911 | 3.95E-05 |
| A29/- | TT | 56 | 681 | 0.203 | 0.167 | 2.316 | 1.522 | 3.539 | 4.51E-05 |
| A29/Aw19 | CC | 13 | 94 | 0.047 | 0.023 | 3.891 | 1.861 | 7.644 | 2.13E-04 |
| A29/Aw19 | CT | 17 | 119 | 0.062 | 0.029 | 4.019 | 2.092 | 7.413 | 2.32E-05 |
| A29/Aw19 | TT | 12 | 34 | 0.043 | 0.008 | 9.902 | 4.378 | 21.197 | 1.16E-07 |

Figure 8

| Aw19 | ERAP1-rs27432 | cases number | controls number | cases freq. | controls freq. | OR | OR CI_low | OR CI_high | P |
|------|---------------|--------------|-----------------|-------------|----------------|-----|-----------|------------|---|
| A29/- | AA | 9 | 298 | 0.033 | 0.073 | 1.000 | NA | NA | NA |
| A29/- | AG | 58 | 1550 | 0.212 | 0.378 | 1.239 | 0.601 | 2.876 | 0.734 |
| A29/- | GG | 164 | 2001 | 0.601 | 0.488 | 2.713 | 1.374 | 6.105 | 1.72E-03 |
| A29/Aw19 | AA | 2 | 24 | 0.007 | 0.006 | 2.747 | 0.274 | 14.391 | 0.209 |
| A29/Aw19 | AG | 15 | 91 | 0.055 | 0.022 | 5.430 | 2.144 | 14.579 | 9.32E-05 |
| A29/Aw19 | GG | 25 | 133 | 0.092 | 0.032 | 6.196 | 2.708 | 15.515 | 1.54E-06 |

Figure 9

| ERAP1-rs27432 | ERAP2-rs10044354 | cases number | controls number | cases freq. | controls freq. | OR | OR_CIlo | OR_CIhi | P |
|---|---|---|---|---|---|---|---|---|---|
| AA | CC | 7 | 255 | 0.026 | 0.063 | 1.000 | NA | NA | NA |
| AA | CT | 4 | 60 | 0.015 | 0.015 | 2.420 | 0.503 | 9.885 | 0.236 |
| AA | TT | 0 | 2 | 0.000 | 0.000 | 0.000 | 0.000 | 208.116 | 1.000 |
| AG | CC | 19 | 687 | 0.070 | 0.170 | 1.007 | 0.400 | 2.871 | 1.000 |
| AG | CT | 49 | 856 | 0.180 | 0.212 | 2.084 | 0.924 | 5.521 | 0.072 |
| AG | TT | 5 | 86 | 0.018 | 0.021 | 2.113 | 0.515 | 7.964 | 0.197 |
| GG | CC | 32 | 443 | 0.118 | 0.109 | 2.628 | 1.118 | 7.160 | 0.024 |
| GG | CT | 94 | 1030 | 0.346 | 0.255 | 3.323 | 1.525 | 8.594 | 8.29E-04 |
| GG | TT | 62 | 627 | 0.228 | 0.155 | 3.598 | 1.617 | 9.446 | 4.03E-04 |

Figure 10

| Aw19 | ERAP1-rs27432 | ERAP2-rs10044354 | cases number | controls number | cases freq. | controls freq. | OR | OR_CIlo | OR_CIhi | P | Absolute risk |
|---|---|---|---|---|---|---|---|---|---|---|---|
| A29/- | 0 | 0 | 5 | 237 | 0.018 | 0.059 | NA | NA | NA | NA | 3.43E-05 |
| A29/- | 0/1 | 0/1 | 60 | 1510 | 0.220 | 0.373 | 1.883 | 0.752 | 6.071 | 0.197 | 6.45E-05 |
| A29/- | 2_either | 2_either | 113 | 1457 | 0.414 | 0.360 | 3.674 | 1.506 | 11.653 | 1.16E-03 | 1.26E-04 |
| A29/- | 2_both | 2_both | 53 | 596 | 0.194 | 0.147 | 4.211 | 1.666 | 13.665 | 6.26E-04 | 1.44E-04 |
| A29/Aw19 | 0 | 0 | 2 | 18 | 0.007 | 0.004 | 5.204 | 0.465 | 34.701 | 0.092 | 1.78E-04 |
| A29/Aw19 | 0/1 | 0/1 | 12 | 93 | 0.044 | 0.023 | 6.079 | 1.929 | 22.651 | 5.23E-04 | 2.08E-04 |
| A29/Aw19 | 2_either | 2_either | 19 | 104 | 0.070 | 0.026 | 8.604 | 3.002 | 30.314 | 3.09E-06 | 2.95E-04 |
| A29/Aw19 | 2_both | 2_both | 9 | 31 | 0.033 | 0.008 | 13.527 | 3.791 | 54.766 | 1.17E-05 | 4.63E-04 |

Figure 11

| Allele\position | 9 | 17 | 56 | 62 | 63 | 70 | 73 | 76 | 77 | 79 | 80 | 81 | 82 | 83 | 97 | 105 | 109 | 114 | 116 | 152 |
|---|---|---|---|---|---|---|---|---|---|---|---|---|---|---|---|---|---|---|---|---|
| | F | R | G | Q | E | H | T | A | N | G | T | L | R | G | I | P | F | R | D | A |
| A*01:01:01:01 | | | | | | Q | | | | | | | | | | | | | | |
| A*29:02:01:03 | T | ' | ' | L | Q | ' | ' | ' | ' | ' | ' | ' | ' | ' | M | S | ' | ' | ' | V |
| A*30:02:01:01 | S | S | R | ' | ' | ' | ' | E | ' | ' | ' | ' | ' | ' | ' | S | ' | E | H | R |
| A*31:01:02:01 | T | ' | R | ' | ' | ' | — | V | Q | R | ' | A | L | R | M | S | L | Q | ' | V |
| A*32:01:01:01 | ' | ' | ' | R | N | ' | ' | E | S | ' | ' | ' | ' | R | M | ' | ' | Q | ' | V |
| A*33:01:01:01 | T | ' | ' | ' | ' | ' | — | V | Q | ' | ' | ' | ' | ' | M | S | ' | Q | ' | V |
| A*74:01:01:01 | ' | ' | ' | ' | ' | ' | ' | V | D | ' | ' | ' | ' | ' | M | ' | L | Q | ' | V |

MODULATION OF ENDOPLASMIC RETICULUM AMINOPEPTIDASE 2 (ERAP2)-MEDIATED IMMUNE RESPONSE

REFERENCE TO SEQUENCE LISTING

This application includes a Sequence Listing filed electronically as a text file named 18923805101SEQ, created on Jul. 23, 2021, with a size of 1,243 kilobytes. The Sequence Listing is incorporated herein by reference.

FIELD

The present disclosure is directed, in part, to methods of treating subjects having an immune disorder by administering a therapeutically effective amount of an Endoplasmic Reticulum Aminopeptidase 2 (ERAP2) inhibitor to the subject, and optionally an Endoplasmic Reticulum Aminopeptidase 1 (ERAP1) agonist or inhibitor and/or an HLA-Aw19 inhibitor, and also provides methods of identifying subjects having an increased risk for developing an MHC-I-opathy.

BACKGROUND

The cellular immune response in humans relies at least partly on the presentation of small peptides that are 8 to 10 amino acids long, which are bound proteins of the major histocompatibility complex (MHC) (i.e., class I MHC molecules). These small peptides are derived from the proteolytic degradation of proteins (foreign antigens and self-antigens). One source of these antigens come from infected or malignantly transformed cells that express particular protein molecules that, upon degradation, yield distinct antigenic peptides that are presented on the cell surface complexed with MHC class I molecules (MHCl). Cytotoxic T cells can recognize these complexes of MHC molecules with degraded protein antigens and induce apoptotic cell death. Aberrant generation of antigenic peptides can lead to immune system evasion or to autoimmune reactions.

Although most antigenic peptides are initially produced by the proteasome, many of them are larger than the final antigenic epitope and contain one or more additional amino acids at their N-termini. These antigenic peptide precursors are transported into the endoplasmic reticulum (ER), where they are further degraded by at least two different amino-peptidases, ERAP1 and ERAP2, to generate the mature antigenic peptides for complexing with MHC class I molecules. Thus, the activity of ERAP1 and ERAP2 can directly affect the presentation of antigenic peptides complexed with particular MHC molecules in a beneficial or adverse manner, thus altering the immune response. Accordingly, there continues to be a need for identifying subjects that have particular MHC-I-opathies related to ERAP2 activity and treatment of the same.

Birdshot Chorioretinopathy (BSCR) is a rare autoimmune uveitis predominately affecting individuals over the age of 50 of European descent and treated with immunomodulatory therapies. The disease presents with vitritis and gradual decline in vision due to choroidal and retinal inflammatory lesions and atrophy. T cells have been identified in the retinal and choroidal tissues as well as the vitreous of affected BSCR eyes.

SUMMARY

The present disclosure provides methods of treating a subject having an immune disorder, the methods comprising administering to the subject a therapeutically effective amount of an ERAP2 inhibitor. Optionally, an ERAP1 agonist or inhibitor and/or an HLA-Aw19 inhibitor is also administered to the subject. The immune disorder can be an MHC-I-opathy or an MHC-II-opathy. The MHC-I-opathy can be BSCR, Ankylosing Spondylitis (AS), Behçet's disease, psoriasis, Juvenile Idiopathic Arthritis (JIA), inflammatory bowel disease (IBD), or Crohn's disease (CD).

The present disclosure also provides methods of treating a subject having an MHC-I-opathy, the methods comprising: performing or having performed an assay on a biological sample from the subject to determine whether the subject comprises: i) an MHC-I-opathy-related HLA genotype; and ii) a functional ERAP2 protein or a nucleic acid molecule encoding a functional ERAP2 protein; and administering to the subject a therapeutically effective amount of an ERAP2 inhibitor, wherein the subject comprises both an MHC-I-opathy-related HLA genotype and a functional ERAP2 protein or a nucleic acid molecule encoding a functional ERAP2 protein; wherein the presence of both the MHC-I-opathy-related HLA genotype and the functional ERAP2 protein or a nucleic acid molecule encoding a functional ERAP2 protein indicates that the subject is a candidate for treating the MHC-I-opathy by inhibiting ERAP2. The assay performed or having been performed on the biological sample from the subject can further determine whether the subject comprises a functional ERAP1 protein or a nucleic acid molecule encoding a functional ERAP1 protein; and the methods can further comprise administering to the subject a therapeutically effective amount of an ERAP1 agonist or inhibitor, wherein the subject comprises an MHC-I-opathy-related HLA genotype and does or does not comprise a functional ERAP1 protein or a nucleic acid molecule encoding a functional ERAP1 protein; wherein the presence of an MHC-I-opathy-related HLA genotype and the absence of a functional ERAP1 protein or a nucleic acid molecule encoding a functional ERAP1 protein indicates that the subject is a candidate for treating the MHC-I-opathy by activating ERAP1; wherein the presence of an MHC-I-opathy-related HLA genotype and the presence of a functional ERAP1 protein or a nucleic acid molecule encoding a functional ERAP1 protein indicates that the subject is a candidate for treating the MHC-I-opathy by inhibiting ERAP1.

The present disclosure also provides methods of identifying a subject having an increased risk for developing an MHC-I-opathy, the methods comprising: performing or having performed an assay on a biological sample from the subject to determine whether the subject comprises: i) an MHC-I-opathy-related HLA genotype; and ii) a functional ERAP2 protein or a nucleic acid molecule encoding a functional ERAP2 protein; wherein: when the subject has both the MHC-I-opathy-related HLA genotype and the functional ERAP2 protein or the nucleic acid molecule encoding the functional ERAP2 protein, then the subject has an increased risk of developing the MHC-I-opathy; when the subject lacks the MHC-I-opathy-related HLA genotype, or lacks the functional ERAP2 protein or the nucleic acid molecule encoding the functional ERAP2 protein, or lacks both, then the subject has a decreased risk of developing the MHC-I-opathy; and when the subject comprises two copies of the MHC-I-opathy-related HLA genotype, then the subject has an increased risk of developing the MHC-I-opathy compared to comprising a single copy of the MHC-I-opathy-related HLA genotype. The assay performed or having been performed on the biological sample from the subject can further determine whether the subject comprises a functional ERAP1 protein or a nucleic acid molecule encoding a functional ERAP1 protein. When the subject has the MHC-I-opathy-related HLA genotype and lacks the functional ERAP1 protein or the nucleic acid molecule encoding the functional ERAP1 protein, then the subject has an increased risk of developing the MHC-I-opathy; and when the subject lacks the MHC-I-opathy-related HLA genotype, or has the functional ERAP1 protein or the nucleic acid molecule encoding the functional ERAP1 protein, or both, then the subject has a decreased risk of developing the MHC-I-opathy.

BRIEF DESCRIPTION OF THE DRAWINGS

FIG. 1 shows a table of HLA-A 2nd allele frequencies in the French cohort compared to UKB and GHS EUR A29 carriers. Alleles belonging to the Aw19 broad antigen group that increase risk are A29, A30, A31 and A33 (red) and A32 exhibits protection (green). A Fisher's exact test combining all Aw19 risk alleles presents the strongest enrichment in all comparisons. Only alleles that have three or more case carriers are presented. Table is sorted by p-values when comparing case frequencies against A29 controls in UKB.

FIG. 3 shows a table of HLA-A 2nd allele frequencies in the French cohort compared to UKB and GHS EUR A29 carriers. Alleles belonging to the Aw19 broad antigen group that increase risk are A29, A30, A31 and A33 (red) and A32 exhibits protection (green). A logistic regression test with covariates included for sex and six principal components, calculated based on genetic array data for each analytic set. Results are presented for all HLA-A alleles that have three or more case carriers. Alleles are sorted as in FIG. 1. *Three principal components.

FIG. 4 shows a table of haplotype analysis of ERAP1. Haplotype analysis examining the association of all eight ERAP1 haplotypes with the case-control status, showing that Hap1 and Hap2 are strongly associated with protection from BSCR.

FIG. 5 shows a table of top SNPs in ERAP1 and ERAP2 regions. Variants in ERAP1 and ERAP2 are genome-wide significant when analyzed together with previous results (125 cases and 670 controls (Kuiper 2014). Rs10044354 is the top association in the ERAP1-ERAP2 locus in the previous GWAS of Dutch and Spanish cohorts, while rs27432 is the top association in the region in the current French cohort. The LD between the two loci is also presented. *The reference A-allele is the minor allele, risk is the G-allele.

FIG. 6 shows ERAP2 splice region variant is protective for BSCR. The common ERAP2 splice region variant rs2248374 that disrupts ERAP2 expression is protective in the current BSCR cohort and the previous Spanish and Dutch cohorts.

FIG. 8 shows a table of the combined risk of ERAP2 and Aw19. Utilizing 286 Birdshot cases and 4,014 controls from GHS cohort #1 to calculate additive risk while combining risk factors in ERAP2 and Aw19. An additive genotype model of ERAP2 risk signal tagged by rs10044354 and single (A29/-) or double (A29/Aw19) Aw19 copies relative to lowest risk combination of rs10044354-CC and one copy of Aw19 allele (A29).

FIG. 9 shows a table of the combined risk of ERAP1 and Aw19. Utilizing 286 Birdshot cases and 4,014 controls from GHS cohort #1 to calculate additive risk while combining risk factors in ERAP1 and Aw19. An additive genotype model of ERAP1 risk signal tagged by rs27432 and single (A29/-) or double (A29/Aw19) Aw19 copies relative to lowest risk combination of rs27432-AA and one copy of Aw19 allele (A29).

FIG. 10 shows a table of the combined risk of ERAP1 and ERAP2. Utilizing 286 Birdshot cases and 4,014 controls from GHS cohort #1 to calculate additive risk while combining risk factors in ERAP1 and ERAP2. An additive genotype model of ERAP1 risk signal tagged by rs27432 and ERAP2 signal tagged by rs10044354 relative to lowest risk combination of rs27432-AA and rs10044354-CC.

FIG. 11 shows a table of the combined risk of ERAP1, ERAP2 and Aw19. Utilizing 286 Birdshot cases and 4,014 controls from GHS cohort #1 to calculate additive risk while combining risk factors in ERAP1, ERAP2 and Aw19. An additive genotype model of ERAP1 and ERAP2 risk signals and single (A29/-) or double (A29/Aw19) Aw19 copies relative to lowest risk combination. The genotypes are combined as following: 0=ERAP1 and ERAP2 homozygous for protective allele. 1/[01],[01]/1=either homozygous protective or heterozygous genotypes of both ERAP1 and ERAP2. 2/ . . . /2=homozygous risk allele of either ERAP1 or ERAP2. 2/2=homozygous risk allele of both ERAP1 and ERAP2.

FIG. 12 shows differences between risk Aw19 alleles and A32. Panel A) Sequence differences between risk Aw19 alleles (red) and protective A32 allele (green). A32 exhibits F at position 9 as is the reference A:01:01 allele, while risk alleles are either T or S at that position. The Bw4 epitope sequence is apparent at positions 79-83 or A32 only.

DESCRIPTION OF EMBODIMENTS

Figure 2:
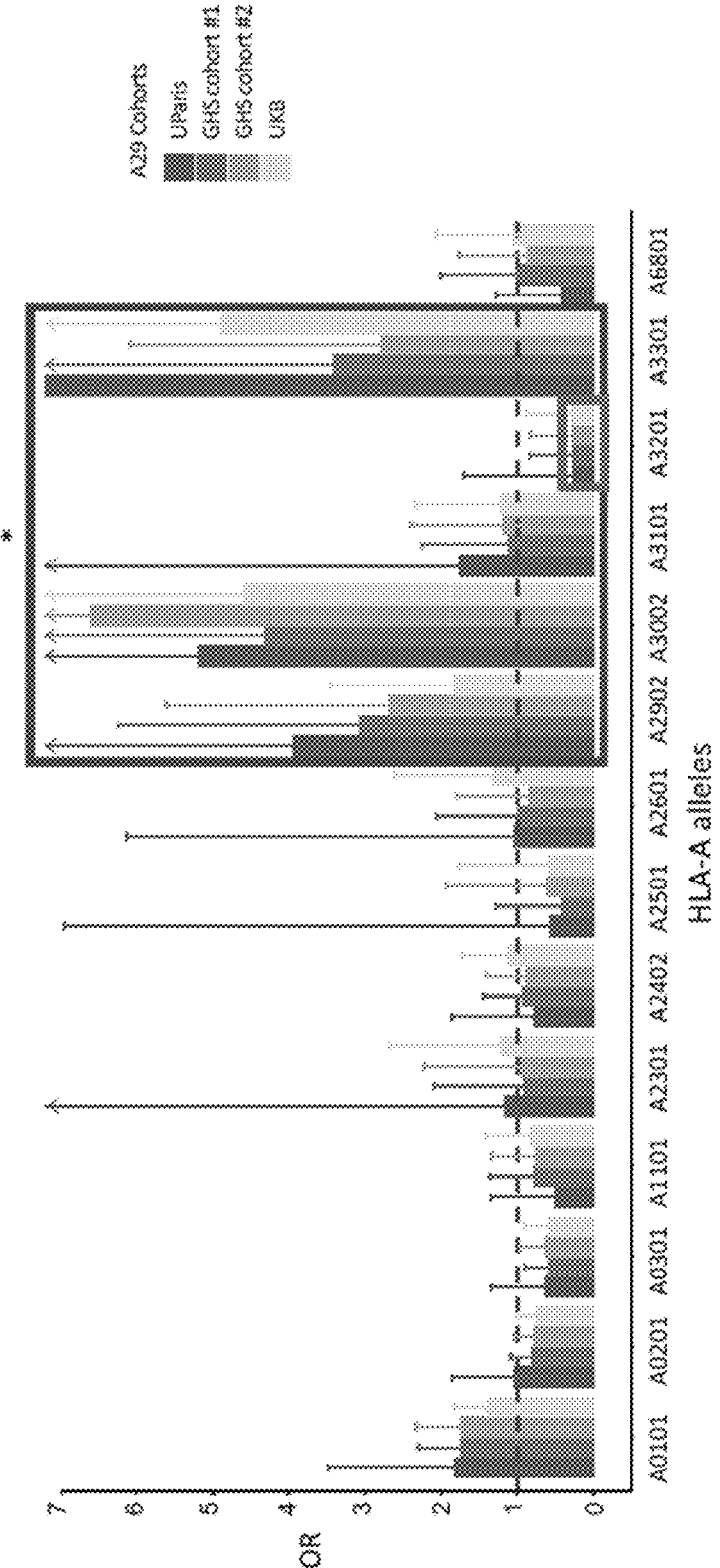
FIG. 2 shows Aw19 enrichment in Birdshot cases. Odds-ratio for BSCR, comparing frequencies of 14 HLA-A alleles that are present in three or more cases (>1%, x-axis) in 286 UParis cases compared with 108 UParis controls (Blue), GHS control cohort #1 (n=4,014, dark green), GHS control cohort #2 (n=2,829, bright green) and UKB controls (n=38, 543, yellow). Aw19 alleles show the highest ORs (red box) that replicates with large A29 control cohorts, with the exception of A32 that is depleted in cases (green box). * p<0.01

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

The present disclosure provides methods of treating a subject having an immune disorder, the methods comprising administering to the subject an ERAP2 inhibitor. In some embodiments, the immune disorder is an MHC-I-opathy. In some embodiments, the immune disorder is an MHC-II-opathy. In some embodiments, the MHC-I-opathy is Birdshot Chorioretinopathy (BSCR), Ankylosing Spondylitis (AS), Behçet's disease, psoriasis, Juvenile Idiopathic Arthritis (JIA), inflammatory bowel disease (IBD), or Crohn's disease (CD). In some embodiments, the MHC-I-opathy is BSCR. In some embodiments, the MHC-I-opathy is AS. In some embodiments, the MHC-I-opathy is Behçet's disease. In some embodiments, the MHC-I-opathy is psoriasis. In some embodiments, the MHC-I-opathy is JIA. In some embodiments, the MHC-I-opathy is IBD. In some embodiments, the MHC-I-opathy is CD.

In some embodiments, the MHC-I-opathy is BSCR. In some embodiments, the method further comprises detecting the presence or absence of an HLA-Aw19 allele in a biological sample obtained from the subject. In some embodiments, the subject is HLA-Aw19$^+$. In some embodiments, the subject is or is suspected of being HLA-A*29$^+$, HLA-A*30$^+$, HLA-A*31$^+$, or HLA-A*33$^+$, or any combination thereof. In some embodiments, the method further comprises determining whether the subject has one or two copies of an HLA-Aw19 allele. In some embodiments, the subject has a single copy of HLA-Aw19. In some embodiments, the subject has two copies of HLA-Aw19. In some embodiments, the subject is HLA-A*29$^+$/HLA-A*30$^+$. In some embodiments, the subject is HLA-A*29$^+$/HLA-A*31$^+$. In some embodiments, the subject is HLA-A*29$^+$/HLA-A*33$^+$.

In some embodiments, the subject having BSCR is not HLA-A*29$^+$.

In some embodiments, the subject having BSCR has a copy of at least any two of HLA-A*29, HLA-A*30, HLA-A*31, or HLA-A*33. In some embodiments, the subject having BSCR has a copy of at least any three of HLA-A*29, HLA-A*30, HLA-A*31, or HLA-A*33. In some embodiments, the subject having BSCR has a copy of all of HLA-A*29, HLA-A*30, HLA-A*31, or HLA-A*33.

In some embodiments, the subject having BSCR has one copy of each HLA-A*29 and HLA-A*30. In some embodiments, the subject having BSCR has one copy of each HLA-A*29 and HLA-A*31. In some embodiments, the subject having BSCR has one copy of each HLA-A*29 and HLA-A*33. In some embodiments, the subject having BSCR has one copy of each HLA-A*30 and HLA-A*31. In some embodiments, the subject having BSCR has one copy of each HLA-A*30 and HLA-A*33. In some embodiments, the subject having BSCR has one copy of each HLA-A*31 and HLA-A*33.

In some embodiments, the subject having BSCR has one copy of HLA-A*29 and two copies of HLA-A*30. In some embodiments, the subject having BSCR has one copy of HLA-A*29 and two copies of HLA-A*31. In some embodiments, the subject having BSCR has one copy of HLA-A*29 and two copies of HLA-A*33. In some embodiments, the subject having BSCR has one copy of HLA-A*30 and two copies of HLA-A*31. In some embodiments, the subject having BSCR has one copy of HLA-A*30 and two copies HLA-A*33. In some embodiments, the subject having BSCR has one copy of HLA-A*31 and two copies of HLA-A*33.

In some embodiments, the subject having BSCR has two copies of HLA-A*29 and one copy of HLA-A*30. In some embodiments, the subject having BSCR has two copies of HLA-A*29 and one copy of HLA-A*31. In some embodiments, the subject having BSCR has two copies of HLA-A*29 and one copy of HLA-A*33. In some embodiments, the subject having BSCR has two copies of HLA-A*30 and one copy of HLA-A*31. In some embodiments, the subject having BSCR has two copies of HLA-A*30 and one copy of HLA-A*33. In some embodiments, the subject having BSCR has two copies of HLA-A*31 and one copy of HLA-A*33.

In some embodiments, the subject having BSCR or suspected of having BSCR has two copies of HLA-A*29 and two copies of HLA-A*30. In some embodiments, the subject having BSCR or suspected of having BSCR has two copies of HLA-A*29 and two copies of HLA-A*31. In some embodiments, the subject having BSCR or suspected of having BSCR has two copies of HLA-A*29 and two copies of HLA-A*33. In some embodiments, the subject having BSCR or suspected of having BSCR has two copies of HLA-A*30 and two copies of HLA-A*31. In some embodiments, the subject having BSCR or suspected of having BSCR has two copies of HLA-A*30 and two copies of HLA-A*33. In some embodiments, the subject having BSCR or suspected of having BSCR has two copies of HLA-A*31 and two copies of HLA-A*33.

In some embodiments, the method further comprises administering to the subject an HLA-Aw19 inhibitor. In some embodiments, the HLA-Aw19 inhibitor is an antibody. In some embodiments, the antibody is an anti-HLA-A*29 antibody. In some embodiments, the HLA-Aw19 inhibitor comprises a small molecule degrader or an inhibitory nucleic acid molecule. In some embodiments, the inhibitory nucleic acid molecule is an antisense nucleic acid molecule, a small interfering RNA (siRNA), or a short hairpin RNA (shRNA) that hybridizes to an HLA-Aw19. In some embodiments, the HLA-Aw19 is HLA-A*29.

In some embodiments, the MHC-I-opathy is AS. In some embodiments, the method further comprises detecting the presence or absence of HLA-B*27 or HLA-B*40 in a biological sample obtained from the subject. In some embodiments, the subject is or is suspected of being HLA-B*27$^+$. In some embodiments, the subject is or is suspected of being HLA-B*40$^+$. In some embodiments, the method further comprises determining whether the subject has one or two copies of HLA-B*27 or HLA-B*40. In some embodiments, the subject has a single copy of HLA-B*27 or HLA-B*40. In some embodiments, the subject has two copies of HLA-B*27 or HLA-B*40. In some embodiments, the method further comprises administering to the subject an HLA-B*27 inhibitor or an HLA-B*40 inhibitor. In some embodiments, the HLA-B*27 inhibitor or HLA-B*40 inhibitor is an antibody. In some embodiments, the antibody is an anti-HLA-B*27 antibody or an anti-HLA-B*40 antibody. In some embodiments, the HLA-B*27 inhibitor or HLA-B*40 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*27 or an HLA-B*40.

In some embodiments, the MHC-I-opathy is Behçet's disease. In some embodiments, the method further comprises detecting the presence or absence of HLA-B*51 in a biological sample obtained from the subject. In some embodiments, the subject is or is suspected of being HLA-B*51$^+$. In some embodiments, the method further comprises determining whether the subject has one or two copies of HLA-B*51. In some embodiments, the subject has a single copy of HLA-B*51. In some embodiments, the subject has two copies of HLA-B*51. In some embodiments, the method further comprises administering to the subject an HLA-B*51 inhibitor. In some embodiments, the HLA-B*51 inhibitor is an antibody. In some embodiments, the antibody is an anti-HLA-B*51 antibody. In some embodiments, the HLA-B*51 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*51.

In some embodiments, the MHC-I-opathy is psoriasis. In some embodiments, the method further comprises detecting the presence or absence of HLA-C*06 in a biological sample obtained from the subject. In some embodiments, the subject is or is suspected of being HLA-C*06$^+$. In some embodiments, the method further comprises determining whether the subject has one or two copies of HLA-C*06. In some embodiments, the subject has a single copy of HLA-C*06. In some embodiments, the subject has two copies of HLA-C*06. In some embodiments, the method further comprises administering to the subject an HLA-C*06 inhibitor. In some embodiments, the HLA-C*06 inhibitor is an antibody. In some embodiments, the antibody is an anti-HLA-C*06 antibody. In some embodiments, the HLA-C*06 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-C*06.

In some embodiments, the MHC-I-opathy is JIA. In some embodiments, the method further comprises detecting the presence or absence of HLA-B*27 and/or DRB1 in a biological sample obtained from the subject. In some embodiments, the subject is or is suspected of being HLA-B*27$^+$ and/or DRB1$^+$. In some embodiments, the method further comprises determining whether the subject has one or two copies of HLA-B*27 and/or DRB1. In some embodiments, the subject has a single copy of HLA-B*27 and/or DRB1. In some embodiments, the subject has two copies of HLA-B*27 and/or DRB1. In some embodiments, the method further comprises administering to the subject an HLA-B*27 inhibitor and/or a DRB1 inhibitor. In some embodiments, the HLA-B*27 inhibitor and/or DRB1 inhibitor is an antibody. In some embodiments, the antibody is an anti-HLA-B*27 antibody or an anti-DRB1 antibody. In some embodiments, the HLA-B*27 inhibitor and/or DRB1 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*27 and/or an DRB1.

In some embodiments, the MHC-I-opathy is IBD or CD. In some embodiments, the method further comprises detecting the presence or absence of HLA-C*07 in a biological sample obtained from the subject. In some embodiments, the subject is or is suspected of being HLA-C*07$^+$. In some embodiments, the method further comprises determining whether the subject has one or two copies of HLA-C*07. In some embodiments, the subject has a single copy of HLA-C*07. In some embodiments, the subject has two copies of HLA-C*07. In some embodiments, the method further comprises administering to the subject an HLA-C*07 inhibitor. In some embodiments, the HLA-C*07 inhibitor is an antibody. In some embodiments, the antibody is an anti-HLA-C*07 antibody. In some embodiments, the HLA-C*07 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-C*07.

In some embodiments, the ERAP2 inhibitor comprises a small molecule degrader, a proteoloysis-targeting chimera, an immunomodulatory drug, or an inhibitory nucleic acid molecule. In some embodiments, the inhibitory nucleic acid molecule is an antisense nucleic acid molecule, an siRNA, or an shRNA that hybridizes to ERAP2 mRNA. In some embodiments, the inhibitory nucleic acid molecule is an antisense nucleic acid molecule that hybridizes to ERAP2 mRNA. In some embodiments, the inhibitory nucleic acid molecule is an siRNA that hybridizes to ERAP2 mRNA. In some embodiments, the inhibitory nucleic acid molecule is an shRNA that hybridizes to ERAP2 mRNA. In some embodiments, the ERAP2 inhibitor comprises an anti-ERAP2 antibody. In some embodiments, the ERAP2 inhibitor comprises a pseudopeptide. In some embodiments, the pseudopeptide is a phosphinic pseudopeptide. In some embodiments, the phosphinic pseudopeptide is DG002 or DG013 (see, for example, Zervoudi et al., Proc. Natl. Acad. Sci. USA, 2013, 110, 19890-19895). In some embodiments, the phosphinic pseudopeptide is DG002. In some embodiments, the phosphinic pseudopeptide is DG013. In some embodiments, the ERAP2 inhibitor comprises a small molecule. In some embodiments, the ERAP2 inhibitor is compound 4, compound 15, compound 16, compound 5, or analogues of compound 5, which are drug-like carboxylic acids and bioisosters screened for enhanced selectivity for ERAP2 over ERAP1 (see, Medve et al., European Journal of Medicinal Chemistry, 2021, 211, 113053). In some embodiments, the ERAP2 inhibitor is a phosphonic or phosphinic acid compound with higher affinity for ERAP2 than ERAP1 (see, Weglarz-Tomczak et al., Bioorg. Med. Chem. Lett., 2016, 26, 4122-4126). Additional ERAP2 inhibitors are described in, for example, Georgiadis et al., Curr. Medic. Chem., 2019, 26, 2715-2729.

In any of the embodiments described herein, the methods can further comprise administering to the subject an ERAP1 agonist or inhibitor, depending upon the MHC-I-opathy. For AS and psoriasis, an ERAP1 inhibitor can be administered. For the remaining MHC-I-opathies, an ERAP1 agonist can be administered.

In some embodiments, the ERAP1 agonist comprises an oligonucleotide. In some embodiments, the oligonucleotide is ODN1826. In some embodiments, the ERAP1 agonist comprises a peptide. In some embodiments, the ERAP1 agonist comprises a lipopeptide. In some embodiments, the lipopeptide is Pam3CSK4 or FSL-1. In some embodiments, the lipopeptide is Pam3CSK4. In some embodiments, the lipopeptide is FSL-1. In some embodiments, the ERAP1 agonist comprises a small molecule. In some embodiments, the ERAP1 agonist can comprise an ERAP1-specific transcriptional activator, an ERAP1 protein stabilizer, an agonist of ERAP1 enzymatic activity, or an activator of ERAP1 secretion. In some embodiments, the ERAP1 agonist can comprise an ERAP1-specific transcriptional activator. In some embodiments, the ERAP1 agonist can comprise an ERAP1 protein stabilizer. In some embodiments, the ERAP1 agonist can comprise an agonist of ERAP1 enzymatic activity. In some embodiments, the ERAP1 agonist can comprise an activator of ERAP1 secretion. Additional examples of ERAP1 agonists are described in, for example, Goto et al., J. Immunol., 2014, 192, 4443-4452.

In some embodiments, the ERAP1 inhibitor comprises a small molecule degrader, a proteoloysis-targeting chimera, an immunomodulatory drug, or an inhibitory nucleic acid molecule. In some embodiments, the inhibitory nucleic acid molecule is an antisense nucleic acid molecule, an siRNA, or an shRNA that hybridizes to ERAP1 mRNA. In some embodiments, the inhibitory nucleic acid molecule is an antisense nucleic acid molecule that hybridizes to ERAP1 mRNA. In some embodiments, the inhibitory nucleic acid molecule is an siRNA that hybridizes to ERAP1 mRNA. In some embodiments, the inhibitory nucleic acid molecule is an shRNA that hybridizes to ERAP1 mRNA. In some embodiments, the ERAP1 inhibitor comprises an anti-ERAP1 antibody. In some embodiments, the ERAP1 inhibitor is DG002 and DG013 (see, Zervoudi et al., Proc. Nat'l Acad. Sci. USA, 2013, 110, 19890-19895). In some embodiments, the ERAP1 inhibitor is a phosphinic dipeptide or tripeptide analog (see, Weglarz-Tomczak et al., Bioorg. Med. Che, Lett., 2016, 26, 4122-4126). In some embodiments, the ERAP1 inhibitor is (N—(N-(2-(1H-indol-3-yl) ethyl)carbamimidoyl)-2,5-difluorobenzenesulfonamide), (1-(1-(4-acetylpiperazine-1-carbonyl)cyclohexyl)-3-(p-tolyl) urea), or (4-methoxy-3-(N-(2-(piperidin-1-yl)-5-(trifluoromethyl)phenyl) sulfamoyl)benzoic acid (see, Maben et al., J. Med. Chem., 2020, 63, 103-121). In some embodiments, the ERAP1 inhibitor is (4aR,5S,6R,8S,8aR)-5-(2-(Furan-3-yl)ethyl)-8-hydroxy-5,6,8a-trimethyl-3,4,4a, 5,6,7,8,8a-octahydronaphthalene-1-carboxylic acid (see, Liddle et al., J. Med. Chem., 2020, 63, 3348-3358). In some embodiments, the ERAP1 inhibitor is DG013A or a phosphinic tripeptide or dipeptide or an aminophosphonic derivative, or 3,4-diaminobenzoic (DABA) derivative, or a derivative of thimerosal, (see, Georgiadis et al., Cur. Med. Chem., 2019, 26, 2715-2729). In some embodiments, the ERAP1 inhibitor is a benzofuran or 7-Benzofuran amide variation (see, Deddouche-Grass et al., ACS Med. Chem. Lett., 2021, 12, 1137-1142).

In any of the embodiments described herein, any of the inhibitors or other agents described herein can form a component of an antibody-drug-conjugate (ADC). For example, an ERAP1 inhibitor or an ERAP2 inhibitor can be conjugated to an antibody, or antigen-binding fragment thereof. The inhibitor can comprise a small molecule degrader, a proteoloysis-targeting chimera, an immunomodulatory drug, or an inhibitory nucleic acid molecule.

The present disclosure also provides methods of treating a subject having an MHC-I-opathy. In some embodiments, the method comprises performing or having performed an assay on a biological sample from the subject to determine whether the subject comprises: i) an MHC-I-opathy-related HLA genotype; and ii) a functional ERAP2 protein or a nucleic acid molecule encoding a functional ERAP2 protein. In some embodiments, the method comprises administering to the subject a therapeutically effective amount of an ERAP2 inhibitor, wherein the subject comprises both an MHC-I-opathy-related HLA genotype and a functional ERAP2 protein or a nucleic acid molecule encoding a functional ERAP2 protein. The presence of both the MHC-I-opathy-related HLA genotype and the functional ERAP2 protein or a nucleic acid molecule encoding a functional ERAP2 protein indicates that the subject is a candidate for treating the MHC-I-opathy by inhibiting ERAP2.

In some embodiments, the MHC-I-opathy is BSCR and the MHC-I-opathy-related HLA genotype comprises an HLA-Aw19 allele. In some embodiments, the HLA-Aw19 allele is an HLA-A*29 allele, an HLA-A*30 allele, an HLA-A*31 allele, or an HLA-A*33 allele, or any combination thereof. In some embodiments, the subject has a single copy of the HLA-Aw19 allele. In some embodiments, the HLA-Aw19 allele is an HLA-A*29 allele. In some embodiments, the HLA-Aw19 allele is an HLA-A*30 allele. In some embodiments, the HLA-Aw19 allele is an HLA-A*31 allele. In some embodiments, the HLA-Aw19 allele is an HLA-A*33 allele. In some embodiments, the subject has two copies of the HLA-Aw19 allele. In some embodiments, the subject is or is suspected of being HLA-A*29$^+$/HLA-A*30$^+$. In some embodiments, the subject is or is suspected of being HLA-A*29$^+$/HLA-A*31$^+$. In some embodiments, the subject is or is suspected of being HLA-A*29$^+$/HLA-A*33$^+$.

In some embodiments, the subject having BSCR is not HLA-A*29$^+$.

In some embodiments, the subject having BSCR has a copy of at least any two of HLA-A*29, HLA-A*30, HLA-A*31, or HLA-A*33. In some embodiments, the subject having BSCR has a copy of at least any three of HLA-A*29, HLA-A*30, HLA-A*31, or HLA-A*33. In some embodiments, the subject having BSCR has a copy of all of HLA-A*29, HLA-A*30, HLA-A*31, or HLA-A*33.

In some embodiments, the subject having BSCR has one copy of each HLA-A*29 and HLA-A*30. In some embodiments, the subject having BSCR has one copy of each HLA-A*29 and HLA-A*31. In some embodiments, the subject having BSCR has one copy of each HLA-A*29 and HLA-A*33. In some embodiments, the subject having BSCR has one copy of each HLA-A*30 and HLA-A*31. In some embodiments, the subject having BSCR has one copy of each HLA-A*30 and HLA-A*33. In some embodiments, the subject having BSCR has one copy of each HLA-A*31 and HLA-A*33.

In some embodiments, the subject having BSCR has one copy of HLA-A*29 and two copies of HLA-A*30. In some embodiments, the subject having BSCR has one copy of HLA-A*29 and two copies of HLA-A*31. In some embodiments, the subject having BSCR has one copy of HLA-A*29 and two copies of HLA-A*33. In some embodiments, the subject having BSCR has one copy of HLA-A*30 and two copies of HLA-A*31. In some embodiments, the subject having BSCR has one copy of HLA-A*30 and two copies HLA-A*33. In some embodiments, the subject having BSCR has one copy of HLA-A*31 and two copies of HLA-A*33.

In some embodiments, the subject having BSCR has two copies of HLA-A*29 and one copy of HLA-A*30. In some embodiments, the subject having BSCR has two copies of HLA-A*29 and one copy of HLA-A*31. In some embodiments, the subject having BSCR has two copies of HLA-A*29 and one copy of HLA-A*33. In some embodiments, the subject having BSCR has two copies of HLA-A*30 and one copy of HLA-A*31. In some embodiments, the subject having BSCR has two copies of HLA-A*30 and one copy of HLA-A*33. In some embodiments, the subject having BSCR has two copies of HLA-A*31 and one copy of HLA-A*33.

In some embodiments, the subject having BSCR or suspected of having BSCR has two copies of HLA-A*29 and two copies of HLA-A*30. In some embodiments, the subject having BSCR or suspected of having BSCR has two copies of HLA-A*29 and two copies of HLA-A*31. In some embodiments, the subject having BSCR or suspected of having BSCR has two copies of HLA-A*29 and two copies of HLA-A*33. In some embodiments, the subject having BSCR or suspected of having BSCR has two copies of HLA-A*30 and two copies of HLA-A*31. In some embodiments, the subject having BSCR or suspected of having BSCR has two copies of HLA-A*30 and two copies of HLA-A*33. In some embodiments, the subject having BSCR or suspected of having BSCR has two copies of HLA-A*31 and two copies of HLA-A*33.

In some embodiments, the method further comprises administering to the subject an HLA-Aw19 inhibitor. In some embodiments, the HLA-Aw19 inhibitor is an antibody. In some embodiments, the antibody is an anti-HLA-A*29 antibody. In some embodiments, the HLA-Aw19 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-Aw19. In some embodiments, the HLA-Aw19 is HLA-A*29.

In some embodiments, the MHC-I-opathy is AS and the MHC-I-opathy-related HLA genotype comprises an HLA-B*27 allele or an HLA-B*40 allele. In some embodiments, the subject has a single copy of HLA-B*27 or HLA-B*40. In some embodiments, the subject has two copies of HLA-B*27 or HLA-B*40. In some embodiments, the method further comprises administering to the subject an HLA-B*27 inhibitor or an HLA-B*40 inhibitor. In some embodiments, the HLA-B*27 inhibitor or HLA-B*40 inhibitor is an antibody. In some embodiments, the antibody is an anti-HLA-B*27 antibody or an anti-HLA-B*40 antibody. In some embodiments, the HLA-B*27 inhibitor or HLA-B*40 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*27 or an HLA-B*40.

In some embodiments, the MHC-I-opathy is Behçet's disease and the MHC-I-opathy-related HLA genotype comprises an HLA-B*51 allele. In some embodiments, the subject has a single copy of HLA-B*51. In some embodiments, the subject has two copies of HLA-B*51. In some embodiments, the method further comprises administering to the subject an HLA-B*51 inhibitor. In some embodiments, the HLA-B*51 inhibitor is an antibody. In some embodiments, the antibody is an anti-HLA-B*51 antibody. In some embodiments, the HLA-B*51 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*51.

In some embodiments, the MHC-I-opathy is psoriasis and the MHC-I-opathy-related HLA genotype comprises an HLA-C*06 allele. In some embodiments, the subject has a single copy of HLA-C*06. In some embodiments, the subject has two copies of HLA-C*06. In some embodiments, the method further comprises administering to the subject an HLA-C*06 inhibitor. In some embodiments, the HLA-C*06 inhibitor is an antibody. In some embodiments, the antibody is an anti-HLA-C*06 antibody. In some embodiments, the HLA-C*06 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-C*06.

In some embodiments, the MHC-I-opathy is JIA and the MHC-I-opathy-related HLA genotype comprises an HLA-B*27 and/or DRB1. In some embodiments, the subject has a single copy of HLA-B*27 and/or DRB1. In some embodiments, the subject has two copies of HLA-B*27 and/or. In some embodiments, the method further comprises administering to the subject an HLA-B*27 inhibitor and/or a DRB1 inhibitor. In some embodiments, the HLA-B*27 inhibitor and/or DRB1 inhibitor is an antibody. In some embodiments, the antibody is an anti-HLA-B*27 antibody and/or a DRB1 antibody. In some embodiments, the HLA-B*27 inhibitor and/or DRB1 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*27 or DRB1.

In some embodiments, the MHC-I-opathy is IBD or CD and the MHC-I-opathy-related HLA genotype comprises an HLA-C*07 allele. In some embodiments, the subject has a single copy of HLA-C*07. In some embodiments, the subject has two copies of HLA-C*07. In some embodiments, the method further comprising administering to the subject an HLA-C*07 inhibitor. In some embodiments, the HLA-C*07 inhibitor is an antibody. In some embodiments, the antibody is an anti-HLA-C*07 antibody. In some embodiments, the HLA-C*07 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-C*07.

In any of the embodiments described herein, the nucleic acid molecule comprises genomic DNA, mRNA, or cDNA obtained from mRNA. In some embodiments, the nucleic acid molecule comprises genomic DNA. In some embodiments, the nucleic acid molecule comprises mRNA. In some embodiments, the nucleic acid molecule comprises cDNA obtained from mRNA.

In any of the embodiments described herein, the ERAP2 inhibitor comprises a small molecule degrader, a proteoloy-sis-targeting chimera, an immunomodulatory drug, or an inhibitory nucleic acid molecule. In some embodiments, the inhibitory nucleic acid molecule is an antisense nucleic acid molecule, an siRNA, or an shRNA that hybridizes to ERAP2 mRNA. In some embodiments, the inhibitory nucleic acid molecule is an antisense nucleic acid molecule that hybrid-izes to ERAP2 mRNA. In some embodiments, the inhibitory nucleic acid molecule is an siRNA that hybridizes to ERAP2 mRNA. In some embodiments, the inhibitory nucleic acid molecule is an shRNA that hybridizes to ERAP2 mRNA. In some embodiments, the ERAP2 inhibitor comprises an anti-ERAP2 antibody. In some embodiments, the ERAP2 inhibitor comprises a pseudopeptide. In some embodiments, the pseudopeptide is a phosphinic pseudopeptide. In some embodiments, the phosphinic pseudopeptide is DG002 or DG013. In some embodiments, the ERAP2 inhibitor com-prises a small molecule.

In any of the embodiments described herein, the assay performed or having been performed on the biological sample from the subject can further determine whether the subject comprises a functional ERAP1 protein or a nucleic acid molecule encoding a functional ERAP1 protein. In some embodiments, the method further comprises adminis-tering to the subject a therapeutically effective amount of an ERAP1 agonist or inhibitor (depending upon the MHC-I-opathy), wherein the subject comprises an MHC-I-opathy-related HLA genotype and does or does not comprise a functional ERAP1 protein or a nucleic acid molecule encod-ing a functional ERAP1 protein. The presence of an MHC-I-opathy-related HLA genotype and the absence of a func-tional ERAP1 protein or a nucleic acid molecule encoding a functional ERAP1 protein indicates that the subject is a candidate for treating the MHC-I-opathy by activating ERAP1. The presence of an MHC-I-opathy-related HLA genotype and the presence of a functional ERAP1 protein or a nucleic acid molecule encoding a functional ERAP1 protein indicates that the subject is a candidate for treating the MHC-I-opathy by inhibiting ERAP1.

In any of the embodiments described herein, the ERAP1 agonist comprises an oligonucleotide. In some embodi-ments, the oligonucleotide is ODN1826. In some embodi-ments, the ERAP1 agonist comprises a peptide. In some embodiments, the ERAP1 agonist comprises a lipopeptide. In some embodiments, the lipopeptide is Pam3CSK4 or FSL-1. In some embodiments, the lipopeptide is Pam3CSK4. In some embodiments, the lipopeptide is FSL-1. In some embodiments, the ERAP1 agonist comprises a small molecule. In some embodiments, the ERAP1 agonist can comprise an ERAP1-specific transcriptional activator, an ERAP1 protein stabilizer, an agonist of ERAP1 enzy-matic activity, or an activator of ERAP1 secretion. In some embodiments, the ERAP1 agonist can comprise an ERAP1-specific transcriptional activator. In some embodiments, the ERAP1 agonist can comprise an ERAP1 protein stabilizer. In some embodiments, the ERAP1 agonist can comprise an agonist of ERAP1 enzymatic activity. In some embodi-ments, the ERAP1 agonist can comprise an activator of ERAP1 secretion. Additional examples of ERAP1 agonists are described in, for example, Goto et al., J. Immunol., 2014, 192, 4443-4452.

In any of the embodiments described herein, the ERAP1 inhibitor comprises a small molecule degrader, a proteoloysis-targeting chimera, an immunomodulatory drug, or an inhibitory nucleic acid molecule. In some embodiments, the inhibitory nucleic acid molecule is an antisense nucleic acid molecule, an siRNA, or an shRNA that hybridizes to ERAP1 mRNA. In some embodiments, the inhibitory nucleic acid molecule is an antisense nucleic acid molecule that hybrid-izes to ERAP1 mRNA. In some embodiments, the inhibitory nucleic acid molecule is an siRNA that hybridizes to ERAP1 mRNA. In some embodiments, the inhibitory nucleic acid molecule is an shRNA that hybridizes to ERAP1 mRNA. In some embodiments, the ERAP1 inhibitor comprises an anti-ERAP1 antibody.

HLA-class-I antibodies can be generated by numerous methodologies with different degrees of antigen/allele speci-ficity attained and are reported to be used for in vitro assays. HLA-B*27 antibodies can be generated by numerous meth-odologies. In addition, three commercially available anti-bodies for HLA-B27 flow cytometric screening include the monoclonal mouse anti-human ABC-m3, FD705, and GS145.2 which have been shown to each have differing levels of cross-reactivity to other HLA-B antigens/alleles (Levering et al., Cytometry B Clin. Cytom., 2003, 54, 28-38). HLA-B*51 antibodies can also be generated by numerous methodologies. For example, antibodies to a broader HLA-Bw4 epitope can be obtained from clone REA274 (e.g., HLA-B members: B5, B5102, B5103, B13, B17, B37, B38, B44, B47, B49, B51, B52, B53, B57, B58, B59, B63, and B77; HLA-A members: A9, A23, A24, A25, and A*32). In addition, antibodies to HLA-B*51/B*52/B*35 can be obtained from clone HDG8D9 (Drabbels et al., Blood, 2011, 118, e149-55). HLA-C*06 antibodies can also be generated by numerous methodologies. For example, pan HLA-C antibodies can be obtained from clone DT-9 (which also recognizes HLA-E) (Braud et al., Curr. Biol., 1998, 8, 1-10). Broad anti-HLA-C antibodies can be obtained from clone L31 (which also recognizes some HLA-B alleles) (Setini et al., Hum. Immunol., 1996, 46, 69-81). HLA-Cw6 scFv can also be generated which has weak binding to HLA-Cw2,4,5 (Marget et al., Mol. Immunol., 2005, 42, 643-649).

In some embodiments, the assay for determining whether the subject comprises an MHC-I-opathy-related and/or MHC-II-opathy-related HLA genotype and a functional ERAP2 protein and/or ERAP1 protein, or a nucleic acid molecule encoding a functional ERAP2 protein and/or ERAP1 protein, is a genotyping assay or sequencing assay. In some embodiments, the nucleic acid molecule encoding a functional ERAP2 protein and/or ERAP1 protein com-prises genomic DNA, mRNA, or cDNA obtained from mRNA. By comparing the nucleotide or protein sequence of the ERAP2 protein and/or ERAP1 protein in the sample from a subject to the wild type sequence for ERAP2 protein and/or ERAP1 protein or nucleic acid molecule, or to published sequences of variant ERAP2 proteins and/or ERAP1 proteins or nucleic acid molecules having reduced or no activity, a determination can be made whether the subject comprises a functional ERAP2 protein and/or ERAP1 protein, or a nucleic acid molecule encoding a functional ERAP2 protein and/or ERAP1 protein. In addi-tion, although an individual ERAP2 protein and/or ERAP1 protein may have biological activity, the overall function of the ERAP2 protein and/or ERAP1 protein may not be functional due to reduced levels of expression. Thus, as used herein, an ERAP2 protein and/or ERAP1 protein can be determined not to be functional because the ERAP2 protein and/or ERAP1 protein lacks or had reduced biological activity or because the expression level is reduced.

Determining whether a subject has an MHC-I-opathy-related and/or MHC-II-opathy-related HLA genotype and/or a functional ERAP2 protein and/or ERAP1 protein, or a nucleic acid molecule encoding a functional ERAP2 protein and/or ERAP1 protein, in a biological sample from a subject can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a biological sample obtained from the subject.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any particular nucleic acid molecule, preliminary processing designed to isolate or enrich the biological sample for the particular nucleic acid molecule can be employed. A variety of techniques may be used for this purpose. Various methods to detect the presence or level of an mRNA molecule or the presence of a particular genomic DNA locus can be used.

In some embodiments, the biological sample comprises a cell or cell lysate. Such methods can further comprise, for example, obtaining a biological sample from the subject comprising genomic nucleic acid molecules or mRNA molecules, and if mRNA, optionally reverse transcribing the mRNA into cDNA. In some embodiments, the method is an in vitro method. In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Administration of any of the therapeutic agents described herein (including the ERAP2 inhibitor, the ERAP1 agonist or inhibitor, and/or the HLA inhibitor) can be in a therapeutically effective amount to be determined by a health care professional. Administration of any of the therapeutic agents can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of any of the therapeutic agents can occur by any suitable route including, but not limited to, parenteral, intravenous, oral, subcutaneous, intra-arterial, intracranial, intrathecal, intraperitoneal, topical, intranasal, intra-articular, intravitreal, intracameral, subretinal, suprachoroidal, or intramuscular.

Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in an MHC-I-opathy and/or MHC-II-opathy, a decrease/reduction in the severity of an MHC-I-opathy and/or MHC-II-opathy (such as, for example, a reduction or inhibition of development of an MHC-I-opathy and/or MHC-II-opathy), a decrease/reduction in symptoms and MHC-I-opathy-related effects and/or MHC-II-opathy-related effects, delaying the onset of symptoms and MHC-I-opathy-related effects and/or MHC-II-opathy-related effects, reducing the severity of symptoms of MHC-I-opathy-related effects and/or MHC-II-opathy-related effects, reducing the severity of an acute episode, reducing the number of symptoms and MHC-I-opathy-related effects and/or MHC-II-opathy-related effects, reducing the latency of symptoms and MHC-I-opathy-related effects and/or MHC-II-opathy-related effects, an amelioration of symptoms and MHC-I-opathy-related effects and/or MHC-II-opathy-related effects, reducing secondary symptoms, reducing secondary infections, preventing relapse to an MHC-I-opathy and/or MHC-II-opathy, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the subject, following administration of the agent or composition comprising the agent. A prophylactic effect may comprise a complete or partial avoidance/inhibition or a delay of an MHC-I-opathy and/or MHC-II-opathy development/progression (such as, for example, a complete or partial avoidance/inhibition or a delay), and an increased survival time of the affected subject, following administration of a therapeutic protocol. Treatment of an MHC-I-opathy and/or MHC-II-opathy encompasses the treatment of subjects already diagnosed as having any form of the MHC-I-opathy and/or MHC-II-opathy at any clinical stage or manifestation, the delay of the onset or evolution or aggravation or deterioration of the symptoms or signs of an MHC-I-opathy and/or MHC-II-opathy, and/or preventing and/or reducing the severity of an MHC-I-opathy and/or MHC-II-opathy.

In some embodiments, the antisense nucleic acid molecules targeted to ERAP2 comprise or consist of the nucleotide sequences shown in Table 1.

TABLE 1

| Sequence | SEQ ID NO: |
|---|---|
| AUCUGCCUGUUUGAGUUGGG | 1 |
| UAUCUGCCUGUUUGAGUUGG | 2 |
| UUAUCUGCCUGUUUGAGUUG | 3 |
| CUUUAUCUGCCUGUUUGAGU | 4 |
| UGAUCUCUCUUUAUCUGCCU | 5 |
| UUGAUCUCUCUUUAUCUGCC | 6 |
| UCAUGCUCAUCUCUUUGAUC | 7 |
| CUCAUGCUCAUCUCUUUGAU | 8 |
| GGACUGUAUCUCAUGCUCAU | 9 |
| GGGACUGUAUCUCAUGCUCA | 10 |
| CGGGCAGCUUCUGUGAUCUU | 11 |
| UUUAAUCAAACACCUCCCGG | 12 |
| AUUUAAUCAAACACCUCCCG | 13 |
| CUCCAGUUAUGUCACAUGGG | 14 |
| GGCUCCAGUUAUGUCACAUG | 15 |
| CUGGCUCCAGUUAUGUCACA | 16 |
| AGUUCUUCAUGGCACUGCAC | 17 |
| UAGUUCUUCAUGGCACUGCA | 18 |
| AGACAAGUUAAUAUCCAGGC | 19 |
| GCAGAAGAAUGGAACAUGAA | 20 |
| GUGUGAAUUAACCAUUGCAG | 21 |
| CUGUGUGAAUUAACCAUUGC | 22 |
| AGCAGUAAAAUCCUCUGUGA | 23 |
| AAGCAGUAAAAUCCUCUGUG | 24 |
| GGCUGUUAAGCAGUAAAAUC | 25 |
| GAUGGCUGUUAAGCAGUAAA | 26 |
| AAGAUGGCUGUUAAGCAGUA | 27 |
| CAAGAUGGCUGUUAAGCAGU | 28 |
| CACUGAGAACUGAGAACAAA | 29 |
| AUGGCACUGAGAACUGAGAA | 30 |
| GAUGGCACUGAGAACUGAGA | 31 |
| UAGAUGGCACUGAGAACUGA | 32 |
| CUAGAUGGCACUGAGAACUG | 33 |
| GAUAACUAGAUGGCACUGAG | 34 |
| UGAUAACUAGAUGGCACUGA | 35 |

TABLE 1-continued

| Sequence | SEQ ID NO: |
|---|---|
| GUGAUAACUAGAUGGCACUG | 36 |
| GAAGUGAUAACUAGAUGGCA | 37 |
| UGAAGUGAUAACUAGAUGGC | 38 |
| GUGAAGUGAUAACUAGAUGG | 39 |
| CUCAGUGAAGUGAUAACUAG | 40 |
| CCUCAGUGAAGUGAUAACUA | 41 |
| UCCUCAGUGAAGUGAUAACU | 42 |
| GAUCCUCAGUGAAGUGAUAA | 43 |
| UUAGUGGCUACUGGGAAAGC | 44 |
| AUUAGUGGCUACUGGGAAAG | 45 |
| CAUUAGUGGCUACUGGGAAA | 46 |
| CCAUUAGUGGCUACUGGGAA | 47 |

In some embodiments, the antisense nucleic acid molecules targeted to ERAP2 comprise or consist of the nucleotide sequences shown in Table 2.

TABLE 2

| Sequence | SEQ ID NO: |
|---|---|
| AUCUUAAAUCAUGCUGCUGC | 48 |
| CUCCAGUUAUGUCACAUGGG | 49 |
| GGCUCCAGUUAUGUCACAUG | 50 |
| CUGGCUCCAGUUAUGUCACA | 51 |
| AGUUCUUCAUGGCACUGCAC | 52 |
| UAGUUCUUCAUGGCACUGCA | 53 |
| AGACAAGUUAAUAUCCAGGC | 54 |
| GCAGAAGAAUGGAACAUGAA | 55 |
| GUGUGAAUUAACCAUUGCAG | 56 |
| CUGUGUGAAUUAACCAUUGC | 57 |
| AGCAGUAAAAUCCUCUGUGA | 58 |
| AAGCAGUAAAAUCCUCUGUG | 59 |
| GGCUGUUAAGCAGUAAAAUC | 60 |
| GAUGGCUGUUAAGCAGUAAA | 61 |
| AAGAUGGCUGUUAAGCAGUA | 62 |
| CAAGAUGGCUGUUAAGCAGU | 63 |
| CACUGAGAACUGAGAACAAA | 64 |
| AUGGCACUGAGAACUGAGAA | 65 |
| GAUGGCACUGAGAACUGAGA | 66 |
| UAGAUGGCACUGAGAACUGA | 67 |
| CUAGAUGGCACUGAGAACUG | 68 |
| GAUAACUAGAUGGCACUGAG | 69 |

TABLE 2-continued

| Sequence | SEQ ID NO: |
| --- | --- |
| UGAUAACUAGAUGGCACUGA | 70 |
| GUGAUAACUAGAUGGCACUG | 71 |
| GAAGUGAUAACUAGAUGGCA | 72 |
| UGAAGUGAUAACUAGAUGGC | 73 |
| GUGAAGUGAUAACUAGAUGG | 74 |
| CUCAGUGAAGUGAUAACUAG | 75 |
| CCUCAGUGAAGUGAUAACUA | 76 |
| UCCUCAGUGAAGUGAUAACU | 77 |
| GAUCCUCAGUGAAGUGAUAA | 78 |
| UUAGUGGCUACUGGGAAAGC | 79 |
| AUUAGUGGCUACUGGGAAAG | 80 |
| CAUUAGUGGCUACUGGGAAA | 81 |
| CCAUUAGUGGCUACUGGGAA | 82 |
| UAAUGGAGAGGAAUGACCAC | 83 |
| AUAAUGGAGAGGAAUGACCA | 84 |
| AGAGGUCAUAAUGGAGAGGA | 85 |
| AAGAGGUCAUAAUGGAGAGG | 86 |
| AAAGAGGUCAUAAUGGAGAG | 87 |
| CAAAGAGGUCAUAAUGGAGA | 88 |
| ACAAAGAGGUCAUAAUGGAG | 89 |
| GGACAAAGAGGUCAUAAUGG | 90 |
| AAAGUCCAGAGAGGUGAGAU | 91 |
| CAAAGUCCAGAGAGGUGAGA | 92 |
| AUGCAACAAAGUCCAGAGAG | 93 |
| GAUGCAACAAAGUCCAGAGA | 94 |
| AGAUGCAACAAAGUCCAGAG | 95 |
| CUCAGAUGCAACAAAGUCCA | 96 |
| UUCUCAGAUGCAACAAAGUC | 97 |
| CUUCUCAGAUGCAACAAAGU | 98 |
| AGCAUUGCUGACCAAGACUU | 99 |
| UAGCAUUGCUGACCAAGACU | 100 |
| GUAGCAUUGCUGACCAAGAC | 101 |
| GGUAGCAUUGCUGACCAAGA | 102 |
| GGGUAGCAUUGCUGACCAAG | 103 |
| UGGGUAGCAUUGCUGACCAA | 104 |
| AAACUGGGUAGCAUUGCUGA | 105 |
| UAAACUGGGUAGCAUUGCUG | 106 |
| UGAUAAACUGGGUAGCAUUG | 107 |
| AGAUGAUAAACUGGGUAGCA | 108 |

TABLE 2-continued

| Sequence | SEQ ID NO: |
| --- | --- |
| AAGAUGAUAAACUGGGUAGC | 109 |
| CAAGAUGAUAAACUGGGUAG | 110 |
| GCAAGAUGAUAAACUGGGUA | 111 |
| GUGCAAGAUGAUAAACUGGG | 112 |
| UGUGCAAGAUGAUAAACUGG | 113 |
| CUGUGCAAGAUGAUAAACUG | 114 |
| GCUGUGCAAGAUGAUAAACU | 115 |
| GGCAUUCGUGAUUUCAAGAU | 116 |
| UGGCAUUCGUGAUUUCAAGA | 117 |
| GUGGCAUUCGUGAUUUCAAG | 118 |
| GGUGGCAUUCGUGAUUUCAA | 119 |
| GGGUGGCAUUCGUGAUUUCA | 120 |
| AGGGUGGCAUUCGUGAUUUC | 121 |
| AAGGGUGGCAUUCGUGAUUU | 122 |
| CUGAAGGGUGGCAUUCGUGA | 123 |
| ACUGAAGGGUGGCAUUCGUG | 124 |
| GACUGAAGGGUGGCAUUCGU | 125 |
| UGACUGAAGGGUGGCAUUCG | 126 |
| CUGACUGAAGGGUGGCAUUC | 127 |
| UCUGACUGAAGGGUGGCAUU | 128 |
| CUCUGACUGAAGGGUGGCAU | 129 |
| CCUCUGACUGAAGGGUGGCA | 130 |
| UCCUCUGACUGAAGGGUGGC | 131 |
| UUCCUCUGACUGAAGGGUGG | 132 |
| UUGAAUCUUCCUCUGACUGA | 133 |
| CUUGAAUCUUCCUCUGACUG | 134 |
| UCUUGAAUCUUCCUCUGACU | 135 |
| GUAUCUUGAAUCUUCCUCUG | 136 |
| UCCUGGUUUCAUGUAUCUUG | 137 |
| GCAGGGUAACUCAAAACUUU | 138 |
| AGCAGGGUAACUCAAAACUU | 139 |
| GAGCAGGGUAACUCAAAACU | 140 |
| AGCAGUGCAAUUUGUUCAUG | 141 |
| CAGCAGUGCAAUUUGUUCAU | 142 |
| CCAGCAGUGCAAUUUGUUCA | 143 |
| ACCAGCAGUGCAAUUUGUUC | 144 |
| AACCAGCAGUGCAAUUUGUU | 145 |
| GAACCAGCAGUGCAAUUUGU | 146 |
| GGAACCAGCAGUGCAAUUUG | 147 |

21

22

TABLE 2-continued

TABLE 2-continued

| Sequence | SEQ ID NO: |
|----------|------------|
| UCUGGAACCAGCAGUGCAAU | 148 |
| UCUCUGGAACCAGCAGUGCA | 149 |
| UUCUCUGGAACCAGCAGUGC | 150 |
| UUUCUCUGGAACCAGCAGUG | 151 |
| CGUAAGUUUCUCUGGAACCA | 152 |
| GCGUAAGUUUCUCUGGAACC | 153 |
| GGCGUAAGUUUCUCUGGAAC | 154 |
| AGGCGUAAGUUUCUCUGGAA | 155 |
| GAGGCGUAAGUUUCUCUGGA | 156 |
| UGAGGCGUAAGUUUCUCUGG | 157 |
| GUGAGGCGUAAGUUUCUCUG | 158 |
| GGUGAGGCGUAAGUUUCUCU | 159 |
| AGGUGAGGCGUAAGUUUCUC | 160 |
| CAGGUGAGGCGUAAGUUUCU | 161 |
| UCAGGUGAGGCGUAAGUUUC | 162 |
| UUCAGGUGAGGCGUAAGUUU | 163 |
| UUUCAGGUGAGGCGUAAGUU | 164 |
| AUUUCAGGUGAGGCGUAAGU | 165 |
| UAUUUCAGGUGAGGCGUAAG | 166 |
| GUAUUUCAGGUGAGGCGUAA | 167 |
| AGUAUUUCAGGUGAGGCGUA | 168 |
| AUAGUAUUUCAGGUGAGGCG | 169 |
| CAUAGUAUUUCAGGUGAGGC | 170 |
| CACAUAGUAUUUCAGGUGAG | 171 |
| AGCCACAUAGUAUUUCAGGU | 172 |
| UAGCCACAUAGUAUUUCAGG | 173 |
| CCAUAGCCACAUAGUAUUUC | 174 |
| AGUCCAUAGCCACAUAGUAU | 175 |
| AAGUCCAUAGCCACAUAGUA | 176 |
| GAAGUCCAUAGCCACAUAGU | 177 |
| GGAAGUCCAUAGCCACAUAG | 178 |
| UGGAAGUCCAUAGCCACAUA | 179 |
| GCUUGGAAGUCCAUAGCCAC | 180 |
| UUGGCUUGGAAGUCCAUAGC | 181 |
| CACCUAACUUGGCUUGGAAG | 182 |
| AUCACCUAACUUGGCUUGGA | 183 |
| CAUCACCUAACUUGGCUUGG | 184 |
| CCAUCACCUAACUUGGCUUG | 185 |
| CAAAGCCAUCACCUAACUUG | 186 |

| Sequence | SEQ ID NO: |
|----------|------------|
| UCAAAGCCAUCACCUAACUU | 187 |
| UUCAAAGCCAUCACCUAACU | 188 |
| CUUCAAAGCCAUCACCUAAC | 189 |
| ACCCUUCAAAGCCAUCACCU | 190 |
| AACCCUUCAAAGCCAUCACC | 191 |
| CAAGAGUUCUGUAUGUGCUU | 192 |
| CCAAGAGUUCUGUAUGUGCU | 193 |
| ACCAAGAGUUCUGUAUGUGC | 194 |
| CACCAAGAGUUCUGUAUGUG | 195 |
| CCACCAAGAGUUCUGUAUGU | 196 |
| ACCACCAAGAGUUCUGUAUG | 197 |
| GGCUCAAAAUCUGUUACUGC | 198 |
| UGGCUCAAAAUCUGUUACUG | 199 |
| UGGGUUGGCUCAAAAUCUGU | 200 |
| CUGGGUUGGCUCAAAAUCUG | 201 |
| CCUGGGUUGGCUCAAAAUCU | 202 |
| UGCCUGGGUUGGCUCAAAAU | 203 |
| GUGCCUGGGUUGGCUCAAAA | 204 |
| CGUGCCUGGGUUGGCUCAAA | 205 |
| AAGCCAUGCGUGCCUGGGUU | 206 |
| AAAGCCAUGCGUGCCUGGGU | 207 |
| AGGGAAAGCCAUGCGUGCCU | 208 |
| AAGGGAAAGCCAUGCGUGCC | 209 |
| GCAAGGGAAAGCCAUGCGUG | 210 |
| AAGCAAGGGAAAGCCAUGCG | 211 |
| CAAAGCAAGGGAAAGCCAUG | 212 |
| CAUCAAAGCAAGGGAAAGCC | 213 |
| GUUCAUCAAAGCAAGGGAAA | 214 |
| CUCUCUUCGUAUCUUGAUUG | 215 |
| GCUCUCUUCGUAUCUUGA | 216 |
| CCUGCUCUCUCUUCGUAUCU | 217 |
| GCCUGCUCUCUCUUCGUAUC | 218 |
| GUGCAAUAUGCCUGCUCUCU | 219 |
| AGUGCAAUAUGCCUGCUCUC | 220 |
| UAGUGCAAUAUGCCUGCUCU | 221 |
| AUAGUGCAAUAUGCCUGCUC | 222 |
| UGGAUAGUGCAAUAUGCCUG | 223 |
| UUGGAUAGUGCAAUAUGCCU | 224 |
| GUUGGAUAGUGCAAUAUGCC | 225 |

TABLE 2-continued

| Sequence | SEQ ID NO: |
|---|---|
| UGUUGGAUAGUGCAAUAUGC | 226 |
| GCAUGUUGGAUAGUGCAAUA | 227 |
| GGCAUGUUGGAUAGUGCAAU | 228 |
| UGGCAUGUUGGAUAGUGCAA | 229 |
| UUGGCAUGUUGGAUAGUGCA | 230 |
| UUUGGCAUGUUGGAUAGUGC | 231 |
| CUUUGGCAUGUUGGAUAGUG | 232 |
| GACCUCCUUCAAGUUCAAUU | 233 |
| CAAAAGACCUCCUUCAAGUU | 234 |
| UCCAAAAGACCUCCUUCAAG | 235 |
| CUUCCAAAAGACCUCCUUCA | 236 |
| UCACAAACUAUGUAGGCUAC | 237 |
| AGAGAGUGGAAAUCACAAAC | 238 |
| UCAGAGAGUGGAAAUCACAA | 239 |
| CCCUGAUGAAGUGAAGCCAC | 240 |
| AUAGAUGGACACCUUGACCC | 241 |
| CAUAGAUGGACACCUUGACC | 242 |
| GCAUAGAUGGACACCUUGAC | 243 |
| UGCAUAGAUGGACACCUUGA | 244 |
| UUUGAUUCCGUUUGUCUGGG | 245 |
| GUUUGAUUCCGUUUGUCUGG | 246 |
| UGUUUGAUUCCGUUUGUCUG | 247 |
| GUGUUUGAUUCCGUUUGUCU | 248 |
| GCAUAAUGUGUUUGAUUCCG | 249 |
| UCAGUGAUGCCUGCAAAGCA | 250 |
| GUAGCUUCAGUGAUGCCUGC | 251 |
| AGUAGCUUCAGUGAUGCCUG | 252 |
| GGAGAGUGGAUAGUAGAUAU | 253 |
| UGGAGAGUGGAUAGUAGAUA | 254 |
| UUGGAGAGUGGAUAGUAGAU | 255 |
| UUUGGAGAGUGGAUAGUAGA | 256 |
| GUUUGGAGAGUGGAUAGUAG | 257 |
| CAGUUUGGAGAGUGGAUAGU | 258 |
| GCAAAGUCAGGAAUAGCAAU | 259 |
| UGCAAAGUCAGGAAUAGCAA | 260 |
| GUGCAAAGUCAGGAAUAGCA | 261 |
| GGUGCAAAGUCAGGAAUAGC | 262 |
| AGGUGCAAAGUCAGGAAUAG | 263 |
| CAGGUGCAAAGUCAGGAAUA | 264 |

TABLE 2-continued

| Sequence | SEQ ID NO: |
|---|---|
| CCAGGUGCAAAGUCAGGAAU | 265 |
| UCCAGGUGCAAAGUCAGGAA | 266 |
| CUCCAGGUGCAAAGUCAGGA | 267 |
| GCUCCAGGUGCAAAGUCAGG | 268 |
| GGCUCCAGGUGCAAAGUCAG | 269 |
| CUCCCUAUAUGUAAUGAGGC | 270 |
| GGAAGCAGAAGAGGUCUUGG | 271 |
| CGGAAGCAGAAGAGGUCUUG | 272 |
| UCGGAAGCAGAAGAGGUCUU | 273 |
| AUCGGAAGCAGAAGAGGUCU | 274 |
| UAUCGGAAGCAGAAGAGGUC | 275 |
| UUAUCGGAAGCAGAAGAGGU | 276 |
| UUUAUCGGAAGCAGAAGAGG | 277 |
| GUUUAUCGGAAGCAGAAGAG | 278 |
| AGUUUAUCGGAAGCAGAAGA | 279 |
| CAGUUUAUCGGAAGCAGAAG | 280 |
| CCACAGUUUAUCGGAAGCAG | 281 |
| CCCACAGUUUAUCGGAAGCA | 282 |
| ACCCACAGUUUAUCGGAAGC | 283 |
| GACCCACAGUUUAUCGGAAG | 284 |
| UGACCCACAGUUUAUCGGAA | 285 |
| GUGACCCACAGUUUAUCGGA | 286 |
| GGUGACCCACAGUUUAUCGG | 287 |
| UGGUGACCCACAGUUUAUCG | 288 |
| CUGGUGACCCACAGUUUAUC | 289 |
| CUCUGGUGACCCACAGUUUA | 290 |
| ACUCUGGUGACCCACAGUUU | 291 |
| GACUCUGGUGACCCACAGUU | 292 |
| AUGACUCUGGUGACCCACAG | 293 |
| UAUGACUCUGGUGACCCACA | 294 |
| CUAUGACUCUGGUGACCCAC | 295 |
| GGCUAUGACUCUGGUGACCC | 296 |
| GGGCUAUGACUCUGGUGACC | 297 |
| UGGGCUAUGACUCUGGUGAC | 298 |
| AUGGGCUAUGACUCUGGUGA | 299 |
| GCGCCAGUUCAUGGGCUAUG | 300 |
| GUGCGCCAGUUCAUGGGCUA | 301 |
| UUGCCAAACCACUGGUGCGC | 302 |
| GUUGCCAAACCACUGGUGCG | 303 |

TABLE 2-continued

| Sequence | SEQ ID NO: |
|---|---|
| UUGUGACCAGGUUGCCAAAC | 304 |
| AUUGUGACCAGGUUGCCAAA | 305 |
| CAUUGUGACCAGGUUGCCAA | 306 |
| UCCAUUGUGACCAGGUUGCC | 307 |
| UUCCAUUGUGACCAGGUUGC | 308 |
| AUUCCAUUGUGACCAGGUUG | 309 |
| CCAUUCCAUUGUGACCAGGU | 310 |
| ACCAUUCCAUUGUGACCAGG | 311 |
| CACCAUUCCAUUGUGACCAG | 312 |
| CCACCAUUCCAUUGUGACCA | 313 |
| UCCACCAUUCCAUUGUGACC | 314 |
| UUCCACCAUUCCAUUGUGAC | 315 |
| CAGCGAUAAGUUCCAUGUAU | 316 |
| ACAGCGAUAAGUUCCAUGUA | 317 |
| AACAGCGAUAAGUUCCAUGU | 318 |
| UAACAGCGAUAAGUUCCAUG | 319 |
| CAUUAACAGCGAUAAGUUCC | 320 |
| GCAUUAACAGCGAUAAGUUC | 321 |
| GUAGCAUUAACAGCGAUAAG | 322 |
| GAUAUGUAGCAUUAACAGCG | 323 |
| GCUCUGGAUAUGUAGCAUUA | 324 |
| GUUUCCGCUGGUUUGGAGAU | 325 |
| GGUUUCCGCUGGUUUGGAGA | 326 |
| GGGUUUCCGCUGGUUUGGAG | 327 |
| CAUUUCCUGUAUUUGAGUCG | 328 |
| CCCUUGUUAUAGGAAACUUC | 329 |
| CUCCCUUGUUAUAGGAAACU | 330 |
| GCUCCCUUGUUAUAGGAAAC | 331 |
| AGCUCCCUUGUUAUAGGAAA | 332 |
| AAGCUCCCUUGUUAUAGGAA | 333 |
| CCCAGAAAAUCCUUGAGCAU | 334 |
| CUCACCCAGAAAAUCCUUGA | 335 |
| CUCCUCACCCAGAAAAUCCU | 336 |
| UCUCCUCACCCAGAAAAUCC | 337 |
| CCACAAGUCAUCAUUCUUAG | 338 |
| CUGCUCCACAAGUCAUCAUU | 339 |
| ACUGCUCCACAAGUCAUCAU | 340 |
| UGACAGACUGCUCCACAAGU | 341 |
| UUGACAGACUGCUCCACAAG | 342 |

TABLE 2-continued

| Sequence | SEQ ID NO: |
|---|---|
| AUUUGACAGACUGCUCCACA | 343 |
| UAUUUGACAGACUGCUCCAC | 344 |
| CUAUUUGACAGACUGCUCCA | 345 |
| ACUAUUUGACAGACUGCUCC | 346 |
| AACUAUUUGACAGACUGCUC | 347 |
| CAACUAUUUGACAGACUGCU | 348 |
| ACAACUAUUUGACAGACUGC | 349 |
| CCACCAGAUGUAAAAUCACU | 350 |
| UCCACCAGAUGUAAAAUCAC | 351 |
| GACAAACUCCACCAGAUGUA | 352 |
| CGAAUGACAAACUCCACCAG | 353 |
| CCGAAUGACAAACUCCACCA | 354 |
| GAUCCGAAUGACAAACUCCA | 355 |
| AUGUUACUUGUCAUCUUGGG | 356 |
| GCAUGUUACUUGUCAUCUUG | 357 |
| GAGCAUGUUACUUGUCAUCU | 358 |
| CGAGCAUGUUACUUGUCAUC | 359 |
| GCGAGCAUGUUACUUGUCAU | 360 |
| GGCGAGCAUGUUACUUGUCA | 361 |
| AGGCGAGCAUGUUACUUGUC | 362 |
| AAGGCGAGCAUGUUACUUGU | 363 |
| AAAGGCGAGCAUGUUACUUG | 364 |
| GAAAGGCGAGCAUGUUACUU | 365 |
| AGAAAGGCGAGCAUGUUACU | 366 |
| CAGAAAGGCGAGCAUGUUAC | 367 |
| CCAGAAAGGCGAGCAUGUUA | 368 |
| CCCAGAAAGGCGAGCAUGUU | 369 |
| UCUUUGACCUCUGCAUUUUC | 370 |
| AUCAUCUCUUUGACCUCUGC | 371 |
| CCAUGUAGUCAUCAUCUCUU | 372 |
| AGAGUCCAUGUAGUCAUCAU | 373 |
| GAGAGUCCAUGUAGUCAUCA | 374 |
| GGAGAGUCCAUGUAGUCAUC | 375 |
| GAUUCCUUUCUGGAGAGUCC | 376 |
| UUGUUUAACCACCAGCAGGG | 377 |
| CUUGUUUAACCACCAGCAGG | 378 |
| UCUUGUUUAACCACCAGCAG | 379 |
| CGUCUUGUUUAACCACCAGC | 380 |
| CCGUCUUGUUUAACCACCAG | 381 |

TABLE 2-continued

| Sequence | SEQ ID NO: |
|---|---|
| CCCGUCUUGUUUAACCACCA | 382 |
| ACCCGUCUUGUUUAACCACC | 383 |
| CACCCGUCUUGUUUAACCAC | 384 |
| ACACCCGUCUUGUUUAACCA | 385 |
| GGAGUGAACACCCGUCUUGU | 386 |
| CGGAGUGAACACCCGUCUUG | 387 |
| UCGGAGUGAACACCCGUCUU | 388 |
| GUCGGAGUGAACACCCGUCU | 389 |
| AGUCGGAGUGAACACCCGUC | 390 |
| CAGUCGGAGUGAACACCCGU | 391 |
| UGCAGUCGGAGUGAACACCC | 392 |
| UUGCAGUCGGAGUGAACACC | 393 |
| GUUGCAGUCGGAGUGAACAC | 394 |
| CCUCCAUUCAGGGUCUUCCU | 395 |
| AUGGGAUAUGCCACAGGUAC | 396 |
| AAUGGGAUAUGCCACAGGUA | 397 |
| CAAUGGGAUAUGCCACAGGU | 398 |
| UCAAUGGGAUAUGCCACAGG | 399 |
| GUAGGUCAAUGGGAUAUGCC | 400 |
| AGUAGGUCAAUGGGAUAUGC | 401 |
| GAGUAGGUCAAUGGGAUAUG | 402 |
| GGAGUAGGUCAAUGGGAUAU | 403 |
| UGGAGUAGGUCAAUGGGAUA | 404 |
| CGUGGAGUAGGUCAAUGGGA | 405 |
| UCGUGGAGUAGGUCAAUGGG | 406 |
| CUCGUGGAGUAGGUCAAUGG | 407 |
| CAUUAGAAGAACUCGUGGAG | 408 |
| ACAUUAGAAGAACUCGUGGA | 409 |
| UCACAUUAGAAGAACUCGUG | 410 |
| GAUCACAUUAGAAGAACUCG | 411 |
| GGAUCACAUUAGAAGAACUC | 412 |
| GUGGAUCACAUUAGAAGAAC | 413 |
| AGAAUGUGUCUGUGGAUCAC | 414 |
| UAGAAUGUGUCUGUGGAUCA | 415 |
| UUUCAGGUAGAUCCAGAGUA | 416 |
| UUUUCAGGUAGAUCCAGAGU | 417 |
| UCUUUUCAGGUAGAUCCAGA | 418 |
| GUCUUUUCAGGUAGAUCCAG | 419 |
| GGUCUUUUCAGGUAGAUCCA | 420 |

TABLE 2-continued

| Sequence | SEQ ID NO: |
|---|---|
| CUGGUCUUUUCAGGUAGAUC | 421 |
| CCAACUGGUCUUUUCAGGUA | 422 |
| CCCAACUGGUCUUUUCAGGU | 423 |
| ACCCAACUGGUCUUUUCAGG | 424 |
| CACCCAACUGGUCUUUUCAG | 425 |
| UUCACCCAACUGGUCUUUUC | 426 |
| UUUCACCCAACUGGUCUUUU | 427 |
| AUUUCACCCAACUGGUCUUU | 428 |
| AAUUUCACCCAACUGGUCUU | 429 |
| GUAACCAUUUGAGUCCACAU | 430 |
| AGUAACCAUUUGAGUCCACA | 431 |
| GUAGUAACCAUUUGAGUCCA | 432 |
| UGUAGUAACCAUUUGAGUCC | 433 |
| CGAUGUAGUAACCAUUUGAG | 434 |
| AGUGAACGAUGUAGUAACCA | 435 |
| UAGUGAACGAUGUAGUAACC | 436 |
| CUCAUAGUGAACGAUGUAGU | 437 |
| CCUCAUAGUGAACGAUGUAG | 438 |
| CCCUCAUAGUGAACGAUGUA | 439 |
| ACCCUCAUAGUGAACGAUGU | 440 |
| GACCCUCAUAGUGAACGAUG | 441 |
| UGACCCUCAUAGUGAACGAU | 442 |
| GAGUUGGUCCCAUCCAUGAC | 443 |
| AUGAGUUGGUCCCAUCCAUG | 444 |
| AAUGAGUUGGUCCCAUCCAU | 445 |
| UAAUGAGUUGGUCCCAUCCA | 446 |
| GUAAUGAGUUGGUCCCAUCC | 447 |
| UGUAAUGAGUUGGUCCCAUC | 448 |
| GUGUAAUGAGUUGGUCCCAU | 449 |
| UGUGUAAUGAGUUGGUCCCA | 450 |
| CUGUGUAAUGAGUUGGUCCC | 451 |
| GCUGUGUAAUGAGUUGGUCC | 452 |
| AGCUGUGUAAUGAGUUGGUC | 453 |
| GUGUGUGGUUCUGAUUCAGC | 454 |
| AAGUGUGUGGUUCUGAUUCA | 455 |
| CUUAGGUCUGAGAAGUGUGU | 456 |
| CCUUAGGUCUGAGAAGUGUG | 457 |
| UCCUUAGGUCUGAGAAGUGU | 458 |
| GUCCUUAGGUCUGAGAAGUG | 459 |

TABLE 2-continued

| Sequence | SEQ ID NO: |
|----------|------------|
| UGUCCUUAGGUCUGAGAAGU | 460 |
| ACUCUGUCCUUAGGUCUGAG | 461 |
| UACUCUGUCCUUAGGUCUGA | 462 |
| CUACUCUGUCCUUAGGUCUG | 463 |
| UCAGUCUCCCUGCACCAACU | 464 |
| GUCAGUCUCCCUGCACCAAC | 465 |
| GGUCAGUCUCCCUGCACCAA | 466 |
| UUGUCUAGGGUCAGUCUCCC | 467 |
| UUUGUCUAGGGUCAGUCUCC | 468 |
| CUUUGUCUAGGGUCAGUCUC | 469 |
| GCUUUGUCUAGGGUCAGUCU | 470 |
| AGCUUUGUCUAGGGUCAGUC | 471 |
| GAGCUUUGUCUAGGGUCAGU | 472 |
| AAGAGCUUUGUCUAGGGUCA | 473 |
| CAAGAGCUUUGUCUAGGGUC | 474 |
| UCAAGAGCUUUGUCUAGGGU | 475 |
| UGUCAAGAGCUUUGUCUAGG | 476 |
| AUGUCAAGAGCUUUGUCUAG | 477 |
| CAUGUCAAGAGCUUUGUCUA | 478 |
| GUCAUGUCAAGAGCUUUGUC | 479 |
| AAGUCAUGUCAAGAGCUUUG | 480 |
| GUAAGUCAUGUCAAGAGCUU | 481 |
| AGUAAGUCAUGUCAAGAGCU | 482 |
| UAGUAAGUCAUGUCAAGAGC | 483 |
| GUAGUAAGUCAUGUCAAGAG | 484 |
| GGUAGUAAGUCAUGUCAAGA | 485 |
| AGGUAGUAAGUCAUGUCAAG | 486 |
| GGAGGUAGUAAGUCAUGUCA | 487 |
| UGGAGGUAGUAAGUCAUGUC | 488 |
| UUGGAGGUAGUAAGUCAUGU | 489 |
| GUUGGAGGUAGUAAGUCAUG | 490 |
| UGUUGGAGGUAGUAAGUCAU | 491 |
| AGACCUUCGAGAAGUGCGGG | 492 |
| CAGACCUUCGAGAAGUGCGG | 493 |
| ACUCAGACCUUCGAGAAGUG | 494 |
| AACUCAGACCUUCGAGAAGU | 495 |
| UAACUCAGACCUUCGAGAAG | 496 |
| GUAACUCAGACCUUCGAGAA | 497 |
| AGUAACUCAGACCUUCGAGA | 498 |

TABLE 2-continued

| Sequence | SEQ ID NO: |
|----------|------------|
| UCCAAGUAACUCAGACCUUC | 499 |
| UUCCAAGUAACUCAGACCUU | 500 |
| GAUUCCAAGUAACUCAGACC | 501 |
| CGAUUCCAAGUAACUCAGAC | 502 |
| GUGGUAAAACGAUUCCAAGU | 503 |
| UGUGGUAAAACGAUUCCAAG | 504 |
| CAUGUGGUAAAACGAUUCCA | 505 |
| UCAUGUGGUAAAACGAUUCC | 506 |
| CCAUCAUGUGGUAAAACGAU | 507 |
| CUGUCCAUCAUGUGGUAAAA | 508 |
| UCUGUCCAUCAUGUGGUAAA | 509 |
| UUCUGUCCAUCAUGUGGUAA | 510 |
| CCUUCUGUCCAUCAUGUGGU | 511 |
| CGCUUGAGGUUUUCAGAGAU | 512 |
| AACGCUUGAGGUUUUCAGAG | 513 |
| UAACGCUUGAGGUUUUCAGA | 514 |
| GUAACGCUUGAGGUUUUCAG | 515 |
| GGUAACGCUUGAGGUUUUCA | 516 |
| AGGUAACGCUUGAGGUUUUC | 517 |
| AAGGUAACGCUUGAGGUUUU | 518 |
| GAAGGUAACGCUUGAGGUUU | 519 |
| AGAAGGUAACGCUUGAGGUU | 520 |
| AAGAAGGUAACGCUUGAGGU | 521 |
| GAAGAAGGUAACGCUUGAGG | 522 |
| UGAAGAAGGUAACGCUUGAG | 523 |
| CUGAAGAAGGUAACGCUUGA | 524 |
| ACUGAAGAAGGUAACGCUUG | 525 |
| UACUGAAGAAGGUAACGCUU | 526 |
| CUGUCAAUCACUGGCUUAAA | 527 |
| CCUGUCAAUCACUGGCUUAA | 528 |
| GCCUGUCAAUCACUGGCUUA | 529 |
| UGCCUGUCAAUCACUGGCUU | 530 |
| UUGCCUGUCAAUCACUGGCU | 531 |
| UUUGCCUGUCAAUCACUGGC | 532 |
| GCUUUGCCUGUCAAUCACUG | 533 |
| AGCUUUGCCUGUCAAUCACU | 534 |
| CAGCUUUGCCUGUCAAUCAC | 535 |
| CCAGCUUUGCCUGUCAAUCA | 536 |
| UCCAGCUUUGCCUGUCAAUC | 537 |

TABLE 2-continued

| Sequence | SEQ ID NO: |
|---|---|
| CUCCAGCUUUGCCUGUCAAU | 538 |
| CACUCCAGCUUUGCCUGUCA | 539 |
| UCACUCCAGCUUUGCCUGUC | 540 |
| UUGUCACUCCAGCUUUGCCU | 541 |
| CUUGUCACUCCAGCUUUGCC | 542 |
| AGCAUCCUGUCCCAGACUGA | 543 |
| UCACAGGCCAGCUUCAAGAG | 544 |
| GGUCACAGGCCAGCUUCAAG | 545 |
| AGGUCACAGGCCAGCUUCAA | 546 |
| UCAGGUCACAGGCCAGCUUC | 547 |
| GUUCAGGUCACAGGCCAGCU | 548 |
| UGGUUCAGGUCACAGGCCAG | 549 |
| AUGGUUCAGGUCACAGGCCA | 550 |
| CAUGGUUCAGGUCACAGGCC | 551 |
| GAGCAUGGUUCAGGUCACAG | 552 |
| GGAGCAUGGUUCAGGUCACA | 553 |
| CAAGGAGCAUGGUUCAGGUC | 554 |
| GCAAGGAGCAUGGUUCAGGU | 555 |
| UGCAAGGAGCAUGGUUCAGG | 556 |
| CUUUCUGGAUGCAAGGAGCA | 557 |
| GCUUUCUGGAUGCAAGGAGC | 558 |
| GCAGCUUUCUGGAUGCAAGG | 559 |
| AGCAGCUUUCUGGAUGCAAG | 560 |
| CAGCAGCUUUCUGGAUGCAA | 561 |
| UCAGCAGCUUUCUGGAUGCA | 562 |
| GAGUUCAGCAGCUUUCUGGA | 563 |
| AAGAGUUCAGCAGCUUUCUG | 564 |
| AGAAGAGUUCAGCAGCUUUC | 565 |
| GAGAAGAGUUCAGCAGCUUU | 566 |
| UGAGCACCCACAGAAUACAC | 567 |
| UGUUGUCUGAGCACCCACAG | 568 |
| CUGUUGUCUGAGCACCCACA | 569 |
| GCUGUUGUCUGAGCACCCAC | 570 |
| AAAAGGUAAUUCCAUCCUGC | 571 |
| CACUUGACAUUGACAGUUCA | 572 |
| GCACUUGACAUUGACAGUUC | 573 |
| AGCACUUGACAUUGACAGUU | 574 |
| UUCAGCACUUGACAUUGACA | 575 |
| UGUUCAGCACUUGACAUUGA | 576 |

TABLE 2-continued

| Sequence | SEQ ID NO: |
|---|---|
| UUGUUCAGCACUUGACAUUG | 577 |
| CUCGUUGACAAAGCAUACAG | 578 |
| GCUCGUUGACAAAGCAUACA | 579 |
| AUGCUUGCUCGUUGACAAAG | 580 |
| GAUGCUUGCUCGUUGACAAA | 581 |
| UGAUGCUUGCUCGUUGACAA | 582 |
| CUGAUGCUUGCUCGUUGACA | 583 |
| CCUGAUGCUUGCUCGUUGAC | 584 |
| UCCUGAUGCUUGCUCGUUGA | 585 |
| UUCCUGAUGCUUGCUCGUUG | 586 |
| UUUCCUGAUGCUUGCUCGUU | 587 |
| UUUUCCUGAUGCUUGCUCGU | 588 |
| CUUUUCCUGAUGCUUGCUCG | 589 |
| CUUGAUAACCUUUCCUUCCA | 590 |
| UCUUGAUAACCUUUCCUUCC | 591 |
| GUCUUGAUAACCUUUCCUUC | 592 |
| GUGUCUUGAUAACCUUUCCU | 593 |
| GUUCUGUGUCUUGAUAACCU | 594 |
| GCUGCCAAGUUCUGUGUCUU | 595 |
| AGCUGCCAAGUUCUGUGUCU | 596 |
| AGAGCUGCCAAGUUCUGUGU | 597 |
| GGAGAGCUGCCAAGUUCUGU | 598 |
| AAGGAGAGCUGCCAAGUUCU | 599 |
| GAAGGAGAGCUGCCAAGUUC | 600 |
| AUGAAGGAGAGCUGCCAAGU | 601 |
| CAUGAAGGAGAGCUGCCAAG | 602 |
| GCAUGAAGGAGAGCUGCCAA | 603 |
| CGCAUGAAGGAGAGCUGCCA | 604 |
| UCGCAUGAAGGAGAGCUGCC | 605 |
| AUCGCAUGAAGGAGAGCUGC | 606 |
| CAAUCGCAUGAAGGAGAGCU | 607 |
| GCAAUCGCAUGAAGGAGAGC | 608 |
| GGCAAUCGCAUGAAGGAGAG | 609 |
| CUGGCAAUCGCAUGAAGGAG | 610 |
| UCUGGCAAUCGCAUGAAGGA | 611 |
| GUCUGGCAAUCGCAUGAAGG | 612 |
| CGUCUGGCAAUCGCAUGAAG | 613 |
| ACGUCUGGCAAUCGCAUGAA | 614 |
| UCUCUUACAAAAUCCCAUGC | 615 |

33

34

TABLE 2-continued

TABLE 2-continued

| Sequence | SEQ ID NO: |
|---|---|
| AGAAGAUGGGUCCAAUUUUC | 616 |
| CAGAAGAUGGGUCCAAUUUU | 617 |
| UCAGAAGAUGGGUCCAAUUU | 618 |
| UUCAGAAGAUGGGUCCAAUU | 619 |
| AAGUGAGCUGUUGUGCCAGA | 620 |
| AGAAAGUGAGCUGUUGUGC | 621 |
| GAAGAAAGUGAGCUGUUGU | 622 |
| GAGCCUCAAGAGAUUCAAAA | 623 |
| UGAGCCUCAAGAGAUUCAAA | 624 |
| CAGAUGUGAUCCUUGAGCCU | 625 |
| CCAGAUGUGAUCCUUGAGCC | 626 |
| UCCAGAUGUGAUCCUUGAGC | 627 |
| GUUAUCGUUUCCAGAACAGU | 628 |
| GGUUAUCGUUUCCAGAACAG | 629 |
| UGGUUAUCGUUUCCAGAACA | 630 |
| UUGGUUAUCGUUUCCAGAAC | 631 |
| UAACCAUUAGCCAAGUCCUC | 632 |
| UUAACCAUUAGCCAAGUCCU | 633 |
| AUUAACCAUUAGCCAAGUCC | 634 |
| AUUACAGGCGUGAGCCACCG | 635 |
| GAUUACAGGCGUGAGCCACC | 636 |
| GGAUUACAGGCGUGAGCCAC | 637 |
| GGGAUUACAGGCGUGAGCCA | 638 |
| UGGGAUUACAGGCGUGAGCC | 639 |
| CUGGGAUUACAGGCGUGAGC | 640 |
| GCUGGGAUUACAGGCGUGAG | 641 |
| UGCUGGGAUUACAGGCGUGA | 642 |
| GUGCUGGGAUUACAGGCGUG | 643 |
| AGUGCUGGGAUUACAGGCGU | 644 |
| AAGUGCUGGGAUUACAGGCG | 645 |
| AAAGUGCUGGGAUUACAGGC | 646 |
| CAAAGUGCUGGGAUUACAGG | 647 |
| CCAAAGUGCUGGGAUUACAG | 648 |
| UCUCAGCCUCCCAAAGUGCU | 649 |
| UUCUCAGCCUCCCAAAGUGC | 650 |
| CUUCUCAGCCUCCCAAAGUG | 651 |
| CCUUCUCAGCCUCCCAAAGU | 652 |
| CCCUUCUCAGCCUCCCAAAG | 653 |
| AUCUCCUGACCUCGUGAUCC | 654 |

| Sequence | SEQ ID NO: |
|---|---|
| CAUCUCCUGACCUCGUGAUC | 655 |
| CCAUCUCCUGACCUCGUGAU | 656 |
| UCCAUCUCCUGACCUCGUGA | 657 |
| CUCCAUCUCCUGACCUCGUG | 658 |
| UCUCCAUCUCCUGACCUCGU | 659 |
| CUCACCGUGUUAGCCAGGAU | 660 |
| UCUCACCGUGUUAGCCAGGA | 661 |
| GUCUCACCGUGUUAGCCAGG | 662 |
| GGUCUCACCGUGUUAGCCAG | 663 |
| GGGUCUCACCGUGUUAGCCA | 664 |
| UACAGGCACCUGCCACCAUG | 665 |
| CUACAGGCACCUGCCACCAU | 666 |
| ACUACAGGCACCUGCCACCA | 667 |
| AGCUGGGACUACAGGCACCU | 668 |
| UAGCUGGGACUACAGGCACC | 669 |
| CUGCCGAGUAGCUGGGACUA | 670 |
| CUCACUGCAAGCUCCACCUC | 671 |
| GCUCACUGCAAGCUCCACCU | 672 |
| UCGGCUCACUGCAAGCUCCA | 673 |
| UCUCGGCUCACUGCAAGCUC | 674 |
| AUCUCGGCUCACUGCAAGCU | 675 |
| AAUCUCGGCUCACUGCAAGC | 676 |
| CAAUCUCGGCUCACUGCAAG | 677 |
| GCAAUCUCGGCUCACUGCAA | 678 |
| GUGCAAUCUCGGCUCACUGC | 679 |
| GGUGCAAUCUCGGCUCACUG | 680 |
| UGGUGCAAUCUCGGCUCACU | 681 |
| GUGGUGCAAUCUCGGCUCAC | 682 |
| AGUGGUGCAAUCUCGGCUCA | 683 |
| CAGUGGUGCAAUCUCGGCUC | 684 |
| GCAGUGGUGCAAUCUCGGCU | 685 |
| AGGCUGGAAUGCAGUGGUGC | 686 |
| CAGGCUGGAAUGCAGUGGUG | 687 |
| CCAGGCUGGAAUGCAGUGGU | 688 |
| ACCCAGGCUGGAAUGCAGUG | 689 |
| CACCCAGGCUGGAAUGCAGU | 690 |
| UCACCCAGGCUGGAAUGCAG | 691 |
| GUCACCCAGGCUGGAAUGCA | 692 |
| AGUCACCCAGGCUGGAAUGC | 693 |

TABLE 2-continued

| Sequence | SEQ ID NO: |
|---|---|
| CAGUCACCCAGGCUGGAAUG | 694 |
| UCAGUCACCCAGGCUGGAAU | 695 |
| CUCAGUCACCCAGGCUGGAA | 696 |
| GACAGAGUCUCGCUCAGUCA | 697 |
| GUCAUGUCUGAUGUACCUUU | 698 |
| AGUCAUGUCUGAUGUACCUU | 699 |
| CAGUCAUGUCUGAUGUACCU | 700 |
| GCAGUCAUGUCUGAUGUACC | 701 |
| GGCAGUCAUGUCUGAUGUAC | 702 |
| AGGCAGUCAUGUCUGAUGUA | 703 |
| CAGGCAGUCAUGUCUGAUGU | 704 |
| GCAGGCAGUCAUGUCUGAUG | 705 |
| UGCAGGCAGUCAUGUCUGAU | 706 |
| CUGUUUGACUUCAUGCAGGC | 707 |
| UACCCUGUUUGACUUCAUGC | 708 |
| GUUACCCUGUUUGACUUCAU | 709 |
| GGUGUUACCCUGUUUGACUU | 710 |
| UGGUGUUACCCUGUUUGACU | 711 |
| CUGGUGUUACCCUGUUUGAC | 712 |
| ACUGGUGUUACCCUGUUUGA | 713 |
| CACUGGUGUUACCCUGUUUG | 714 |
| UCACUGGUGUUACCCUGUUU | 715 |
| UUCACUGGUGUUACCCUGUU | 716 |
| CUUCACUGGUGUUACCCUGU | 717 |
| AGCUUCACUGGUGUUACCCU | 718 |
| UUGAGCUUCACUGGUGUUAC | 719 |
| CUUGAGCUUCACUGGUGUUA | 720 |
| ACUUGAGCUUCACUGGUGUU | 721 |
| GACUUGAGCUUCACUGGUGU | 722 |
| CUCUUGACUUGAGCUUCACU | 723 |
| UCCACAGCUCUUGACUUGAG | 724 |
| AUCCACAGCUCUUGACUUGA | 725 |
| UAUCCACAGCUCUUGACUUG | 726 |
| GACAAAAUAUCCACAGCUCU | 727 |
| AGACAAAAUAUCCACAGCUC | 728 |
| GACUUCUUGUUGGUUAGACA | 729 |
| UGAGACUUCUUGUUGGUUAG | 730 |
| CUUGAGACUUCUUGUUGGUU | 731 |
| UCUUGAGACUUCUUGUUGGU | 732 |

TABLE 2-continued

| Sequence | SEQ ID NO: |
|---|---|
| UUCUUGAGACUUCUUGUUGG | 733 |
| GCCUGAUUUCUUGAGACUUC | 734 |
| UGCCUGAUUUCUUGAGACUU | 735 |
| CAUCUUUUGGCUGGAUACGA | 736 |
| GCAUCUUUUGGCUGGAUACG | 737 |
| CCACCACUCCAUCAUCAUGC | 738 |
| CCCACCACUCCAUCAUCAUG | 739 |
| GAUACUGAACUGGCCUUCCC | 740 |
| UAGGAUACUGAACUGGCCUU | 741 |
| AUAGGAUACUGAACUGGCCU | 742 |
| AAUAGGAUACUGAACUGGCC | 743 |
| AAAUAGGAUACUGAACUGGC | 744 |
| GGAGAAAGUCACUUGAGGCU | 745 |
| UGGAGAAAGUCACUUGAGGC | 746 |
| AAUGGAGAAAGUCACUUGAG | 747 |
| AGCAAUGGAGAAAGUCACUU | 748 |
| UAGCGUGAAGCAAUGGAGAA | 749 |
| AUAGCGUGAAGCAAUGGAGA | 750 |
| CAUAGCGUGAAGCAAUGGAG | 751 |
| GCAUAGCGUGAAGCAAUGGA | 752 |
| GGCAUAGCGUGAAGCAAUGG | 753 |
| UGGCAUAGCGUGAAGCAAUG | 754 |
| GUGGCAUAGCGUGAAGCAAU | 755 |
| AGUGGCAUAGCGUGAAGCAA | 756 |
| UAGUGGCAUAGCGUGAAGCA | 757 |
| AUAGUGGCAUAGCGUGAAGC | 758 |
| AAUAGUGGCAUAGCGUGAAG | 759 |
| AAAUAGUGGCAUAGCGUGAA | 760 |
| AAAAUAGUGGCAUAGCGUGA | 761 |
| GCAAAAUAGUGGCAUAGCGU | 762 |
| AGCAAAAUAGUGGCAUAGCG | 763 |
| AAGCAAAAUAGUGGCAUAGC | 764 |
| AACUGGUUGGGCAAACUAUA | 765 |
| AAACUGGUUGGGCAAACUAU | 766 |
| AAAACUGGUUGGGCAAACUA | 767 |
| UAAAACUGGUUGGGCAAACU | 768 |
| GUAAAACUGGUUGGGCAAAC | 769 |
| CGUAAAACUGGUUGGGCAAA | 770 |
| GACGUAAAACUGGUUGGGCA | 771 |

37

38

TABLE 2-continued

TABLE 2-continued

| Sequence | SEQ ID NO: |
| --- | --- |
| GGACGUAAAACUGGUUGGGC | 772 |
| UGGACGUAAAACUGGUUGGG | 773 |
| UUGGACGUAAAACUGGUUGG | 774 |
| CUUGGACGUAAAACUGGUUG | 775 |
| CCUUGGACGUAAAACUGGUU | 776 |
| UCCUUGGACGUAAAACUGGU | 777 |
| UUCCUUGGACGUAAAACUGG | 778 |
| UUUCCUUGGACGUAAAACUG | 779 |
| GGCUAAUUUUCCUUGGACGU | 780 |
| UGGCUAAUUUUCCUUGGACG | 781 |
| GCAUUGGCUAAUUUUCCUUG | 782 |
| UUCCUGAUCCUUGCCUUUCA | 783 |
| UCUGGUUUCCUGAUCCUUGC | 784 |
| UCUCUGGUUUCCUGAUCCUU | 785 |
| GUCUCUGGUUUCCUGAUCCU | 786 |
| AGUCUCUGGUUUCCUGAUCC | 787 |
| AAGUCUCUGGUUUCCUGAUC | 788 |
| CCUGACACCUAGUUUCUAAU | 789 |
| AACCCUGACACCUAGUUUCU | 790 |
| AUAAACCCUGACACCUAGUU | 791 |
| GAUAAACCCUGACACCUAGU | 792 |
| UGAUAAACCCUGACACCUAG | 793 |
| CUUGAUAAACCCUGACACCU | 794 |
| UCUUGAUAAACCCUGACACC | 795 |
| UUCUUGAUAAACCCUGACAC | 796 |
| CUUCUUGAUAAACCCUGACA | 797 |
| CCUUCUUGAUAAACCCUGAC | 798 |
| GCCUUCUUGAUAAACCCUGA | 799 |
| GGCCUUCUUGAUAAACCCUG | 800 |
| UGGCCUUCUUGAUAAACCCU | 801 |
| UUCCUGGCCUUCUUGAUAAA | 802 |
| CAGAGACCAUUCAUUUGGAA | 803 |
| CCAGAGACCAUUCAUUUGGA | 804 |
| ACCAGAGACCAUUCAUUUGG | 805 |
| UGACCAGAGACCAUUCAUUU | 806 |
| UUGACCAGAGACCAUUCAUU | 807 |
| UUUGACCAGAGACCAUUCAU | 808 |
| AUUUGACCAGAGACCAUUCA | 809 |
| CAUUUGACCAGAGACCAUUC | 810 |

| Sequence | SEQ ID NO: |
| --- | --- |
| AUUCAUUUGACCAGAGACCA | 811 |
| UUGUAUCUCUGUGAGGGCAG | 812 |
| GUAAGGCUUAAACCAAAUGG | 813 |
| CAGAUUCGACUUCAUUUGGA | 814 |
| GGCAGAUUCGACUUCAUUUG | 815 |
| GGGCAGAUUCGACUUCAUUU | 816 |
| AGGGCAGAUUCGACUUCAUU | 817 |
| GAGGGCAGAUUCGACUUCAU | 818 |
| UGAGGGCAGAUUCGACUUCA | 819 |
| GUGAGGGCAGAUUCGACUUC | 820 |
| UGUGAGGGCAGAUUCGACUU | 821 |
| CUGUGAGGGCAGAUUCGACU | 822 |
| CUUGUGUCUCUGUGAGGGCA | 823 |
| UUCUUGUGUCUCUGUGAGGG | 824 |
| AUUUCAGAGAGCAAGAAGCG | 825 |
| CAUUUCAGAGAGCAAGAAGC | 826 |
| GGCAUUUCAGAGAGCAAGAA | 827 |
| CAUUUAGCAGGGCAUUUCAG | 828 |
| GCAUUUAGCAGGGCAUUUCA | 829 |
| AGCAUUUAGCAGGGCAUUUC | 830 |
| AGAAGCAUUUAGCAGGGCAU | 831 |
| GAGAAGCAUUUAGCAGGGCA | 832 |
| CUCUUGACCCAACAUCCCAA | 833 |
| CCUCUUGACCCAACAUCCCA | 834 |
| UGGAUUGACUAACACUUUCC | 835 |
| GUGGAUUGACUAACACUUUC | 836 |
| CUGUGGCAUCAAAGAAAGGU | 837 |
| UCUGACUGUGGCAUCAAAGA | 838 |
| UCUCUGACUGUGGCAUCAAA | 839 |
| GGCCACCCAAACUGUAUUCU | 840 |
| ACCACCAAGUCAAAGUUAGA | 841 |
| CACCACCAAGUCAAAGUUAG | 842 |
| GUCCACCACCAAGUCAAAGU | 843 |
| GGUCCACCACCAAGUCAAAG | 844 |
| AGGAAGGUCCACCACCAAGU | 845 |
| AAGGAAGGUCCACCACCAAG | 846 |
| CAAGGAAGGUCCACCACCAA | 847 |
| CCAAGGAAGGUCCACCACCA | 848 |
| ACCAAGGAAGGUCCACCACC | 849 |

TABLE 2-continued

| Sequence | SEQ ID NO: |
|---|---|
| AACCAAGGAAGGUCCACCAC | 850 |
| AAACCAAGGAAGGUCCACCA | 851 |
| GUUGAUGGUACAGUUCUACU | 852 |
| UGUUGAUGGUACAGUUCUAC | 853 |
| CAUUGUUGAUGGUACAGUUC | 854 |

TABLE 2-continued

| Sequence | SEQ ID NO: |
|---|---|
| GGAAACAUUGUUGAUGGUAC | 855 |
| GUAUUGGCACAGUAAUUCUC | 856 |
| CAGUAUUGGCACAGUAAUUC | 857 |
| UCAAAACAGUAUUGGCACAG | 858 |

In some embodiments, the siRNA molecules targeted to ERAP2 comprise or consist of the nucleotide sequences (sense and antisense strands) shown in Table 3.

TABLE 3

| Sense Sequence | SEQ ID NO: | Antisense Sequence | SEQ ID NO: |
|---|---|---|---|
| AAAGAUCACAGAAGCUGCC | 859 | GGCAGCUUCUGUGAUCUUU | 860 |
| AAGAUCACAGAAGCUGCCC | 861 | GGGCAGCUUCUGUGAUCUU | 862 |
| AGAUCACAGAAGCUGCCCG | 863 | CGGGCAGCUUCUGUGAUCU | 864 |
| CCGGGAGGUGUUUGAUUAA | 865 | UUAAUCAAACACCUCCCGG | 866 |
| CGGGAGGUGUUUGAUUAAA | 867 | UUUAAUCAAACACCUCCCG | 868 |
| GGGAGGUGUUUGAUUAAAU | 869 | AUUUAAUCAAACACCUCCC | 870 |
| GGAGGUGUUUGAUUAAAUU | 871 | AAUUUAAUCAAACACCUCC | 872 |
| GAGGUGUUUGAUUAAAUUC | 873 | GAAUUUAAUCAAACACCUC | 874 |
| AUGUGACAUAACUGGAGCC | 875 | GGCUCCAGUUAUGUCACAU | 876 |
| UGUGACAUAACUGGAGCCA | 877 | UGGCUCCAGUUAUGUCACA | 878 |
| UGGAGCCAGUGCAGUGCCA | 879 | UGGCACUGCACUGGCUCCA | 880 |
| GCCAGUGCAGUGCCAUGAA | 881 | UUCAUGGCACUGCACUGGC | 882 |
| CCAGUGCAGUGCCAUGAAG | 883 | CUUCAUGGCACUGCACUGG | 884 |
| CAGUGCAGUGCCAUGAAGA | 885 | UCUUCAUGGCACUGCACUG | 886 |
| AGUGCAGUGCCAUGAAGAA | 887 | UUCUUCAUGGCACUGCACU | 888 |
| AGAUUAGCCUGGAUAUUAA | 889 | UUAAUAUCCAGGCUAAUCU | 890 |
| GAUUAGCCUGGAUAUUAAC | 891 | GUUAAUAUCCAGGCUAAUC | 892 |
| AUUAGCCUGGAUAUUAACU | 893 | AGUUAAUAUCCAGGCUAAU | 894 |
| UUAGCCUGGAUAUUAACUU | 895 | AAGUUAAUAUCCAGGCUAA | 896 |
| UAGCCUGGAUAUUAACUUG | 897 | CAAGUUAAUAUCCAGGCUA | 898 |
| GCCUGGAUAUUAACUUGUC | 899 | GACAAGUUAAUAUCCAGGC | 900 |
| CCUGGAUAUUAACUUGUCU | 901 | AGACAAGUUAAUAUCCAGG | 902 |
| CUGGAUAUUAACUUGUCUU | 903 | AAGACAAGUUAAUAUCCAG | 904 |
| UGGAUAUUAACUUGUCUUC | 905 | GAAGACAAGUUAAUAUCCA | 906 |
| GGAUAUUAACUUGUCUUCU | 907 | AGAAGACAAGUUAAUAUCC | 908 |
| AUUAACUUGUCUUCUAGAG | 909 | CUCUAGAAGACAAGUUAAU | 910 |
| AGAAUAGAUUUCAUGUUCC | 911 | GGAACAUGAAAUCUAUUCU | 912 |
| GAAUAGAUUUCAUGUUCCA | 913 | UGGAACAUGAAAUCUAUUC | 914 |
| UAGAUUUCAUGUUCCAUUC | 915 | GAAUGGAACAUGAAAUCUA | 916 |
| GAUUUCAUGUUCCAUUCUU | 917 | AAGAAUGGAACAUGAAAUC | 918 |

TABLE 3-continued

| Sense Sequence | SEQ ID NO: | Antisense Sequence | SEQ ID NO: |
|---|---|---|---|
| AUUUCAUGUUCCAUUCUUC | 919 | GAAGAAUGGAACAUGAAAU | 920 |
| UUUCAUGUUCCAUUCUUCU | 921 | AGAAGAAUGGAACAUGAAA | 922 |
| UUCAUGUUCCAUUCUUCUG | 923 | CAGAAGAAUGGAACAUGAA | 924 |
| UCAUGUUCCAUUCUUCUGC | 925 | GCAGAAGAAUGGAACAUGA | 926 |
| CAUGUUCCAUUCUUCUGCA | 927 | UGCAGAAGAAUGGAACAUG | 928 |
| UCUUCUGCAAUGGUUAAUU | 929 | AAUUAACCAUUGCAGAAGA | 930 |
| UUCUGCAAUGGUUAAUUCA | 931 | UGAAUUAACCAUUGCAGAA | 932 |
| CAUUCACAGAGGAUUUUAC | 933 | GUAAAAUCCUCUGUGAAUG | 934 |
| AUUCACAGAGGAUUUUACU | 935 | AGUAAAAUCCUCUGUGAAU | 936 |
| ACAGAGGAUUUUACUGCUU | 937 | AAGCAGUAAAAUCCUCUGU | 938 |
| CAGAGGAUUUUACUGCUUA | 939 | UAAGCAGUAAAAUCCUCUG | 940 |
| AGAGGAUUUUACUGCUUAA | 941 | UUAAGCAGUAAAAUCCUCU | 942 |
| GAGGAUUUUACUGCUUAAC | 943 | GUUAAGCAGUAAAAUCCUC | 944 |
| AUAUGCAUUUGUUCUCAGU | 945 | ACUGAGAACAAAUGCAUAU | 946 |
| AUGCAUUUGUUCUCAGUUC | 947 | GAACUGAGAACAAAUGCAU | 948 |
| UUUGUUCUCAGUUCUCAGU | 949 | ACUGAGAACUGAGAACAAA | 950 |
| UUGUUCUCAGUUCUCAGUG | 951 | CACUGAGAACUGAGAACAA | 952 |
| GUUCUCAGUUCUCAGUGCC | 953 | GGCACUGAGAACUGAGAAC | 954 |
| UUCUCAGUUCUCAGUGCCA | 955 | UGGCACUGAGAACUGAGAA | 956 |
| CAGUUCUCAGUGCCAUCUA | 957 | UAGAUGGCACUGAGAACUG | 958 |
| AGUUCUCAGUGCCAUCUAG | 959 | CUAGAUGGCACUGAGAACU | 960 |
| UCAGUGCCAUCUAGUUAUC | 961 | GAUAACUAGAUGGCACUGA | 962 |
| CAGUGCCAUCUAGUUAUCA | 963 | UGAUAACUAGAUGGCACUG | 964 |
| AGUGCCAUCUAGUUAUCAC | 965 | GUGAUAACUAGAUGGCACU | 966 |
| GUGCCAUCUAGUUAUCACU | 967 | AGUGAUAACUAGAUGGCAC | 968 |
| UGCCAUCUAGUUAUCACUU | 969 | AAGUGAUAACUAGAUGGCA | 970 |
| GCCAUCUAGUUAUCACUUC | 971 | GAAGUGAUAACUAGAUGGC | 972 |
| CCAUCUAGUUAUCACUUCA | 973 | UGAAGUGAUAACUAGAUGG | 974 |
| CAUCUAGUUAUCACUUCAC | 975 | GUGAAGUGAUAACUAGAUG | 976 |
| AUCUAGUUAUCACUUCACU | 977 | AGUGAAGUGAUAACUAGAU | 978 |
| UCUAGUUAUCACUUCACUG | 979 | CAGUGAAGUGAUAACUAGA | 980 |
| CUAGUUAUCACUUCACUGA | 981 | UCAGUGAAGUGAUAACUAG | 982 |
| UAGUUAUCACUUCACUGAG | 983 | CUCAGUGAAGUGAUAACUA | 984 |
| AGUUAUCACUUCACUGAGG | 985 | CCUCAGUGAAGUGAUAACU | 986 |
| GUUAUCACUUCACUGAGGA | 987 | UCCUCAGUGAAGUGAUAAC | 988 |
| UUAUCACUUCACUGAGGAU | 989 | AUCCUCAGUGAAGUGAUAA | 990 |
| UAUCACUUCACUGAGGAUC | 991 | GAUCCUCAGUGAAGUGAUA | 992 |
| AUCACUUCACUGAGGAUCC | 993 | GGAUCCUCAGUGAAGUGAU | 994 |
| UCACUUCACUGAGGAUCCU | 995 | AGGAUCCUCAGUGAAGUGA | 996 |

TABLE 3-continued

| Sense Sequence | SEQ ID NO: | Antisense Sequence | SEQ ID NO: |
|---|---|---|---|
| GCUUUCCCAGUAGCCACUA | 997 | UAGUGGCUACUGGGAAAGC | 998 |
| CUUUCCCAGUAGCCACUAA | 999 | UUAGUGGCUACUGGGAAAG | 1000 |
| UUUCCCAGUAGCCACUAAU | 1001 | AUUAGUGGCUACUGGGAAA | 1002 |
| UUCCCAGUAGCCACUAAUG | 1003 | CAUUAGUGGCUACUGGGAA | 1004 |
| UCCCAGUAGCCACUAAUGG | 1005 | CCAUUAGUGGCUACUGGGA | 1006 |
| CUUGGCAGGAGCUAAGGCU | 1007 | AGCCUUAGCUCCUGCCAAG | 1008 |

In some embodiments, the siRNA molecules targeted to ERAP2 comprise or consist of the nucleotide sequences (sense and antisense strands) shown in Table 4.

TABLE 4

| Sense Sequence | SEQ ID NO: | Antisense Sequence | SEQ ID NO: |
|---|---|---|---|
| UCAAAUCUGCAGCAGCAUG | 1009 | CAUGCUGCUGCAGAUUUGA | 1010 |
| CAAAUCUGCAGCAGCAUGA | 1011 | UCAUGCUGCUGCAGAUUUG | 1012 |
| AAAUCUGCAGCAGCAUGAU | 1013 | AUCAUGCUGCUGCAGAUUU | 1014 |
| AUGUGACAUAACUGGAGCC | 1015 | GGCUCCAGUUAUGUCACAU | 1016 |
| UGUGACAUAACUGGAGCCA | 1017 | UGGCUCCAGUUAUGUCACA | 1018 |
| UGGAGCCAGUGCAGUGCCA | 1019 | UGGCACUGCACUGGCUCCA | 1020 |
| GCCAGUGCAGUGCCAUGAA | 1021 | UUCAUGGCACUGCACUGGC | 1022 |
| CCAGUGCAGUGCCAUGAAG | 1023 | CUUCAUGGCACUGCACUGG | 1024 |
| CAGUGCAGUGCCAUGAAGA | 1025 | UCUUCAUGGCACUGCACUG | 1026 |
| AGUGCAGUGCCAUGAAGAA | 1027 | UUCUUCAUGGCACUGCACU | 1028 |
| AGAUUAGCCUGGAUAUUAA | 1029 | UUAAUAUCCAGGCUAAUCU | 1030 |
| GAUUAGCCUGGAUAUUAAC | 1031 | GUUAAUAUCCAGGCUAAUC | 1032 |
| AUUAGCCUGGAUAUUAACU | 1033 | AGUUAAUAUCCAGGCUAAU | 1034 |
| UUAGCCUGGAUAUUAACUU | 1035 | AAGUUAAUAUCCAGGCUAA | 1036 |
| UAGCCUGGAUAUUAACUUG | 1037 | CAAGUUAAUAUCCAGGCUA | 1038 |
| GCCUGGAUAUUAACUUGUC | 1039 | GACAAGUUAAUAUCCAGGC | 1040 |
| CCUGGAUAUUAACUUGUCU | 1041 | AGACAAGUUAAUAUCCAGG | 1042 |
| CUGGAUAUUAACUUGUCUU | 1043 | AAGACAAGUUAAUAUCCAG | 1044 |
| UGGAUAUUAACUUGUCUUC | 1045 | GAAGACAAGUUAAUAUCCA | 1046 |
| GGAUAUUAACUUGUCUUCU | 1047 | AGAAGACAAGUUAAUAUCC | 1048 |
| AUUAACUUGUCUUCUAGAG | 1049 | CUCUAGAAGACAAGUUAAU | 1050 |
| AGAAUAGAUUUCAUGUUCC | 1051 | GGAACAUGAAAUCUAUUCU | 1052 |
| GAAUAGAUUUCAUGUUCCA | 1053 | UGGAACAUGAAAUCUAUUC | 1054 |
| UAGAUUUCAUGUUCCAUUC | 1055 | GAAUGGAACAUGAAAUCUA | 1056 |
| GAUUUCAUGUUCCAUUCUU | 1057 | AAGAAUGGAACAUGAAAUC | 1058 |
| AUUUCAUGUUCCAUUCUUC | 1059 | GAAGAAUGGAACAUGAAAU | 1060 |
| UUUCAUGUUCCAUUCUUCU | 1061 | AGAAGAAUGGAACAUGAAA | 1062 |
| UUCAUGUUCCAUUCUUCUG | 1063 | CAGAAGAAUGGAACAUGAA | 1064 |

TABLE 4-continued

| Sense Sequence | SEQ ID NO: | Antisense Sequence | SEQ ID NO: |
|---|---|---|---|
| UCAUGUUCCAUUCUUCUGC | 1065 | GCAGAAGAAUGGAACAUGA | 1066 |
| CAUGUUCCAUUCUUCUGCA | 1067 | UGCAGAAGAAUGGAACAUG | 1068 |
| UCUUCUGCAAUGGUUAAUU | 1069 | AAUUAACCAUUGCAGAAGA | 1070 |
| UUCUGCAAUGGUUAAUUCA | 1071 | UGAAUUAACCAUUGCAGAA | 1072 |
| CAUUCACAGAGGAUUUUAC | 1073 | GUAAAAUCCUCUGUGAAUG | 1074 |
| AUUCACAGAGGAUUUUACU | 1075 | AGUAAAAUCCUCUGUGAAU | 1076 |
| ACAGAGGAUUUUACUGCUU | 1077 | AAGCAGUAAAAUCCUCUGU | 1078 |
| CAGAGGAUUUUACUGCUUA | 1079 | UAAGCAGUAAAAUCCUCUG | 1080 |
| AGAGGAUUUUACUGCUUAA | 1081 | UUAAGCAGUAAAAUCCUCU | 1082 |
| GAGGAUUUUACUGCUUAAC | 1083 | GUUAAGCAGUAAAAUCCUC | 1084 |
| AUAUGCAUUUGUUCUCAGU | 1085 | ACUGAGAACAAAUGCAUAU | 1086 |
| AUGCAUUUGUUCUCAGUUC | 1087 | GAACUGAGAACAAAUGCAU | 1088 |
| UUUGUUCUCAGUUCUCAGU | 1089 | ACUGAGAACUGAGAACAAA | 1090 |
| UUGUUCUCAGUUCUCAGUG | 1091 | CACUGAGAACUGAGAACAA | 1092 |
| GUUCUCAGUUCUCAGUGCC | 1093 | GGCACUGAGAACUGAGAAC | 1094 |
| UUCUCAGUUCUCAGUGCCA | 1095 | UGGCACUGAGAACUGAGAA | 1096 |
| CAGUUCUCAGUGCCAUCUA | 1097 | UAGAUGGCACUGAGAACUG | 1098 |
| AGUUCUCAGUGCCAUCUAG | 1099 | CUAGAUGGCACUGAGAACU | 1100 |
| UCAGUGCCAUCUAGUUAUC | 1101 | GAUAACUAGAUGGCACUGA | 1102 |
| CAGUGCCAUCUAGUUAUCA | 1103 | UGAUAACUAGAUGGCACUG | 1104 |
| AGUGCCAUCUAGUUAUCAC | 1105 | GUGAUAACUAGAUGGCACU | 1106 |
| GUGCCAUCUAGUUAUCACU | 1107 | AGUGAUAACUAGAUGGCAC | 1108 |
| UGCCAUCUAGUUAUCACUU | 1109 | AAGUGAUAACUAGAUGGCA | 1110 |
| GCCAUCUAGUUAUCACUUC | 1111 | GAAGUGAUAACUAGAUGGC | 1112 |
| CCAUCUAGUUAUCACUUCA | 1113 | UGAAGUGAUAACUAGAUGG | 1114 |
| CAUCUAGUUAUCACUUCAC | 1115 | GUGAAGUGAUAACUAGAUG | 1116 |
| AUCUAGUUAUCACUUCACU | 1117 | AGUGAAGUGAUAACUAGAU | 1118 |
| UCUAGUUAUCACUUCACUG | 1119 | CAGUGAAGUGAUAACUAGA | 1120 |
| CUAGUUAUCACUUCACUGA | 1121 | UCAGUGAAGUGAUAACUAG | 1122 |
| UAGUUAUCACUUCACUGAG | 1123 | CUCAGUGAAGUGAUAACUA | 1124 |
| AGUUAUCACUUCACUGAGG | 1125 | CCUCAGUGAAGUGAUAACU | 1126 |
| GUUAUCACUUCACUGAGGA | 1127 | UCCUCAGUGAAGUGAUAAC | 1128 |
| UUAUCACUUCACUGAGGAU | 1129 | AUCCUCAGUGAAGUGAUAA | 1130 |
| UAUCACUUCACUGAGGAUC | 1131 | GAUCCUCAGUGAAGUGAUA | 1132 |
| AUCACUUCACUGAGGAUCC | 1133 | GGAUCCUCAGUGAAGUGAU | 1134 |
| UCACUUCACUGAGGAUCCU | 1135 | AGGAUCCUCAGUGAAGUGA | 1136 |
| GCUUUCCCAGUAGCCACUA | 1137 | UAGUGGCUACUGGGAAAGC | 1138 |
| CUUUCCCAGUAGCCACUAA | 1139 | UUAGUGGCUACUGGGAAAG | 1140 |
| UUUCCCAGUAGCCACUAAU | 1141 | AUUAGUGGCUACUGGGAAA | 1142 |

TABLE 4-continued

| Sense Sequence | SEQ ID NO: | Antisense Sequence | SEQ ID NO: |
|---|---|---|---|
| UUCCCAGUAGCCACUAAUG | 1143 | CAUUAGUGGCUACUGGGAA | 1144 |
| UCCCAGUAGCCACUAAUGG | 1145 | CCAUUAGUGGCUACUGGGA | 1146 |
| CUUGGCAGGAGCUAAGGCU | 1147 | AGCCUUAGCUCCUGCCAAG | 1148 |
| CCAGUGUGGUCAUUCCUCU | 1149 | AGAGGAAUGACCACACUGG | 1150 |
| GUCAUUCCUCUCCAUUAUG | 1151 | CAUAAUGGAGAGGAAUGAC | 1152 |
| CAUUCCUCUCCAUUAUGAC | 1153 | GUCAUAAUGGAGAGGAAUG | 1154 |
| AUUCCUCUCCAUUAUGACC | 1155 | GGUCAUAAUGGAGAGGAAU | 1156 |
| CUCUCCAUUAUGACCUCUU | 1157 | AAGAGGUCAUAAUGGAGAG | 1158 |
| UCUCCAUUAUGACCUCUUU | 1159 | AAAGAGGUCAUAAUGGAGA | 1160 |
| CUCCAUUAUGACCUCUUUG | 1161 | CAAAGAGGUCAUAAUGGAG | 1162 |
| UCCAUUAUGACCUCUUUGU | 1163 | ACAAAGAGGUCAUAAUGGA | 1164 |
| CCAUUAUGACCUCUUUGUC | 1165 | GACAAAGAGGUCAUAAUGG | 1166 |
| CAUUAUGACCUCUUUGUCC | 1167 | GGACAAAGAGGUCAUAAUG | 1168 |
| CCCAAUCUCACCUCUCUGG | 1169 | CCAGAGAGGUGAGAUUGGG | 1170 |
| UCUCACCUCUCUGGACUUU | 1171 | AAAGUCCAGAGAGGUGAGA | 1172 |
| CUCACCUCUCUGGACUUUG | 1173 | CAAAGUCCAGAGAGGUGAG | 1174 |
| UCACCUCUCUGGACUUUGU | 1175 | ACAAAGUCCAGAGAGGUGA | 1176 |
| UCUCUGGACUUUGUUGCAU | 1177 | AUGCAACAAAGUCCAGAGA | 1178 |
| CUCUGGACUUUGUUGCAUC | 1179 | GAUGCAACAAAGUCCAGAG | 1180 |
| CUGGACUUUGUUGCAUCUG | 1181 | CAGAUGCAACAAAGUCCAG | 1182 |
| GGACUUUGUUGCAUCUGAG | 1183 | CUCAGAUGCAACAAAGUCC | 1184 |
| GAAGUCUUGGUCAGCAAUG | 1185 | CAUUGCUGACCAAGACUUC | 1186 |
| AAGUCUUGGUCAGCAAUGC | 1187 | GCAUUGCUGACCAAGACUU | 1188 |
| AGUCUUGGUCAGCAAUGCU | 1189 | AGCAUUGCUGACCAAGACU | 1190 |
| GUCUUGGUCAGCAAUGCUA | 1191 | UAGCAUUGCUGACCAAGAC | 1192 |
| UCUUGGUCAGCAAUGCUAC | 1193 | GUAGCAUUGCUGACCAAGA | 1194 |
| CUUGGUCAGCAAUGCUACC | 1195 | GGUAGCAUUGCUGACCAAG | 1196 |
| UUGGUCAGCAAUGCUACCC | 1197 | GGGUAGCAUUGCUGACCAA | 1198 |
| UGGUCAGCAAUGCUACCCA | 1199 | UGGGUAGCAUUGCUGACCA | 1200 |
| GGUCAGCAAUGCUACCCAG | 1201 | CUGGGUAGCAUUGCUGACC | 1202 |
| GUCAGCAAUGCUACCCAGU | 1203 | ACUGGGUAGCAUUGCUGAC | 1204 |
| UCAGCAAUGCUACCCAGUU | 1205 | AACUGGGUAGCAUUGCUGA | 1206 |
| CAGCAAUGCUACCCAGUUU | 1207 | AAACUGGGUAGCAUUGCUG | 1208 |
| AGCAAUGCUACCCAGUUUA | 1209 | UAAACUGGGUAGCAUUGCU | 1210 |
| CAAUGCUACCCAGUUUAUC | 1211 | GAUAAACUGGGUAGCAUUG | 1212 |
| AAUGCUACCCAGUUUAUCA | 1213 | UGAUAAACUGGGUAGCAUU | 1214 |
| AUGCUACCCAGUUUAUCAU | 1215 | AUGAUAAACUGGGUAGCAU | 1216 |
| UGCUACCCAGUUUAUCAUC | 1217 | GAUGAUAAACUGGGUAGCA | 1218 |
| GCUACCCAGUUUAUCAUCU | 1219 | AGAUGAUAAACUGGGUAGC | 1220 |

TABLE 4-continued

| Sense Sequence | SEQ ID NO: | Antisense Sequence | SEQ ID NO: |
|---|---|---|---|
| CUACCCAGUUUAUCAUCUU | 1221 | AAGAUGAUAAACUGGGUAG | 1222 |
| UACCCAGUUUAUCAUCUUG | 1223 | CAAGAUGAUAAACUGGGUA | 1224 |
| ACCCAGUUUAUCAUCUUGC | 1225 | GCAAGAUGAUAAACUGGGU | 1226 |
| CCCAGUUUAUCAUCUUGCA | 1227 | UGCAAGAUGAUAAACUGGG | 1228 |
| GUUUAUCAUCUUGCACAGC | 1229 | GCUGUGCAAGAUGAUAAAC | 1230 |
| UUUAUCAUCUUGCACAGCA | 1231 | UGCUGUGCAAGAUGAUAAA | 1232 |
| UCACGAAUGCCACCCUUCA | 1233 | UGAAGGGUGGCAUUCGUGA | 1234 |
| CACGAAUGCCACCCUUCAG | 1235 | CUGAAGGGUGGCAUUCGUG | 1236 |
| ACGAAUGCCACCCUUCAGU | 1237 | ACUGAAGGGUGGCAUUCGU | 1238 |
| CGAAUGCCACCCUUCAGUC | 1239 | GACUGAAGGGUGGCAUUCG | 1240 |
| GAAUGCCACCCUUCAGUCA | 1241 | UGACUGAAGGGUGGCAUUC | 1242 |
| UUCAGUCAGAGGAAGAUUC | 1243 | GAAUCUUCCUCUGACUGAA | 1244 |
| UCAGUCAGAGGAAGAUUCA | 1245 | UGAAUCUUCCUCUGACUGA | 1246 |
| CAGUCAGAGGAAGAUUCAA | 1247 | UUGAAUCUUCCUCUGACUG | 1248 |
| AGUCAGAGGAAGAUUCAAG | 1249 | CUUGAAUCUUCCUCUGACU | 1250 |
| GUCAGAGGAAGAUUCAAGA | 1251 | UCUUGAAUCUUCCUCUGAC | 1252 |
| CAGAGGAAGAUUCAAGAUA | 1253 | UAUCUUGAAUCUUCCUCUG | 1254 |
| AGAGGAAGAUUCAAGAUAC | 1255 | GUAUCUUGAAUCUUCCUCU | 1256 |
| GAGGAAGAUUCAAGAUACA | 1257 | UGUAUCUUGAAUCUUCCUC | 1258 |
| AGGAAGAUUCAAGAUACAU | 1259 | AUGUAUCUUGAAUCUUCCU | 1260 |
| GGAAGAUUCAAGAUACAUG | 1261 | CAUGUAUCUUGAAUCUUCC | 1262 |
| GAAGAUUCAAGAUACAUGA | 1263 | UCAUGUAUCUUGAAUCUUC | 1264 |
| AAAGUUUUGAGUUACCCUG | 1265 | CAGGGUAACUCAAAACUUU | 1266 |
| CAAAUUGCACUGCUGGUUC | 1267 | GAACCAGCAGUGCAAUUUG | 1268 |
| AAAUUGCACUGCUGGUUCC | 1269 | GGAACCAGCAGUGCAAUUU | 1270 |
| AAUUGCACUGCUGGUUCCA | 1271 | UGGAACCAGCAGUGCAAUU | 1272 |
| AUUGCACUGCUGGUUCCAG | 1273 | CUGGAACCAGCAGUGCAAU | 1274 |
| UUGCACUGCUGGUUCCAGA | 1275 | UCUGGAACCAGCAGUGCAA | 1276 |
| AAAUACUAUGUGGCUAUGG | 1277 | CCAUAGCCACAUAGUAUUU | 1278 |
| AAUACUAUGUGGCUAUGGA | 1279 | UCCAUAGCCACAUAGUAUU | 1280 |
| AUACUAUGUGGCUAUGGAC | 1281 | GUCCAUAGCCACAUAGUAU | 1282 |
| UACUAUGUGGCUAUGGACU | 1283 | AGUCCAUAGCCACAUAGUA | 1284 |
| ACUAUGUGGCUAUGGACUU | 1285 | AAGUCCAUAGCCACAUAGU | 1286 |
| CUAUGUGGCUAUGGACUUC | 1287 | GAAGUCCAUAGCCACAUAG | 1288 |
| UAUGUGGCUAUGGACUUCC | 1289 | GGAAGUCCAUAGCCACAUA | 1290 |
| AUGUGGCUAUGGACUUCCA | 1291 | UGGAAGUCCAUAGCCACAU | 1292 |
| UGUGGCUAUGGACUUCCAA | 1293 | UUGGAAGUCCAUAGCCACA | 1294 |
| GUGGCUAUGGACUUCCAAG | 1295 | CUUGGAAGUCCAUAGCCAC | 1296 |
| UGGCUAUGGACUUCCAAGC | 1297 | GCUUGGAAGUCCAUAGCCA | 1298 |

TABLE 4-continued

| Sense Sequence | SEQ ID NO: | Antisense Sequence | SEQ ID NO: |
|---|---|---|---|
| GCUAUGGACUUCCAAGCCA | 1299 | UGGCUUGGAAGUCCAUAGC | 1300 |
| CUAUGGACUUCCAAGCCAA | 1301 | UUGGCUUGGAAGUCCAUAG | 1302 |
| UAUGGACUUCCAAGCCAAG | 1303 | CUUGGCUUGGAAGUCCAUA | 1304 |
| CUUCCAAGCCAAGUUAGGU | 1305 | ACCUAACUUGGCUUGGAAG | 1306 |
| UUCCAAGCCAAGUUAGGUG | 1307 | CACCUAACUUGGCUUGGAA | 1308 |
| UCCAAGCCAAGUUAGGUGA | 1309 | UCACCUAACUUGGCUUGGA | 1310 |
| CCAAGCCAAGUUAGGUGAU | 1311 | AUCACCUAACUUGGCUUGG | 1312 |
| CAAGCCAAGUUAGGUGAUG | 1313 | CAUCACCUAACUUGGCUUG | 1314 |
| AAGCCAAGUUAGGUGAUGG | 1315 | CCAUCACCUAACUUGGCUU | 1316 |
| CCAAGUUAGGUGAUGGCUU | 1317 | AAGCCAUCACCUAACUUGG | 1318 |
| CAAGUUAGGUGAUGGCUUU | 1319 | AAAGCCAUCACCUAACUUG | 1320 |
| UUAGGUGAUGGCUUUGAAG | 1321 | CUUCAAAGCCAUCACCUAA | 1322 |
| GUGAUGGCUUUGAAGGGUU | 1323 | AACCCUUCAAAGCCAUCAC | 1324 |
| UGAUGGCUUUGAAGGGUUU | 1325 | AAACCCUUCAAAGCCAUCA | 1326 |
| GAUGGCUUUGAAGGGUUUU | 1327 | AAAACCCUUCAAAGCCAUC | 1328 |
| AUGGCUUUGAAGGGUUUUA | 1329 | UAAAACCCUUCAAAGCCAU | 1330 |
| UGGCUUUGAAGGGUUUUAU | 1331 | AUAAAACCCUUCAAAGCCA | 1332 |
| UGAAGGGUUUUAUAAAAGC | 1333 | GCUUUUAUAAAACCCUUCA | 1334 |
| GAAGGGUUUUAUAAAAGCA | 1335 | UGCUUUUAUAAAACCCUUC | 1336 |
| AAGGGUUUUAUAAAAGCAC | 1337 | GUGCUUUUAUAAAACCCUU | 1338 |
| AGAUUUUGAGCCAACCCAG | 1339 | CUGGGUUGGCUCAAAAUCU | 1340 |
| GAUUUUGAGCCAACCCAGG | 1341 | CCUGGGUUGGCUCAAAAUC | 1342 |
| AUUUUGAGCCAACCCAGGC | 1343 | GCCUGGGUUGGCUCAAAAU | 1344 |
| AGCCAACCCAGGCACGCAU | 1345 | AUGCGUGCCUGGGUUGGCU | 1346 |
| AACCCAGGCACGCAUGGCU | 1347 | AGCCAUGCGUGCCUGGGUU | 1348 |
| ACCCAGGCACGCAUGGCUU | 1349 | AAGCCAUGCGUGCCUGGGU | 1350 |
| CCCAGGCACGCAUGGCUUU | 1351 | AAAGCCAUGCGUGCCUGGG | 1352 |
| CCAGGCACGCAUGGCUUUC | 1353 | GAAAGCCAUGCGUGCCUGG | 1354 |
| CAGGCACGCAUGGCUUUCC | 1355 | GGAAAGCCAUGCGUGCCUG | 1356 |
| CACGCAUGGCUUUCCCUUG | 1357 | CAAGGGAAAGCCAUGCGUG | 1358 |
| CAUGGCUUUCCCUUGCUUU | 1359 | AAAGCAAGGGAAAGCCAUG | 1360 |
| GCUUUCCCUUGCUUUGAUG | 1361 | CAUCAAAGCAAGGGAAAGC | 1362 |
| CUUUCCCUUGCUUUGAUGA | 1363 | UCAUCAAAGCAAGGGAAAG | 1364 |
| UUUCCCUUGCUUUGAUGAA | 1365 | UUCAUCAAAGCAAGGGAAA | 1366 |
| AAGCCAACUUUUCAAUCAA | 1367 | UUGAUUGAAAAGUUGGCUU | 1368 |
| AGCCAACUUUUCAAUCAAG | 1369 | CUUGAUUGAAAAGUUGGCU | 1370 |
| GCCAACUUUUCAAUCAAGA | 1371 | UCUUGAUUGAAAAGUUGGC | 1372 |
| CCAACUUUUCAAUCAAGAU | 1373 | AUCUUGAUUGAAAAGUUGG | 1374 |
| ACUUUUCAAUCAAGAUACG | 1375 | CGUAUCUUGAUUGAAAAGU | 1376 |

53

54

TABLE 4-continued

| Sense Sequence | SEQ ID NO: | Antisense Sequence | SEQ ID NO: |
|---|---|---|---|
| CUUUUCAAUCAAGAUACGA | 1377 | UCGUAUCUUGAUUGAAAAG | 1378 |
| UUUCAAUCAAGAUACGAAG | 1379 | CUUCGUAUCUUGAUUGAAA | 1380 |
| UUCAAUCAAGAUACGAAGA | 1381 | UCUUCGUAUCUUGAUUGAA | 1382 |
| UCAAUCAAGAUACGAAGAG | 1383 | CUCUUCGUAUCUUGAUUGA | 1384 |
| GCAGGCAUAUUGCACUAUC | 1385 | GAUAGUGCAAUAUGCCUGC | 1386 |
| CAGGCAUAUUGCACUAUCC | 1387 | GGAUAGUGCAAUAUGCCUG | 1388 |
| CUUGAAGGAGGUCUUUUGG | 1389 | CCAAAAGACCUCCUUCAAG | 1390 |
| UUGAAGGAGGUCUUUUGGA | 1391 | UCCAAAAGACCUCCUUCAA | 1392 |
| GAAGGAGGUCUUUUGGAAG | 1393 | CUUCCAAAAGACCUCCUUC | 1394 |
| UUUGGAAGAUCACUUUGAA | 1395 | UUCAAAGUGAUCUUCCAAA | 1396 |
| AAAAUGAGUACAUACCUUG | 1397 | CAAGGUAUGUACUCAUUUU | 1398 |
| AAAUGAGUACAUACCUUGU | 1399 | ACAAGGUAUGUACUCAUUU | 1400 |
| GUAGCCUACAUAGUUUGUG | 1401 | CACAAACUAUGUAGGCUAC | 1402 |
| AUAGUUUGUGAUUUCCACU | 1403 | AGUGGAAAUCACAAACUAU | 1404 |
| UAGUUUGUGAUUUCCACUC | 1405 | GAGUGGAAAUCACAAACUA | 1406 |
| AGUUUGUGAUUUCCACUCU | 1407 | AGAGUGGAAAUCACAAACU | 1408 |
| GUUUGUGAUUUCCACUCUC | 1409 | GAGAGUGGAAAUCACAAAC | 1410 |
| UUUGUGAUUUCCACUCUCU | 1411 | AGAGAGUGGAAAUCACAAA | 1412 |
| UUGUGAUUUCCACUCUCUG | 1413 | CAGAGAGUGGAAAUCACAA | 1414 |
| UGUGAUUUCCACUCUCUGA | 1415 | UCAGAGAGUGGAAAUCACA | 1416 |
| GUGAUUUCCACUCUCUGAG | 1417 | CUCAGAGAGUGGAAAUCAC | 1418 |
| GGGUCAAGGUGUCCAUCUA | 1419 | UAGAUGGACACCUUGACCC | 1420 |
| GGUCAAGGUGUCCAUCUAU | 1421 | AUAGAUGGACACCUUGACC | 1422 |
| GUCAAGGUGUCCAUCUAUG | 1423 | CAUAGAUGGACACCUUGAC | 1424 |
| UCAAGGUGUCCAUCUAUGC | 1425 | GCAUAGAUGGACACCUUGA | 1426 |
| UGCUUUGCAGGCAUCACUG | 1427 | CAGUGAUGCCUGCAAAGCA | 1428 |
| GCUUUGCAGGCAUCACUGA | 1429 | UCAGUGAUGCCUGCAAAGC | 1430 |
| CUUUGCAGGCAUCACUGAA | 1431 | UUCAGUGAUGCCUGCAAAG | 1432 |
| UUUGCAGGCAUCACUGAAG | 1433 | CUUCAGUGAUGCCUGCAAA | 1434 |
| UUGCAGGCAUCACUGAAGC | 1435 | GCUUCAGUGAUGCCUGCAA | 1436 |
| CAGGCAUCACUGAAGCUAC | 1437 | GUAGCUUCAGUGAUGCCUG | 1438 |
| AGGCAUCACUGAAGCUACU | 1439 | AGUAGCUUCAGUGAUGCCU | 1440 |
| GGCAUCACUGAAGCUACUU | 1441 | AAGUAGCUUCAGUGAUGCC | 1442 |
| AUAUCUACUAUCCACUCUC | 1443 | GAGAGUGGAUAGUAGAUAU | 1444 |
| CUACUAUCCACUCUCCAAA | 1445 | UUUGGAGAGUGGAUAGUAG | 1446 |
| CUGGAUUUAAUUGCUAUUC | 1447 | GAAUAGCAAUUAAAUCCAG | 1448 |
| UGGAUUUAAUUGCUAUUCC | 1449 | GGAAUAGCAAUUAAAUCCA | 1450 |
| GGAUUUAAUUGCUAUUCCU | 1451 | AGGAAUAGCAAUUAAAUCC | 1452 |
| UUAAUUGCUAUUCCUGACU | 1453 | AGUCAGGAAUAGCAAUUAA | 1454 |

TABLE 4-continued

| Sense Sequence | SEQ ID NO: | Antisense Sequence | SEQ ID NO: |
|---|---|---|---|
| UAAUUGCUAUUCCUGACUU | 1455 | AAGUCAGGAAUAGCAAUUA | 1456 |
| AAUUGCUAUUCCUGACUUU | 1457 | AAAGUCAGGAAUAGCAAUU | 1458 |
| AUUGCUAUUCCUGACUUUG | 1459 | CAAAGUCAGGAAUAGCAAU | 1460 |
| UUGCUAUUCCUGACUUUGC | 1461 | GCAAAGUCAGGAAUAGCAA | 1462 |
| UGCUAUUCCUGACUUUGCA | 1463 | UGCAAAGUCAGGAAUAGCA | 1464 |
| CCUGACUUUGCACCUGGAG | 1465 | CUCCAGGUGCAAAGUCAGG | 1466 |
| CUGACUUUGCACCUGGAGC | 1467 | GCUCCAGGUGCAAAGUCAG | 1468 |
| GACUUUGCACCUGGAGCCA | 1469 | UGGCUCCAGGUGCAAAGUC | 1470 |
| UUGCACCUGGAGCCAUGGA | 1471 | UCCAUGGCUCCAGGUGCAA | 1472 |
| UGCACCUGGAGCCAUGGAA | 1473 | UUCCAUGGCUCCAGGUGCA | 1474 |
| GGGCCUCAUUACAUAUAGG | 1475 | CCUAUAUGUAAUGAGGCCC | 1476 |
| GGCCUCAUUACAUAUAGGG | 1477 | CCCUAUAUGUAAUGAGGCC | 1478 |
| GCCUCAUUACAUAUAGGGA | 1479 | UCCCUAUAUGUAAUGAGGC | 1480 |
| CCAAGACCUCUUCUGCUUC | 1481 | GAAGCAGAAGAGGUCUUGG | 1482 |
| CAAGACCUCUUCUGCUUCC | 1483 | GGAAGCAGAAGAGGUCUUG | 1484 |
| AAGACCUCUUCUGCUUCCG | 1485 | CGGAAGCAGAAGAGGUCUU | 1486 |
| AGACCUCUUCUGCUUCCGA | 1487 | UCGGAAGCAGAAGAGGUCU | 1488 |
| GACCUCUUCUGCUUCCGAU | 1489 | AUCGGAAGCAGAAGAGGUC | 1490 |
| ACCUCUUCUGCUUCCGAUA | 1491 | UAUCGGAAGCAGAAGAGGU | 1492 |
| CCUCUUCUGCUUCCGAUAA | 1493 | UUAUCGGAAGCAGAAGAGG | 1494 |
| CUCUUCUGCUUCCGAUAAA | 1495 | UUUAUCGGAAGCAGAAGAG | 1496 |
| CUGUGGGUCACCAGAGUCA | 1497 | UGACUCUGGUGACCCACAG | 1498 |
| UGUGGGUCACCAGAGUCAU | 1499 | AUGACUCUGGUGACCCACA | 1500 |
| GUGGGUCACCAGAGUCAUA | 1501 | UAUGACUCUGGUGACCCAC | 1502 |
| UGGGUCACCAGAGUCAUAG | 1503 | CUAUGACUCUGGUGACCCA | 1504 |
| UCACCAGAGUCAUAGCCCA | 1505 | UGGGCUAUGACUCUGGUGA | 1506 |
| ACCAGAGUCAUAGCCCAUG | 1507 | CAUGGGCUAUGACUCUGGU | 1508 |
| GCGCACCAGUGGUUUGGCA | 1509 | UGCCAAACCACUGGUGCGC | 1510 |
| CGCACCAGUGGUUUGGCAA | 1511 | UUGCCAAACCACUGGUGCG | 1512 |
| GCACCAGUGGUUUGGCAAC | 1513 | GUUGCCAAACCACUGGUGC | 1514 |
| GUUUGGCAACCUGGUCACA | 1515 | UGUGACCAGGUUGCCAAAC | 1516 |
| AAUGGUGGAAUGAUAUUUG | 1517 | CAAAUAUCAUUCCACCAUU | 1518 |
| AUGGUGGAAUGAUAUUUGG | 1519 | CCAAAUAUCAUUCCACCAU | 1520 |
| UGGUGGAAUGAUAUUUGGC | 1521 | GCCAAAUAUCAUUCCACCA | 1522 |
| GGUGGAAUGAUAUUUGGCU | 1523 | AGCCAAAUAUCAUUCCACC | 1524 |
| GUGGAAUGAUAUUUGGCUU | 1525 | AAGCCAAAUAUCAUUCCAC | 1526 |
| UGGAAUGAUAUUUGGCUUA | 1527 | UAAGCCAAAUAUCAUUCCA | 1528 |
| GGAAUGAUAUUUGGCUUAA | 1529 | UUAAGCCAAAUAUCAUUCC | 1530 |
| GAGGGUUUUGCAAAAUACA | 1531 | UGUAUUUUGCAAAACCCUC | 1532 |

TABLE 4-continued

| Sense Sequence | SEQ ID NO: | Antisense Sequence | SEQ ID NO: |
|---|---|---|---|
| AGGGUUUUGCAAAAUACAU | 1533 | AUGUAUUUUGCAAAACCCU | 1534 |
| GGGUUUUGCAAAAUACAUG | 1535 | CAUGUAUUUUGCAAAACCC | 1536 |
| GGUUUUGCAAAAUACAUGG | 1537 | CCAUGUAUUUUGCAAAACC | 1538 |
| GUUUUGCAAAAUACAUGGA | 1539 | UCCAUGUAUUUUGCAAAAC | 1540 |
| AACUUAUCGCUGUUAAUGC | 1541 | GCAUUAACAGCGAUAAGUU | 1542 |
| ACUUAUCGCUGUUAAUGCU | 1543 | AGCAUUAACAGCGAUAAGU | 1544 |
| CUUAUCGCUGUUAAUGCUA | 1545 | UAGCAUUAACAGCGAUAAG | 1546 |
| UUAUCGCUGUUAAUGCUAC | 1547 | GUAGCAUUAACAGCGAUAA | 1548 |
| UAUCGCUGUUAAUGCUACA | 1549 | UGUAGCAUUAACAGCGAUA | 1550 |
| UUGAAUGUGUGUUUUGAAG | 1551 | CUUCAAAACACACAUUCAA | 1552 |
| UGAAUGUGUGUUUUGAAGU | 1553 | ACUUCAAAACACACAUUCA | 1554 |
| GAAUGUGUGUUUUGAAGUA | 1555 | UACUUCAAAACACACAUUC | 1556 |
| UUCAUUGAAUUCAUCCCGC | 1557 | GCGGGAUGAAUUCAAUGAA | 1558 |
| AAUGUUUGAUGAAGUUUCC | 1559 | GGAAACUUCAUCAAACAUU | 1560 |
| AAGGGAGCUUGUAUUUUGA | 1561 | UCAAAAUACAAGCUCCCUU | 1562 |
| GGGAGCUUGUAUUUUGAAU | 1563 | AUUCAAAAUACAAGCUCCC | 1564 |
| GAAUAUGCUCAAGGAUUUU | 1565 | AAAAUCCUUGAGCAUAUUC | 1566 |
| AAUAUGCUCAAGGAUUUUC | 1567 | GAAAAUCCUUGAGCAUAUU | 1568 |
| AUAUGCUCAAGGAUUUUCU | 1569 | AGAAAAUCCUUGAGCAUAU | 1570 |
| UAUGCUCAAGGAUUUUCUG | 1571 | CAGAAAAUCCUUGAGCAUA | 1572 |
| AUGCUCAAGGAUUUUCUGG | 1573 | CCAGAAAAUCCUUGAGCAU | 1574 |
| GCUCAAGGAUUUUCUGGGU | 1575 | ACCCAGAAAAUCCUUGAGC | 1576 |
| CUCAAGGAUUUUCUGGGUG | 1577 | CACCCAGAAAAUCCUUGAG | 1578 |
| UCAAGGAUUUUCUGGGUGA | 1579 | UCACCCAGAAAAUCCUUGA | 1580 |
| CAAGGAUUUUCUGGGUGAG | 1581 | CUCACCCAGAAAAUCCUUG | 1582 |
| AAGGAUUUUCUGGGUGAGG | 1583 | CCUCACCCAGAAAAUCCUU | 1584 |
| AGGAUUUUCUGGGUGAGGA | 1585 | UCCUCACCCAGAAAAUCCU | 1586 |
| GGAUUUUCUGGGUGAGGAG | 1587 | CUCCUCACCCAGAAAAUCC | 1588 |
| UAAAGAAGUUCAGCUAUAG | 1589 | CUAUAGCUGAACUUCUUUA | 1590 |
| AAAGAAGUUCAGCUAUAGA | 1591 | UCUAUAGCUGAACUUCUUU | 1592 |
| AAGAAGUUCAGCUAUAGAA | 1593 | UUCUAUAGCUGAACUUCUU | 1594 |
| AAAUGCUAAGAAUGAUGAC | 1595 | GUCAUCAUUCUUAGCAUUU | 1596 |
| AAUGCUAAGAAUGAUGACU | 1597 | AGUCAUCAUUCUUAGCAUU | 1598 |
| AAGAAUGAUGACUUGUGGA | 1599 | UCCACAAGUCAUCAUUCUU | 1600 |
| AGAAUGAUGACUUGUGGAG | 1601 | CUCCACAAGUCAUCAUUCU | 1602 |
| AAUGAUGACUUGUGGAGCA | 1603 | UGCUCCACAAGUCAUCAUU | 1604 |
| AUGAUGACUUGUGGAGCAG | 1605 | CUGCUCCACAAGUCAUCAU | 1606 |
| UGAUGACUUGUGGAGCAGU | 1607 | ACUGCUCCACAAGUCAUCA | 1608 |
| ACUUGUGGAGCAGUCUGUC | 1609 | GACAGACUGCUCCACAAGU | 1610 |

TABLE 4-continued

| Sense Sequence | SEQ ID NO: | Antisense Sequence | SEQ ID NO: |
|---|---|---|---|
| CUUGUGGAGCAGUCUGUCA | 1611 | UGACAGACUGCUCCACAAG | 1612 |
| UUGUGGAGCAGUCUGUCAA | 1613 | UUGACAGACUGCUCCACAA | 1614 |
| UGUGGAGCAGUCUGUCAAA | 1615 | UUUGACAGACUGCUCCACA | 1616 |
| GUGGAGCAGUCUGUCAAAU | 1617 | AUUUGACAGACUGCUCCAC | 1618 |
| UGGAGCAGUCUGUCAAAUA | 1619 | UAUUUGACAGACUGCUCCA | 1620 |
| GCAGUCUGUCAAAUAGUUG | 1621 | CAACUAUUUGACAGACUGC | 1622 |
| CAGUCUGUCAAAUAGUUGU | 1623 | ACAACUAUUUGACAGACUG | 1624 |
| AGUCUGUCAAAUAGUUGUU | 1625 | AACAACUAUUUGACAGACU | 1626 |
| GUCUGUCAAAUAGUUGUUU | 1627 | AAACAACUAUUUGACAGAC | 1628 |
| CUGUCAAAUAGUUGUUUAG | 1629 | CUAAACAACUAUUUGACAG | 1630 |
| GUGAUUUUACAUCUGGUGG | 1631 | CCACCAGAUGUAAAAUCAC | 1632 |
| UGAUUUUACAUCUGGUGGA | 1633 | UCCACCAGAUGUAAAAUCA | 1634 |
| GAUUUUACAUCUGGUGGAG | 1635 | CUCCACCAGAUGUAAAAUC | 1636 |
| UACAUCUGGUGGAGUUUGU | 1637 | ACAAACUCCACCAGAUGUA | 1638 |
| ACAUCUGGUGGAGUUUGUC | 1639 | GACAAACUCCACCAGAUGU | 1640 |
| CAUCUGGUGGAGUUUGUCA | 1641 | UGACAAACUCCACCAGAUG | 1642 |
| UGGUGGAGUUUGUCAUUCG | 1643 | CGAAUGACAAACUCCACCA | 1644 |
| GGUGGAGUUUGUCAUUCGG | 1645 | CCGAAUGACAAACUCCACC | 1646 |
| GUGGAGUUUGUCAUUCGGA | 1647 | UCCGAAUGACAAACUCCAC | 1648 |
| UGGAGUUUGUCAUUCGGAU | 1649 | AUCCGAAUGACAAACUCCA | 1650 |
| GGAGUUUGUCAUUCGGAUC | 1651 | GAUCCGAAUGACAAACUCC | 1652 |
| GAGUUUGUCAUUCGGAUCC | 1653 | GGAUCCGAAUGACAAACUC | 1654 |
| AGUUUGUCAUUCGGAUCCC | 1655 | GGGAUCCGAAUGACAAACU | 1656 |
| UGUCAUUCGGAUCCCAAGA | 1657 | UCUUGGGAUCCGAAUGACA | 1658 |
| GUCAUUCGGAUCCCAAGAU | 1659 | AUCUUGGGAUCCGAAUGAC | 1660 |
| UCAUUCGGAUCCCAAGAUG | 1661 | CAUCUUGGGAUCCGAAUGA | 1662 |
| CAUUCGGAUCCCAAGAUGA | 1663 | UCAUCUUGGGAUCCGAAUG | 1664 |
| AUUCGGAUCCCAAGAUGAC | 1665 | GUCAUCUUGGGAUCCGAAU | 1666 |
| UUCGGAUCCCAAGAUGACA | 1667 | UGUCAUCUUGGGAUCCGAA | 1668 |
| ACAUGCUCGCCUUUCUGGG | 1669 | CCCAGAAAGGCGAGCAUGU | 1670 |
| AAAAUGCAGAGGUCAAAGA | 1671 | UCUUUGACCUCUGCAUUUU | 1672 |
| AGAUGAUGACUACAUGGAC | 1673 | GUCCAUGUAGUCAUCAUCU | 1674 |
| AUGAUGACUACAUGGACUC | 1675 | GAGUCCAUGUAGUCAUCAU | 1676 |
| UGAUGACUACAUGGACUCU | 1677 | AGAGUCCAUGUAGUCAUCA | 1678 |
| GAUGACUACAUGGACUCUC | 1679 | GAGAGUCCAUGUAGUCAUC | 1680 |
| GACGGGUGUUCACUCCGAC | 1681 | GUCGGAGUGAACACCCGUC | 1682 |
| ACGGGUGUUCACUCCGACU | 1683 | AGUCGGAGUGAACACCCGU | 1684 |
| CGGGUGUUCACUCCGACUG | 1685 | CAGUCGGAGUGAACACCCG | 1686 |
| GGGUGUUCACUCCGACUGC | 1687 | GCAGUCGGAGUGAACACCC | 1688 |

TABLE 4-continued

| Sense Sequence | SEQ ID NO: | Antisense Sequence | SEQ ID NO: |
|---|---|---|---|
| GGUGUUCACUCCGACUGCA | 1689 | UGCAGUCGGAGUGAACACC | 1690 |
| GUGUUCACUCCGACUGCAA | 1691 | UUGCAGUCGGAGUGAACAC | 1692 |
| UGUUCACUCCGACUGCAAC | 1693 | GUUGCAGUCGGAGUGAACA | 1694 |
| AGAGGUACCUGUGGCAUAU | 1695 | AUAUGCCACAGGUACCUCU | 1696 |
| CCUGUGGCAUAUCCCAUUG | 1697 | CAAUGGGAUAUGCCACAGG | 1698 |
| CUGUGGCAUAUCCCAUUGA | 1699 | UCAAUGGGAUAUGCCACAG | 1700 |
| CAUAUCCCAUUGACCUACU | 1701 | AGUAGGUCAAUGGGAUAUG | 1702 |
| AUAUCCCAUUGACCUACUC | 1703 | GAGUAGGUCAAUGGGAUAU | 1704 |
| UAUCCCAUUGACCUACUCC | 1705 | GGAGUAGGUCAAUGGGAUA | 1706 |
| CCAUUGACCUACUCCACGA | 1707 | UCGUGGAGUAGGUCAAUGG | 1708 |
| CAUUGACCUACUCCACGAG | 1709 | CUCGUGGAGUAGGUCAAUG | 1710 |
| CUCCACGAGUUCUUCUAAU | 1711 | AUUAGAAGAACUCGUGGAG | 1712 |
| UCCACGAGUUCUUCUAAUG | 1713 | CAUUAGAAGAACUCGUGGA | 1714 |
| AGUUCUUCUAAUGUGAUCC | 1715 | GGAUCACAUUAGAAGAACU | 1716 |
| GUUCUUCUAAUGUGAUCCA | 1717 | UGGAUCACAUUAGAAGAAC | 1718 |
| UUCUUCUAAUGUGAUCCAC | 1719 | GUGGAUCACAUUAGAAGAA | 1720 |
| AAAAGACCAGUUGGGUGAA | 1721 | UUCACCCAACUGGUCUUUU | 1722 |
| UUUAAUGUGGACUCAAAUG | 1723 | CAUUUGAGUCCACAUUAAA | 1724 |
| UUAAUGUGGACUCAAAUGG | 1725 | CCAUUUGAGUCCACAUUAA | 1726 |
| UAAUGUGGACUCAAAUGGU | 1727 | ACCAUUUGAGUCCACAUUA | 1728 |
| AAUGUGGACUCAAAUGGUU | 1729 | AACCAUUUGAGUCCACAUU | 1730 |
| AUGUGGACUCAAAUGGUUA | 1731 | UAACCAUUUGAGUCCACAU | 1732 |
| UGUGGACUCAAAUGGUUAC | 1733 | GUAACCAUUUGAGUCCACA | 1734 |
| GUGGACUCAAAUGGUUACU | 1735 | AGUAACCAUUUGAGUCCAC | 1736 |
| UGGACUCAAAUGGUUACUA | 1737 | UAGUAACCAUUUGAGUCCA | 1738 |
| GGACUCAAAUGGUUACUAC | 1739 | GUAGUAACCAUUUGAGUCC | 1740 |
| GACUCAAAUGGUUACUACA | 1741 | UGUAGUAACCAUUUGAGUC | 1742 |
| CAAAUGGUUACUACAUCGU | 1743 | ACGAUGUAGUAACCAUUUG | 1744 |
| AAUGGUUACUACAUCGUUC | 1745 | GAACGAUGUAGUAACCAUU | 1746 |
| AUGGUUACUACAUCGUUCA | 1747 | UGAACGAUGUAGUAACCAU | 1748 |
| UGGUUACUACAUCGUUCAC | 1749 | GUGAACGAUGUAGUAACCA | 1750 |
| GGUUACUACAUCGUUCACU | 1751 | AGUGAACGAUGUAGUAACC | 1752 |
| GUUACUACAUCGUUCACUA | 1753 | UAGUGAACGAUGUAGUAAC | 1754 |
| UUACUACAUCGUUCACUAU | 1755 | AUAGUGAACGAUGUAGUAA | 1756 |
| UACUACAUCGUUCACUAUG | 1757 | CAUAGUGAACGAUGUAGUA | 1758 |
| ACAUCGUUCACUAUGAGGG | 1759 | CCCUCAUAGUGAACGAUGU | 1760 |
| CAUCGUUCACUAUGAGGGU | 1761 | ACCCUCAUAGUGAACGAUG | 1762 |
| UGAGGGUCAUGGAUGGGAC | 1763 | GUCCCAUCCAUGACCCUCA | 1764 |
| CACACUUCUCAGACCUAAG | 1765 | CUUAGGUCUGAGAAGUGUG | 1766 |

TABLE 4-continued

| Sense Sequence | SEQ ID NO: | Antisense Sequence | SEQ ID NO: |
|---|---|---|---|
| ACACUUCUCAGACCUAAGG | 1767 | CCUUAGGUCUGAGAAGUGU | 1768 |
| CACUUCUCAGACCUAAGGA | 1769 | UCCUUAGGUCUGAGAAGUG | 1770 |
| ACUUCUCAGACCUAAGGAC | 1771 | GUCCUUAGGUCUGAGAAGU | 1772 |
| UUCUCAGACCUAAGGACAG | 1773 | CUGUCCUUAGGUCUGAGAA | 1774 |
| UCUCAGACCUAAGGACAGA | 1775 | UCUGUCCUUAGGUCUGAGA | 1776 |
| CUCAGACCUAAGGACAGAG | 1777 | CUCUGUCCUUAGGUCUGAG | 1778 |
| UCAGACCUAAGGACAGAGU | 1779 | ACUCUGUCCUUAGGUCUGA | 1780 |
| CAGACCUAAGGACAGAGUA | 1781 | UACUCUGUCCUUAGGUCUG | 1782 |
| AGACCUAAGGACAGAGUAG | 1783 | CUACUCUGUCCUUAGGUCU | 1784 |
| UCUGAUUCAUGAUGUGUUU | 1785 | AAACACAUCAUGAAUCAGA | 1786 |
| AUUCAUGAUGUGUUUCAGC | 1787 | GCUGAAACACAUCAUGAAU | 1788 |
| CAAAGCUCUUGACAUGACU | 1789 | AGUCAUGUCAAGAGCUUUG | 1790 |
| AAAGCUCUUGACAUGACUU | 1791 | AAGUCAUGUCAAGAGCUUU | 1792 |
| AAGCUCUUGACAUGACUUA | 1793 | UAAGUCAUGUCAAGAGCUU | 1794 |
| AGCUCUUGACAUGACUUAC | 1795 | GUAAGUCAUGUCAAGAGCU | 1796 |
| GCUCUUGACAUGACUUACU | 1797 | AGUAAGUCAUGUCAAGAGC | 1798 |
| CUCUUGACAUGACUUACUA | 1799 | UAGUAAGUCAUGUCAAGAG | 1800 |
| UCUUGACAUGACUUACUAC | 1801 | GUAGUAAGUCAUGUCAAGA | 1802 |
| CUUGACAUGACUUACUACC | 1803 | GGUAGUAAGUCAUGUCAAG | 1804 |
| CCCGCACUUCUCGAAGGUC | 1805 | GACCUUCGAGAAGUGCGGG | 1806 |
| CCGCACUUCUCGAAGGUCU | 1807 | AGACCUUCGAGAAGUGCGG | 1808 |
| GCACUUCUCGAAGGUCUGA | 1809 | UCAGACCUUCGAGAAGUGC | 1810 |
| CACUUCUCGAAGGUCUGAG | 1811 | CUCAGACCUUCGAGAAGUG | 1812 |
| UCUCGAAGGUCUGAGUUAC | 1813 | GUAACUCAGACCUUCGAGA | 1814 |
| CUCGAAGGUCUGAGUUACU | 1815 | AGUAACUCAGACCUUCGAG | 1816 |
| UCGAAGGUCUGAGUUACUU | 1817 | AAGUAACUCAGACCUUCGA | 1818 |
| CGAAGGUCUGAGUUACUUG | 1819 | CAAGUAACUCAGACCUUCG | 1820 |
| AAGGUCUGAGUUACUUGGA | 1821 | UCCAAGUAACUCAGACCUU | 1822 |
| AGGUCUGAGUUACUUGGAA | 1823 | UUCCAAGUAACUCAGACCU | 1824 |
| GGUCUGAGUUACUUGGAAU | 1825 | AUUCCAAGUAACUCAGACC | 1826 |
| GUCUGAGUUACUUGGAAUC | 1827 | GAUUCCAAGUAACUCAGAC | 1828 |
| UCUGAGUUACUUGGAAUCG | 1829 | CGAUUCCAAGUAACUCAGA | 1830 |
| CUGAGUUACUUGGAAUCGU | 1831 | ACGAUUCCAAGUAACUCAG | 1832 |
| UGAGUUACUUGGAAUCGUU | 1833 | AACGAUUCCAAGUAACUCA | 1834 |
| GAGUUACUUGGAAUCGUUU | 1835 | AAACGAUUCCAAGUAACUC | 1836 |
| AGUUACUUGGAAUCGUUUU | 1837 | AAAACGAUUCCAAGUAACU | 1838 |
| GUUACUUGGAAUCGUUUUA | 1839 | UAAAACGAUUCCAAGUAAC | 1840 |
| UUACUUGGAAUCGUUUUAC | 1841 | GUAAAACGAUUCCAAGUAA | 1842 |
| UACUUGGAAUCGUUUUACC | 1843 | GGUAAAACGAUUCCAAGUA | 1844 |

TABLE 4-continued

| Sense Sequence | SEQ ID NO: | Antisense Sequence | SEQ ID NO: |
|---|---|---|---|
| ACUUGGAAUCGUUUUACCA | 1845 | UGGUAAAACGAUUCCAAGU | 1846 |
| CUUGGAAUCGUUUUACCAC | 1847 | GUGGUAAAACGAUUCCAAG | 1848 |
| UUGGAAUCGUUUUACCACA | 1849 | UGUGGUAAAACGAUUCCAA | 1850 |
| AAUCGUUUUACCACAUGAU | 1851 | AUCAUGUGGUAAAACGAUU | 1852 |
| AUCGUUUUACCACAUGAUG | 1853 | CAUCAUGUGGUAAAACGAU | 1854 |
| UCGUUUUACCACAUGAUGG | 1855 | CCAUCAUGUGGUAAAACGA | 1856 |
| CGUUUUACCACAUGAUGGA | 1857 | UCCAUCAUGUGGUAAAACG | 1858 |
| GUUUUACCACAUGAUGGAC | 1859 | GUCCAUCAUGUGGUAAAAC | 1860 |
| UUUACCACAUGAUGGACAG | 1861 | CUGUCCAUCAUGUGGUAAA | 1862 |
| UUACCACAUGAUGGACAGA | 1863 | UCUGUCCAUCAUGUGGUAA | 1864 |
| UACCACAUGAUGGACAGAA | 1865 | UUCUGUCCAUCAUGUGGUA | 1866 |
| ACCACAUGAUGGACAGAAG | 1867 | CUUCUGUCCAUCAUGUGGU | 1868 |
| CAUGAUGGACAGAAGGAAU | 1869 | AUUCCUUCUGUCCAUCAUG | 1870 |
| UGAUGGACAGAAGGAAUAU | 1871 | AUAUUCCUUCUGUCCAUCA | 1872 |
| GAUGGACAGAAGGAAUAUU | 1873 | AAUAUUCCUUCUGUCCAUC | 1874 |
| AUGGACAGAAGGAAUAUUU | 1875 | AAAUAUUCCUUCUGUCCAU | 1876 |
| UGGACAGAAGGAAUAUUUC | 1877 | GAAAUAUUCCUUCUGUCCA | 1878 |
| CAGAAGGAAUAUUUCAGAU | 1879 | AUCUGAAAUAUUCCUUCUG | 1880 |
| CUCAAGCGUUACCUUCUUC | 1881 | GAAGAAGGUAACGCUUGAG | 1882 |
| AGCGUUACCUUCUUCAGUA | 1883 | UACUGAAGAAGGUAACGCU | 1884 |
| GCGUUACCUUCUUCAGUAU | 1885 | AUACUGAAGAAGGUAACGC | 1886 |
| CCUUCUUCAGUAUUUUAAG | 1887 | CUUAAAAUACUGAAGAAGG | 1888 |
| UUCUUCAGUAUUUUAAGCC | 1889 | GGCUUAAAAUACUGAAGAA | 1890 |
| UCUUCAGUAUUUUAAGCCA | 1891 | UGGCUUAAAAUACUGAAGA | 1892 |
| AUUUUAAGCCAGUGAUUGA | 1893 | UCAAUCACUGGCUUAAAAU | 1894 |
| UUUUAAGCCAGUGAUUGAC | 1895 | GUCAAUCACUGGCUUAAAA | 1896 |
| UUUAAGCCAGUGAUUGACA | 1897 | UGUCAAUCACUGGCUUAAA | 1898 |
| UUAAGCCAGUGAUUGACAG | 1899 | CUGUCAAUCACUGGCUUAA | 1900 |
| UAAGCCAGUGAUUGACAGG | 1901 | CCUGUCAAUCACUGGCUUA | 1902 |
| AAGCCAGUGAUUGACAGGC | 1903 | GCCUGUCAAUCACUGGCUU | 1904 |
| CAGUGAUUGACAGGCAAAG | 1905 | CUUUGCCUGUCAAUCACUG | 1906 |
| AGUGAUUGACAGGCAAAGC | 1907 | GCUUUGCCUGUCAAUCACU | 1908 |
| AUUGACAGGCAAAGCUGGA | 1909 | UCCAGCUUUGCCUGUCAAU | 1910 |
| UUGACAGGCAAAGCUGGAG | 1911 | CUCCAGCUUUGCCUGUCAA | 1912 |
| GCUCGGCUCUCUUGAAGCU | 1913 | AGCUUCAAGAGAGCCGAGC | 1914 |
| UCGGCUCUCUUGAAGCUGG | 1915 | CCAGCUUCAAGAGAGCCGA | 1916 |
| CGGCUCUCUUGAAGCUGGC | 1917 | GCCAGCUUCAAGAGAGCCG | 1918 |
| GGCUCUCUUGAAGCUGGCC | 1919 | GGCCAGCUUCAAGAGAGCC | 1920 |
| GCUCUCUUGAAGCUGGCCU | 1921 | AGGCCAGCUUCAAGAGAGC | 1922 |

TABLE 4-continued

| Sense Sequence | SEQ ID NO: | Antisense Sequence | SEQ ID NO: |
|---|---|---|---|
| CUCUCUUGAAGCUGGCCUG | 1923 | CAGGCCAGCUUCAAGAGAG | 1924 |
| UCUCUUGAAGCUGGCCUGU | 1925 | ACAGGCCAGCUUCAAGAGA | 1926 |
| AGCUGGCCUGUGACCUGAA | 1927 | UUCAGGUCACAGGCCAGCU | 1928 |
| AGAUUGUGUAUUCUGUGGG | 1929 | CCCACAGAAUACACAAUCU | 1930 |
| CAGCAGGAUGGAAUUACCU | 1931 | AGGUAAUUCCAUCCUGCUG | 1932 |
| CAGGAUGGAAUUACCUUUU | 1933 | AAAAGGUAAUUCCAUCCUG | 1934 |
| AGGAUGGAAUUACCUUUUA | 1935 | UAAAAGGUAAUUCCAUCCU | 1936 |
| GGAUGGAAUUACCUUUUAG | 1937 | CUAAAAGGUAAUUCCAUCC | 1938 |
| GAUGGAAUUACCUUUUAGA | 1939 | UCUAAAAGGUAAUUCCAUC | 1940 |
| AUGGAAUUACCUUUUAGAG | 1941 | CUCUAAAAGGUAAUUCCAU | 1942 |
| GGAAUUACCUUUUAGAGCA | 1943 | UGCUCUAAAAGGUAAUUCC | 1944 |
| GAAUUACCUUUUAGAGCAA | 1945 | UUGCUCUAAAAGGUAAUUC | 1946 |
| ACCUUUUAGAGCAAUAUGA | 1947 | UCAUAUUGCUCUAAAAGGU | 1948 |
| CCUUUUAGAGCAAUAUGAA | 1949 | UUCAUAUUGCUCUAAAAGG | 1950 |
| AACUGUCAAUGUCAAGUGC | 1951 | GCACUUGACAUUGACAGUU | 1952 |
| ACUGUCAAUGUCAAGUGCU | 1953 | AGCACUUGACAUUGACAGU | 1954 |
| AAUUCUGUAUGCUUUGUCA | 1955 | UGACAAAGCAUACAGAAUU | 1956 |
| CUGUAUGCUUUGUCAACGA | 1957 | UCGUUGACAAAGCAUACAG | 1958 |
| UGUAUGCUUUGUCAACGAG | 1959 | CUCGUUGACAAAGCAUACA | 1960 |
| GUAUGCUUUGUCAACGAGC | 1961 | GCUCGUUGACAAAGCAUAC | 1962 |
| CUUUGUCAACGAGCAAGCA | 1963 | UGCUUGCUCGUUGACAAAG | 1964 |
| UUUGUCAACGAGCAAGCAU | 1965 | AUGCUUGCUCGUUGACAAA | 1966 |
| UUGUCAACGAGCAAGCAUC | 1967 | GAUGCUUGCUCGUUGACAA | 1968 |
| UGUCAACGAGCAAGCAUCA | 1969 | UGAUGCUUGCUCGUUGACA | 1970 |
| AACUUGGCAGCUCUCCUUC | 1971 | GAAGGAGAGCUGCCAAGUU | 1972 |
| CUUGGCAGCUCUCCUUCAU | 1973 | AUGAAGGAGAGCUGCCAAG | 1974 |
| UUGGCAGCUCUCCUUCAUG | 1975 | CAUGAAGGAGAGCUGCCAA | 1976 |
| UGGCAGCUCUCCUUCAUGC | 1977 | GCAUGAAGGAGAGCUGCCA | 1978 |
| GGCAGCUCUCCUUCAUGCG | 1979 | CGCAUGAAGGAGAGCUGCC | 1980 |
| GCAGCUCUCCUUCAUGCGA | 1981 | UCGCAUGAAGGAGAGCUGC | 1982 |
| CAGCUCUCCUUCAUGCGAU | 1983 | AUCGCAUGAAGGAGAGCUG | 1984 |
| AGCUCUCCUUCAUGCGAUU | 1985 | AAUCGCAUGAAGGAGAGCU | 1986 |
| GCUCUCCUUCAUGCGAUUG | 1987 | CAAUCGCAUGAAGGAGAGC | 1988 |
| CUCUCCUUCAUGCGAUUGC | 1989 | GCAAUCGCAUGAAGGAGAG | 1990 |
| UCUCCUUCAUGCGAUUGCC | 1991 | GGCAAUCGCAUGAAGGAGA | 1992 |
| CUCCUUCAUGCGAUUGCCA | 1993 | UGGCAAUCGCAUGAAGGAG | 1994 |
| UCCUUCAUGCGAUUGCCAG | 1995 | CUGGCAAUCGCAUGAAGGA | 1996 |
| CCUUCAUGCGAUUGCCAGA | 1997 | UCUGGCAAUCGCAUGAAGG | 1998 |
| CUUCAUGCGAUUGCCAGAC | 1999 | GUCUGGCAAUCGCAUGAAG | 2000 |

TABLE 4-continued

| Sense Sequence | SEQ ID NO: | Antisense Sequence | SEQ ID NO: |
|---|---|---|---|
| UUCAUGCGAUUGCCAGACG | 2001 | CGUCUGGCAAUCGCAUGAA | 2002 |
| UCAUGCGAUUGCCAGACGU | 2003 | ACGUCUGGCAAUCGCAUGA | 2004 |
| CAUGCGAUUGCCAGACGUC | 2005 | GACGUCUGGCAAUCGCAUG | 2006 |
| AUGCGAUUGCCAGACGUCC | 2007 | GGACGUCUGGCAAUCGCAU | 2008 |
| UGCGAUUGCCAGACGUCCA | 2009 | UGGACGUCUGGCAAUCGCA | 2010 |
| GCGAUUGCCAGACGUCCAA | 2011 | UUGGACGUCUGGCAAUCGC | 2012 |
| CGAUUGCCAGACGUCCAAA | 2013 | UUUGGACGUCUGGCAAUCG | 2014 |
| UAGCAUGGGAUUUUGUAAG | 2015 | CUUACAAAAUCCCAUGCUA | 2016 |
| GCAUGGGAUUUUGUAAGAG | 2017 | CUCUUACAAAAUCCCAUGC | 2018 |
| AAAAUUGGACCCAUCUUCU | 2019 | AGAAGAUGGGUCCAAUUUU | 2020 |
| AAAUUGGACCCAUCUUCUG | 2021 | CAGAAGAUGGGUCCAAUUU | 2022 |
| AAUUGGACCCAUCUUCUGA | 2023 | UCAGAAGAUGGGUCCAAUU | 2024 |
| AUUGGACCCAUCUUCUGAA | 2025 | UUCAGAAGAUGGGUCCAAU | 2026 |
| AAAAUUUGACUUGGGCUCA | 2027 | UGAGCCCAAGUCAAAUUUU | 2028 |
| AAAUUUGACUUGGGCUCAU | 2029 | AUGAGCCCAAGUCAAAUUU | 2030 |
| AAUUUGACUUGGGCUCAUA | 2031 | UAUGAGCCCAAGUCAAAUU | 2032 |
| AUUUGACUUGGGCUCAUAU | 2033 | AUAUGAGCCCAAGUCAAAU | 2034 |
| UUUGACUUGGGCUCAUAUG | 2035 | CAUAUGAGCCCAAGUCAAA | 2036 |
| UUGACUUGGGCUCAUAUGA | 2037 | UCAUAUGAGCCCAAGUCAA | 2038 |
| UGACUUGGGCUCAUAUGAC | 2039 | GUCAUAUGAGCCCAAGUCA | 2040 |
| GACUUGGGCUCAUAUGACA | 2041 | UGUCAUAUGAGCCCAAGUC | 2042 |
| ACUUGGGCUCAUAUGACAU | 2043 | AUGUCAUAUGAGCCCAAGU | 2044 |
| UUGGGCUCAUAUGACAUAA | 2045 | UUAUGUCAUAUGAGCCCAA | 2046 |
| UGGGCUCAUAUGACAUAAG | 2047 | CUUAUGUCAUAUGAGCCCA | 2048 |
| GGGCUCAUAUGACAUAAGG | 2049 | CCUUAUGUCAUAUGAGCCC | 2050 |
| GGCUCAUAUGACAUAAGGA | 2051 | UCCUUAUGUCAUAUGAGCC | 2052 |
| CAUAUGACAUAAGGAUGAU | 2053 | AUCAUCCUUAUGUCAUAUG | 2054 |
| AUAUGACAUAAGGAUGAUC | 2055 | GAUCAUCCUUAUGUCAUAU | 2056 |
| UAUGACAUAAGGAUGAUCA | 2057 | UGAUCAUCCUUAUGUCAUA | 2058 |
| AGCUCACUUUUCUUCCAAG | 2059 | CUUGGAAGAAAAGUGAGCU | 2060 |
| CUUUUCUUCCAAGGAUAAG | 2061 | CUUAUCCUUGGAAGAAAAG | 2062 |
| UUUCUUCCAAGGAUAAGUU | 2063 | AACUUAUCCUUGGAAGAAA | 2064 |
| UUCUUCCAAGGAUAAGUUG | 2065 | CAACUUAUCCUUGGAAGAA | 2066 |
| UCUUCCAAGGAUAAGUUGC | 2067 | GCAACUUAUCCUUGGAAGA | 2068 |
| CUUCCAAGGAUAAGUUGCA | 2069 | UGCAACUUAUCCUUGGAAG | 2070 |
| UUCCAAGGAUAAGUUGCAA | 2071 | UUGCAACUUAUCCUUGGAA | 2072 |
| UCCAAGGAUAAGUUGCAAG | 2073 | CUUGCAACUUAUCCUUGGA | 2074 |
| CCAAGGAUAAGUUGCAAGA | 2075 | UCUUGCAACUUAUCCUUGG | 2076 |
| CAAGGAUAAGUUGCAAGAG | 2077 | CUCUUGCAACUUAUCCUUG | 2078 |

TABLE 4-continued

| Sense Sequence | SEQ ID NO: | Antisense Sequence | SEQ ID NO: |
|---|---|---|---|
| AAGGAUAAGUUGCAAGAGG | 2079 | CCUCUUGCAACUUAUCCUU | 2080 |
| AGGAUAAGUUGCAAGAGGU | 2081 | ACCUCUUGCAACUUAUCCU | 2082 |
| GGAUAAGUUGCAAGAGGUG | 2083 | CACCUCUUGCAACUUAUCC | 2084 |
| GAUAAGUUGCAAGAGGUGA | 2085 | UCACCUCUUGCAACUUAUC | 2086 |
| AUAAGUUGCAAGAGGUGAA | 2087 | UUCACCUCUUGCAACUUAU | 2088 |
| UUUUGAAUCUCUUGAGGCU | 2089 | AGCCUCAAGAGAUUCAAAA | 2090 |
| UUUGAAUCUCUUGAGGCUC | 2091 | GAGCCUCAAGAGAUUCAAA | 2092 |
| UUGAAUCUCUUGAGGCUCA | 2093 | UGAGCCUCAAGAGAUUCAA | 2094 |
| GAGGCUCAAGGAUCACAUC | 2095 | GAUGUGAUCCUUGAGCCUC | 2096 |
| AGGCUCAAGGAUCACAUCU | 2097 | AGAUGUGAUCCUUGAGCCU | 2098 |
| GGCUCAAGGAUCACAUCUG | 2099 | CAGAUGUGAUCCUUGAGCC | 2100 |
| AGGAUCACAUCUGGAUAUU | 2101 | AAUAUCCAGAUGUGAUCCU | 2102 |
| GAUCACAUCUGGAUAUUUU | 2103 | AAAAUAUCCAGAUGUGAUC | 2104 |
| AAAUAUAAAAUGGCUGGAG | 2105 | CUCCAGCCAUUUUAUAUUU | 2106 |
| GAGGACUUGGCUAAUGGUU | 2107 | AACCAUUAGCCAAGUCCUC | 2108 |
| AGGACUUGGCUAAUGGUUA | 2109 | UAACCAUUAGCCAAGUCCU | 2110 |
| GGACUUGGCUAAUGGUUAA | 2111 | UUAACCAUUAGCCAAGUCC | 2112 |
| GACUUGGCUAAUGGUUAAU | 2113 | AUUAACCAUUAGCCAAGUC | 2114 |
| ACUUGGCUAAUGGUUAAUA | 2115 | UAUUAACCAUUAGCCAAGU | 2116 |
| CUUGGCUAAUGGUUAAUAC | 2117 | GUAUUAACCAUUAGCCAAG | 2118 |
| UUGGCUAAUGGUUAAUACU | 2119 | AGUAUUAACCAUUAGCCAA | 2120 |
| UGGCUAAUGGUUAAUACUU | 2121 | AAGUAUUAACCAUUAGCCA | 2122 |
| CGGUGGCUCACGCCUGUAA | 2123 | UUACAGGCGUGAGCCACCG | 2124 |
| GGUGGCUCACGCCUGUAAU | 2125 | AUUACAGGCGUGAGCCACC | 2126 |
| GUGGCUCACGCCUGUAAUC | 2127 | GAUUACAGGCGUGAGCCAC | 2128 |
| UGGCUCACGCCUGUAAUCC | 2129 | GGAUUACAGGCGUGAGCCA | 2130 |
| GGCUCACGCCUGUAAUCCC | 2131 | GGGAUUACAGGCGUGAGCC | 2132 |
| ACGCCUGUAAUCCCAGCAC | 2133 | GUGCUGGGAUUACAGGCGU | 2134 |
| AGCACUUUGGGAGGCUGAG | 2135 | CUCAGCCUCCCAAAGUGCU | 2136 |
| CAUGGUGGCAGGUGCCUGU | 2137 | ACAGGCACCUGCCACCAUG | 2138 |
| AUGGUGGCAGGUGCCUGUA | 2139 | UACAGGCACCUGCCACCAU | 2140 |
| UGGCAGGUGCCUGUAGUCC | 2141 | GGACUACAGGCACCUGCCA | 2142 |
| GCAGGUGCCUGUAGUCCCA | 2143 | UGGGACUACAGGCACCUGC | 2144 |
| GUGCCUGUAGUCCCAGCUA | 2145 | UAGCUGGGACUACAGGCAC | 2146 |
| UAGUCCCAGCUACUCGGCA | 2147 | UGCCGAGUAGCUGGGACUA | 2148 |
| AGUCCCAGCUACUCGGCAG | 2149 | CUGCCGAGUAGCUGGGACU | 2150 |
| GAGCUUGCAGUGAGCCGAG | 2151 | CUCGGCUCACUGCAAGCUC | 2152 |
| ACUGCAUUCCAGCCUGGGU | 2153 | ACCCAGGCUGGAAUGCAGU | 2154 |
| CUGCAUUCCAGCCUGGGUG | 2155 | CACCCAGGCUGGAAUGCAG | 2156 |

TABLE 4-continued

| Sense Sequence | SEQ ID NO: | Antisense Sequence | SEQ ID NO: |
|---|---|---|---|
| UGCAUUCCAGCCUGGGUGA | 2157 | UCACCCAGGCUGGAAUGCA | 2158 |
| GCAUUCCAGCCUGGGUGAC | 2159 | GUCACCCAGGCUGGAAUGC | 2160 |
| CAUUCCAGCCUGGGUGACU | 2161 | AGUCACCCAGGCUGGAAUG | 2162 |
| AUUCCAGCCUGGGUGACUG | 2163 | CAGUCACCCAGGCUGGAAU | 2164 |
| UUCCAGCCUGGGUGACUGA | 2165 | UCAGUCACCCAGGCUGGAA | 2166 |
| UCCAGCCUGGGUGACUGAG | 2167 | CUCAGUCACCCAGGCUGGA | 2168 |
| AAGGUACAUCAGACAUGAC | 2169 | GUCAUGUCUGAUGUACCUU | 2170 |
| AGGUACAUCAGACAUGACU | 2171 | AGUCAUGUCUGAUGUACCU | 2172 |
| GGUACAUCAGACAUGACUG | 2173 | CAGUCAUGUCUGAUGUACC | 2174 |
| GUACAUCAGACAUGACUGC | 2175 | GCAGUCAUGUCUGAUGUAC | 2176 |
| AUCAGACAUGACUGCCUGC | 2177 | GCAGGCAGUCAUGUCUGAU | 2178 |
| UCAGACAUGACUGCCUGCA | 2179 | UGCAGGCAGUCAUGUCUGA | 2180 |
| CAGACAUGACUGCCUGCAU | 2181 | AUGCAGGCAGUCAUGUCUG | 2182 |
| AUGACUGCCUGCAUGAAGU | 2183 | ACUUCAUGCAGGCAGUCAU | 2184 |
| ACUGCCUGCAUGAAGUCAA | 2185 | UUGACUUCAUGCAGGCAGU | 2186 |
| CUGCCUGCAUGAAGUCAAA | 2187 | UUUGACUUCAUGCAGGCAG | 2188 |
| ACACCAGUGAAGCUCAAGU | 2189 | ACUUGAGCUUCACUGGUGU | 2190 |
| CACCAGUGAAGCUCAAGUC | 2191 | GACUUGAGCUUCACUGGUG | 2192 |
| ACCAGUGAAGCUCAAGUCA | 2193 | UGACUUGAGCUUCACUGGU | 2194 |
| GUGAAGCUCAAGUCAAGAG | 2195 | CUCUUGACUUGAGCUUCAC | 2196 |
| CUCAAGUCAAGAGCUGUGG | 2197 | CCACAGCUCUUGACUUGAG | 2198 |
| UCAAGUCAAGAGCUGUGGA | 2199 | UCCACAGCUCUUGACUUGA | 2200 |
| CAAGUCAAGAGCUGUGGAU | 2201 | AUCCACAGCUCUUGACUUG | 2202 |
| AAGUCAAGAGCUGUGGAUA | 2203 | UAUCCACAGCUCUUGACUU | 2204 |
| AGUCAAGAGCUGUGGAUAU | 2205 | AUAUCCACAGCUCUUGACU | 2206 |
| GUCAAGAGCUGUGGAUAUU | 2207 | AAUAUCCACAGCUCUUGAC | 2208 |
| CAAGAGCUGUGGAUAUUUU | 2209 | AAAAUAUCCACAGCUCUUG | 2210 |
| AAGAGCUGUGGAUAUUUUG | 2211 | CAAAAUAUCCACAGCUCUU | 2212 |
| AGAGCUGUGGAUAUUUUGU | 2213 | ACAAAAUAUCCACAGCUCU | 2214 |
| GAGCUGUGGAUAUUUUGUC | 2215 | GACAAAAUAUCCACAGCUC | 2216 |
| AGCUGUGGAUAUUUUGUCU | 2217 | AGACAAAAUAUCCACAGCU | 2218 |
| GCUGUGGAUAUUUUGUCUA | 2219 | UAGACAAAAUAUCCACAGC | 2220 |
| CUGUGGAUAUUUUGUCUAA | 2221 | UUAGACAAAAUAUCCACAG | 2222 |
| UGUGGAUAUUUUGUCUAAC | 2223 | GUUAGACAAAAUAUCCACA | 2224 |
| GUGGAUAUUUUGUCUAACC | 2225 | GGUUAGACAAAAUAUCCAC | 2226 |
| UGGAUAUUUUGUCUAACCA | 2227 | UGGUUAGACAAAAUAUCCA | 2228 |
| GGAUAUUUUGUCUAACCAA | 2229 | UUGGUUAGACAAAAUAUCC | 2230 |
| UCGUAUCCAGCCAAAAGAU | 2231 | AUCUUUUGGCUGGAUACGA | 2232 |
| CGUAUCCAGCCAAAAGAUG | 2233 | CAUCUUUUGGCUGGAUACG | 2234 |

TABLE 4-continued

| Sense Sequence | SEQ ID NO: | Antisense Sequence | SEQ ID NO: |
|---|---|---|---|
| GUAUCCAGCCAAAAGAUGC | 2235 | GCAUCUUUUGGCUGGAUAC | 2236 |
| UAUCCAGCCAAAAGAUGCA | 2237 | UGCAUCUUUUGGCUGGAUA | 2238 |
| AUCCAGCCAAAAGAUGCAU | 2239 | AUGCAUCUUUUGGCUGGAU | 2240 |
| AGCCAAAAGAUGCAUGAUG | 2241 | CAUCAUGCAUCUUUUGGCU | 2242 |
| GCCAAAAGAUGCAUGAUGA | 2243 | UCAUCAUGCAUCUUUUGGC | 2244 |
| CCAAAAGAUGCAUGAUGAU | 2245 | AUCAUCAUGCAUCUUUUGG | 2246 |
| CAAAAGAUGCAUGAUGAUG | 2247 | CAUCAUCAUGCAUCUUUUG | 2248 |
| AAAAGAUGCAUGAUGAUGG | 2249 | CCAUCAUCAUGCAUCUUUU | 2250 |
| AAAGAUGCAUGAUGAUGGA | 2251 | UCCAUCAUCAUGCAUCUUU | 2252 |
| GCAUGAUGAUGGAGUGGUG | 2253 | CACCACUCCAUCAUCAUGC | 2254 |
| CAUGAUGAUGGAGUGGUGG | 2255 | CCACCACUCCAUCAUCAUG | 2256 |
| AUGAUGAUGGAGUGGUGGG | 2257 | CCCACCACUCCAUCAUCAU | 2258 |
| GGGAAGGCCAGUUCAGUAU | 2259 | AUACUGAACUGGCCUUCCC | 2260 |
| GGAAGGCCAGUUCAGUAUC | 2261 | GAUACUGAACUGGCCUUCC | 2262 |
| GAAGGCCAGUUCAGUAUCC | 2263 | GGAUACUGAACUGGCCUUC | 2264 |
| AGGCCAGUUCAGUAUCCUA | 2265 | UAGGAUACUGAACUGGCCU | 2266 |
| GGCCAGUUCAGUAUCCUAU | 2267 | AUAGGAUACUGAACUGGCC | 2268 |
| GCCAGUUCAGUAUCCUAUU | 2269 | AAUAGGAUACUGAACUGGC | 2270 |
| CCAGUUCAGUAUCCUAUUU | 2271 | AAAUAGGAUACUGAACUGG | 2272 |
| CAGUUCAGUAUCCUAUUUA | 2273 | UAAAUAGGAUACUGAACUG | 2274 |
| AACUUCCUGAAUAAUGGAU | 2275 | AUCCAUUAUUCAGGAAGUU | 2276 |
| ACUUCCUGAAUAAUGGAUA | 2277 | UAUCCAUUAUUCAGGAAGU | 2278 |
| CUUCCUGAAUAAUGGAUAU | 2279 | AUAUCCAUUAUUCAGGAAG | 2280 |
| GAAUAAUGGAUAUAUGUGG | 2281 | CCACAUAUAUCCAUUAUUC | 2282 |
| AUAAUGGAUAUAUGUGGAG | 2283 | CUCCACAUAUAUCCAUUAU | 2284 |
| AGAUAUAUAGAUACAGCUG | 2285 | CAGCUGUAUCUAUAUAUCU | 2286 |
| GAUAUAUAGAUACAGCUGU | 2287 | ACAGCUGUAUCUAUAUAUC | 2288 |
| ACAGCUGUAAUUAUUUAGC | 2289 | GCUAAAUAAUUACAGCUGU | 2290 |
| CAGCUGUAAUUAUUUAGCC | 2291 | GGCUAAAUAAUUACAGCUG | 2292 |
| AGCUGUAAUUAUUUAGCCU | 2293 | AGGCUAAAUAAUUACAGCU | 2294 |
| GUAAUUAUUUAGCCUCAAG | 2295 | CUUGAGGCUAAAUAAUUAC | 2296 |
| AAUUAUUUAGCCUCAAGUG | 2297 | CACUUGAGGCUAAAUAAUU | 2298 |
| AUUAUUUAGCCUCAAGUGA | 2299 | UCACUUGAGGCUAAAUAAU | 2300 |
| UUUAGCCUCAAGUGACUUU | 2301 | AAAGUCACUUGAGGCUAAA | 2302 |
| AAGUGACUUUCUCCAUUGC | 2303 | GCAAUGGAGAAAGUCACUU | 2304 |
| AGUGACUUUCUCCAUUGCU | 2305 | AGCAAUGGAGAAAGUCACU | 2306 |
| GUGACUUUCUCCAUUGCUU | 2307 | AAGCAAUGGAGAAAGUCAC | 2308 |
| UUUCUCCAUUGCUUCACGC | 2309 | GCGUGAAGCAAUGGAGAAA | 2310 |
| UUCUCCAUUGCUUCACGCU | 2311 | AGCGUGAAGCAAUGGAGAA | 2312 |

TABLE 4-continued

| Sense Sequence | SEQ ID NO: | Antisense Sequence | SEQ ID NO: |
|---|---|---|---|
| UCUCCAUUGCUUCACGCUA | 2313 | UAGCGUGAAGCAAUGGAGA | 2314 |
| CUCCAUUGCUUCACGCUAU | 2315 | AUAGCGUGAAGCAAUGGAG | 2316 |
| UCCAUUGCUUCACGCUAUG | 2317 | CAUAGCGUGAAGCAAUGGA | 2318 |
| CCAUUGCUUCACGCUAUGC | 2319 | GCAUAGCGUGAAGCAAUGG | 2320 |
| CAUUGCUUCACGCUAUGCC | 2321 | GGCAUAGCGUGAAGCAAUG | 2322 |
| AUUGCUUCACGCUAUGCCA | 2323 | UGGCAUAGCGUGAAGCAAU | 2324 |
| UUGCUUCACGCUAUGCCAC | 2325 | GUGGCAUAGCGUGAAGCAA | 2326 |
| UGCUUCACGCUAUGCCACU | 2327 | AGUGGCAUAGCGUGAAGCA | 2328 |
| GCUUCACGCUAUGCCACUA | 2329 | UAGUGGCAUAGCGUGAAGC | 2330 |
| CUUCACGCUAUGCCACUAU | 2331 | AUAGUGGCAUAGCGUGAAG | 2332 |
| UUCACGCUAUGCCACUAUU | 2333 | AAUAGUGGCAUAGCGUGAA | 2334 |
| UCACGCUAUGCCACUAUUU | 2335 | AAAUAGUGGCAUAGCGUGA | 2336 |
| CACGCUAUGCCACUAUUUU | 2337 | AAAAUAGUGGCAUAGCGUG | 2338 |
| CGCUAUGCCACUAUUUUGC | 2339 | GCAAAAUAGUGGCAUAGCG | 2340 |
| GCUAUGCCACUAUUUUGCU | 2341 | AGCAAAAUAGUGGCAUAGC | 2342 |
| CUAUGCCACUAUUUUGCUU | 2343 | AAGCAAAAUAGUGGCAUAG | 2344 |
| UAUGCCACUAUUUUGCUUC | 2345 | GAAGCAAAAUAGUGGCAUA | 2346 |
| AUGCCACUAUUUUGCUUCU | 2347 | AGAAGCAAAAUAGUGGCAU | 2348 |
| UGCCACUAUUUUGCUUCUU | 2349 | AAGAAGCAAAAUAGUGGCA | 2350 |
| AACCUUGCUUAGUAUUCUA | 2351 | UAGAAUACUAAGCAAGGUU | 2352 |
| CCUUGCUUAGUAUUCUAUA | 2353 | UAUAGAAUACUAAGCAAGG | 2354 |
| AGUAUUCUAUAGUUUGCCC | 2355 | GGGCAAACUAUAGAAUACU | 2356 |
| GUAUUCUAUAGUUUGCCCA | 2357 | UGGGCAAACUAUAGAAUAC | 2358 |
| UAUUCUAUAGUUUGCCCAA | 2359 | UUGGGCAAACUAUAGAAUA | 2360 |
| AUUCUAUAGUUUGCCCAAC | 2361 | GUUGGGCAAACUAUAGAAU | 2362 |
| UAUAGUUUGCCCAACCAGU | 2363 | ACUGGUUGGGCAAACUAUA | 2364 |
| AUAGUUUGCCCAACCAGUU | 2365 | AACUGGUUGGGCAAACUAU | 2366 |
| UAGUUUGCCCAACCAGUUU | 2367 | AAACUGGUUGGGCAAACUA | 2368 |
| AGUUUGCCCAACCAGUUUU | 2369 | AAAACUGGUUGGGCAAACU | 2370 |
| GUUUGCCCAACCAGUUUUA | 2371 | UAAAACUGGUUGGGCAAAC | 2372 |
| UUUGCCCAACCAGUUUUAC | 2373 | GUAAAACUGGUUGGGCAAA | 2374 |
| UUGCCCAACCAGUUUUACG | 2375 | CGUAAAACUGGUUGGGCAA | 2376 |
| UGCCCAACCAGUUUUACGU | 2377 | ACGUAAAACUGGUUGGGCA | 2378 |
| GCCCAACCAGUUUUACGUC | 2379 | GACGUAAAACUGGUUGGGC | 2380 |
| CCCAACCAGUUUUACGUCC | 2381 | GGACGUAAAACUGGUUGGG | 2382 |
| CCAACCAGUUUUACGUCCA | 2383 | UGGACGUAAAACUGGUUGG | 2384 |
| CAACCAGUUUUACGUCCAA | 2385 | UUGGACGUAAAACUGGUUG | 2386 |
| AACCAGUUUUACGUCCAAG | 2387 | CUUGGACGUAAAACUGGUU | 2388 |
| GCCAAUGCAUAAAAUAUAC | 2389 | GUAUAUUUUAUGCAUUGGC | 2390 |

TABLE 4-continued

| Sense Sequence | SEQ ID NO: | Antisense Sequence | SEQ ID NO: |
|---|---|---|---|
| AACUAGGUGUCAGGGUUUA | 2391 | UAAACCCUGACACCUAGUU | 2392 |
| ACUAGGUGUCAGGGUUUAU | 2393 | AUAAACCCUGACACCUAGU | 2394 |
| CUAGGUGUCAGGGUUUAUC | 2395 | GAUAAACCCUGACACCUAG | 2396 |
| UAGGUGUCAGGGUUUAUCA | 2397 | UGAUAAACCCUGACACCUA | 2398 |
| AGGUGUCAGGGUUUAUCAA | 2399 | UUGAUAAACCCUGACACCU | 2400 |
| GGUGUCAGGGUUUAUCAAG | 2401 | CUUGAUAAACCCUGACACC | 2402 |
| GUGUCAGGGUUUAUCAAGA | 2403 | UCUUGAUAAACCCUGACAC | 2404 |
| UGUCAGGGUUUAUCAAGAA | 2405 | UUCUUGAUAAACCCUGACA | 2406 |
| GUCAGGGUUUAUCAAGAAG | 2407 | CUUCUUGAUAAACCCUGAC | 2408 |
| GGUUUAUCAAGAAGGCCAG | 2409 | CUGGCCUUCUUGAUAAACC | 2410 |
| UAUCAAGAAGGCCAGGAAG | 2411 | CUUCCUGGCCUUCUUGAUA | 2412 |
| UCAAGAAGGCCAGGAAGGC | 2413 | GCCUUCCUGGCCUUCUUGA | 2414 |
| GCCAGGAAGGCCUUUUGGG | 2415 | CCCAAAAGGCCUUCCUGGC | 2416 |
| CCAGGAAGGCCUUUUGGGU | 2417 | ACCCAAAAGGCCUUCCUGG | 2418 |
| CAGGAAGGCCUUUUGGGUU | 2419 | AACCCAAAAGGCCUUCCUG | 2420 |
| AGGAAGGCCUUUUGGGUUA | 2421 | UAACCCAAAAGGCCUUCCU | 2422 |
| GGAAGGCCUUUUGGGUUAA | 2423 | UUAACCCAAAAGGCCUUCC | 2424 |
| GAAGGCCUUUUGGGUUAAG | 2425 | CUUAACCCAAAAGGCCUUC | 2426 |
| AAGGCCUUUUGGGUUAAGC | 2427 | GCUUAACCCAAAAGGCCUU | 2428 |
| AGGCCUUUUGGGUUAAGCC | 2429 | GGCUUAACCCAAAAGGCCU | 2430 |
| GGCCUUUUGGGUUAAGCCU | 2431 | AGGCUUAACCCAAAAGGCC | 2432 |
| UUCCAAAUGAAUGGUCUCU | 2433 | AGAGACCAUUCAUUUGGAA | 2434 |
| UCCAAAUGAAUGGUCUCUG | 2435 | CAGAGACCAUUCAUUUGGA | 2436 |
| CCAAAUGAAUGGUCUCUGG | 2437 | CCAGAGACCAUUCAUUUGG | 2438 |
| CAAAUGAAUGGUCUCUGGU | 2439 | ACCAGAGACCAUUCAUUUG | 2440 |
| AAAUGAAUGGUCUCUGGUC | 2441 | GACCAGAGACCAUUCAUUU | 2442 |
| AAUGAAUGGUCUCUGGUCA | 2443 | UGACCAGAGACCAUUCAUU | 2444 |
| AUGAAUGGUCUCUGGUCAA | 2445 | UUGACCAGAGACCAUUCAU | 2446 |
| UGAAUGGUCUCUGGUCAAA | 2447 | UUUGACCAGAGACCAUUCA | 2448 |
| GAAUGGUCUCUGGUCAAAU | 2449 | AUUUGACCAGAGACCAUUC | 2450 |
| AAUGGUCUCUGGUCAAAUG | 2451 | CAUUUGACCAGAGACCAUU | 2452 |
| GUCAAAUGAAUGAAUGGUC | 2453 | GACCAUUCAUUCAUUUGAC | 2454 |
| UCAAAUGAAUGAAUGGUCA | 2455 | UGACCAUUCAUUCAUUUGA | 2456 |
| CAAAUGAAUGAAUGGUCAA | 2457 | UUGACCAUUCAUUCAUUUG | 2458 |
| AUGAAUGAAUGGUCAAAUG | 2459 | CAUUUGACCAUUCAUUCAU | 2460 |
| GGUCAAAUGAAUAAAUCUG | 2461 | CAGAUUUAUUCAUUUGACC | 2462 |
| GUCAAAUGAAUAAAUCUGC | 2463 | GCAGAUUUAUUCAUUUGAC | 2464 |
| UCAAAUGAAUAAAUCUGCC | 2465 | GGCAGAUUUAUUCAUUUGA | 2466 |
| CAAAUGAAUAAAUCUGCCC | 2467 | GGGCAGAUUUAUUCAUUUG | 2468 |

TABLE 4-continued

| Sense Sequence | SEQ ID NO: | Antisense Sequence | SEQ ID NO: |
| --- | --- | --- | --- |
| AAAUGAAUAAAUCUGCCCU | 2469 | AGGGCAGAUUUAUUCAUUU | 2470 |
| AAUGAAUAAAUCUGCCCUC | 2471 | GAGGGCAGAUUUAUUCAUU | 2472 |
| AUGAAUAAAUCUGCCCUCA | 2473 | UGAGGGCAGAUUUAUUCAU | 2474 |
| GAAUAAAUCUGCCCUCACA | 2475 | UGUGAGGGCAGAUUUAUUC | 2476 |
| AAUAAAUCUGCCCUCACAG | 2477 | CUGUGAGGGCAGAUUUAUU | 2478 |
| UCAUACCAUUUGGUUUAAG | 2479 | CUUAAACCAAAUGGUAUGA | 2480 |
| AUACCAUUUGGUUUAAGCC | 2481 | GGCUUAAACCAAAUGGUAU | 2482 |
| UACCAUUUGGUUUAAGCCU | 2483 | AGGCUUAAACCAAAUGGUA | 2484 |
| ACCAUUUGGUUUAAGCCUU | 2485 | AAGGCUUAAACCAAAUGGU | 2486 |
| CCAUUUGGUUUAAGCCUUA | 2487 | UAAGGCUUAAACCAAAUGG | 2488 |
| CAUUUGGUUUAAGCCUUAC | 2489 | GUAAGGCUUAAACCAAAUG | 2490 |
| AUUUGGUUUAAGCCUUACA | 2491 | UGUAAGGCUUAAACCAAAU | 2492 |
| GUUUAAGCCUUACAUUCAU | 2493 | AUGAAUGUAAGGCUUAAAC | 2494 |
| UUUAAGCCUUACAUUCAUG | 2495 | CAUGAAUGUAAGGCUUAAA | 2496 |
| UUCCAAAUGAAGUCGAAUC | 2497 | GAUUCGACUUCAUUUGGAA | 2498 |
| UCCAAAUGAAGUCGAAUCU | 2499 | AGAUUCGACUUCAUUUGGA | 2500 |
| CCAAAUGAAGUCGAAUCUG | 2501 | CAGAUUCGACUUCAUUUGG | 2502 |
| AAAUGAAGUCGAAUCUGCC | 2503 | GGCAGAUUCGACUUCAUUU | 2504 |
| AAUGAAGUCGAAUCUGCCC | 2505 | GGGCAGAUUCGACUUCAUU | 2506 |
| AUGAAGUCGAAUCUGCCCU | 2507 | AGGGCAGAUUCGACUUCAU | 2508 |
| UGAAGUCGAAUCUGCCCUC | 2509 | GAGGGCAGAUUCGACUUCA | 2510 |
| GAAGUCGAAUCUGCCCUCA | 2511 | UGAGGGCAGAUUCGACUUC | 2512 |
| AAGUCGAAUCUGCCCUCAC | 2513 | GUGAGGGCAGAUUCGACUU | 2514 |
| AGUCGAAUCUGCCCUCACA | 2515 | UGUGAGGGCAGAUUCGACU | 2516 |
| GUCGAAUCUGCCCUCACAG | 2517 | CUGUGAGGGCAGAUUCGAC | 2518 |
| UUGUAUUGUGUAUUUUCGG | 2519 | CCGAAAAUACACAAUACAA | 2520 |
| UGUAUUGUGUAUUUUCGGU | 2521 | ACCGAAAAUACACAAUACA | 2522 |
| GUAUUGUGUAUUUUCGGUU | 2523 | AACCGAAAAUACACAAUAC | 2524 |
| AAAUAUUUAGAUGCAGCAC | 2525 | GUGCUGCAUCUAAAUAUUU | 2526 |
| AUUUAGAUGCAGCACCAUA | 2527 | UAUGGUGCUGCAUCUAAAU | 2528 |
| UUUAGAUGCAGCACCAUAU | 2529 | AUAUGGUGCUGCAUCUAAA | 2530 |
| UUAGAUGCAGCACCAUAUU | 2531 | AAUAUGGUGCUGCAUCUAA | 2532 |
| UAGAUGCAGCACCAUAUUU | 2533 | AAAUAUGGUGCUGCAUCUA | 2534 |
| AGAUGCAGCACCAUAUUUU | 2535 | AAAAUAUGGUGCUGCAUCU | 2536 |
| GAUGCAGCACCAUAUUUUA | 2537 | UAAAAUAUGGUGCUGCAUC | 2538 |
| AUGCAGCACCAUAUUUUAU | 2539 | AUAAAAUAUGGUGCUGCAU | 2540 |
| AGCACCAUAUUUUAUAACC | 2541 | GGUUAUAAAAUAUGGUGCU | 2542 |
| GCACCAUAUUUUAUAACCC | 2543 | GGGUUAUAAAAUAUGGUGC | 2544 |
| ACCAUAUUUUAUAACCCAG | 2545 | CUGGGUUAUAAAAUAUGGU | 2546 |

TABLE 4-continued

| Sense Sequence | SEQ ID NO: | Antisense Sequence | SEQ ID NO: |
|---|---|---|---|
| CCAUAUUUUAUAACCCAGC | 2547 | GCUGGGUUAUAAAAUAUGG | 2548 |
| CAUAUUUUAUAACCCAGCU | 2549 | AGCUGGGUUAUAAAAUAUG | 2550 |
| UUAUAACCCAGCUUUAGCA | 2551 | UGCUAAAGCUGGGUUAUAA | 2552 |
| ACCCAGCUUUAGCAUUUCU | 2553 | AGAAAUGCUAAAGCUGGGU | 2554 |
| CCAGCUUUAGCAUUUCUUC | 2555 | GAAGAAAUGCUAAAGCUGG | 2556 |
| GGCGCUUCUUGCUCUCUGA | 2557 | UCAGAGAGCAAGAAGCGCC | 2558 |
| GCGCUUCUUGCUCUCUGAA | 2559 | UUCAGAGAGCAAGAAGCGC | 2560 |
| AAAUGCCCUGCUAAAUGCU | 2561 | AGCAUUUAGCAGGGCAUUU | 2562 |
| AAUGCCCUGCUAAAUGCUU | 2563 | AAGCAUUUAGCAGGGCAUU | 2564 |
| AUGCCCUGCUAAAUGCUUC | 2565 | GAAGCAUUUAGCAGGGCAU | 2566 |
| UGCCCUGCUAAAUGCUUCU | 2567 | AGAAGCAUUUAGCAGGGCA | 2568 |
| UUUGAAUAAGGUAGUUUGG | 2569 | CCAAACUACCUUAUUCAAA | 2570 |
| UUGAAUAAGGUAGUUUGGA | 2571 | UCCAAACUACCUUAUUCAA | 2572 |
| UGAAUAAGGUAGUUUGGAA | 2573 | UUCCAAACUACCUUAUUCA | 2574 |
| GAAUAAGGUAGUUUGGAAU | 2575 | AUUCCAAACUACCUUAUUC | 2576 |
| AGGUAGUUUGGAAUAAAGA | 2577 | UCUUUAUUCCAAACUACCU | 2578 |
| GAUCACUCUACAUACAGAU | 2579 | AUCUGUAUGUAGAGUGAUC | 2580 |
| AUCACUCUACAUACAGAUA | 2581 | UAUCUGUAUGUAGAGUGAU | 2582 |
| UCACUCUACAUACAGAUAG | 2583 | CUAUCUGUAUGUAGAGUGA | 2584 |
| CACUCUACAUACAGAUAGU | 2585 | ACUAUCUGUAUGUAGAGUG | 2586 |
| ACUCUACAUACAGAUAGUA | 2587 | UACUAUCUGUAUGUAGAGU | 2588 |
| CUCUACAUACAGAUAGUAA | 2589 | UUACUAUCUGUAUGUAGAG | 2590 |
| UGUAAAUGACUGAUGUUUG | 2591 | CAAACAUCAGUCAUUUACA | 2592 |
| GUAAAUGACUGAUGUUUGC | 2593 | GCAAACAUCAGUCAUUUAC | 2594 |
| UAAAUGACUGAUGUUUGCA | 2595 | UGCAAACAUCAGUCAUUUA | 2596 |
| AAAUGACUGAUGUUUGCAU | 2597 | AUGCAAACAUCAGUCAUUU | 2598 |
| GAUGUUUGCAUUAUUAAGG | 2599 | CCUUAAUAAUGCAAACAUC | 2600 |
| ACUUGGGAUGUUGGGUCAA | 2601 | UUGACCCAACAUCCCAAGU | 2602 |
| UUGGGAUGUUGGGUCAAGA | 2603 | UCUUGACCCAACAUCCCAA | 2604 |
| UGGGAUGUUGGGUCAAGAG | 2605 | CUCUUGACCCAACAUCCCA | 2606 |
| GGGAUGUUGGGUCAAGAGG | 2607 | CCUCUUGACCCAACAUCCC | 2608 |
| AAAGUGUUAGUCAAUCCAC | 2609 | GUGGAUUGACUAACACUUU | 2610 |
| GAAGGUCAAUUAUAAUUCC | 2611 | GGAAUUAUAAUUGACCUUC | 2612 |
| CCAUAUACCUUUCUUUGAU | 2613 | AUCAAAGAAAGGUAUAUGG | 2614 |
| CAUAUACCUUUCUUUGAUG | 2615 | CAUCAAAGAAAGGUAUAUG | 2616 |
| AUAUACCUUUCUUUGAUGC | 2617 | GCAUCAAAGAAAGGUAUAU | 2618 |
| UAUACCUUUCUUUGAUGCC | 2619 | GGCAUCAAAGAAAGGUAUA | 2620 |
| ACCUUUCUUUGAUGCCACA | 2621 | UGUGGCAUCAAAGAAAGGU | 2622 |
| AGAAUACAGUUUGGGUGGC | 2623 | GCCACCCAAACUGUAUUCU | 2624 |

TABLE 4-continued

| Sense Sequence | SEQ ID NO: | Antisense Sequence | SEQ ID NO: |
|---|---|---|---|
| GAAUACAGUUUGGGUGGCC | 2625 | GGCCACCCAAACUGUAUUC | 2626 |
| AAUACAGUUUGGGUGGCCA | 2627 | UGGCCACCCAAACUGUAUU | 2628 |
| AUACAGUUUGGGUGGCCAU | 2629 | AUGGCCACCCAAACUGUAU | 2630 |
| UACAGUUUGGGUGGCCAUG | 2631 | CAUGGCCACCCAAACUGUA | 2632 |
| ACAGUUUGGGUGGCCAUGG | 2633 | CCAUGGCCACCCAAACUGU | 2634 |
| CAGUUUGGGUGGCCAUGGA | 2635 | UCCAUGGCCACCCAAACUG | 2636 |
| AGUUUGGGUGGCCAUGGAU | 2637 | AUCCAUGGCCACCCAAACU | 2638 |
| GUUUGGGUGGCCAUGGAUG | 2639 | CAUCCAUGGCCACCCAAAC | 2640 |
| UUUGGGUGGCCAUGGAUGU | 2641 | ACAUCCAUGGCCACCCAAA | 2642 |
| UCAGAUCAUUUCAUGGAAU | 2643 | AUUCCAUGAAAUGAUCUGA | 2644 |
| CAGAUCAUUUCAUGGAAUC | 2645 | GAUUCCAUGAAAUGAUCUG | 2646 |
| GAUCAUUUCAUGGAAUCUU | 2647 | AAGAUUCCAUGAAAUGAUC | 2648 |
| AAGUAUCUUUGACUCUAAC | 2649 | GUUAGAGUCAAAGAUACUU | 2650 |
| AGUAUCUUUGACUCUAACU | 2651 | AGUUAGAGUCAAAGAUACU | 2652 |
| GUAUCUUUGACUCUAACUU | 2653 | AAGUUAGAGUCAAAGAUAC | 2654 |
| AUCUUUGACUCUAACUUUG | 2655 | CAAAGUUAGAGUCAAAGAU | 2656 |
| UCUUUGACUCUAACUUUGA | 2657 | UCAAAGUUAGAGUCAAAGA | 2658 |
| CUUUGACUCUAACUUUGAC | 2659 | GUCAAAGUUAGAGUCAAAG | 2660 |
| UUUGACUCUAACUUUGACU | 2661 | AGUCAAAGUUAGAGUCAAA | 2662 |
| UUGACUCUAACUUUGACUU | 2663 | AAGUCAAAGUUAGAGUCAA | 2664 |
| CUCUAACUUUGACUUGGUG | 2665 | CACCAAGUCAAAGUUAGAG | 2666 |
| UCUAACUUUGACUUGGUGG | 2667 | CCACCAAGUCAAAGUUAGA | 2668 |
| CUAACUUUGACUUGGUGGU | 2669 | ACCACCAAGUCAAAGUUAG | 2670 |
| UAACUUUGACUUGGUGGUG | 2671 | CACCACCAAGUCAAAGUUA | 2672 |
| ACUUUGACUUGGUGGUGGA | 2673 | UCCACCACCAAGUCAAAGU | 2674 |
| CUUUGACUUGGUGGUGGAC | 2675 | GUCCACCACCAAGUCAAAG | 2676 |
| UUUGACUUGGUGGUGGACC | 2677 | GGUCCACCACCAAGUCAAA | 2678 |
| UUGACUUGGUGGUGGACCU | 2679 | AGGUCCACCACCAAGUCAA | 2680 |
| UGACUUGGUGGUGGACCUU | 2681 | AAGGUCCACCACCAAGUCA | 2682 |
| UUGGUGGUGGACCUUCCUU | 2683 | AAGGAAGGUCCACCACCAA | 2684 |
| UGGUGGUGGACCUUCCUUG | 2685 | CAAGGAAGGUCCACCACCA | 2686 |
| GGUGGUGGACCUUCCUUGG | 2687 | CCAAGGAAGGUCCACCACC | 2688 |
| GUGGUGGACCUUCCUUGGU | 2689 | ACCAAGGAAGGUCCACCAC | 2690 |
| UGGUGGACCUUCCUUGGUU | 2691 | AACCAAGGAAGGUCCACCA | 2692 |
| GGUGGACCUUCCUUGGUUU | 2693 | AAACCAAGGAAGGUCCACC | 2694 |
| GUGGACCUUCCUUGGUUUU | 2695 | AAAACCAAGGAAGGUCCAC | 2696 |
| CAUGUAUUUUAGCAUAAGG | 2697 | CCUUAUGCUAAAAUACAUG | 2698 |
| AAAUGUGUAUGAGUUUCAG | 2699 | CUGAAACUCAUACACAUUU | 2700 |
| AAUGUGUAUGAGUUUCAGU | 2701 | ACUGAAACUCAUACACAUU | 2702 |

TABLE 4-continued

| Sense Sequence | SEQ ID NO: | Antisense Sequence | SEQ ID NO: |
|---|---|---|---|
| AUGUGUAUGAGUUUCAGUA | 2703 | UACUGAAACUCAUACACAU | 2704 |
| GUGUAUGAGUUUCAGUAGA | 2705 | UCUACUGAAACUCAUACAC | 2706 |
| UGUAUGAGUUUCAGUAGAA | 2707 | UUCUACUGAAACUCAUACA | 2708 |
| UUCCAUAAAUAUGCAGAGU | 2709 | ACUCUGCAUAUUUAUGGAA | 2710 |
| CCAUAAAUAUGCAGAGUUC | 2711 | GAACUCUGCAUAUUUAUGG | 2712 |
| UGAAUGCAUUUGCAAUUUC | 2713 | GAAAUUGCAAAUGCAUUCA | 2714 |
| GAAUGCAUUUGCAAUUUCU | 2715 | AGAAAUUGCAAAUGCAUUC | 2716 |
| AUGCAUUUGCAAUUUCUAG | 2717 | CUAGAAAUUGCAAAUGCAU | 2718 |
| UGCAUUUGCAAUUUCUAGG | 2719 | CCUAGAAAUUGCAAAUGCA | 2720 |
| GCAUUUGCAAUUUCUAGGA | 2721 | UCCUAGAAAUUGCAAAUGC | 2722 |
| CAUUUGCAAUUUCUAGGAU | 2723 | AUCCUAGAAAUUGCAAAUG | 2724 |
| UUUGCAAUUUCUAGGAUUC | 2725 | GAAUCCUAGAAAUUGCAAA | 2726 |
| UGCAAUUUCUAGGAUUCUA | 2727 | UAGAAUCCUAGAAAUUGCA | 2728 |
| GCAAUUUCUAGGAUUCUAA | 2729 | UUAGAAUCCUAGAAAUUGC | 2730 |
| UCUAAAGAAUUGAGUACAG | 2731 | CUGUACUCAAUUCUUUAGA | 2732 |
| CUAAAGAAUUGAGUACAGA | 2733 | UCUGUACUCAAUUCUUUAG | 2734 |
| AGAAUUACUGUGCCAAUAC | 2735 | GUAUUGGCACAGUAAUUCU | 2736 |
| GAAUUACUGUGCCAAUACU | 2737 | AGUAUUGGCACAGUAAUUC | 2738 |
| AAUUACUGUGCCAAUACUG | 2739 | CAGUAUUGGCACAGUAAUU | 2740 |
| CUGUGCCAAUACUGUUUUG | 2741 | CAAAACAGUAUUGGCACAG | 2742 |
| UGUGCCAAUACUGUUUUGA | 2743 | UCAAAACAGUAUUGGCACA | 2744 |
| GUGCCAAUACUGUUUUGAU | 2745 | AUCAAAACAGUAUUGGCAC | 2746 |
| GCCAAUACUGUUUUGAUAA | 2747 | UUAUCAAAACAGUAUUGGC | 2748 |

In some embodiments, the antisense nucleic acid molecules targeted to ERAP1 comprise or consist of the nucleotide sequences shown in Table 5.

TABLE 5

| Sequence | SEQ ID NO: |
|---|---|
| CGCCUUUCUGAACGCGGAUC | 2749 |
| ACGCCUUUCUGAACGCGGAU | 2750 |
| CACGCCUUUCUGAACGCGGA | 2751 |
| UGCACGCCUUUCUGAACGCG | 2752 |
| GAUCAGGCGUAGGAAGUGCA | 2753 |
| GGAUCAGGCGUAGGAAGUGC | 2754 |
| GGGAUCAGGCGUAGGAAGUG | 2755 |
| GAAGCUGCGAGGUUGCGAUG | 2756 |
| GGAAGCUGCGAGGUUGCGAU | 2757 |
| GGGAAUUGGUAAAUGAGCGC | 2758 |

TABLE 5-continued

| Sequence | SEQ ID NO: |
|---|---|
| AGGGAAUUGGUAAAUGAGCG | 2759 |
| GAAGGGAAUUGGUAAAUGAG | 2760 |
| GGAAGGGAAUUGGUAAAUGA | 2761 |
| CCAGGAAGGGAAUUGGUAAA | 2762 |
| CCCAGGAAGGGAAUUGGUAA | 2763 |
| AAGCCGCAACUCCCAGGAAG | 2764 |
| GAAGCCGCAACUCCCAGGAA | 2765 |
| AAAGGGUAAACGGGAGUGGG | 2766 |
| GAAAGGGUAAACGGGAGUGG | 2767 |
| GGAAAGGGUAAACGGGAGUG | 2768 |
| GAAAGUGAAAGUGGAGCCCG | 2769 |
| GGACCGAAAGUGAAAGUGGA | 2770 |

89

TABLE 5-continued

| Sequence | SEQ ID NO: |
|---|---|
| AGGACCGAAAGUGAAAGUGG | 2771 |
| CAGGACCGAAAGUGAAAGUG | 2772 |
| CCAGGACCGAAAGUGAAAGU | 2773 |
| UCUUGCUCUACCUACCUGGG | 2774 |
| UUCUUGCUCUACCUACCUGG | 2775 |
| CUUCUUGCUCUACCUACCUG | 2776 |
| CACCAUCUUCUUGCUCUACC | 2777 |
| ACACCAUCUUCUUGCUCUAC | 2778 |
| AACACCAUCUUCUUGCUCUA | 2779 |
| AAACACCAUCUUCUUGCUCU | 2780 |
| GUUAAGAGAGCCAACAGUGA | 2781 |
| AGUUAAGAGAGCCAACAGUG | 2782 |
| ACACAGUUAAGAGAGCCAAC | 2783 |
| UGGACACAGUUAAGAGAGCC | 2784 |
| AGUGGACACAGUUAAGAGAG | 2785 |
| UGAAGGAGUGGACACAGUUA | 2786 |
| AUGAAGGAGUGGACACAGUU | 2787 |
| ACCAUGAAGGAGUGGACACA | 2788 |
| ACACCAUGAAGGAGUGGACA | 2789 |
| GACACCAUGAAGGAGUGGAC | 2790 |
| UGACACCAUGAAGGAGUGGA | 2791 |
| CUGACACCAUGAAGGAGUGG | 2792 |
| CUCUGACACCAUGAAGGAGU | 2793 |
| GCUCUGACACCAUGAAGGAG | 2794 |
| UGCUCUGACACCAUGAAGGA | 2795 |
| GUGCUCUGACACCAUGAAGG | 2796 |
| GGAGAUGCUUCAGUGCUCUG | 2797 |
| UGGAGAUGCUUCAGUGCUCU | 2798 |
| GUUUUGGAGAUGCUUCAGUG | 2799 |
| UACGUUUUGGAGAUGCUUCA | 2800 |
| CUACGUUUUGGAGAUGCUUC | 2801 |
| ACUACGUUUUGGAGAUGCUU | 2802 |
| CACUACGUUUUGGAGAUGCU | 2803 |
| AUCACUACGUUUUGGAGAUG | 2804 |
| CAUCACUACGUUUUGGAGAU | 2805 |
| CCAUCACUACGUUUUGGAGA | 2806 |
| CCCAUCACUACGUUUUGGAG | 2807 |
| UCCCAUCACUACGUUUUGGA | 2808 |
| GUCCCAUCACUACGUUUUGG | 2809 |

90

TABLE 5-continued

| Sequence | SEQ ID NO: |
|---|---|
| UGUCCCAUCACUACGUUUUG | 2810 |
| GUGUCCCAUCACUACGUUUU | 2811 |
| GGUGUCCCAUCACUACGUUU | 2812 |
| UGGUGUCCCAUCACUACGUU | 2813 |
| AUUCCAAGGAAAUGGUGUCC | 2814 |
| UAUUCCAAGGAAAUGGUGUC | 2815 |
| GAUCAUAAUGAACUGGGAUG | 2816 |
| GAGAUCAUAAUGAACUGGGA | 2817 |
| AGAGAUCAUAAUGAACUGGG | 2818 |
| GUCAGCGUGGUAAGGUUUGC | 2819 |
| GGUCAGCGUGGUAAGGUUUG | 2820 |
| AGGUCAGCGUGGUAAGGUUU | 2821 |
| AAGGUCAGCGUGGUAAGGUU | 2822 |
| GAAGGUCAGCGUGGUAAGGU | 2823 |
| AGAAGGUCAGCGUGGUAAGG | 2824 |
| CCAGAAGGUCAGCGUGGUAA | 2825 |
| CCCAGAAGGUCAGCGUGGUA | 2826 |
| UUUCUACUUUCGUGGUUCCC | 2827 |
| AUUUCUACUUUCGUGGUUCC | 2828 |
| GAUUUCUACUUUCGUGGUUC | 2829 |
| GUGAUUUCUACUUUCGUGGU | 2830 |
| ACUGGCUGUGAUUUCUACUU | 2831 |
| GACUGGCUGUGAUUUCUACU | 2832 |
| CUGACUGGCUGUGAUUUCUA | 2833 |
| UGCAGGAUGAUGGUGCUGGU | 2834 |
| AUGCAGGAUGAUGGUGCUGG | 2835 |
| CUAUGCAGGAUGAUGGUGCU | 2836 |
| UGACUAUGCAGGAUGAUGGU | 2837 |
| GUGACUAUGCAGGAUGAUGG | 2838 |
| GGUGACUAUGCAGGAUGAUG | 2839 |
| UGGUGACUAUGCAGGAUGAU | 2840 |
| GUGGUGACUAUGCAGGAUGA | 2841 |
| GGUGGUGACUAUGCAGGAUG | 2842 |
| AGGUGGUGACUAUGCAGGAU | 2843 |
| CAGGUGGUGACUAUGCAGGA | 2844 |
| GCAGGUGGUGACUAUGCAGG | 2845 |
| UCCGAUAGCCUCUCUCCAGC | 2846 |
| UUCCGAUAGCCUCUCUCCAG | 2847 |
| CUUCCGAUAGCCUCUCUCCA | 2848 |

TABLE 5-continued

| Sequence | SEQ ID NO: |
|----------|------------|
| UCUUCCGAUAGCCUCUCUCC | 2849 |
| UUCUUCCGAUAGCCUCUCUC | 2850 |
| GUUCUUCCGAUAGCCUCUCU | 2851 |
| GGUUCUUCCGAUAGCCUCUC | 2852 |
| GGGUUCUUCCGAUAGCCUCU | 2853 |
| GAGCCAGCAGUGCAAUUUGC | 2854 |
| UCGGGAGCCAGCAGUGCAAU | 2855 |
| UGUGUACGGGAGCCCGACAA | 2856 |
| AACUGUGUACGGGAGCCCGA | 2857 |
| ACAACUGUGUACGGGAGCCC | 2858 |
| GACAACUGUGUACGGGAGCC | 2859 |
| UGACAACUGUGUACGGGAGC | 2860 |
| AUGACAACUGUGUACGGGAG | 2861 |
| AAUGACAACUGUGUACGGGA | 2862 |
| GAAUGACAACUGUGUACGGG | 2863 |
| GUGAAUGACAACUGUGUACG | 2864 |
| CAUAGUGAAUGACAACUGUG | 2865 |
| GCAUAGUGAAUGACAACUGU | 2866 |
| AGCAUAGUGAAUGACAACUG | 2867 |
| CAGCAUAGUGAAUGACAACU | 2868 |
| CCAGCAUAGUGAAUGACAAC | 2869 |
| GCCAGCAUAGUGAAUGACAA | 2870 |
| UGCCAGCAUAGUGAAUGACA | 2871 |
| UUGCCAGCAUAGUGAAUGAC | 2872 |
| AAAGAUUGCCAGCAUAGUGA | 2873 |
| GAAAGAUUGCCAGCAUAGUG | 2874 |
| UAAAAUCCGUGGAAAGUCUC | 2875 |
| GUAAAAUCCGUGGAAAGUCU | 2876 |
| UGUAAAAUCCGUGGAAAGUC | 2877 |
| GCUUUUGUAAAAUCCGUGGA | 2878 |
| UGCUUUUGUAAAAUCCGUGG | 2879 |
| AGGUGCUUUUGUAAAAUCCG | 2880 |
| GUUCUGUAGGUGCUUUUGUA | 2881 |
| GGUUCUGUAGGUGCUUUUGU | 2882 |
| UUCCUUGGUUCUGUAGGUGC | 2883 |
| CUUCCUUGGUUCUGUAGGUG | 2884 |
| CCCUUCCUUGGUUCUGUAGG | 2885 |
| UGCUAGUAUCCUCAGUUCCC | 2886 |
| AUGCUAGUAUCCUCAGUUCC | 2887 |

TABLE 5-continued

| Sequence | SEQ ID NO: |
|----------|------------|
| GAUGCUAGUAUCCUCAGUUC | 2888 |
| UGAUGCUAGUAUCCUCAGUU | 2889 |
| UUGAUGCUAGUAUCCUCAGU | 2890 |
| GUUGAUGCUAGUAUCCUCAG | 2891 |
| UGUUGAUGCUAGUAUCCUCA | 2892 |
| GUGUUGAUGCUAGUAUCCUC | 2893 |
| AGGGAAAGGCCAUUCUAGCU | 2894 |
| CAGGGAAAGGCCAUUCUAGC | 2895 |
| AAAGCAGGGAAAGGCCAUUC | 2896 |
| CAUCAAAGCAGGGAAAGGCC | 2897 |
| GUUCAUCAAAGCAGGGAAAG | 2898 |
| CAGGUUCAUCAAAGCAGGGA | 2899 |
| AGGCAGGUUCAUCAAAGCAG | 2900 |
| AAGGCAGGUUCAUCAAAGCA | 2901 |
| GAAGGCAGGUUCAUCAAAGC | 2902 |
| AAACUUGCUUUGAAGGCAGG | 2903 |
| GAAACUUGCUUUGAAGGCAG | 2904 |
| AGAAACUUGCUUUGAAGGCA | 2905 |
| UGCCUUGGCUCUCUUCUAAU | 2906 |
| GUGCCUUGGCUCUCUUCUAA | 2907 |
| UAGGUGCCUUGGCUCUCUUC | 2908 |
| UGGCUAGGUGCCUUGGCUCU | 2909 |
| AUGGCUAGGUGCCUUGGCUC | 2910 |
| GAUGGCUAGGUGCCUUGGCU | 2911 |
| AGAUGGCUAGGUGCCUUGGC | 2912 |
| GAGAUGGCUAGGUGCCUUGG | 2913 |
| GGAGAUGGCUAGGUGCCUUG | 2914 |
| UUGGAGAUGGCUAGGUGCCU | 2915 |
| AUUGGAGAUGGCUAGGUGCC | 2916 |
| UAUUGGAGAUGGCUAGGUGC | 2917 |
| CAUAUUGGAGAUGGCUAGGU | 2918 |
| GCAUAUUGGAGAUGGCUAGG | 2919 |
| GGCAUAUUGGAGAUGGCUAG | 2920 |
| AUGGCAUAUUGGAGAUGGCU | 2921 |
| CAGAUUUCACCAUGGCAUA | 2922 |
| ACAGAUUUCACCAUGGCAU | 2923 |
| CACAGAUUUCACCAUGGCA | 2924 |
| UCACAGAUUUCACCAUGGC | 2925 |
| GUCACAGAUUUCACCAUGG | 2926 |

TABLE 5-continued

| Sequence | SEQ ID NO: |
|----------|------------|
| AGUCACAGAUUUCACCAAUG | 2927 |
| CAGUCACAGAUUUCACCAAU | 2928 |
| ACAGUCACAGAUUUCACCAA | 2929 |
| UUCAGCAACAGUCACAGAUU | 2930 |
| CUUCAGCAACAGUCACAGAU | 2931 |
| GUCCUUCAGCAACAGUCACA | 2932 |
| AGUCCUUCAGCAACAGUCAC | 2933 |
| GAGUCCUUCAGCAACAGUCA | 2934 |
| CUAUGAGUCCUUCAGCAACA | 2935 |
| UCUAUGAGUCCUUCAGCAAC | 2936 |
| UUCUAUGAGUCCUUCAGCAA | 2937 |
| CUUCUAUGAGUCCUUCAGCA | 2938 |
| GUCUUCUAUGAGUCCUUCAG | 2939 |
| AAUGGUCUUCUAUGAGUCCU | 2940 |
| AAAUGGUCUUCUAUGAGUCC | 2941 |
| UCACAGUGACAUCAAAAUGG | 2942 |
| UCAUCUUCACAGUGACAUCA | 2943 |
| GCUCAUCUUCACAGUGACAU | 2944 |
| UGCUCAUCUUCACAGUGACA | 2945 |
| GGUGCUCAUCUUCACAGUGA | 2946 |
| AGGUGCUCAUCUUCACAGUG | 2947 |
| AUAGGUGCUCAUCUUCACAG | 2948 |
| GAUAGGUGCUCAUCUUCACA | 2949 |
| AUGAAGGCCACCAGAUAGGU | 2950 |
| UGAUGAAGGCCACCAGAUAG | 2951 |
| AUGAUGAAGGCCACCAGAUA | 2952 |
| AAUGAUGAAGGCCACCAGAU | 2953 |
| GAAAUGAUGAAGGCCACCAG | 2954 |
| UGAAAUGAUGAAGGCCACCA | 2955 |
| UGCUGACAGACUCAAAAUCU | 2956 |
| UCUUGCUGACAGACUCAAAA | 2957 |
| GUUAUCUUGCUGACAGACUC | 2958 |
| GGUUAUCUUGCUGACAGACU | 2959 |
| UGGUUAUCUUGCUGACAGAC | 2960 |
| CUUGGUUAUCUUGCUGACAG | 2961 |
| CUCUUGGUUAUCUUGCUGAC | 2962 |
| ACUCUUGGUUAUCUUGCUGA | 2963 |
| CACUCUUGGUUAUCUUGCUG | 2964 |
| CCACUCUUGGUUAUCUUGCU | 2965 |

TABLE 5-continued

| Sequence | SEQ ID NO: |
|----------|------------|
| GACUCCACUCUUGGUUAUCU | 2966 |
| UGACUCCACUCUUGGUUAUC | 2967 |
| UUGACUCCACUCUUGGUUAU | 2968 |
| CUUGACUCCACUCUUGGUUA | 2969 |
| ACCUUGACUCCACUCUUGGU | 2970 |
| AACCUUGACUCCACUCUUGG | 2971 |
| AAACCUUGACUCCACUCUUG | 2972 |
| AGAAACCUUGACUCCACUCU | 2973 |
| CAGAAACCUUGACUCCACUC | 2974 |
| AAACAGAAACCUUGACUCCA | 2975 |
| UAAACAGAAACCUUGACUCC | 2976 |
| GCAUAAACAGAAACCUUGAC | 2977 |
| CAGCAUAAACAGAAACCUUG | 2978 |
| UCUUGUCUGGCACAGCAUAA | 2979 |
| CAGUGCAUAAUCUGCUUGAU | 2980 |
| CCAGUGCAUAAUCUGCUUGA | 2981 |
| UCCAGUGCAUAAUCUGCUUG | 2982 |
| AUCCAGUGCAUAAUCUGCUU | 2983 |
| CAUCCAGUGCAUAAUCUGCU | 2984 |
| GCAUCCAGUGCAUAAUCUGC | 2985 |
| AGCAUCCAGUGCAUAAUCUG | 2986 |
| CGCAGCAUCCAGUGCAUAAU | 2987 |
| CACCGCAGCAUCCAGUGCAU | 2988 |
| UCACCGCAGCAUCCAGUGCA | 2989 |
| AGUCACCGCAGCAUCCAGUG | 2990 |
| GAGUCACCGCAGCAUCCAGU | 2991 |
| AGAGUCACCGCAGCAUCCAG | 2992 |
| AAGAGUCACCGCAGCAUCCA | 2993 |
| GAAGAGUCACCGCAGCAUCC | 2994 |
| AGAAGAGUCACCGCAGCAUC | 2995 |
| UAGAAGAGUCACCGCAGCAU | 2996 |
| CUAGAAGAGUCACCGCAGCA | 2997 |
| UCGGGAAUAGCAGCAAGAUC | 2998 |
| AAGUCGGGAAUAGCAGCAAG | 2999 |
| AAAGUCGGGAAUAGCAGCAA | 3000 |
| GAAAGUCGGGAAUAGCAGCA | 3001 |
| UGAAAGUCGGGAAUAGCAGC | 3002 |
| CUGAAAGUCGGGAAUAGCAG | 3003 |
| ACUGAAAGUCGGGAAUAGCA | 3004 |

95

TABLE 5-continued

| Sequence | SEQ ID NO: |
|---|---|
| CAUAGCACCAGACUGAAAGU | 3005 |
| UCCAUAGCACCAGACUGAAA | 3006 |
| UUCCAUAGCACCAGACUGAA | 3007 |
| UUUCCAUAGCACCAGACUGA | 3008 |
| UUUUCCAUAGCACCAGACUG | 3009 |
| GUUUUCCAUAGCACCAGACU | 3010 |
| AGUUUUCCAUAGCACCAGAC | 3011 |
| CAGUUUUCCAUAGCACCAGA | 3012 |
| CCAGUUUUCCAUAGCACCAG | 3013 |
| CUCUAUAUGUUGUCAGUCCC | 3014 |
| CUUGAUGCAGAAGACUUUUC | 3015 |
| GCUUACUUGAUGCAGAAGAC | 3016 |
| CAGUUCAUGGGCCACAGUCA | 3017 |
| GCCAGUUCAUGGGCCACAGU | 3018 |
| UAGUGACCAGGUUCCCAAAC | 3019 |
| AUAGUGACCAGGUUCCCAAA | 3020 |
| UCCAUAGUGACCAGGUUCCC | 3021 |
| UUCCAUAGUGACCAGGUUCC | 3022 |
| AUUCCAUAGUGACCAGGUUC | 3023 |
| CAUUCCAUAGUGACCAGGUU | 3024 |
| CCAUUCCAUAGUGACCAGGU | 3025 |
| ACCAUUCCAUAGUGACCAGG | 3026 |
| CACCAUUCCAUAGUGACCAG | 3027 |
| CCACCAUUCCAUAGUGACCA | 3028 |
| UCCACCAUUCCAUAGUGACC | 3029 |
| AUUCCACCAUUCCAUAGUGA | 3030 |
| AUCAUUCCACCAUUCCAUAG | 3031 |
| GAUCAUUCCACCAUUCCAUA | 3032 |
| AAGAUCAUUCCACCAUUCCA | 3033 |
| AAAGAUCAUUCCACCAUUCC | 3034 |
| CAAAGAUCAUUCCACCAUUC | 3035 |
| CCAAAGAUCAUUCCACCAUU | 3036 |
| GCCAAAGAUCAUUCCACCAU | 3037 |
| AGCCAAAGAUCAUUCCACCA | 3038 |
| UAGCCAAAGAUCAUUCCACC | 3039 |
| GACAGACACAAACUCCAUAA | 3040 |
| GUUCAGGAUGGGUCACACUG | 3041 |
| AGUUCAGGAUGGGUCACACU | 3042 |
| CAGUUCAGGAUGGGUCACAC | 3043 |

96

TABLE 5-continued

| Sequence | SEQ ID NO: |
|---|---|
| UCAGUUCAGGAUGGGUCACA | 3044 |
| CUUUCAGUUCAGGAUGGGUC | 3045 |
| AAAGCAUCUACCUCCAUUGC | 3046 |
| UUUCCACAGGUGUAGACACA | 3047 |
| UUUUCCACAGGUGUAGACAC | 3048 |
| AUUUUCCACAGGUGUAGACA | 3049 |
| AGGAUUUUCCACAGGUGUAG | 3050 |
| GCAGGAUUUUCCACAGGUGU | 3051 |
| AGCAGGAUUUUCCACAGGUG | 3052 |
| GAGCAGGAUUUUCCACAGGU | 3053 |
| UGAGCAGGAUUUUCCACAGG | 3054 |
| CUGAGCAGGAUUUUCCACAG | 3055 |
| CGGAUCUGAGCAGGAUUUUC | 3056 |
| CUCCCGGAUCUGAGCAGGAU | 3057 |
| ACAUCUCCCGGAUCUGAGCA | 3058 |
| AAACAUCUCCCGGAUCUGAG | 3059 |
| CAAACAUCUCCCGGAUCUGA | 3060 |
| UCAAACAUCUCCCGGAUCUG | 3061 |
| AUCAAACAUCUCCCGGAUCU | 3062 |
| CAUCAAACAUCUCCCGGAUC | 3063 |
| UCAUCAAACAUCUCCCGGAU | 3064 |
| CAUCAUCAAACAUCUCCCGG | 3065 |
| ACAUCAUCAAACAUCUCCCG | 3066 |
| AACAUCAUCAAACAUCUCCC | 3067 |
| GAAUACAAGCUCCCUUAUCA | 3068 |
| AGAAUACAAGCUCCCUUAUC | 3069 |
| CAGAAUACAAGCUCCCUUAU | 3070 |
| UCAGAAUACAAGCUCCCUUA | 3071 |
| UUCAGAAUACAAGCUCCCUU | 3072 |
| AUUCAGAAUACAAGCUCCCU | 3073 |
| CUCCCUUAGCAUAUUCAGAA | 3074 |
| ACUCCCUUAGCAUAUUCAGA | 3075 |
| UGCUUCUGGAGAUACUGUAC | 3076 |
| AUGCUUCUGGAGAUACUGUA | 3077 |
| UAUGCUUCUGGAGAUACUGU | 3078 |
| AUCCCACAGGUCCUCGUUUU | 3079 |
| UAUCCCACAGGUCCUCGUUU | 3080 |
| CUAUCCCACAGGUCCUCGUU | 3081 |
| UACUAUCCCACAGGUCCUCG | 3082 |

97

98

TABLE 5-continued

TABLE 5-continued

| Sequence | SEQ ID NO: |
| --- | --- |
| AUACUAUCCCACAGGUCCUC | 3083 |
| CCAUACUAUCCCACAGGUCC | 3084 |
| GCCAUACUAUCCCACAGGUC | 3085 |
| UGCCAUACUAUCCCACAGGU | 3086 |
| UUGCCAUACUAUCCCACAGG | 3087 |
| CUUGCCAUACUAUCCCACAG | 3088 |
| ACUUGCCAUACUAUCCCACA | 3089 |
| UACUUGCCAUACUAUCCCAC | 3090 |
| AUACUUGCCAUACUAUCCCA | 3091 |
| AAUACUUGCCAUACUAUCCC | 3092 |
| AUCUGUAGGGCAAAUACUUG | 3093 |
| CAUCUGUAGGGCAAAUACUU | 3094 |
| CCAUCUGUAGGGCAAAUACU | 3095 |
| ACCAUCUGUAGGGCAAAUAC | 3096 |
| CACCAUCUGUAGGGCAAAUA | 3097 |
| ACACCAUCUGUAGGGCAAAU | 3098 |
| AUCCCUUUUACACCAUCUGU | 3099 |
| AUCCAUCCCUUUUACACCAU | 3100 |
| CAUCCAUCCCUUUUACACCA | 3101 |
| CCAUCCAUCCCUUUUACACC | 3102 |
| UAGAGCAAAAGCCAUCCAUC | 3103 |
| CUAGAGCAAAAGCCAUCCAU | 3104 |
| CAAUGUGAGGAUGAAGAUGA | 3105 |
| CCAAUGUGAGGAUGAAGAUG | 3106 |
| GCCAAUGUGAGGAUGAAGAU | 3107 |
| UGCCAAUGUGAGGAUGAAGA | 3108 |
| AUGCCAAUGUGAGGAUGAAG | 3109 |
| GAUGCCAAUGUGAGGAUGAA | 3110 |
| CUGAUGCCAAUGUGAGGAUG | 3111 |
| CCUGAUGCCAAUGUGAGGAU | 3112 |
| UCAUGGUUUUCACAUCCACC | 3113 |
| AUCAUGGUUUUCACAUCCAC | 3114 |
| CAUCAUGGUUUUCACAUCCA | 3115 |
| UCAUCAUGGUUUUCACAUCC | 3116 |
| CCAAGUGUUCAUCAUGGUUU | 3117 |
| UCCAAGUGUUCAUCAUGGUU | 3118 |
| CACUGUGAUGGUUAUUAGGG | 3119 |
| CUCACUGUGAUGGUUAUUAG | 3120 |
| GUGCUCUUGCUUCAUGUGUA | 3121 |

| Sequence | SEQ ID NO: |
| --- | --- |
| AGUGCUCUUGCUUCAUGUGU | 3122 |
| UAGUGCUCUUGCUUCAUGUG | 3123 |
| GUAGUGCUCUUGCUUCAUGU | 3124 |
| UGUAGUGCUCUUGCUUCAUG | 3125 |
| AUGUAGUGCUCUUGCUUCAU | 3126 |
| CAUGUAGUGCUCUUGCUUCA | 3127 |
| CCUUCAUGUAGUGCUCUUGC | 3128 |
| CCCUUCAUGUAGUGCUCUUG | 3129 |
| GCCCUUCAUGUAGUGCUCUU | 3130 |
| AGCCCUUCAUGUAGUGCUCU | 3131 |
| AGAGCCCUUCAUGUAGUGCU | 3132 |
| CAGAGCCCUUCAUGUAGUGC | 3133 |
| UCAGAGCCCUUCAUGUAGUG | 3134 |
| CGUCAGAGCCCUUCAUGUAG | 3135 |
| CCGUCAGAGCCCUUCAUGUA | 3136 |
| AUGGAACAUGCCACAGGUAC | 3137 |
| AAUGGAACAUGCCACAGGUA | 3138 |
| CAAUGGAACAUGCCACAGGU | 3139 |
| UCAAUGGAACAUGCCACAGG | 3140 |
| GUCAAUGGAACAUGCCACAG | 3141 |
| UGUCAAUGGAACAUGCCACA | 3142 |
| UUGCUGGUGAUGAAUGUCAA | 3143 |
| CCAUUCCACCUCUUCUGGGA | 3144 |
| AAUUUGAUCCAUUCCACCUC | 3145 |
| CCAUUCAUGCCCACAUUAAA | 3146 |
| GCCAUUCAUGCCCACAUUAA | 3147 |
| AGCCAUUCAUGCCCACAUUA | 3148 |
| UAGCCAUUCAUGCCCACAUU | 3149 |
| AUAGCCAUUCAUGCCCACAU | 3150 |
| GUAAUAGCCAUUCAUGCCCA | 3151 |
| UCCUCGUAAUGCACAAUGUA | 3152 |
| AUCCUCGUAAUGCACAAUGU | 3153 |
| CAUCCUCGUAAUGCACAAUG | 3154 |
| UCAUCCUCGUAAUGCACAAU | 3155 |
| AUCAUCCUCGUAAUGCACAA | 3156 |
| CAUCAUCCUCGUAAUGCACA | 3157 |
| CCAUCAUCCUCGUAAUGCAC | 3158 |
| UCCAUCAUCCUCGUAAUGCA | 3159 |
| AUCCAUCAUCCUCGUAAUGC | 3160 |

TABLE 5-continued

| Sequence | SEQ ID NO: |
|---|---|
| CAUCCAUCAUCCUCGUAAUG | 3161 |
| CCAUCCAUCAUCCUCGUAAU | 3162 |
| CCCAUCCAUCAUCCUCGUAA | 3163 |
| GUCCCAUCCAUCAUCCUCGU | 3164 |
| AGUCCCAUCCAUCAUCCUCG | 3165 |
| GAGUCCCAUCCAUCAUCCUC | 3166 |
| CAAAGAGUCCCAUCCAUCAU | 3167 |
| UCAAAGAGUCCCAUCCAUCA | 3168 |
| AGUCAAAGAGUCCCAUCCAU | 3169 |
| CAGUCAAAGAGUCCCAUCCA | 3170 |
| CCAGUCAAAGAGUCCCAUCC | 3171 |
| GCCAGUCAAAGAGUCCCAUC | 3172 |
| GGCCAGUCAAAGAGUCCCAU | 3173 |
| AGGCCAGUCAAAGAGUCCCA | 3174 |
| AAGGCCAGUCAAAGAGUCCC | 3175 |
| AAAGGCCAGUCAAAGAGUCC | 3176 |
| UAAAAGGCCAGUCAAAGAGU | 3177 |
| UUAAAAGGCCAGUCAAAGAG | 3178 |
| UUACUGCUGACUGCUGUGUG | 3179 |
| CAUUACUGCUGACUGCUGUG | 3180 |
| UCAUUACUGCUGACUGCUGU | 3181 |
| AUCAUUACUGCUGACUGCUG | 3182 |
| GAUCAUUACUGCUGACUGCU | 3183 |
| CGAUCAUUACUGCUGACUGC | 3184 |
| CCGAUCAUUACUGCUGACUG | 3185 |
| UCAAUGGACAGCUUCCCAAU | 3186 |
| UUCAAUGGACAGCUUCCCAA | 3187 |
| UUUUCAAUGGACAGCUUCCC | 3188 |
| CUUUUCAAUGGACAGCUUCC | 3189 |
| UACAGGGAUAAAUCCAAGGC | 3190 |
| GUACAGGGAUAAAUCCAAGG | 3191 |
| AGUACAGGGAUAAAUCCAAG | 3192 |
| CAAGUACAGGGAUAAAUCCA | 3193 |
| UCAAGUACAGGGAUAAAUCC | 3194 |
| CGGGCAUAAUUUCAGUUUCA | 3195 |
| ACGGGCAUAAUUUCAGUUUC | 3196 |
| CACGGGCAUAAUUUCAGUUU | 3197 |
| ACACGGGCAUAAUUUCAGUU | 3198 |
| AACACGGGCAUAAUUUCAGU | 3199 |

TABLE 5-continued

| Sequence | SEQ ID NO: |
|---|---|
| AAACACGGGCAUAAUUUCAG | 3200 |
| CUUGAAACACGGGCAUAAUU | 3201 |
| CCUUGAAACACGGGCAUAAU | 3202 |
| ACCUUGAAACACGGGCAUAA | 3203 |
| AACCUUGAAACACGGGCAUA | 3204 |
| AAACCUUGAAACACGGGCAU | 3205 |
| CAAACCUUGAAACACGGGCA | 3206 |
| CCUUGAAUUGAGUUUCCACU | 3207 |
| GCCUUGAAUUGAGUUUCCAC | 3208 |
| GGCCUUGAAUUGAGUUUCCA | 3209 |
| UUAGCAGCCUGAUGAGGAAG | 3210 |
| GAGGUCCCUUAGCAGCCUGA | 3211 |
| AUGAGGUCCCUUAGCAGCCU | 3212 |
| UCAAUGAGGUCCCUUAGCAG | 3213 |
| AUCAAUGAGGUCCCUUAGCA | 3214 |
| UAUCAAUGAGGUCCCUUAGC | 3215 |
| UUAUCAAUGAGGUCCCUUAG | 3216 |
| UGCUUAUCAAUGAGGUCCCU | 3217 |
| CUGCUUAUCAAUGAGGUCCC | 3218 |
| UCUGCUUAUCAAUGAGGUCC | 3219 |
| GUCUGCUUAUCAAUGAGGUC | 3220 |
| UGUCUGCUUAUCAAUGAGGU | 3221 |
| CAUGUCUGCUUAUCAAUGAG | 3222 |
| CUGUCCAUGUCUGCUUAUCA | 3223 |
| UCUGUCCAUGUCUGCUUAUC | 3224 |
| UCGUCUGUCCAUGUCUGCUU | 3225 |
| CUCGUCUGUCCAUGUCUGCU | 3226 |
| GCCCUCGUCUGUCCAUGUCU | 3227 |
| AGCCCUCGUCUGUCCAUGUC | 3228 |
| GAGCCCUCGUCUGUCCAUGU | 3229 |
| CUGAGCCCUCGUCUGUCCAU | 3230 |
| ACUGAGCCCUCGUCUGUCCA | 3231 |
| ACAGGCGAGGAGUAGUAGUU | 3232 |
| CACAGGCGAGGAGUAGUAGU | 3233 |
| ACACAGGCGAGGAGUAGUAG | 3234 |
| CACACAGGCGAGGAGUAGUA | 3235 |
| GCACACAGGCGAGGAGUAGU | 3236 |
| UGCACACAGGCGAGGAGUAG | 3237 |
| UAGCCUUCUGCCCUCUGUAC | 3238 |

101

TABLE 5-continued

| Sequence | SEQ ID NO: |
|---|---|
| AAAUAGCCUUCUGCCCUCUG | 3239 |
| GAAAUAGCCUUCUGCCCUCU | 3240 |
| CUGAAAUAGCCUUCUGCCCU | 3241 |
| UUUCUGAAAUAGCCUUCUGC | 3242 |
| UUCCACUUUCUGAAAUAGCC | 3243 |
| GCUCAAGUUUCCAUUGGAUU | 3244 |
| GGCUCAAGUUUCCAUUGGAU | 3245 |
| AGGCUCAAGUUUCCAUUGGA | 3246 |
| CACUGCCAAGGUCACGUCGA | 3247 |
| ACACUGCCAAGGUCACGUCG | 3248 |
| AACACUGCCAAGGUCACGUC | 3249 |
| AAACACUGCCAAGGUCACGU | 3250 |
| CAGCAAACACUGCCAAGGUC | 3251 |
| CCACAGCAAACACUGCCAAG | 3252 |
| UAAAGAAAAUCCCAGCCUUC | 3253 |
| GUACUGGACAAAGAAAACUG | 3254 |
| UGCAGAGGGCAAAUUCAAUU | 3255 |
| AUCUAGUAGCCAUUGAAGCU | 3256 |
| CAUCUAGUAGCCAUUGAAGC | 3257 |
| UCAUCUAGUAGCCAUUGAAG | 3258 |
| CUUUCAUCUAGUAGCCAUUG | 3259 |
| GCUUUCAUCUAGUAGCCAUU | 3260 |
| AGCUUUCAUCUAGUAGCCAU | 3261 |
| CUGCCAAUGAGUGUAAGAAU | 3262 |
| CCUGCCAAUGAGUGUAAGAA | 3263 |
| UCCUGCCAAUGAGUGUAAGA | 3264 |
| UUCCUGCCAAUGAGUGUAAG | 3265 |
| GUUCCUGCCAAUGAGUGUAA | 3266 |
| GGUUCCUGCCAAUGAGUGUA | 3267 |
| GGGUUCCUGCCAAUGAGUGU | 3268 |
| UGGGUUCCUGCCAAUGAGUG | 3269 |
| UACUGGGUUCCUGCCAAUGA | 3270 |
| AUCCUACUGGGUUCCUGCCA | 3271 |
| UAUCCUACUGGGUUCCUGCC | 3272 |
| GUAUCCUACUGGGUUCCUGC | 3273 |
| GGUAUCCUACUGGGUUCCUG | 3274 |
| GGGUAUCCUACUGGGUUCCU | 3275 |
| UGGGUAUCCUACUGGGUUCC | 3276 |
| UCCUCAGAAAUUGCCAGGCC | 3277 |

102

TABLE 5-continued

| Sequence | SEQ ID NO: |
|---|---|
| UUCCUCAGAAAUUGCCAGGC | 3278 |
| AGAUGAGCCAAGUUCAAACU | 3279 |
| AAGAUGAGCCAAGUUCAAAC | 3280 |
| GAAGAUGAGCCAAGUUCAAA | 3281 |
| GGAAGAUGAGCCAAGUUCAA | 3282 |
| UGGAAGAUGAGCCAAGUUCA | 3283 |
| AUGGAAGAUGAGCCAAGUUC | 3284 |
| UGUGGGCUAUGGAAGAUGAG | 3285 |
| CCAUUACCAUGUGGGCUAUG | 3286 |
| GUUGUACCCAUUACCAUGUG | 3287 |
| UGUUGUACCCAUUACCAUGU | 3288 |
| UUGUUGUACCCAUUACCAUG | 3289 |
| AAGCCGUGUUCUUGUGGAGA | 3290 |
| CCUCUUCAAGCCGUGUUCUU | 3291 |
| ACCUCUUCAAGCCGUGUUCU | 3292 |
| UACCUCUUCAAGCCGUGUUC | 3293 |
| UUACCUCUUCAAGCCGUGUU | 3294 |
| UUUACCUCUUCAAGCCGUGU | 3295 |
| UUUUACCUCUUCAAGCCGUG | 3296 |
| CUUUUACCUCUUCAAGCCGU | 3297 |
| CCUUUUACCUCUUCAAGCCG | 3298 |
| AUCCUUUUACCUCUUCAAGC | 3299 |
| CUGAAGAAUCCUUUUACCUC | 3300 |
| GCUGAAGAAUCCUUUUACCU | 3301 |
| AGCUGAAGAAUCCUUUUACC | 3302 |
| ACGGAGCUGAGAACCAUUUU | 3303 |
| AACGGAGCUGAGAACCAUUU | 3304 |
| CAACGGAGCUGAGAACCAUU | 3305 |
| ACAACGGAGCUGAGAACCAU | 3306 |
| CACAACGGAGCUGAGAACCA | 3307 |
| ACACAACGGAGCUGAGAACC | 3308 |
| GACACAACGGAGCUGAGAAC | 3309 |
| GGACACAACGGAGCUGAGAA | 3310 |
| UGGACACAACGGAGCUGAGA | 3311 |
| UUGGACACAACGGAGCUGAG | 3312 |
| ACCGAUGUUUUCUUCAAUGG | 3313 |
| CCAACCGAUGUUUUCUUCAA | 3314 |
| UCCAACCGAUGUUUUCUUCA | 3315 |
| AUCCAACCGAUGUUUUCUUC | 3316 |

TABLE 5-continued

| Sequence | SEQ ID NO: |
|---|---|
| UUCUUAUCCAUCCAACCGAU | 3317 |
| AUUCUUAUCCAUCCAACCGA | 3318 |
| CAGCCACACUCUGAUUUUAU | 3319 |
| UCACUUUGCAGCCACACUCU | 3320 |
| UUCACUUUGCAGCCACACUC | 3321 |
| CUUUUCACUUUGCAGCCACA | 3322 |
| GCUUUUCACUUUGCAGCCAC | 3323 |
| UUCAGGAUCAUGUUCAAGCU | 3324 |
| CUUCAGGAUCAUGUUCAAGC | 3325 |
| GCUUCAGGAUCAUGUUCAAG | 3326 |
| CAGCUUCAGGAUCAUGUUCA | 3327 |
| UCAGCUUCAGGAUCAUGUUC | 3328 |
| GUCAGCUUCAGGAUCAUGUU | 3329 |
| GCGUCAGCUUCAGGAUCAUG | 3330 |
| UGCGUCAGCUUCAGGAUCAU | 3331 |
| UUGCGUCAGCUUCAGGAUCA | 3332 |
| GUUGCGUCAGCUUCAGGAUC | 3333 |
| UGUUGCGUCAGCUUCAGGAU | 3334 |
| CUGUUGCGUCAGCUUCAGGA | 3335 |
| UCCUGUUGCGUCAGCUUCAG | 3336 |
| AUCCUGUUGCGUCAGCUUCA | 3337 |
| UCAUCCUGUUGCGUCAGCUU | 3338 |
| UUCAUCCUGUUGCGUCAGCU | 3339 |
| UUUCAUCCUGUUGCGUCAGC | 3340 |
| UUUUCAUCCUGUUGCGUCAG | 3341 |
| AUUUUCAUCCUGUUGCGUCA | 3342 |
| CAUUCCGUUUGAUGUAGCAU | 3343 |
| UUGCUAGAUGGAGAUGAAGU | 3344 |
| UUUGCUAGAUGGAGAUGAAG | 3345 |
| CAUUUGCUAGAUGGAGAUGA | 3346 |
| UCAUUUGCUAGAUGGAGAUG | 3347 |
| GCCUCAUUUGCUAGAUGGAG | 3348 |
| UGCCUCAUUUGCUAGAUGGA | 3349 |
| GUGCCUCAUUUGCUAGAUGG | 3350 |
| AGAACAGUGCCUCAUUUGCU | 3351 |
| GAGAACAGUGCCUCAUUUGC | 3352 |
| UUGGUUGAGAACAGUGCCUC | 3353 |
| UUUGGUUGAGAACAGUGCCU | 3354 |
| CUUUGGUUGAGAACAGUGCC | 3355 |

TABLE 5-continued

| Sequence | SEQ ID NO: |
|---|---|
| GACCACAGCACAUCAAAUUA | 3356 |
| CAAGGAGACCACAGCACAUC | 3357 |
| CCAAGGAGACCACAGCACAU | 3358 |
| ACCAAGGAGACCACAGCACA | 3359 |
| UUACCAAGGAGACCACAGCA | 3360 |
| CAUUACCAAGGAGACCACAG | 3361 |
| ACAUUACCAAGGAGACCACA | 3362 |
| UACAUUACCAAGGAGACCAC | 3363 |
| AUACAUUACCAAGGAGACCA | 3364 |
| CACCUGUGCAAUACCAAAUU | 3365 |
| UCACCUGUGCAAUACCAAAU | 3366 |
| AUCACCUGUGCAAUACCAAA | 3367 |
| AAUCACCUGUGCAAUACCAA | 3368 |
| ACUAAUCACCUGUGCAAUAC | 3369 |
| GACUAAUCACCUGUGCAAUA | 3370 |
| UGACUAAUCACCUGUGCAAU | 3371 |
| UUGACUAAUCACCUGUGCAA | 3372 |
| CCUUGACUAAUCACCUGUGC | 3373 |
| UCCUUGACUAAUCACCUGUG | 3374 |
| UUCCUUGACUAAUCACCUGU | 3375 |
| CUUCCUUGACUAAUCACCUG | 3376 |
| ACUUCCUUGACUAAUCACCU | 3377 |
| GACUUCCUUGACUAAUCACC | 3378 |
| AGACUUCCUUGACUAAUCAC | 3379 |
| CAGACUUCCUUGACUAAUCA | 3380 |
| AAGGCUGUGGGACCAAAGCU | 3381 |
| GCAAGGCUGUGGGACCAAAG | 3382 |
| GGCAAGGCUGUGGGACCAAA | 3383 |
| UGCUGUGAGGCAAGGCUGUG | 3384 |
| CAUGCUGUGAGGCAAGGCUG | 3385 |
| ACAUGCUGUGAGGCAAGGCU | 3386 |
| UUUACAUGCUGUGAGGCAAG | 3387 |
| AUUUACAUGCUGUGAGGCAA | 3388 |
| GAAGAACCUCAGCAUCAAUA | 3389 |
| AGAAGAACCUCAGCAUCAAU | 3390 |
| UAGAAGAACCUCAGCAUCAA | 3391 |
| CAGUAGAAGAACCUCAGCAU | 3392 |
| CUAGCAGUAGAAGAACCUCA | 3393 |
| ACUAGCAGUAGAAGAACCUC | 3394 |

TABLE 5-continued

| Sequence | SEQ ID NO: |
|---|---|
| GUCACUUUCAUACUAGCAGU | 3395 |
| CCCAAUUCACACCAGUAAAA | 3396 |
| UCCCAAUUCACACCAGUAAA | 3397 |
| CUUCCCAAUUCACACCAGUA | 3398 |
| CGUCAUGGAAUAGCAUUGUU | 3399 |
| ACGUCAUGGAAUAGCAUUGU | 3400 |
| CAAACGUCAUGGAAUAGCAU | 3401 |
| ACAAACGUCAUGGAAUAGCA | 3402 |
| UACAAACGUCAUGGAAUAGC | 3403 |
| CACAUAGUCAAGGACCUUAA | 3404 |
| ACACAUAGUCAAGGACCUUA | 3405 |
| UACACAUAGUCAAGGACCUU | 3406 |
| GUACACAUAGUCAAGGACCU | 3407 |
| CGAGAUGGCAGAGAUUAACU | 3408 |
| GCGAGAUGGCAGAGAUUAAC | 3409 |
| AUUUAGCGAGAUGGCAGAGA | 3410 |
| GAUUUAGCGAGAUGGCAGAG | 3411 |
| UGAUUUAGCGAGAUGGCAGA | 3412 |
| AUGAUUUAGCGAGAUGGCAG | 3413 |
| GAUGAUUUAGCGAGAUGGCA | 3414 |
| UGAUGAUUUAGCGAGAUGGC | 3415 |
| CUGAUGAUUUAGCGAGAUGG | 3416 |
| ACUGAUGAUUUAGCGAGAUG | 3417 |
| GACUGAUGAUUUAGCGAGAU | 3418 |
| AGACUGAUGAUUUAGCGAGA | 3419 |
| GAUCAGGCACCUUCUAUUUC | 3420 |
| AGAUCAGGCACCUUCUAUUU | 3421 |
| UUAGGAAGAUCAGGCACCUU | 3422 |
| AUUAGGAAGAUCAGGCACCU | 3423 |
| UAUUAGGAAGAUCAGGCACC | 3424 |
| GCAGCACAUCUUAUUUGGGA | 3425 |
| AGCAGCACAUCUUAUUUGGG | 3426 |
| AAGCAGCACAUCUUAUUUGG | 3427 |
| CUCGGUAAGCAGCACAUCUU | 3428 |
| CCUCGGUAAGCAGCACAUCU | 3429 |
| ACCUCGGUAAGCAGCACAUC | 3430 |
| UACCUCGGUAAGCAGCACAU | 3431 |
| AUACCUCGGUAAGCAGCACA | 3432 |
| GAUACCUCGGUAAGCAGCAC | 3433 |

TABLE 5-continued

| Sequence | SEQ ID NO: |
|---|---|
| UGAUACCUCGGUAAGCAGCA | 3434 |
| GUGAUACCUCGGUAAGCAGC | 3435 |
| CGUGAUACCUCGGUAAGCAG | 3436 |
| CCGUGAUACCUCGGUAAGCA | 3437 |
| CCCGUGAUACCUCGGUAAGC | 3438 |
| UCAACGACCCAAGCUGGAGC | 3439 |
| UUCAACGACCCAAGCUGGAG | 3440 |
| CUUCAACGACCCAAGCUGGA | 3441 |
| CCCAGCUUCAACGACCCAAG | 3442 |
| UCUCUGAAGUGGUUUCCCAA | 3443 |
| AUCUCUGAAGUGGUUUCCCA | 3444 |
| CAUCUCUGAAGUGGUUUCCC | 3445 |
| GAUGGCAUUGUGCUCAUAAU | 3446 |
| UGAUGGCAUUGUGCUCAUAA | 3447 |
| GUGAUGGCAUUGUGCUCAUA | 3448 |
| GUUAAGUGAUGGCAUUGUGC | 3449 |
| AGUUAAGUGAUGGCAUUGUG | 3450 |
| GAGUCUAUUUGGUCAAGAGA | 3451 |
| UGAGUCUAUUUGGUCAAGAG | 3452 |
| CCAUAACUCACUCACUAGAA | 3453 |
| AGCACCAUAACUCACUCACU | 3454 |
| CCAGCACCAUAACUCACUCA | 3455 |
| GCCAGCACCAUAACUCACUC | 3456 |
| AGCCAGCACCAUAACUCACU | 3457 |
| UAGCCAGCACCAUAACUCAC | 3458 |
| AUAGCCAGCACCAUAACUCA | 3459 |
| UAUAGCCAGCACCAUAACUC | 3460 |
| AAUAUAGCCAGCACCAUAAC | 3461 |
| CAAAAUAUAGCCAGCACCAU | 3462 |
| GCAAAAUAUAGCCAGCACCA | 3463 |
| GCAACAUUUGAGAGGGCAGU | 3464 |
| AGCAACAUUUGAGAGGGCAG | 3465 |
| UAGCAACAUUUGAGAGGGCA | 3466 |
| CUAGCAACAUUUGAGAGGGC | 3467 |
| CCUAGCAACAUUUGAGAGGG | 3468 |
| UCCUAGCAACAUUUGAGAGG | 3469 |
| UUCCUAGCAACAUUUGAGAG | 3470 |
| AAAUUCUGGCAAGCAAGGCC | 3471 |
| UCAAAUUCUGGCAAGCAAGG | 3472 |

TABLE 5-continued

| Sequence | SEQ ID NO: |
|---|---|
| AGUCAAAUUCUGGCAAGCAA | 3473 |
| AAGUCAAAUUCUGGCAAGCA | 3474 |
| AAAGUCAAAUUCUGGCAAGC | 3475 |
| CUGAAACCUGACACCGUAUA | 3476 |
| CCUGAAACCUGACACCGUAU | 3477 |
| CCCUGAAACCUGACACCGUA | 3478 |
| ACCCUGAAACCUGACACCGU | 3479 |
| CACCAAAGAGUUCUGGACUU | 3480 |
| UCACCAAAGAGUUCUGGACU | 3481 |
| GUCACCAAAGAGUUCUGGAC | 3482 |
| AGUCACCAAAGAGUUCUGGA | 3483 |
| AAAACGGCUUUACAGGGUAU | 3484 |
| GACCAUAGGUUGUUUCAUAC | 3485 |
| CAGACCAUAGGUUGUUUCAU | 3486 |

TABLE 5-continued

| Sequence | SEQ ID NO: |
|---|---|
| CCAGACCAUAGGUUGUUUCA | 3487 |
| UCCAGACCAUAGGUUGUUUC | 3488 |
| UUCCAGACCAUAGGUUGUUU | 3489 |
| UUUCCAGACCAUAGGUUGUU | 3490 |
| AUUUCCAGACCAUAGGUUGU | 3491 |
| AAUUUCCAGACCAUAGGUUG | 3492 |
| CACAUAUAGCUUUGCGAUAC | 3493 |
| GCACAUAUAGCUUUGCGAUA | 3494 |
| UGCACAUAUAGCUUUGCGAU | 3495 |
| AUGCACAUAUAGCUUUGCGA | 3496 |
| UAUGCACAUAUAGCUUUGCG | 3497 |
| GCAAACUCAAAGCAUAGAUC | 3498 |

In some embodiments, the siRNA molecules targeted to ERAP1 comprise or consist of the nucleotide sequences (sense and antisense strands) shown in Table 6.

TABLE 6

| Sense Sequence | SEQ ID NO: | Antisense Sequence | SEQ ID NO: |
|---|---|---|---|
| AAAGGCGUGCACUUCCUAC | 3499 | GUAGGAAGUGCACGCCUUU | 3500 |
| AAGGCGUGCACUUCCUACG | 3501 | CGUAGGAAGUGCACGCCUU | 3502 |
| CGUGCACUUCCUACGCCUG | 3503 | CAGGCGUAGGAAGUGCACG | 3504 |
| GUGCACUUCCUACGCCUGA | 3505 | UCAGGCGUAGGAAGUGCAC | 3506 |
| UGCACUUCCUACGCCUGAU | 3507 | AUCAGGCGUAGGAAGUGCA | 3508 |
| UCGCAACCUCGCAGCUUCC | 3509 | GGAAGCUGCGAGGUUGCGA | 3510 |
| CGGCGUGCAGCGCUCAUUU | 3511 | AAAUGAGCGCUGCACGCCG | 3512 |
| GGCGUGCAGCGCUCAUUUA | 3513 | UAAAUGAGCGCUGCACGCC | 3514 |
| GCGUGCAGCGCUCAUUUAC | 3515 | GUAAAUGAGCGCUGCACGC | 3516 |
| CGUGCAGCGCUCAUUUACC | 3517 | GGUAAAUGAGCGCUGCACG | 3518 |
| GUGCAGCGCUCAUUUACCA | 3519 | UGGUAAAUGAGCGCUGCAC | 3520 |
| UGCAGCGCUCAUUUACCAA | 3521 | UUGGUAAAUGAGCGCUGCA | 3522 |
| GCAGCGCUCAUUUACCAAU | 3523 | AUUGGUAAAUGAGCGCUGC | 3524 |
| CAGCGCUCAUUUACCAAUU | 3525 | AAUUGGUAAAUGAGCGCUG | 3526 |
| GCUCAUUUACCAAUUCCCU | 3527 | AGGGAAUUGGUAAAUGAGC | 3528 |
| CUCAUUUACCAAUUCCCUU | 3529 | AAGGGAAUUGGUAAAUGAG | 3530 |
| UCAUUUACCAAUUCCCUUC | 3531 | GAAGGGAAUUGGUAAAUGA | 3532 |
| CAUUUACCAAUUCCCUUCC | 3533 | GGAAGGGAAUUGGUAAAUG | 3534 |
| AUUUACCAAUUCCCUUCCU | 3535 | AGGAAGGGAAUUGGUAAAU | 3536 |
| CUUCCUGGGAGUUGCGGCU | 3537 | AGCCGCAACUCCCAGGAAG | 3538 |
| UUCCUGGGAGUUGCGGCUU | 3539 | AAGCCGCAACUCCCAGGAA | 3540 |
| UCCUGGGAGUUGCGGCUUC | 3541 | GAAGCCGCAACUCCCAGGA | 3542 |

TABLE 6-continued

| Sense Sequence | SEQ ID NO: | Antisense Sequence | SEQ ID NO: |
|---|---|---|---|
| CCCACUCCCGUUUACCCUU | 3543 | AAGGGUAAACGGGAGUGGG | 3544 |
| CCACUCCCGUUUACCCUUU | 3545 | AAAGGGUAAACGGGAGUGG | 3546 |
| GCUCCACUUUCACUUUCGG | 3547 | CCGAAAGUGAAAGUGGAGC | 3548 |
| CUCCACUUUCACUUUCGGU | 3549 | ACCGAAAGUGAAAGUGGAG | 3550 |
| ACUUUCACUUUCGGUCCUG | 3551 | CAGGACCGAAAGUGAAAGU | 3552 |
| CCCAGGUAGGUAGAGCAAG | 3553 | CUUGCUCUACCUACCUGGG | 3554 |
| CCAGGUAGGUAGAGCAAGA | 3555 | UCUUGCUCUACCUACCUGG | 3556 |
| CAGGUAGGUAGAGCAAGAA | 3557 | UUCUUGCUCUACCUACCUG | 3558 |
| AGGUAGGUAGAGCAAGAAG | 3559 | CUUCUUGCUCUACCUACCU | 3560 |
| GGUAGAGCAAGAAGAUGGU | 3561 | ACCAUCUUCUUGCUCUACC | 3562 |
| GUAGAGCAAGAAGAUGGUG | 3563 | CACCAUCUUCUUGCUCUAC | 3564 |
| UAGAGCAAGAAGAUGGUGU | 3565 | ACACCAUCUUCUUGCUCUA | 3566 |
| AGAGCAAGAAGAUGGUGUU | 3567 | AACACCAUCUUCUUGCUCU | 3568 |
| GAGCAAGAAGAUGGUGUUU | 3569 | AAACACCAUCUUCUUGCUC | 3570 |
| GAAGAUGGUGUUUCUGCCC | 3571 | GGGCAGAAACACCAUCUUC | 3572 |
| UCACUGUUGGCUCUCUUAA | 3573 | UUAAGAGAGCCAACAGUGA | 3574 |
| CACUGUUGGCUCUCUUAAC | 3575 | GUUAAGAGAGCCAACAGUG | 3576 |
| ACUGUUGGCUCUCUUAACU | 3577 | AGUUAAGAGAGCCAACAGU | 3578 |
| GGCUCUCUUAACUGUGUCC | 3579 | GGACACAGUUAAGAGAGCC | 3580 |
| GCUCUCUUAACUGUGUCCA | 3581 | UGGACACAGUUAAGAGAGC | 3582 |
| UAACUGUGUCCACUCCUUC | 3583 | GAAGGAGUGGACACAGUUA | 3584 |
| AACUGUGUCCACUCCUUCA | 3585 | UGAAGGAGUGGACACAGUU | 3586 |
| ACUGUGUCCACUCCUUCAU | 3587 | AUGAAGGAGUGGACACAGU | 3588 |
| UGUGUCCACUCCUUCAUGG | 3589 | CCAUGAAGGAGUGGACACA | 3590 |
| GUGUCCACUCCUUCAUGGU | 3591 | ACCAUGAAGGAGUGGACAC | 3592 |
| UGUCCACUCCUUCAUGGUG | 3593 | CACCAUGAAGGAGUGGACA | 3594 |
| GUCCACUCCUUCAUGGUGU | 3595 | ACACCAUGAAGGAGUGGAC | 3596 |
| UCCACUCCUUCAUGGUGUC | 3597 | GACACCAUGAAGGAGUGGA | 3598 |
| CCACUCCUUCAUGGUGUCA | 3599 | UGACACCAUGAAGGAGUGG | 3600 |
| CACUCCUUCAUGGUGUCAG | 3601 | CUGACACCAUGAAGGAGUG | 3602 |
| ACUCCUUCAUGGUGUCAGA | 3603 | UCUGACACCAUGAAGGAGU | 3604 |
| AGCACUGAAGCAUCUCCAA | 3605 | UUGGAGAUGCUUCAGUGCU | 3606 |
| GCACUGAAGCAUCUCCAAA | 3607 | UUUGGAGAUGCUUCAGUGC | 3608 |
| CACUGAAGCAUCUCCAAAA | 3609 | UUUUGGAGAUGCUUCAGUG | 3610 |
| AACGUAGUGAUGGGACACC | 3611 | GGUGUCCCAUCACUACGUU | 3612 |
| ACGUAGUGAUGGGACACCA | 3613 | UGGUGUCCCAUCACUACGU | 3614 |
| GGACACCAUUUCCUUGGAA | 3615 | UUCCAAGGAAAUGGGUUCC | 3616 |
| GACACCAUUUCCUUGGAAU | 3617 | AUUCCAAGGAAAUGGGUGUC | 3618 |
| ACACCAUUUCCUUGGAAUA | 3619 | UAUUCCAAGGAAAUGGUGU | 3620 |

TABLE 6-continued

| Sense Sequence | SEQ ID NO: | Antisense Sequence | SEQ ID NO: |
|---|---|---|---|
| CACCAUUUCCUUGGAAUAA | 3621 | UUAUUCCAAGGAAAUGGUG | 3622 |
| CCAUUUCCUUGGAAUAAAA | 3623 | UUUUAUUCCAAGGAAAUGG | 3624 |
| UUCCUUGGAAUAAAAUACG | 3625 | CGUAUUUUAUUCCAAGGAA | 3626 |
| UCCUUGGAAUAAAAUACGA | 3627 | UCGUAUUUUAUUCCAAGGA | 3628 |
| CCUUGGAAUAAAAUACGAC | 3629 | GUCGUAUUUUAUUCCAAGG | 3630 |
| UGGAAUAAAAUACGACUUC | 3631 | GAAGUCGUAUUUUAUUCCA | 3632 |
| GAAUAAAAUACGACUUCCU | 3633 | AGGAAGUCGUAUUUUAUUC | 3634 |
| GUCAUCCCAGUUCAUUAUG | 3635 | CAUAAUGAACUGGGAUGAC | 3636 |
| CCCAGUUCAUUAUGAUCUC | 3637 | GAGAUCAUAAUGAACUGGG | 3638 |
| CCAGUUCAUUAUGAUCUCU | 3639 | AGAGAUCAUAAUGAACUGG | 3640 |
| CAGUUCAUUAUGAUCUCUU | 3641 | AAGAGAUCAUAAUGAACUG | 3642 |
| UACCACGCUGACCUUCUGG | 3643 | CCAGAAGGUCAGCGUGGUA | 3644 |
| ACCACGCUGACCUUCUGGG | 3645 | CCCAGAAGGUCAGCGUGGU | 3646 |
| AAUCACAGCCAGUCAGCCC | 3647 | GGGCUGACUGGCUGUGAUU | 3648 |
| AUCACAGCCAGUCAGCCCA | 3649 | UGGGCUGACUGGCUGUGAU | 3650 |
| CACCAGCACCAUCAUCCUG | 3651 | CAGGAUGAUGGUGCUGGUG | 3652 |
| ACCAGCACCAUCAUCCUGC | 3653 | GCAGGAUGAUGGUGCUGGU | 3654 |
| CCAGCACCAUCAUCCUGCA | 3655 | UGCAGGAUGAUGGUGCUGG | 3656 |
| CAGCACCAUCAUCCUGCAU | 3657 | AUGCAGGAUGAUGGUGCUG | 3658 |
| AGCACCAUCAUCCUGCAUA | 3659 | UAUGCAGGAUGAUGGUGCU | 3660 |
| GCACCAUCAUCCUGCAUAG | 3661 | CUAUGCAGGAUGAUGGUGC | 3662 |
| CACCAUCAUCCUGCAUAGU | 3663 | ACUAUGCAGGAUGAUGGUG | 3664 |
| ACCAUCAUCCUGCAUAGUC | 3665 | GACUAUGCAGGAUGAUGGU | 3666 |
| CCAUCAUCCUGCAUAGUCA | 3667 | UGACUAUGCAGGAUGAUGG | 3668 |
| CAUCCUGCAUAGUCACCAC | 3669 | GUGGUGACUAUGCAGGAUG | 3670 |
| UAGUCACCACCUGCAGAUA | 3671 | UAUCUGCAGGUGGUGACUA | 3672 |
| AGUCACCACCUGCAGAUAU | 3673 | AUAUCUGCAGGUGGUGACU | 3674 |
| ACCACCUGCAGAUAUCUAG | 3675 | CUAGAUAUCUGCAGGUGGU | 3676 |
| CCACCUGCAGAUAUCUAGG | 3677 | CCUAGAUAUCUGCAGGUGG | 3678 |
| CACCUGCAGAUAUCUAGGG | 3679 | CCCUAGAUAUCUGCAGGUG | 3680 |
| ACCUGCAGAUAUCUAGGGC | 3681 | GCCCUAGAUAUCUGCAGGU | 3682 |
| CCUGCAGAUAUCUAGGGCC | 3683 | GGCCCUAGAUAUCUGCAGG | 3684 |
| CAAAUUGCACUGCUGGCUC | 3685 | GAGCCAGCAGUGCAAUUUG | 3686 |
| UCCUUGUCGGGCUCCCGUA | 3687 | UACGGGAGCCCGACAAGGA | 3688 |
| CUUGUCGGGCUCCCGUACA | 3689 | UGUACGGGAGCCCGACAAG | 3690 |
| CACAGUUGUCAUUCACUAU | 3691 | AUAGUGAAUGACAACUGUG | 3692 |
| ACAGUUGUCAUUCACUAUG | 3693 | CAUAGUGAAUGACAACUGU | 3694 |
| CAGUUGUCAUUCACUAUGC | 3695 | GCAUAGUGAAUGACAACUG | 3696 |
| AGUUGUCAUUCACUAUGCU | 3697 | AGCAUAGUGAAUGACAACU | 3698 |

TABLE 6-continued

| Sense Sequence | SEQ ID NO: | Antisense Sequence | SEQ ID NO: |
|---|---|---|---|
| GUUGUCAUUCACUAUGCUG | 3699 | CAGCAUAGUGAAUGACAAC | 3700 |
| CAUUCACUAUGCUGGCAAU | 3701 | AUUGCCAGCAUAGUGAAUG | 3702 |
| AUUCACUAUGCUGGCAAUC | 3703 | GAUUGCCAGCAUAGUGAAU | 3704 |
| UUCACUAUGCUGGCAAUCU | 3705 | AGAUUGCCAGCAUAGUGAA | 3706 |
| UCACUAUGCUGGCAAUCUU | 3707 | AAGAUUGCCAGCAUAGUGA | 3708 |
| CACUAUGCUGGCAAUCUUU | 3709 | AAAGAUUGCCAGCAUAGUG | 3710 |
| ACUAUGCUGGCAAUCUUUC | 3711 | GAAAGAUUGCCAGCAUAGU | 3712 |
| AGACUUUCCACGGAUUUUA | 3713 | UAAAAUCCGUGGAAAGUCU | 3714 |
| GACUUUCCACGGAUUUUAC | 3715 | GUAAAAUCCGUGGAAAGUC | 3716 |
| ACUUUCCACGGAUUUUACA | 3717 | UGUAAAAUCCGUGGAAAGU | 3718 |
| AACUGAGGAUACUAGCAUC | 3719 | GAUGCUAGUAUCCUCAGUU | 3720 |
| ACUGAGGAUACUAGCAUCA | 3721 | UGAUGCUAGUAUCCUCAGU | 3722 |
| CUGAGGAUACUAGCAUCAA | 3723 | UUGAUGCUAGUAUCCUCAG | 3724 |
| UGAGGAUACUAGCAUCAAC | 3725 | GUUGAUGCUAGUAUCCUCA | 3726 |
| UGCAGCUAGAAUGGCCUUU | 3727 | AAAGGCCAUUCUAGCUGCA | 3728 |
| AAUGGCCUUUCCCUGCUUU | 3729 | AAAGCAGGGAAAGGCCAUU | 3730 |
| GCCUUUCCCUGCUUUGAUG | 3731 | CAUCAAAGCAGGGAAAGGC | 3732 |
| CUUUCCCUGCUUUGAUGAA | 3733 | UUCAUCAAAGCAGGGAAAG | 3734 |
| ACCUGCCUUCAAAGCAAGU | 3735 | ACUUGCUUUGAAGGCAGGU | 3736 |
| CUGCCUUCAAAGCAAGUUU | 3737 | AAACUUGCUUUGAAGGCAG | 3738 |
| UGCCUUCAAAGCAAGUUUC | 3739 | GAAACUUGCUUUGAAGGCA | 3740 |
| GCCUUCAAAGCAAGUUUCU | 3741 | AGAAACUUGCUUUGAAGGC | 3742 |
| CAAAGCAAGUUUCUCAAUC | 3743 | GAUUGAGAAACUUGCUUUG | 3744 |
| AAGCAAGUUUCUCAAUCAA | 3745 | UUGAUUGAGAAACUUGCUU | 3746 |
| AGCAAGUUUCUCAAUCAAA | 3747 | UUUGAUUGAGAAACUUGCU | 3748 |
| GCAAGUUUCUCAAUCAAAA | 3749 | UUUUGAUUGAGAAACUUGC | 3750 |
| GAGCCAAGGCACCUAGCCA | 3751 | UGGCUAGGUGCCUUGGCUC | 3752 |
| GGCACCUAGCCAUCUCCAA | 3753 | UUGGAGAUGGCUAGGUGCC | 3754 |
| GCACCUAGCCAUCUCCAAU | 3755 | AUUGGAGAUGGCUAGGUGC | 3756 |
| CACCUAGCCAUCUCCAAUA | 3757 | UAUUGGAGAUGGCUAGGUG | 3758 |
| ACCUAGCCAUCUCCAAUAU | 3759 | AUAUUGGAGAUGGCUAGGU | 3760 |
| CCUAGCCAUCUCCAAUAUG | 3761 | CAUAUUGGAGAUGGCUAGG | 3762 |
| CUAGCCAUCUCCAAUAUGC | 3763 | GCAUAUUGGAGAUGGCUAG | 3764 |
| UAGCCAUCUCCAAUAUGCC | 3765 | GGCAUAUUGGAGAUGGCUA | 3766 |
| AGCCAUCUCCAAUAUGCCA | 3767 | UGGCAUAUUGGAGAUGGCU | 3768 |
| AAAUCUGUGACUGUUGCUG | 3769 | CAGCAACAGUCACAGAUUU | 3770 |
| AAUCUGUGACUGUUGCUGA | 3771 | UCAGCAACAGUCACAGAUU | 3772 |
| AUCUGUGACUGUUGCUGAA | 3773 | UUCAGCAACAGUCACAGAU | 3774 |
| UCUGUGACUGUUGCUGAAG | 3775 | CUUCAGCAACAGUCACAGA | 3776 |

TABLE 6-continued

| Sense Sequence | SEQ ID NO: | Antisense Sequence | SEQ ID NO: |
|---|---|---|---|
| UGACUGUUGCUGAAGGACU | 3777 | AGUCCUUCAGCAACAGUCA | 3778 |
| ACUGUUGCUGAAGGACUCA | 3779 | UGAGUCCUUCAGCAACAGU | 3780 |
| CUGUUGCUGAAGGACUCAU | 3781 | AUGAGUCCUUCAGCAACAG | 3782 |
| UGUUGCUGAAGGACUCAUA | 3783 | UAUGAGUCCUUCAGCAACA | 3784 |
| GUUGCUGAAGGACUCAUAG | 3785 | CUAUGAGUCCUUCAGCAAC | 3786 |
| UUGCUGAAGGACUCAUAGA | 3787 | UCUAUGAGUCCUUCAGCAA | 3788 |
| UGCUGAAGGACUCAUAGAA | 3789 | UUCUAUGAGUCCUUCAGCA | 3790 |
| GCUGAAGGACUCAUAGAAG | 3791 | CUUCUAUGAGUCCUUCAGC | 3792 |
| CUGAAGGACUCAUAGAAGA | 3793 | UCUUCUAUGAGUCCUUCAG | 3794 |
| UGAAGGACUCAUAGAAGAC | 3795 | GUCUUCUAUGAGUCCUUCA | 3796 |
| AAGGACUCAUAGAAGACCA | 3797 | UGGUCUUCUAUGAGUCCUU | 3798 |
| AGGACUCAUAGAAGACCAU | 3799 | AUGGUCUUCUAUGAGUCCU | 3800 |
| GGACUCAUAGAAGACCAUU | 3801 | AAUGGUCUUCUAUGAGUCC | 3802 |
| GACUCAUAGAAGACCAUUU | 3803 | AAAUGGUCUUCUAUGAGUC | 3804 |
| ACUCAUAGAAGACCAUUUU | 3805 | AAAAUGGUCUUCUAUGAGU | 3806 |
| CUCAUAGAAGACCAUUUUG | 3807 | CAAAAUGGUCUUCUAUGAG | 3808 |
| UCAUAGAAGACCAUUUUGA | 3809 | UCAAAAUGGUCUUCUAUGA | 3810 |
| CAUAGAAGACCAUUUUGAU | 3811 | AUCAAAAUGGUCUUCUAUG | 3812 |
| AUAGAAGACCAUUUUGAUG | 3813 | CAUCAAAAUGGUCUUCUAU | 3814 |
| UAGAAGACCAUUUUGAUGU | 3815 | ACAUCAAAAUGGUCUUCUA | 3816 |
| AGAAGACCAUUUUGAUGUC | 3817 | GACAUCAAAAUGGUCUUCU | 3818 |
| UGAUGUCACUGUGAAGAUG | 3819 | CAUCUUCACAGUGACAUCA | 3820 |
| GAUGUCACUGUGAAGAUGA | 3821 | UCAUCUUCACAGUGACAUC | 3822 |
| AUGUCACUGUGAAGAUGAG | 3823 | CUCAUCUUCACAGUGACAU | 3824 |
| UGUGAAGAUGAGCACCUAU | 3825 | AUAGGUGCUCAUCUUCACA | 3826 |
| GUGAAGAUGAGCACCUAUC | 3827 | GAUAGGUGCUCAUCUUCAC | 3828 |
| ACCUAUCUGGUGGCCUUCA | 3829 | UGAAGGCCACCAGAUAGGU | 3830 |
| CCUAUCUGGUGGCCUUCAU | 3831 | AUGAAGGCCACCAGAUAGG | 3832 |
| CUAUCUGGUGGCCUUCAUC | 3833 | GAUGAAGGCCACCAGAUAG | 3834 |
| UAUCUGGUGGCCUUCAUCA | 3835 | UGAUGAAGGCCACCAGAUA | 3836 |
| AUCUGGUGGCCUUCAUCAU | 3837 | AUGAUGAAGGCCACCAGAU | 3838 |
| UCUGGUGGCCUUCAUCAUU | 3839 | AAUGAUGAAGGCCACCAGA | 3840 |
| CUGGUGGCCUUCAUCAUUU | 3841 | AAAUGAUGAAGGCCACCAG | 3842 |
| UGGUGGCCUUCAUCAUUUC | 3843 | GAAAUGAUGAAGGCCACCA | 3844 |
| GGCCUUCAUCAUUUCAGAU | 3845 | AUCUGAAAUGAUGAAGGCC | 3846 |
| GCCUUCAUCAUUUCAGAUU | 3847 | AAUCUGAAAUGAUGAAGGC | 3848 |
| CCUUCAUCAUUUCAGAUUU | 3849 | AAAUCUGAAAUGAUGAAGG | 3850 |
| AGAUUUUGAGUCUGUCAGC | 3851 | GCUGACAGACUCAAAAUCU | 3852 |
| UUUGAGUCUGUCAGCAAGA | 3853 | UCUUGCUGACAGACUCAAA | 3854 |

TABLE 6-continued

| Sense Sequence | SEQ ID NO: | Antisense Sequence | SEQ ID NO: |
|---|---|---|---|
| UUGAGUCUGUCAGCAAGAU | 3855 | AUCUUGCUGACAGACUCAA | 3856 |
| UGAGUCUGUCAGCAAGAUA | 3857 | UAUCUUGCUGACAGACUCA | 3858 |
| GAGUCUGUCAGCAAGAUAA | 3859 | UUAUCUUGCUGACAGACUC | 3860 |
| AGUCUGUCAGCAAGAUAAC | 3861 | GUUAUCUUGCUGACAGACU | 3862 |
| GUCUGUCAGCAAGAUAACC | 3863 | GGUUAUCUUGCUGACAGAC | 3864 |
| UCUGUCAGCAAGAUAACCA | 3865 | UGGUUAUCUUGCUGACAGA | 3866 |
| UGUCAGCAAGAUAACCAAG | 3867 | CUUGGUUAUCUUGCUGACA | 3868 |
| GUCAGCAAGAUAACCAAGA | 3869 | UCUUGGUUAUCUUGCUGAC | 3870 |
| UCAGCAAGAUAACCAAGAG | 3871 | CUCUUGGUUAUCUUGCUGA | 3872 |
| CAGCAAGAUAACCAAGAGU | 3873 | ACUCUUGGUUAUCUUGCUG | 3874 |
| AGCAAGAUAACCAAGAGUG | 3875 | CACUCUUGGUUAUCUUGCU | 3876 |
| GCAAGAUAACCAAGAGUGG | 3877 | CCACUCUUGGUUAUCUUGC | 3878 |
| CAAGAUAACCAAGAGUGGA | 3879 | UCCACUCUUGGUUAUCUUG | 3880 |
| AAGAUAACCAAGAGUGGAG | 3881 | CUCCACUCUUGGUUAUCUU | 3882 |
| UAACCAAGAGUGGAGUCAA | 3883 | UUGACUCCACUCUUGGUUA | 3884 |
| AACCAAGAGUGGAGUCAAG | 3885 | CUUGACUCCACUCUUGGUU | 3886 |
| ACCAAGAGUGGAGUCAAGG | 3887 | CCUUGACUCCACUCUUGGU | 3888 |
| CCAAGAGUGGAGUCAAGGU | 3889 | ACCUUGACUCCACUCUUGG | 3890 |
| CAAGAGUGGAGUCAAGGUU | 3891 | AACCUUGACUCCACUCUUG | 3892 |
| AAGAGUGGAGUCAAGGUUU | 3893 | AAACCUUGACUCCACUCUU | 3894 |
| AGAGUGGAGUCAAGGUUUC | 3895 | GAAACCUUGACUCCACUCU | 3896 |
| GAGUGGAGUCAAGGUUUCU | 3897 | AGAAACCUUGACUCCACUC | 3898 |
| AGUGGAGUCAAGGUUUCUG | 3899 | CAGAAACCUUGACUCCACU | 3900 |
| GUGGAGUCAAGGUUUCUGU | 3901 | ACAGAAACCUUGACUCCAC | 3902 |
| UGGAGUCAAGGUUUCUGUU | 3903 | AACAGAAACCUUGACUCCA | 3904 |
| GGAGUCAAGGUUUCUGUUU | 3905 | AAACAGAAACCUUGACUCC | 3906 |
| GAGUCAAGGUUUCUGUUUA | 3907 | UAAACAGAAACCUUGACUC | 3908 |
| AGUCAAGGUUUCUGUUUAU | 3909 | AUAAACAGAAACCUUGACU | 3910 |
| GUCAAGGUUUCUGUUUAUG | 3911 | CAUAAACAGAAACCUUGAC | 3912 |
| UCAAGGUUUCUGUUUAUGC | 3913 | GCAUAAACAGAAACCUUGA | 3914 |
| CAAGGUUUCUGUUUAUGCU | 3915 | AGCAUAAACAGAAACCUUG | 3916 |
| AAGGUUUCUGUUUAUGCUG | 3917 | CAGCAUAAACAGAAACCUU | 3918 |
| AGGUUUCUGUUUAUGCUGU | 3919 | ACAGCAUAAACAGAAACCU | 3920 |
| UUUCUGUUUAUGCUGUGCC | 3921 | GGCACAGCAUAAACAGAAA | 3922 |
| UUCUGUUUAUGCUGUGCCA | 3923 | UGGCACAGCAUAAACAGAA | 3924 |
| CUGUUUAUGCUGUGCCAGA | 3925 | UCUGGCACAGCAUAAACAG | 3926 |
| UGUUUAUGCUGUGCCAGAC | 3927 | GUCUGGCACAGCAUAAACA | 3928 |
| GUUUAUGCUGUGCCAGACA | 3929 | UGUCUGGCACAGCAUAAAC | 3930 |
| AUGCACUGGAUGCUGCGGU | 3931 | ACCGCAGCAUCCAGUGCAU | 3932 |

TABLE 6-continued

| Sense Sequence | SEQ ID NO: | Antisense Sequence | SEQ ID NO: |
|---|---|---|---|
| UGCACUGGAUGCUGCGGUG | 3933 | CACCGCAGCAUCCAGUGCA | 3934 |
| GCACUGGAUGCUGCGGUGA | 3935 | UCACCGCAGCAUCCAGUGC | 3936 |
| CACUGGAUGCUGCGGUGAC | 3937 | GUCACCGCAGCAUCCAGUG | 3938 |
| ACUGGAUGCUGCGGUGACU | 3939 | AGUCACCGCAGCAUCCAGU | 3940 |
| CUGGAUGCUGCGGUGACUC | 3941 | GAGUCACCGCAGCAUCCAG | 3942 |
| UGGAUGCUGCGGUGACUCU | 3943 | AGAGUCACCGCAGCAUCCA | 3944 |
| GGAUGCUGCGGUGACUCUU | 3945 | AAGAGUCACCGCAGCAUCC | 3946 |
| GAUGCUGCGGUGACUCUUC | 3947 | GAAGAGUCACCGCAGCAUC | 3948 |
| AUGCUGCGGUGACUCUUCU | 3949 | AGAAGAGUCACCGCAGCAU | 3950 |
| UGCUGCGGUGACUCUUCUA | 3951 | UAGAAGAGUCACCGCAGCA | 3952 |
| GCUGCGGUGACUCUUCUAG | 3953 | CUAGAAGAGUCACCGCAGC | 3954 |
| CUGCGGUGACUCUUCUAGA | 3955 | UCUAGAAGAGUCACCGCAG | 3956 |
| UGCGGUGACUCUUCUAGAA | 3957 | UUCUAGAAGAGUCACCGCA | 3958 |
| GCGGUGACUCUUCUAGAAU | 3959 | AUUCUAGAAGAGUCACCGC | 3960 |
| CGGUGACUCUUCUAGAAUU | 3961 | AAUUCUAGAAGAGUCACCG | 3962 |
| CUUCUAGAAUUUUAUGAGG | 3963 | CCUCAUAAAAUUCUAGAAG | 3964 |
| CAAGAUCUUGCUGCUAUUC | 3965 | GAAUAGCAGCAAGAUCUUG | 3966 |
| AAGAUCUUGCUGCUAUUCC | 3967 | GGAAUAGCAGCAAGAUCUU | 3968 |
| AGAUCUUGCUGCUAUUCCC | 3969 | GGGAAUAGCAGCAAGAUCU | 3970 |
| GAUCUUGCUGCUAUUCCCG | 3971 | CGGGAAUAGCAGCAAGAUC | 3972 |
| UUGCUGCUAUUCCCGACUU | 3973 | AAGUCGGGAAUAGCAGCAA | 3974 |
| UGCUGCUAUUCCCGACUUU | 3975 | AAAGUCGGGAAUAGCAGCA | 3976 |
| GCUGCUAUUCCCGACUUUC | 3977 | GAAAGUCGGGAAUAGCAGC | 3978 |
| CUUUCAGUCUGGUGCUAUG | 3979 | CAUAGCACCAGACUGAAAG | 3980 |
| UUUCAGUCUGGUGCUAUGG | 3981 | CCAUAGCACCAGACUGAAA | 3982 |
| UUCAGUCUGGUGCUAUGGA | 3983 | UCCAUAGCACCAGACUGAA | 3984 |
| UCAGUCUGGUGCUAUGGAA | 3985 | UUCCAUAGCACCAGACUGA | 3986 |
| AAUCUGCUCUGUUGUUUGA | 3987 | UCAAACAACAGAGCAGAUU | 3988 |
| AUCUGCUCUGUUGUUUGAU | 3989 | AUCAAACAACAGAGCAGAU | 3990 |
| UCUGCUCUGUUGUUUGAUG | 3991 | CAUCAAACAACAGAGCAGA | 3992 |
| CUGCUCUGUUGUUUGAUGC | 3993 | GCAUCAAACAACAGAGCAG | 3994 |
| AAAAGUCUUCUGCAUCAAG | 3995 | CUUGAUGCAGAAGACUUUU | 3996 |
| AAGUCUUCUGCAUCAAGUA | 3997 | UACUUGAUGCAGAAGACUU | 3998 |
| AGUCUUCUGCAUCAAGUAA | 3999 | UUACUUGAUGCAGAAGACU | 4000 |
| GUCUUCUGCAUCAAGUAAG | 4001 | CUUACUUGAUGCAGAAGAC | 4002 |
| UCUUCUGCAUCAAGUAAGC | 4003 | GCUUACUUGAUGCAGAAGA | 4004 |
| AACCUGGUCACUAUGGAAU | 4005 | AUUCCAUAGUGACCAGGUU | 4006 |
| ACCUGGUCACUAUGGAAUG | 4007 | CAUUCCAUAGUGACCAGGU | 4008 |
| CCUGGUCACUAUGGAAUGG | 4009 | CCAUUCCAUAGUGACCAGG | 4010 |

TABLE 6-continued

| Sense Sequence | SEQ ID NO: | Antisense Sequence | SEQ ID NO: |
|---|---|---|---|
| CUGGUCACUAUGGAAUGGU | 4011 | ACCAUUCCAUAGUGACCAG | 4012 |
| UGGUCACUAUGGAAUGGUG | 4013 | CACCAUUCCAUAGUGACCA | 4014 |
| GGUCACUAUGGAAUGGUGG | 4015 | CCACCAUUCCAUAGUGACC | 4016 |
| GUCACUAUGGAAUGGUGGA | 4017 | UCCACCAUUCCAUAGUGAC | 4018 |
| UCACUAUGGAAUGGUGGAA | 4019 | UUCCACCAUUCCAUAGUGA | 4020 |
| CACUAUGGAAUGGUGGAAU | 4021 | AUUCCACCAUUCCAUAGUG | 4022 |
| ACUAUGGAAUGGUGGAAUG | 4023 | CAUUCCACCAUUCCAUAGU | 4024 |
| UGGAAUGGUGGAAUGAUCU | 4025 | AGAUCAUUCCACCAUUCCA | 4026 |
| GGAAUGGUGGAAUGAUCUU | 4027 | AAGAUCAUUCCACCAUUCC | 4028 |
| GAAUGGUGGAAUGAUCUUU | 4029 | AAAGAUCAUUCCACCAUUC | 4030 |
| AAUGGUGGAAUGAUCUUUG | 4031 | CAAAGAUCAUUCCACCAUU | 4032 |
| AUGGUGGAAUGAUCUUUGG | 4033 | CCAAAGAUCAUUCCACCAU | 4034 |
| UGGUGGAAUGAUCUUUGGC | 4035 | GCCAAAGAUCAUUCCACCA | 4036 |
| GGUGGAAUGAUCUUUGGCU | 4037 | AGCCAAAGAUCAUUCCACC | 4038 |
| GUGGAAUGAUCUUUGGCUA | 4039 | UAGCCAAAGAUCAUUCCAC | 4040 |
| UGGAAUGAUCUUUGGCUAA | 4041 | UUAGCCAAAGAUCAUUCCA | 4042 |
| GGAAUGAUCUUUGGCUAAA | 4043 | UUUAGCCAAAGAUCAUUCC | 4044 |
| GAAUGAUCUUUGGCUAAAU | 4045 | AUUUAGCCAAAGAUCAUUC | 4046 |
| AAUGAUCUUUGGCUAAAUG | 4047 | CAUUUAGCCAAAGAUCAUU | 4048 |
| AAUUUAUGGAGUUUGUGUC | 4049 | GACACAAACUCCAUAAAUU | 4050 |
| AUUUAUGGAGUUUGUGUCU | 4051 | AGACACAAACUCCAUAAAU | 4052 |
| UUUAUGGAGUUUGUGUCUG | 4053 | CAGACACAAACUCCAUAAA | 4054 |
| UUAUGGAGUUUGUGUCUGU | 4055 | ACAGACACAAACUCCAUAA | 4056 |
| UAUGGAGUUUGUGUCUGUC | 4057 | GACAGACACAAACUCCAUA | 4058 |
| AUGGAGUUUGUGUCUGUCA | 4059 | UGACAGACACAAACUCCAU | 4060 |
| UGGAGUUUGUGUCUGUCAG | 4061 | CUGACAGACACAAACUCCA | 4062 |
| GGAGUUUGUGUCUGUCAGU | 4063 | ACUGACAGACACAAACUCC | 4064 |
| GAGUUUGUGUCUGUCAGUG | 4065 | CACUGACAGACACAAACUC | 4066 |
| AGUUUGUGUCUGUCAGUGU | 4067 | ACACUGACAGACACAAACU | 4068 |
| CAGUGUGACCCAUCCUGAA | 4069 | UUCAGGAUGGGUCACACUG | 4070 |
| GCAAUGGAGGUAGAUGCUU | 4071 | AAGCAUCUACCUCCAUUGC | 4072 |
| AGGUAGAUGCUUUAAAUUC | 4073 | GAAUUUAAAGCAUCUACCU | 4074 |
| GGUAGAUGCUUUAAAUUCC | 4075 | GGAAUUUAAAGCAUCUACC | 4076 |
| GUAGAUGCUUUAAAUUCCU | 4077 | AGGAAUUUAAAGCAUCUAC | 4078 |
| UAGAUGCUUUAAAUUCCUC | 4079 | GAGGAAUUUAAAGCAUCUA | 4080 |
| CCUGUGUCUACACCUGUGG | 4081 | CCACAGGUGUAGACACAGG | 4082 |
| UGUGUCUACACCUGUGGAA | 4083 | UUCCACAGGUGUAGACACA | 4084 |
| UAUGAUAAGGGAGCUUGUA | 4085 | UACAAGCUCCCUUAUCAUA | 4086 |
| AUAAGGGAGCUUGUAUUCU | 4087 | AGAAUACAAGCUCCCUUAU | 4088 |

TABLE 6-continued

| Sense Sequence | SEQ ID NO: | Antisense Sequence | SEQ ID NO: |
|---|---|---|---|
| UAAGGGAGCUUGUAUUCUG | 4089 | CAGAAUACAAGCUCCCUUA | 4090 |
| AAGGGAGCUUGUAUUCUGA | 4091 | UCAGAAUACAAGCUCCCUU | 4092 |
| AGGGAGCUUGUAUUCUGAA | 4093 | UUCAGAAUACAAGCUCCCU | 4094 |
| AUUCUGAAUAUGCUAAGGG | 4095 | CCCUUAGCAUAUUCAGAAU | 4096 |
| GAAUAUGCUAAGGGAGUAU | 4097 | AUACUCCCUUAGCAUAUUC | 4098 |
| AAUAUGCUAAGGGAGUAUC | 4099 | GAUACUCCCUUAGCAUAUU | 4100 |
| AUAUGCUAAGGGAGUAUCU | 4101 | AGAUACUCCCUUAGCAUAU | 4102 |
| UAUGCUAAGGGAGUAUCUU | 4103 | AAGAUACUCCCUUAGCAUA | 4104 |
| GCUGACGCAUUUAAAAGUG | 4105 | CACUUUUAAAUGCGUCAGC | 4106 |
| CUGACGCAUUUAAAAGUGG | 4107 | CCACUUUUAAAUGCGUCAG | 4108 |
| UGACGCAUUUAAAAGUGGU | 4109 | ACCACUUUUAAAUGCGUCA | 4110 |
| GACGCAUUUAAAAGUGGUA | 4111 | UACCACUUUUAAAUGCGUC | 4112 |
| ACGCAUUUAAAAGUGGUAU | 4113 | AUACCACUUUUAAAUGCGU | 4114 |
| CGCAUUUAAAAGUGGUAUU | 4115 | AAUACCACUUUUAAAUGCG | 4116 |
| GCAUUUAAAAGUGGUAUUG | 4117 | CAAUACCACUUUUAAAUGC | 4118 |
| AAAGUGGUAUUGUACAGUA | 4119 | UACUGUACAAUACCACUUU | 4120 |
| AAGUGGUAUUGUACAGUAU | 4121 | AUACUGUACAAUACCACUU | 4122 |
| AGUGGUAUUGUACAGUAUC | 4123 | GAUACUGUACAAUACCACU | 4124 |
| GUGGUAUUGUACAGUAUCU | 4125 | AGAUACUGUACAAUACCAC | 4126 |
| UGGUAUUGUACAGUAUCUC | 4127 | GAGAUACUGUACAAUACCA | 4128 |
| GGUAUUGUACAGUAUCUCC | 4129 | GGAGAUACUGUACAAUACC | 4130 |
| GUAUUGUACAGUAUCUCCA | 4131 | UGGAGAUACUGUACAAUAC | 4132 |
| UAUUGUACAGUAUCUCCAG | 4133 | CUGGAGAUACUGUACAAUA | 4134 |
| AUUGUACAGUAUCUCCAGA | 4135 | UCUGGAGAUACUGUACAAU | 4136 |
| UUGUACAGUAUCUCCAGAA | 4137 | UUCUGGAGAUACUGUACAA | 4138 |
| UGUACAGUAUCUCCAGAAG | 4139 | CUUCUGGAGAUACUGUACA | 4140 |
| CUCCAGAAGCAUAGCUAUA | 4141 | UAUAGCUAUGCUUCUGGAG | 4142 |
| UCCAGAAGCAUAGCUAUAA | 4143 | UUAUAGCUAUGCUUCUGGA | 4144 |
| CCAGAAGCAUAGCUAUAAA | 4145 | UUUAUAGCUAUGCUUCUGG | 4146 |
| ACGAGGACCUGUGGGAUAG | 4147 | CUAUCCCACAGGUCCUCGU | 4148 |
| CGAGGACCUGUGGGAUAGU | 4149 | ACUAUCCCACAGGUCCUCG | 4150 |
| GAGGACCUGUGGGAUAGUA | 4151 | UACUAUCCCACAGGUCCUC | 4152 |
| AGGACCUGUGGGAUAGUAU | 4153 | AUACUAUCCCACAGGUCCU | 4154 |
| GGACCUGUGGGAUAGUAUG | 4155 | CAUACUAUCCCACAGGUCC | 4156 |
| GACCUGUGGGAUAGUAUGG | 4157 | CCAUACUAUCCCACAGGUC | 4158 |
| ACCUGUGGGAUAGUAUGGC | 4159 | GCCAUACUAUCCCACAGGU | 4160 |
| CCUGUGGGAUAGUAUGGCA | 4161 | UGCCAUACUAUCCCACAGG | 4162 |
| CUGUGGGAUAGUAUGGCAA | 4163 | UUGCCAUACUAUCCCACAG | 4164 |
| UGUGGGAUAGUAUGGCAAG | 4165 | CUUGCCAUACUAUCCCACA | 4166 |

TABLE 6-continued

| Sense Sequence | SEQ ID NO: | Antisense Sequence | SEQ ID NO: |
|---|---|---|---|
| GUGGGAUAGUAUGGCAAGU | 4167 | ACUUGCCAUACUAUCCCAC | 4168 |
| UGGGAUAGUAUGGCAAGUA | 4169 | UACUUGCCAUACUAUCCCA | 4170 |
| GGGAUAGUAUGGCAAGUAU | 4171 | AUACUUGCCAUACUAUCCC | 4172 |
| AAGUAUUUGCCCUACAGAU | 4173 | AUCUGUAGGGCAAAUACUU | 4174 |
| AGUAUUUGCCCUACAGAUG | 4175 | CAUCUGUAGGGCAAAUACU | 4176 |
| GUAUUUGCCCUACAGAUGG | 4177 | CCAUCUGUAGGGCAAAUAC | 4178 |
| UAUUUGCCCUACAGAUGGU | 4179 | ACCAUCUGUAGGGCAAAUA | 4180 |
| AUUUGCCCUACAGAUGGUG | 4181 | CACCAUCUGUAGGGCAAAU | 4182 |
| UUUGCCCUACAGAUGGUGU | 4183 | ACACCAUCUGUAGGGCAAA | 4184 |
| UGGUGUAAAAGGGAUGGAU | 4185 | AUCCAUCCCUUUUACACCA | 4186 |
| GGUGUAAAAGGGAUGGAUG | 4187 | CAUCCAUCCCUUUUACACC | 4188 |
| GUGUAAAAGGGAUGGAUGG | 4189 | CCAUCCAUCCCUUUUACAC | 4190 |
| UGUAAAAGGGAUGGAUGGC | 4191 | GCCAUCCAUCCCUUUUACA | 4192 |
| AAGGGAUGGAUGGCUUUUG | 4193 | CAAAAGCCAUCCAUCCCUU | 4194 |
| AGGGAUGGAUGGCUUUUGC | 4195 | GCAAAAGCCAUCCAUCCCU | 4196 |
| GGGAUGGAUGGCUUUUGCU | 4197 | AGCAAAAGCCAUCCAUCCC | 4198 |
| GAUGGAUGGCUUUUGCUCU | 4199 | AGAGCAAAAGCCAUCCAUC | 4200 |
| AUGGAUGGCUUUUGCUCUA | 4201 | UAGAGCAAAAGCCAUCCAU | 4202 |
| UGGAUGGCUUUUGCUCUAG | 4203 | CUAGAGCAAAAGCCAUCCA | 4204 |
| GGAUGGCUUUUGCUCUAGA | 4205 | UCUAGAGCAAAAGCCAUCC | 4206 |
| GAUGGCUUUUGCUCUAGAA | 4207 | UUCUAGAGCAAAAGCCAUC | 4208 |
| AUGGCUUUUGCUCUAGAAG | 4209 | CUUCUAGAGCAAAAGCCAU | 4210 |
| UGGCUUUUGCUCUAGAAGU | 4211 | ACUUCUAGAGCAAAAGCCA | 4212 |
| GGCUUUUGCUCUAGAAGUC | 4213 | GACUUCUAGAGCAAAAGCC | 4214 |
| GCUUUUGCUCUAGAAGUCA | 4215 | UGACUUCUAGAGCAAAAGC | 4216 |
| CUUUUGCUCUAGAAGUCAA | 4217 | UUGACUUCUAGAGCAAAAG | 4218 |
| UUUUGCUCUAGAAGUCAAC | 4219 | GUUGACUUCUAGAGCAAAA | 4220 |
| UUCAUCUUCAUCCUCACAU | 4221 | AUGUGAGGAUGAAGAUGAA | 4222 |
| UCAUCUUCAUCCUCACAUU | 4223 | AAUGUGAGGAUGAAGAUGA | 4224 |
| CAUCUUCAUCCUCACAUUG | 4225 | CAAUGUGAGGAUGAAGAUG | 4226 |
| AUCUUCAUCCUCACAUUGG | 4227 | CCAAUGUGAGGAUGAAGAU | 4228 |
| UCUUCAUCCUCACAUUGGC | 4229 | GCCAAUGUGAGGAUGAAGA | 4230 |
| CUUCAUCCUCACAUUGGCA | 4231 | UGCCAAUGUGAGGAUGAAG | 4232 |
| UUCAUCCUCACAUUGGCAU | 4233 | AUGCCAAUGUGAGGAUGAA | 4234 |
| UCAUCCUCACAUUGGCAUC | 4235 | GAUGCCAAUGUGAGGAUGA | 4236 |
| CAUCCUCACAUUGGCAUCA | 4237 | UGAUGCCAAUGUGAGGAUG | 4238 |
| CCCUAAUAACCAUCACAGU | 4239 | ACUGUGAUGGUUAUUAGGG | 4240 |
| CCUAAUAACCAUCACAGUG | 4241 | CACUGUGAUGGUUAUUAGG | 4242 |
| AGCAAGAGCACUACAUGAA | 4243 | UUCAUGUAGUGCUCUUGCU | 4244 |

TABLE 6-continued

| Sense Sequence | SEQ ID NO: | Antisense Sequence | SEQ ID NO: |
|---|---|---|---|
| GCAAGAGCACUACAUGAAG | 4245 | CUUCAUGUAGUGCUCUUGC | 4246 |
| CACUACAUGAAGGGCUCUG | 4247 | CAGAGCCCUUCAUGUAGUG | 4248 |
| ACUACAUGAAGGGCUCUGA | 4249 | UCAGAGCCCUUCAUGUAGU | 4250 |
| CUACAUGAAGGGCUCUGAC | 4251 | GUCAGAGCCCUUCAUGUAG | 4252 |
| UACAUGAAGGGCUCUGACG | 4253 | CGUCAGAGCCCUUCAUGUA | 4254 |
| ACAUGAAGGGCUCUGACGG | 4255 | CCGUCAGAGCCCUUCAUGU | 4256 |
| CAUGAAGGGCUCUGACGGC | 4257 | GCCGUCAGAGCCCUUCAUG | 4258 |
| AUGAAGGGCUCUGACGGCG | 4259 | CGCCGUCAGAGCCCUUCAU | 4260 |
| CCGGACACUGGGUACCUGU | 4261 | ACAGGUACCCAGUGUCCGG | 4262 |
| CGGACACUGGGUACCUGUG | 4263 | CACAGGUACCCAGUGUCCG | 4264 |
| GGACACUGGGUACCUGUGG | 4265 | CCACAGGUACCCAGUGUCC | 4266 |
| GACACUGGGUACCUGUGGC | 4267 | GCCACAGGUACCCAGUGUC | 4268 |
| ACACUGGGUACCUGUGGCA | 4269 | UGCCACAGGUACCCAGUGU | 4270 |
| CACUGGGUACCUGUGGCAU | 4271 | AUGCCACAGGUACCCAGUG | 4272 |
| ACUGGGUACCUGUGGCAUG | 4273 | CAUGCCACAGGUACCCAGU | 4274 |
| CUGGGUACCUGUGGCAUGU | 4275 | ACAUGCCACAGGUACCCAG | 4276 |
| UGGGUACCUGUGGCAUGUU | 4277 | AACAUGCCACAGGUACCCA | 4278 |
| GGGUACCUGUGGCAUGUUC | 4279 | GAACAUGCCACAGGUACCC | 4280 |
| GGUACCUGUGGCAUGUUCC | 4281 | GGAACAUGCCACAGGUACC | 4282 |
| GUACCUGUGGCAUGUUCCA | 4283 | UGGAACAUGCCACAGGUAC | 4284 |
| UACCUGUGGCAUGUUCCAU | 4285 | AUGGAACAUGCCACAGGUA | 4286 |
| ACCUGUGGCAUGUUCCAUU | 4287 | AAUGGAACAUGCCACAGGU | 4288 |
| CCUGUGGCAUGUUCCAUUG | 4289 | CAAUGGAACAUGCCACAGG | 4290 |
| CUGUGGCAUGUUCCAUUGA | 4291 | UCAAUGGAACAUGCCACAG | 4292 |
| UGUGGCAUGUUCCAUUGAC | 4293 | GUCAAUGGAACAUGCCACA | 4294 |
| GUGGCAUGUUCCAUUGACA | 4295 | UGUCAAUGGAACAUGCCAC | 4296 |
| UGUUCCAUUGACAUUCAUC | 4297 | GAUGAAUGUCAAUGGAACA | 4298 |
| UCCAUUGACAUUCAUCACC | 4299 | GGUGAUGAAUGUCAAUGGA | 4300 |
| CAUUGACAUUCAUCACCAG | 4301 | CUGGUGAUGAAUGUCAAUG | 4302 |
| ACAUUCAUCACCAGCAAAU | 4303 | AUUUGCUGGUGAUGAAUGU | 4304 |
| CUCCCAGAAGAGGUGGAAU | 4305 | AUUCCACCUCUUCUGGGAG | 4306 |
| UCCCAGAAGAGGUGGAAUG | 4307 | CAUUCCACCUCUUCUGGGA | 4308 |
| CCCAGAAGAGGUGGAAUGG | 4309 | CCAUUCCACCUCUUCUGGG | 4310 |
| CCAGAAGAGGUGGAAUGGA | 4311 | UCCAUUCCACCUCUUCUGG | 4312 |
| CAGAAGAGGUGGAAUGGAU | 4313 | AUCCAUUCCACCUCUUCUG | 4314 |
| AGAAGAGGUGGAAUGGAUC | 4315 | GAUCCAUUCCACCUCUUCU | 4316 |
| GAAGAGGUGGAAUGGAUCA | 4317 | UGAUCCAUUCCACCUCUUC | 4318 |
| GAGGUGGAAUGGAUCAAAU | 4319 | AUUUGAUCCAUUCCACCUC | 4320 |
| AGGUGGAAUGGAUCAAAUU | 4321 | AAUUUGAUCCAUUCCACCU | 4322 |

TABLE 6-continued

| Sense Sequence | SEQ ID NO: | Antisense Sequence | SEQ ID NO: |
|---|---|---|---|
| GGUGGAAUGGAUCAAAUUU | 4323 | AAAUUUGAUCCAUUCCACC | 4324 |
| GUGGAAUGGAUCAAAUUUA | 4325 | UAAAUUUGAUCCAUUCCAC | 4326 |
| GAUCAAAUUUAAUGUGGGC | 4327 | GCCCACAUUAAAUUUGAUC | 4328 |
| AUCAAAUUUAAUGUGGGCA | 4329 | UGCCCACAUUAAAUUUGAU | 4330 |
| UCAAAUUUAAUGUGGGCAU | 4331 | AUGCCCACAUUAAAUUUGA | 4332 |
| CAAAUUUAAUGUGGGCAUG | 4333 | CAUGCCCACAUUAAAUUUG | 4334 |
| AAAUUUAAUGUGGGCAUGA | 4335 | UCAUGCCCACAUUAAAUUU | 4336 |
| AAUUUAAUGUGGGCAUGAA | 4337 | UUCAUGCCCACAUUAAAUU | 4338 |
| UAAUGUGGGCAUGAAUGGC | 4339 | GCCAUUCAUGCCCACAUUA | 4340 |
| AAUGUGGGCAUGAAUGGCU | 4341 | AGCCAUUCAUGCCCACAUU | 4342 |
| AUGUGGGCAUGAAUGGCUA | 4343 | UAGCCAUUCAUGCCCACAU | 4344 |
| UGUGGGCAUGAAUGGCUAU | 4345 | AUAGCCAUUCAUGCCCACA | 4346 |
| GUGGGCAUGAAUGGCUAUU | 4347 | AAUAGCCAUUCAUGCCCAC | 4348 |
| UGGGCAUGAAUGGCUAUUA | 4349 | UAAUAGCCAUUCAUGCCCA | 4350 |
| GGGCAUGAAUGGCUAUUAC | 4351 | GUAAUAGCCAUUCAUGCCC | 4352 |
| GGCAUGAAUGGCUAUUACA | 4353 | UGUAAUAGCCAUUCAUGCC | 4354 |
| AUGGCUAUUACAUUGUGCA | 4355 | UGCACAAUGUAAUAGCCAU | 4356 |
| AUUACAUUGUGCAUUACGA | 4357 | UCGUAAUGCACAAUGUAAU | 4358 |
| UUACAUUGUGCAUUACGAG | 4359 | CUCGUAAUGCACAAUGUAA | 4360 |
| UACAUUGUGCAUUACGAGG | 4361 | CCUCGUAAUGCACAAUGUA | 4362 |
| ACAUUGUGCAUUACGAGGA | 4363 | UCCUCGUAAUGCACAAUGU | 4364 |
| CAUUGUGCAUUACGAGGAU | 4365 | AUCCUCGUAAUGCACAAUG | 4366 |
| AUUGUGCAUUACGAGGAUG | 4367 | CAUCCUCGUAAUGCACAAU | 4368 |
| UUGUGCAUUACGAGGAUGA | 4369 | UCAUCCUCGUAAUGCACAA | 4370 |
| UGUGCAUUACGAGGAUGAU | 4371 | AUCAUCCUCGUAAUGCACA | 4372 |
| GUGCAUUACGAGGAUGAUG | 4373 | CAUCAUCCUCGUAAUGCAC | 4374 |
| UGCAUUACGAGGAUGAUGG | 4375 | CCAUCAUCCUCGUAAUGCA | 4376 |
| GCAUUACGAGGAUGAUGGA | 4377 | UCCAUCAUCCUCGUAAUGC | 4378 |
| CAUUACGAGGAUGAUGGAU | 4379 | AUCCAUCAUCCUCGUAAUG | 4380 |
| AUUACGAGGAUGAUGGAUG | 4381 | CAUCCAUCAUCCUCGUAAU | 4382 |
| UUACGAGGAUGAUGGAUGG | 4383 | CCAUCCAUCAUCCUCGUAA | 4384 |
| UACGAGGAUGAUGGAUGGG | 4385 | CCCAUCCAUCAUCCUCGUA | 4386 |
| ACGAGGAUGAUGGAUGGGA | 4387 | UCCCAUCCAUCAUCCUCGU | 4388 |
| CGAGGAUGAUGGAUGGGAC | 4389 | GUCCCAUCCAUCAUCCUCG | 4390 |
| GAGGAUGAUGGAUGGGACU | 4391 | AGUCCCAUCCAUCAUCCUC | 4392 |
| AGGAUGAUGGAUGGGACUC | 4393 | GAGUCCCAUCCAUCAUCCU | 4394 |
| GGAUGAUGGAUGGGACUCU | 4395 | AGAGUCCCAUCCAUCAUCC | 4396 |
| GAUGAUGGAUGGGACUCUU | 4397 | AAGAGUCCCAUCCAUCAUC | 4398 |
| AUGAUGGAUGGGACUCUUU | 4399 | AAAGAGUCCCAUCCAUCAU | 4400 |

TABLE 6-continued

| Sense Sequence | SEQ ID NO: | Antisense Sequence | SEQ ID NO: |
|---|---|---|---|
| UGAUGGAUGGGACUCUUUG | 4401 | CAAAGAGUCCCAUCCAUCA | 4402 |
| GAUGGAUGGGACUCUUUGA | 4403 | UCAAAGAGUCCCAUCCAUC | 4404 |
| AUGGAUGGGACUCUUUGAC | 4405 | GUCAAAGAGUCCCAUCCAU | 4406 |
| UGGAUGGGACUCUUUGACU | 4407 | AGUCAAAGAGUCCCAUCCA | 4408 |
| GGAUGGGACUCUUUGACUG | 4409 | CAGUCAAAGAGUCCCAUCC | 4410 |
| GAUGGGACUCUUUGACUGG | 4411 | CCAGUCAAAGAGUCCCAUC | 4412 |
| AUGGGACUCUUUGACUGGC | 4413 | GCCAGUCAAAGAGUCCCAU | 4414 |
| UGGGACUCUUUGACUGGCC | 4415 | GGCCAGUCAAAGAGUCCCA | 4416 |
| GGGACUCUUUGACUGGCCU | 4417 | AGGCCAGUCAAAGAGUCCC | 4418 |
| GGACUCUUUGACUGGCCUU | 4419 | AAGGCCAGUCAAAGAGUCC | 4420 |
| GACUCUUUGACUGGCCUUU | 4421 | AAAGGCCAGUCAAAGAGUC | 4422 |
| ACUCUUUGACUGGCCUUUU | 4423 | AAAAGGCCAGUCAAAGAGU | 4424 |
| CUCUUUGACUGGCCUUUUA | 4425 | UAAAAGGCCAGUCAAAGAG | 4426 |
| UCUUUGACUGGCCUUUUAA | 4427 | UUAAAAGGCCAGUCAAAGA | 4428 |
| CUUUGACUGGCCUUUUAAA | 4429 | UUUAAAAGGCCAGUCAAAG | 4430 |
| UUUGACUGGCCUUUUAAAA | 4431 | UUUUAAAAGGCCAGUCAAA | 4432 |
| UUGACUGGCCUUUUAAAAG | 4433 | CUUUUAAAAGGCCAGUCAA | 4434 |
| CACAGCAGUCAGCAGUAAU | 4435 | AUUACUGCUGACUGCUGUG | 4436 |
| ACAGCAGUCAGCAGUAAUG | 4437 | CAUUACUGCUGACUGCUGU | 4438 |
| CAGCAGUCAGCAGUAAUGA | 4439 | UCAUUACUGCUGACUGCUG | 4440 |
| AGCAGUCAGCAGUAAUGAU | 4441 | AUCAUUACUGCUGACUGCU | 4442 |
| GCAGUCAGCAGUAAUGAUC | 4443 | GAUCAUUACUGCUGACUGC | 4444 |
| CAGUCAGCAGUAAUGAUCG | 4445 | CGAUCAUUACUGCUGACUG | 4446 |
| AGUCAGCAGUAAUGAUCGG | 4447 | CCGAUCAUUACUGCUGACU | 4448 |
| GUCAGCAGUAAUGAUCGGG | 4449 | CCCGAUCAUUACUGCUGAC | 4450 |
| UCAGCAGUAAUGAUCGGGC | 4451 | GCCCGAUCAUUACUGCUGA | 4452 |
| AGCAUUGGGAAGCUGUCCA | 4453 | UGGACAGCUUCCCAAUGCU | 4454 |
| GCAUUGGGAAGCUGUCCAU | 4455 | AUGGACAGCUUCCCAAUGC | 4456 |
| CAUUGGGAAGCUGUCCAUU | 4457 | AAUGGACAGCUUCCCAAUG | 4458 |
| AUUGGGAAGCUGUCCAUUG | 4459 | CAAUGGACAGCUUCCCAAU | 4460 |
| UUGGGAAGCUGUCCAUUGA | 4461 | UCAAUGGACAGCUUCCCAA | 4462 |
| UGGGAAGCUGUCCAUUGAA | 4463 | UUCAAUGGACAGCUUCCCA | 4464 |
| AAAAGGCCUUGGAUUUAUC | 4465 | GAUAAAUCCAAGGCCUUUU | 4466 |
| AAAGGCCUUGGAUUUAUCC | 4467 | GGAUAAAUCCAAGGCCUUU | 4468 |
| AAGGCCUUGGAUUUAUCCC | 4469 | GGGAUAAAUCCAAGGCCUU | 4470 |
| CCUUGGAUUUAUCCCUGUA | 4471 | UACAGGGAUAAAUCCAAGG | 4472 |
| CUUGGAUUUAUCCCUGUAC | 4473 | GUACAGGGAUAAAUCCAAG | 4474 |
| UUGGAUUUAUCCCUGUACU | 4475 | AGUACAGGGAUAAAUCCAA | 4476 |
| UGGAUUUAUCCCUGUACUU | 4477 | AAGUACAGGGAUAAAUCCA | 4478 |

TABLE 6-continued

| Sense Sequence | SEQ ID NO: | Antisense Sequence | SEQ ID NO: |
|---|---|---|---|
| GGAUUUAUCCCUGUACUUG | 4479 | CAAGUACAGGGAUAAAUCC | 4480 |
| AUUAUGCCCGUGUUUCAAG | 4481 | CUUGAAACACGGGCAUAAU | 4482 |
| UUAUGCCCGUGUUUCAAGG | 4483 | CCUUGAAACACGGGCAUAA | 4484 |
| UAUGCCCGUGUUUCAAGGU | 4485 | ACCUUGAAACACGGGCAUA | 4486 |
| AUGCCCGUGUUUCAAGGUU | 4487 | AACCUUGAAACACGGGCAU | 4488 |
| UGCCCGUGUUUCAAGGUUU | 4489 | AAACCUUGAAACACGGGCA | 4490 |
| CAAGGUUUGAAUGAGCUGA | 4491 | UCAGCUCAUUCAAACCUUG | 4492 |
| CUGAUUCCUAUGUAUAAGU | 4493 | ACUUAUACAUAGGAAUCAG | 4494 |
| CCUAUGUAUAAGUUAAUGG | 4495 | CCAUUAACUUAUACAUAGG | 4496 |
| AACUCAAUUCAAGGCCUUC | 4497 | GAAGGCCUUGAAUUGAGUU | 4498 |
| ACUCAAUUCAAGGCCUUCC | 4499 | GGAAGGCCUUGAAUUGAGU | 4500 |
| CUCAAUUCAAGGCCUUCCU | 4501 | AGGAAGGCCUUGAAUUGAG | 4502 |
| UCAAUUCAAGGCCUUCCUC | 4503 | GAGGAAGGCCUUGAAUUGA | 4504 |
| UUCAAGGCCUUCCUCAUCA | 4505 | UGAUGAGGAAGGCCUUGAA | 4506 |
| UCCUCAUCAGGCUGCUAAG | 4507 | CUUAGCAGCCUGAUGAGGA | 4508 |
| CCUCAUCAGGCUGCUAAGG | 4509 | CCUUAGCAGCCUGAUGAGG | 4510 |
| UCAGGCUGCUAAGGGACCU | 4511 | AGGUCCCUUAGCAGCCUGA | 4512 |
| CAGGCUGCUAAGGGACCUC | 4513 | GAGGUCCCUUAGCAGCCUG | 4514 |
| AGGCUGCUAAGGGACCUCA | 4515 | UGAGGUCCCUUAGCAGCCU | 4516 |
| GGCUGCUAAGGGACCUCAU | 4517 | AUGAGGUCCCUUAGCAGCC | 4518 |
| GCUGCUAAGGGACCUCAUU | 4519 | AAUGAGGUCCCUUAGCAGC | 4520 |
| CUGCUAAGGGACCUCAUUG | 4521 | CAAUGAGGUCCCUUAGCAG | 4522 |
| UGCUAAGGGACCUCAUUGA | 4523 | UCAAUGAGGUCCCUUAGCA | 4524 |
| GCUAAGGGACCUCAUUGAU | 4525 | AUCAAUGAGGUCCCUUAGC | 4526 |
| CUAAGGGACCUCAUUGAUA | 4527 | UAUCAAUGAGGUCCCUUAG | 4528 |
| AAGGGACCUCAUUGAUAAG | 4529 | CUUAUCAAUGAGGUCCCUU | 4530 |
| AGGGACCUCAUUGAUAAGC | 4531 | GCUUAUCAAUGAGGUCCCU | 4532 |
| GGGACCUCAUUGAUAAGCA | 4533 | UGCUUAUCAAUGAGGUCCC | 4534 |
| GGACCUCAUUGAUAAGCAG | 4535 | CUGCUUAUCAAUGAGGUCC | 4536 |
| GACCUCAUUGAUAAGCAGA | 4537 | UCUGCUUAUCAAUGAGGUC | 4538 |
| AUUGAUAAGCAGACAUGGA | 4539 | UCCAUGUCUGCUUAUCAAU | 4540 |
| GAUAAGCAGACAUGGACAG | 4541 | CUGUCCAUGUCUGCUUAUC | 4542 |
| AUAAGCAGACAUGGACAGA | 4543 | UCUGUCCAUGUCUGCUUAU | 4544 |
| UAAGCAGACAUGGACAGAC | 4545 | GUCUGUCCAUGUCUGCUUA | 4546 |
| AGCAGACAUGGACAGACGA | 4547 | UCGUCUGUCCAUGUCUGCU | 4548 |
| GCAGACAUGGACAGACGAG | 4549 | CUCGUCUGUCCAUGUCUGC | 4550 |
| CAGACAUGGACAGACGAGG | 4551 | CCUCGUCUGUCCAUGUCUG | 4552 |
| AGACAUGGACAGACGAGGG | 4553 | CCCUCGUCUGUCCAUGUCU | 4554 |
| GACAUGGACAGACGAGGGC | 4555 | GCCCUCGUCUGUCCAUGUC | 4556 |

TABLE 6-continued

| Sense Sequence | SEQ ID NO: | Antisense Sequence | SEQ ID NO: |
|---|---|---|---|
| UGGACAGACGAGGGCUCAG | 4557 | CUGAGCCCUCGUCUGUCCA | 4558 |
| GACAGACGAGGGCUCAGUC | 4559 | GACUGAGCCCUCGUCUGUC | 4560 |
| GACGAGGGCUCAGUCUCAG | 4561 | CUGAGACUGAGCCCUCGUC | 4562 |
| ACGAGGGCUCAGUCUCAGA | 4563 | UCUGAGACUGAGCCCUCGU | 4564 |
| AACUACUACUCCUCGCCUG | 4565 | CAGGCGAGGAGUAGUAGUU | 4566 |
| ACUACUACUCCUCGCCUGU | 4567 | ACAGGCGAGGAGUAGUAGU | 4568 |
| CUACUACUCCUCGCCUGUG | 4569 | CACAGGCGAGGAGUAGUAG | 4570 |
| UACUACUCCUCGCCUGUGU | 4571 | ACACAGGCGAGGAGUAGUA | 4572 |
| ACUACUCCUCGCCUGUGUG | 4573 | CACACAGGCGAGGAGUAGU | 4574 |
| CUACUCCUCGCCUGUGUGC | 4575 | GCACACAGGCGAGGAGUAG | 4576 |
| UACUCCUCGCCUGUGUGCA | 4577 | UGCACACAGGCGAGGAGUA | 4578 |
| ACUCCUCGCCUGUGUGCAC | 4579 | GUGCACACAGGCGAGGAGU | 4580 |
| UACAGAGGGCAGAAGGCUA | 4581 | UAGCCUUCUGCCCUCUGUA | 4582 |
| ACAGAGGGCAGAAGGCUAU | 4583 | AUAGCCUUCUGCCCUCUGU | 4584 |
| AGAGGGCAGAAGGCUAUUU | 4585 | AAAUAGCCUUCUGCCCUCU | 4586 |
| GAGGGCAGAAGGCUAUUUC | 4587 | GAAAUAGCCUUCUGCCCUC | 4588 |
| GCAGAAGGCUAUUUCAGAA | 4589 | UUCUGAAAUAGCCUUCUGC | 4590 |
| CCUGUCGACGUGACCUUGG | 4591 | CCAAGGUCACGUCGACAGG | 4592 |
| CUGUCGACGUGACCUUGGC | 4593 | GCCAAGGUCACGUCGACAG | 4594 |
| UGUCGACGUGACCUUGGCA | 4595 | UGCCAAGGUCACGUCGACA | 4596 |
| GUCGACGUGACCUUGGCAG | 4597 | CUGCCAAGGUCACGUCGAC | 4598 |
| UCGACGUGACCUUGGCAGU | 4599 | ACUGCCAAGGUCACGUCGA | 4600 |
| UGACCUUGGCAGUGUUUGC | 4601 | GCAAACACUGCCAAGGUCA | 4602 |
| CCUUGGCAGUGUUUGCUGU | 4603 | ACAGCAAACACUGCCAAGG | 4604 |
| UUGGCAGUGUUUGCUGUGG | 4605 | CCACAGCAAACACUGCCAA | 4606 |
| UGGCAGUGUUUGCUGUGGG | 4607 | CCCACAGCAAACACUGCCA | 4608 |
| CAGAGCACAGAAGGCUGGG | 4609 | CCCAGCCUUCUGUGCUCUG | 4610 |
| AGAGCACAGAAGGCUGGGA | 4611 | UCCCAGCCUUCUGUGCUCU | 4612 |
| GAGCACAGAAGGCUGGGAU | 4613 | AUCCCAGCCUUCUGUGCUC | 4614 |
| AGCACAGAAGGCUGGGAUU | 4615 | AAUCCCAGCCUUCUGUGCU | 4616 |
| GCACAGAAGGCUGGGAUUU | 4617 | AAAUCCCAGCCUUCUGUGC | 4618 |
| ACAGAAGGCUGGGAUUUUC | 4619 | GAAAAUCCCAGCCUUCUGU | 4620 |
| AGUUUUCUUUGUCCAGUAC | 4621 | GUACUGGACAAAGAAAACU | 4622 |
| GUUUUCUUUGUCCAGUACU | 4623 | AGUACUGGACAAAGAAAAC | 4624 |
| UUUUCUUUGUCCAGUACUG | 4625 | CAGUACUGGACAAAGAAAA | 4626 |
| UUUCUUUGUCCAGUACUGA | 4627 | UCAGUACUGGACAAAGAAA | 4628 |
| UUCUUUGUCCAGUACUGAG | 4629 | CUCAGUACUGGACAAAGAA | 4630 |
| AAAAGCUUCAAUGGCUACU | 4631 | AGUAGCCAUUGAAGCUUUU | 4632 |
| AAAGCUUCAAUGGCUACUA | 4633 | UAGUAGCCAUUGAAGCUUU | 4634 |

TABLE 6-continued

| Sense Sequence | SEQ ID NO: | Antisense Sequence | SEQ ID NO: |
|---|---|---|---|
| CUUCAAUGGCUACUAGAUG | 4635 | CAUCUAGUAGCCAUUGAAG | 4636 |
| UUCAAUGGCUACUAGAUGA | 4637 | UCAUCUAGUAGCCAUUGAA | 4638 |
| UCAAUGGCUACUAGAUGAA | 4639 | UUCAUCUAGUAGCCAUUGA | 4640 |
| CAAAUUCUUACACUCAUUG | 4641 | CAAUGAGUGUAAGAAUUUG | 4642 |
| AAAUUCUUACACUCAUUGG | 4643 | CCAAUGAGUGUAAGAAUUU | 4644 |
| AAUUCUUACACUCAUUGGC | 4645 | GCCAAUGAGUGUAAGAAUU | 4646 |
| AUUCUUACACUCAUUGGCA | 4647 | UGCCAAUGAGUGUAAGAAU | 4648 |
| UUCUUACACUCAUUGGCAG | 4649 | CUGCCAAUGAGUGUAAGAA | 4650 |
| UCUUACACUCAUUGGCAGG | 4651 | CCUGCCAAUGAGUGUAAGA | 4652 |
| CUUACACUCAUUGGCAGGA | 4653 | UCCUGCCAAUGAGUGUAAG | 4654 |
| UUACACUCAUUGGCAGGAA | 4655 | UUCCUGCCAAUGAGUGUAA | 4656 |
| UGGCCUGGCAAUUUCUGAG | 4657 | CUCAGAAAUUGCCAGGCCA | 4658 |
| GGCCUGGCAAUUUCUGAGG | 4659 | CCUCAGAAAUUGCCAGGCC | 4660 |
| GCCUGGCAAUUUCUGAGGA | 4661 | UCCUCAGAAAUUGCCAGGC | 4662 |
| ACUUGGCUCAUCUUCCAUA | 4663 | UAUGGAAGAUGAGCCAAGU | 4664 |
| CUUGGCUCAUCUUCCAUAG | 4665 | CUAUGGAAGAUGAGCCAAG | 4666 |
| GCUCAUCUUCCAUAGCCCA | 4667 | UGGGCUAUGGAAGAUGAGC | 4668 |
| CUCAUCUUCCAUAGCCCAC | 4669 | GUGGGCUAUGGAAGAUGAG | 4670 |
| CAUAGCCCACAUGGUAAUG | 4671 | CAUUACCAUGUGGGCUAUG | 4672 |
| AUAGCCCACAUGGUAAUGG | 4673 | CCAUUACCAUGUGGGCUAU | 4674 |
| CCACAUGGUAAUGGGUACA | 4675 | UGUACCCAUUACCAUGUGG | 4676 |
| ACACGGCUUGAAGAGGUAA | 4677 | UUACCUCUUCAAGCCGUGU | 4678 |
| CACGGCUUGAAGAGGUAAA | 4679 | UUUACCUCUUCAAGCCGUG | 4680 |
| ACGGCUUGAAGAGGUAAAA | 4681 | UUUUACCUCUUCAAGCCGU | 4682 |
| CGGCUUGAAGAGGUAAAAG | 4683 | CUUUUACCUCUUCAAGCCG | 4684 |
| GGCUUGAAGAGGUAAAAGG | 4685 | CCUUUUACCUCUUCAAGCC | 4686 |
| GCUUGAAGAGGUAAAAGGA | 4687 | UCCUUUUACCUCUUCAAGC | 4688 |
| GAAGAGGUAAAAGGAUUCU | 4689 | AGAAUCCUUUUACCUCUUC | 4690 |
| AGAGGUAAAAGGAUUCUUC | 4691 | GAAGAAUCCUUUUACCUCU | 4692 |
| GUAAAAGGAUUCUUCAGCU | 4693 | AGCUGAAGAAUCCUUUUAC | 4694 |
| UAAAAGGAUUCUUCAGCUC | 4695 | GAGCUGAAGAAUCCUUUUA | 4696 |
| AAAAGGAUUCUUCAGCUCU | 4697 | AGAGCUGAAGAAUCCUUUU | 4698 |
| AAAGGAUUCUUCAGCUCUU | 4699 | AAGAGCUGAAGAAUCCUUU | 4700 |
| AAGGAUUCUUCAGCUCUUU | 4701 | AAAGAGCUGAAGAAUCCUU | 4702 |
| AGGAUUCUUCAGCUCUUUG | 4703 | CAAAGAGCUGAAGAAUCCU | 4704 |
| GGAUUCUUCAGCUCUUUGA | 4705 | UCAAAGAGCUGAAGAAUCC | 4706 |
| AAAAUGGUUCUCAGCUCCG | 4707 | CGGAGCUGAGAACCAUUUU | 4708 |
| AAAUGGUUCUCAGCUCCGU | 4709 | ACGGAGCUGAGAACCAUUU | 4710 |
| GGUUCUCAGCUCCGUUGUG | 4711 | CACAACGGAGCUGAGAACC | 4712 |

TABLE 6-continued

| Sense Sequence | SEQ ID NO: | Antisense Sequence | SEQ ID NO: |
|---|---|---|---|
| GUUCUCAGCUCCGUUGUGU | 4713 | ACACAACGGAGCUGAGAAC | 4714 |
| UUCUCAGCUCCGUUGUGUC | 4715 | GACACAACGGAGCUGAGAA | 4716 |
| UCUCAGCUCCGUUGUGUCC | 4717 | GGACACAACGGAGCUGAGA | 4718 |
| CUCAGCUCCGUUGUGUCCA | 4719 | UGGACACAACGGAGCUGAG | 4720 |
| UCAGCUCCGUUGUGUCCAA | 4721 | UUGGACACAACGGAGCUGA | 4722 |
| AUCGGUUGGAUGGAUAAGA | 4723 | UCUUAUCCAUCCAACCGAU | 4724 |
| UCGGUUGGAUGGAUAAGAA | 4725 | UUCUUAUCCAUCCAACCGA | 4726 |
| CGGUUGGAUGGAUAAGAAU | 4727 | AUUCUUAUCCAUCCAACCG | 4728 |
| GGUUGGAUGGAUAAGAAUU | 4729 | AAUUCUUAUCCAUCCAACC | 4730 |
| GGAUGGAUAAGAAUUUUGA | 4731 | UCAAAAUUCUUAUCCAUCC | 4732 |
| GAUAAAAUCAGAGUGUGGC | 4733 | GCCACACUCUGAUUUUAUC | 4734 |
| UAAAAUCAGAGUGUGGCUG | 4735 | CAGCCACACUCUGAUUUUA | 4736 |
| AAAAUCAGAGUGUGGCUGC | 4737 | GCAGCCACACUCUGAUUUU | 4738 |
| AAAUCAGAGUGUGGCUGCA | 4739 | UGCAGCCACACUCUGAUUU | 4740 |
| AAUCAGAGUGUGGCUGCAA | 4741 | UUGCAGCCACACUCUGAUU | 4742 |
| UCAGAGUGUGGCUGCAAAG | 4743 | CUUUGCAGCCACACUCUGA | 4744 |
| CAGAGUGUGGCUGCAAAGU | 4745 | ACUUUGCAGCCACACUCUG | 4746 |
| AGAGUGUGGCUGCAAAGUG | 4747 | CACUUUGCAGCCACACUCU | 4748 |
| GAGUGUGGCUGCAAAGUGA | 4749 | UCACUUUGCAGCCACACUC | 4750 |
| AGUGUGGCUGCAAAGUGAA | 4751 | UUCACUUUGCAGCCACACU | 4752 |
| ACAUGAUCCUGAAGCUGAC | 4753 | GUCAGCUUCAGGAUCAUGU | 4754 |
| CAUGAUCCUGAAGCUGACG | 4755 | CGUCAGCUUCAGGAUCAUG | 4756 |
| AUGAUCCUGAAGCUGACGC | 4757 | GCGUCAGCUUCAGGAUCAU | 4758 |
| UGAUCCUGAAGCUGACGCA | 4759 | UGCGUCAGCUUCAGGAUCA | 4760 |
| GAUCCUGAAGCUGACGCAA | 4761 | UUGCGUCAGCUUCAGGAUC | 4762 |
| AUCCUGAAGCUGACGCAAC | 4763 | GUUGCGUCAGCUUCAGGAU | 4764 |
| AAAAUCCAUCAGAAUCUCA | 4765 | UGAGAUUCUGAUGGAUUUU | 4766 |
| CACUAAAUAUGCUUUGAUG | 4767 | CAUCAAAGCAUAUUUAGUG | 4768 |
| ACUAAAUAUGCUUUGAUGC | 4769 | GCAUCAAAGCAUAUUUAGU | 4770 |
| CUAAAUAUGCUUUGAUGCU | 4771 | AGCAUCAAAGCAUAUUUAG | 4772 |
| AAAUAUGCUUUGAUGCUAC | 4773 | GUAGCAUCAAAGCAUAUUU | 4774 |
| AAUAUGCUUUGAUGCUACA | 4775 | UGUAGCAUCAAAGCAUAUU | 4776 |
| CUUCGCUAAAGUUACUUCA | 4777 | UGAAGUAACUUUAGCGAAG | 4778 |
| UUCGCUAAAGUUACUUCAU | 4779 | AUGAAGUAACUUUAGCGAA | 4780 |
| UCGCUAAAGUUACUUCAUC | 4781 | GAUGAAGUAACUUUAGCGA | 4782 |
| CGCUAAAGUUACUUCAUCU | 4783 | AGAUGAAGUAACUUUAGCG | 4784 |
| UACUUCAUCUCCAUCUAGC | 4785 | GCUAGAUGGAGAUGAAGUA | 4786 |
| ACUUCAUCUCCAUCUAGCA | 4787 | UGCUAGAUGGAGAUGAAGU | 4788 |
| CUUCAUCUCCAUCUAGCAA | 4789 | UUGCUAGAUGGAGAUGAAG | 4790 |

TABLE 6-continued

| Sense Sequence | SEQ ID NO: | Antisense Sequence | SEQ ID NO: |
|---|---|---|---|
| UUCAUCUCCAUCUAGCAAA | 4791 | UUUGCUAGAUGGAGAUGAA | 4792 |
| UCAUCUCCAUCUAGCAAAU | 4793 | AUUUGCUAGAUGGAGAUGA | 4794 |
| CAUCUCCAUCUAGCAAAUG | 4795 | CAUUUGCUAGAUGGAGAUG | 4796 |
| UCCAUCUAGCAAAUGAGGC | 4797 | GCCUCAUUUGCUAGAUGGA | 4798 |
| CCAUCUAGCAAAUGAGGCA | 4799 | UGCCUCAUUUGCUAGAUGG | 4800 |
| CAUCUAGCAAAUGAGGCAC | 4801 | GUGCCUCAUUUGCUAGAUG | 4802 |
| GGCACUGUUCUCAACCAAA | 4803 | UUUGGUUGAGAACAGUGCC | 4804 |
| CUGUUCUCAACCAAAGGAG | 4805 | CUCCUUUGGUUGAGAACAG | 4806 |
| CCCUUUAUAAUUUGAUGUG | 4807 | CACAUCAAAUUAUAAAGGG | 4808 |
| CCUUUAUAAUUUGAUGUGC | 4809 | GCACAUCAAAUUAUAAAGG | 4810 |
| AUAAUUUGAUGUGCUGUGG | 4811 | CCACAGCACAUCAAAUUAU | 4812 |
| UUUGAUGUGCUGUGGUCUC | 4813 | GAGACCACAGCACAUCAAA | 4814 |
| AUGUGCUGUGGUCUCCUUG | 4815 | CAAGGAGACCACAGCACAU | 4816 |
| UGUGCUGUGGUCUCCUUGG | 4817 | CCAAGGAGACCACAGCACA | 4818 |
| GUGCUGUGGUCUCCUUGGU | 4819 | ACCAAGGAGACCACAGCAC | 4820 |
| UGCUGUGGUCUCCUUGGUA | 4821 | UACCAAGGAGACCACAGCA | 4822 |
| GCUGUGGUCUCCUUGGUAA | 4823 | UUACCAAGGAGACCACAGC | 4824 |
| CUGUGGUCUCCUUGGUAAU | 4825 | AUUACCAAGGAGACCACAG | 4826 |
| UGUGGUCUCCUUGGUAAUG | 4827 | CAUUACCAAGGAGACCACA | 4828 |
| UAAUUUGGUAUUGCACAGG | 4829 | CCUGUGCAAUACCAAAUUA | 4830 |
| AAUUUGGUAUUGCACAGGU | 4831 | ACCUGUGCAAUACCAAAUU | 4832 |
| AUUUGGUAUUGCACAGGUG | 4833 | CACCUGUGCAAUACCAAAU | 4834 |
| UUUGGUAUUGCACAGGUGA | 4835 | UCACCUGUGCAAUACCAAA | 4836 |
| UUGGUAUUGCACAGGUGAU | 4837 | AUCACCUGUGCAAUACCAA | 4838 |
| UGGUAUUGCACAGGUGAUU | 4839 | AAUCACCUGUGCAAUACCA | 4840 |
| GGUAUUGCACAGGUGAUUA | 4841 | UAAUCACCUGUGCAAUACC | 4842 |
| GUAUUGCACAGGUGAUUAG | 4843 | CUAAUCACCUGUGCAAUAC | 4844 |
| UAUUGCACAGGUGAUUAGU | 4845 | ACUAAUCACCUGUGCAAUA | 4846 |
| AUUGCACAGGUGAUUAGUC | 4847 | GACUAAUCACCUGUGCAAU | 4848 |
| UUGCACAGGUGAUUAGUCA | 4849 | UGACUAAUCACCUGUGCAA | 4850 |
| UGCACAGGUGAUUAGUCAA | 4851 | UUGACUAAUCACCUGUGCA | 4852 |
| GCACAGGUGAUUAGUCAAG | 4853 | CUUGACUAAUCACCUGUGC | 4854 |
| CACAGGUGAUUAGUCAAGG | 4855 | CCUUGACUAAUCACCUGUG | 4856 |
| ACAGGUGAUUAGUCAAGGA | 4857 | UCCUUGACUAAUCACCUGU | 4858 |
| CAGGUGAUUAGUCAAGGAA | 4859 | UUCCUUGACUAAUCACCUG | 4860 |
| AGGUGAUUAGUCAAGGAAG | 4861 | CUUCCUUGACUAAUCACCU | 4862 |
| GGUGAUUAGUCAAGGAAGU | 4863 | ACUUCCUUGACUAAUCACC | 4864 |
| GUGAUUAGUCAAGGAAGUC | 4865 | GACUUCCUUGACUAAUCAC | 4866 |
| UGAUUAGUCAAGGAAGUCU | 4867 | AGACUUCCUUGACUAAUCA | 4868 |

143
144

TABLE 6-continued

| Sense Sequence | SEQ ID NO: | Antisense Sequence | SEQ ID NO: |
|---|---|---|---|
| GAUUAGUCAAGGAAGUCUG | 4869 | CAGACUUCCUUGACUAAUC | 4870 |
| UUAGUCAAGGAAGUCUGGA | 4871 | UCCAGACUUCCUUGACUAA | 4872 |
| UAGUCAAGGAAGUCUGGAA | 4873 | UUCCAGACUUCCUUGACUA | 4874 |
| CCCACAGCCUUGCCUCACA | 4875 | UGUGAGGCAAGGCUGUGGG | 4876 |
| CCACAGCCUUGCCUCACAG | 4877 | CUGUGAGGCAAGGCUGUGG | 4878 |
| CACAGCCUUGCCUCACAGC | 4879 | GCUGUGAGGCAAGGCUGUG | 4880 |
| ACAGCCUUGCCUCACAGCA | 4881 | UGCUGUGAGGCAAGGCUGU | 4882 |
| CAGCCUUGCCUCACAGCAU | 4883 | AUGCUGUGAGGCAAGGCUG | 4884 |
| AGCCUUGCCUCACAGCAUG | 4885 | CAUGCUGUGAGGCAAGGCU | 4886 |
| GCCUUGCCUCACAGCAUGU | 4887 | ACAUGCUGUGAGGCAAGGC | 4888 |
| CCUUGCCUCACAGCAUGUA | 4889 | UACAUGCUGUGAGGCAAGG | 4890 |
| CUUGCCUCACAGCAUGUAA | 4891 | UUACAUGCUGUGAGGCAAG | 4892 |
| UUGCCUCACAGCAUGUAAA | 4893 | UUUACAUGCUGUGAGGCAA | 4894 |
| UGCCUCACAGCAUGUAAAU | 4895 | AUUUACAUGCUGUGAGGCA | 4896 |
| GCCUCACAGCAUGUAAAUA | 4897 | UAUUUACAUGCUGUGAGGC | 4898 |
| CCUCACAGCAUGUAAAUAA | 4899 | UUAUUUACAUGCUGUGAGG | 4900 |
| CAAUAUUGAUGCUGAGGUU | 4901 | AACCUCAGCAUCAAUAUUG | 4902 |
| AAUAUUGAUGCUGAGGUUC | 4903 | GAACCUCAGCAUCAAUAUU | 4904 |
| AUAUUGAUGCUGAGGUUCU | 4905 | AGAACCUCAGCAUCAAUAU | 4906 |
| UAUUGAUGCUGAGGUUCUU | 4907 | AAGAACCUCAGCAUCAAUA | 4908 |
| AUUGAUGCUGAGGUUCUUC | 4909 | GAAGAACCUCAGCAUCAAU | 4910 |
| UUGAUGCUGAGGUUCUUCU | 4911 | AGAAGAACCUCAGCAUCAA | 4912 |
| UGAUGCUGAGGUUCUUCUA | 4913 | UAGAAGAACCUCAGCAUCA | 4914 |
| GAGGUUCUUCUACUGCUAG | 4915 | CUAGCAGUAGAAGAACCUC | 4916 |
| AGGUUCUUCUACUGCUAGU | 4917 | ACUAGCAGUAGAAGAACCU | 4918 |
| UUUUACUGGUGUGAAUUGG | 4919 | CCAAUUCACACCAGUAAAA | 4920 |
| UUUACUGGUGUGAAUUGGG | 4921 | CCCAAUUCACACCAGUAAA | 4922 |
| UUACUGGUGUGAAUUGGGA | 4923 | UCCCAAUUCACACCAGUAA | 4924 |
| UACUGGUGUGAAUUGGGAA | 4925 | UUCCCAAUUCACACCAGUA | 4926 |
| CUGGUGUGAAUUGGGAAGA | 4927 | UCUUCCCAAUUCACACCAG | 4928 |
| UGGUGUGAAUUGGGAAGAA | 4929 | UUCUUCCCAAUUCACACCA | 4930 |
| UGCUAUUCCAUGACGUUUG | 4931 | CAAACGUCAUGGAAUAGCA | 4932 |
| GCUAUUCCAUGACGUUUGU | 4933 | ACAAACGUCAUGGAAUAGC | 4934 |
| CUAUUCCAUGACGUUUGUA | 4935 | UACAAACGUCAUGGAAUAG | 4936 |
| UAUUCCAUGACGUUUGUAA | 4937 | UUACAAACGUCAUGGAAUA | 4938 |
| AUUCCAUGACGUUUGUAAA | 4939 | UUUACAAACGUCAUGGAAU | 4940 |
| UUCCAUGACGUUUGUAAAA | 4941 | UUUUACAAACGUCAUGGAA | 4942 |
| UCCAUGACGUUUGUAAAAU | 4943 | AUUUUACAAACGUCAUGGA | 4944 |
| CCAUGACGUUUGUAAAAUG | 4945 | CAUUUUACAAACGUCAUGG | 4946 |

TABLE 6-continued

| Sense Sequence | SEQ ID NO: | Antisense Sequence | SEQ ID NO: |
|---|---|---|---|
| CAUGACGUUUGUAAAAUGU | 4947 | ACAUUUUACAAACGUCAUG | 4948 |
| CUUGAGGUUAAAUAAUGGG | 4949 | CCCAUUAUUUAACCUCAAG | 4950 |
| UUGAGGUUAAAUAAUGGGU | 4951 | ACCCAUUAUUUAACCUCAA | 4952 |
| UGAGGUUAAAUAAUGGGUA | 4953 | UACCCAUUAUUUAACCUCA | 4954 |
| GAGGUUAAAUAAUGGGUAG | 4955 | CUACCCAUUAUUUAACCUC | 4956 |
| AGGUUAAAUAAUGGGUAGU | 4957 | ACUACCCAUUAUUUAACCU | 4958 |
| GGUUAAAUAAUGGGUAGUA | 4959 | UACUACCCAUUAUUUAACC | 4960 |
| UAAUAUUAAGGUCCUUGAC | 4961 | GUCAAGGACCUUAAUAUUA | 4962 |
| AAUAUUAAGGUCCUUGACU | 4963 | AGUCAAGGACCUUAAUAUU | 4964 |
| AUAUUAAGGUCCUUGACUA | 4965 | UAGUCAAGGACCUUAAUAU | 4966 |
| UAUUAAGGUCCUUGACUAU | 4967 | AUAGUCAAGGACCUUAAUA | 4968 |
| AUUAAGGUCCUUGACUAUG | 4969 | CAUAGUCAAGGACCUUAAU | 4970 |
| AGGUCCUUGACUAUGUGUA | 4971 | UACACAUAGUCAAGGACCU | 4972 |
| GGUCCUUGACUAUGUGUAC | 4973 | GUACACAUAGUCAAGGACC | 4974 |
| UAAUCUCUGCCAUCUCGCU | 4975 | AGCGAGAUGGCAGAGAUUA | 4976 |
| AUCUCUGCCAUCUCGCUAA | 4977 | UUAGCGAGAUGGCAGAGAU | 4978 |
| UCUCUGCCAUCUCGCUAAA | 4979 | UUUAGCGAGAUGGCAGAGA | 4980 |
| CUCUGCCAUCUCGCUAAAU | 4981 | AUUUAGCGAGAUGGCAGAG | 4982 |
| UCUGCCAUCUCGCUAAAUC | 4983 | GAUUUAGCGAGAUGGCAGA | 4984 |
| CUGCCAUCUCGCUAAAUCA | 4985 | UGAUUUAGCGAGAUGGCAG | 4986 |
| UGCCAUCUCGCUAAAUCAU | 4987 | AUGAUUUAGCGAGAUGGCA | 4988 |
| GCCAUCUCGCUAAAUCAUC | 4989 | GAUGAUUUAGCGAGAUGGC | 4990 |
| CCAUCUCGCUAAAUCAUCA | 4991 | UGAUGAUUUAGCGAGAUGG | 4992 |
| AGGUGCCUGAUCUUCCUAA | 4993 | UUAGGAAGAUCAGGCACCU | 4994 |
| GGUGCCUGAUCUUCCUAAU | 4995 | AUUAGGAAGAUCAGGCACC | 4996 |
| GUGCCUGAUCUUCCUAAUA | 4997 | UAUUAGGAAGAUCAGGCAC | 4998 |
| UGCCUGAUCUUCCUAAUAA | 4999 | UUAUUAGGAAGAUCAGGCA | 5000 |
| GAUCUUCCUAAUAAUUCUG | 5001 | CAGAAUUAUUAGGAAGAUC | 5002 |
| AUCUUCCUAAUAAUUCUGC | 5003 | GCAGAAUUAUUAGGAAGAU | 5004 |
| UCUUCCUAAUAAUUCUGCC | 5005 | GGCAGAAUUAUUAGGAAGA | 5006 |
| CUUCCUAAUAAUUCUGCCU | 5007 | AGGCAGAAUUAUUAGGAAG | 5008 |
| UUCCUAAUAAUUCUGCCUA | 5009 | UAGGCAGAAUUAUUAGGAA | 5010 |
| UCCUAAUAAUUCUGCCUAU | 5011 | AUAGGCAGAAUUAUUAGGA | 5012 |
| UUCUGCCUAUUUUCAUUUG | 5013 | CAAAUGAAAAUAGGCAGAA | 5014 |
| UCUGCCUAUUUUCAUUUGC | 5015 | GCAAAUGAAAAUAGGCAGA | 5016 |
| GCCUAUUUUCAUUUGCUUU | 5017 | AAAGCAAAUGAAAAUAGGC | 5018 |
| AUUUUCUUUCUAGUUGUGG | 5019 | CCACAACUAGAAAGAAAAU | 5020 |
| UUUUCUUUCUAGUUGUGGC | 5021 | GCCACAACUAGAAAGAAAA | 5022 |
| UUCUUUCUAGUUGUGGCUG | 5023 | CAGCCACAACUAGAAAGAA | 5024 |

TABLE 6-continued

| Sense Sequence | SEQ ID NO: | Antisense Sequence | SEQ ID NO: |
|---|---|---|---|
| UCUCCCAAAUAAGAUGUGC | 5025 | GCACAUCUUAUUUGGGAGA | 5026 |
| CUCCCAAAUAAGAUGUGCU | 5027 | AGCACAUCUUAUUUGGGAG | 5028 |
| AAGAUGUGCUGCUUACCGA | 5029 | UCGGUAAGCAGCACAUCUU | 5030 |
| AGAUGUGCUGCUUACCGAG | 5031 | CUCGGUAAGCAGCACAUCU | 5032 |
| GAUGUGCUGCUUACCGAGG | 5033 | CCUCGGUAAGCAGCACAUC | 5034 |
| AUGUGCUGCUUACCGAGGU | 5035 | ACCUCGGUAAGCAGCACAU | 5036 |
| UGUGCUGCUUACCGAGGUA | 5037 | UACCUCGGUAAGCAGCACA | 5038 |
| CUGCUUACCGAGGUAUCAC | 5039 | GUGAUACCUCGGUAAGCAG | 5040 |
| UGCUUACCGAGGUAUCACG | 5041 | CGUGAUACCUCGGUAAGCA | 5042 |
| GCUUACCGAGGUAUCACGG | 5043 | CCGUGAUACCUCGGUAAGC | 5044 |
| CUUACCGAGGUAUCACGGG | 5045 | CCCGUGAUACCUCGGUAAG | 5046 |
| GGCUCCAGCUUGGGUCGUU | 5047 | AACGACCCAAGCUGGAGCC | 5048 |
| GCUCCAGCUUGGGUCGUUG | 5049 | CAACGACCCAAGCUGGAGC | 5050 |
| CUCCAGCUUGGGUCGUUGA | 5051 | UCAACGACCCAAGCUGGAG | 5052 |
| UCCAGCUUGGGUCGUUGAA | 5053 | UUCAACGACCCAAGCUGGA | 5054 |
| CCAGCUUGGGUCGUUGAAG | 5055 | CUUCAACGACCCAAGCUGG | 5056 |
| CUUGGGUCGUUGAAGCUGG | 5057 | CCAGCUUCAACGACCCAAG | 5058 |
| UUGGGUCGUUGAAGCUGGG | 5059 | CCCAGCUUCAACGACCCAA | 5060 |
| CAGCAAGUUUAGCAUCUUC | 5061 | GAAGAUGCUAAACUUGCUG | 5062 |
| CAAUGCCAUCACUUAACUA | 5063 | UAGUUAAGUGAUGGCAUUG | 5064 |
| AUGCCAUCACUUAACUAUA | 5065 | UAUAGUUAAGUGAUGGCAU | 5066 |
| UGCCAUCACUUAACUAUAA | 5067 | UUAUAGUUAAGUGAUGGCA | 5068 |
| GCCAUCACUUAACUAUAAC | 5069 | GUUAUAGUUAAGUGAUGGC | 5070 |
| CCAUCACUUAACUAUAACU | 5071 | AGUUAUAGUUAAGUGAUGG | 5072 |
| CAUCACUUAACUAUAACUC | 5073 | GAGUUAUAGUUAAGUGAUG | 5074 |
| UCUCUUGACCAAAUAGACU | 5075 | AGUCUAUUUGGUCAAGAGA | 5076 |
| CUCUUGACCAAAUAGACUC | 5077 | GAGUCUAUUUGGUCAAGAG | 5078 |
| UCUUGACCAAAUAGACUCA | 5079 | UGAGUCUAUUUGGUCAAGA | 5080 |
| CUUGACCAAAUAGACUCAU | 5081 | AUGAGUCUAUUUGGUCAAG | 5082 |
| UUGACCAAAUAGACUCAUA | 5083 | UAUGAGUCUAUUUGGUCAA | 5084 |
| GACCAAAUAGACUCAUAAU | 5085 | AUUAUGAGUCUAUUUGGUC | 5086 |
| UUUCCUGUUGUACAUUUAG | 5087 | CUAAAUGUACAACAGGAAA | 5088 |
| GGUUAUUCAAAGUUUUCAG | 5089 | CUGAAAACUUUGAAUAACC | 5090 |
| UAUUCAAAGUUUUCAGCUC | 5091 | GAGCUGAAAACUUUGAAUA | 5092 |
| AUUCAAAGUUUUCAGCUCU | 5093 | AGAGCUGAAAACUUUGAAU | 5094 |
| UCAGCUCUUUUUAAAAUUGC | 5095 | GCAAUUUUAAAAGAGCUGA | 5096 |
| CAGCUCUUUUUAAAAUUGCU | 5097 | AGCAAUUUUAAAAGAGCUG | 5098 |
| AGCUCUUUUUAAAAUUGCUC | 5099 | GAGCAAUUUUAAAAGAGCU | 5100 |
| GCUCUUUUUAAAAUUGCUCU | 5101 | AGAGCAAUUUUAAAAGAGC | 5102 |

TABLE 6-continued

| Sense Sequence | SEQ ID NO: | Antisense Sequence | SEQ ID NO: |
|---|---|---|---|
| AAUUGCUCUGAAUAAGUUC | 5103 | GAACUUAUUCAGAGCAAUU | 5104 |
| AUUGCUCUGAAUAAGUUCU | 5105 | AGAACUUAUUCAGAGCAAU | 5106 |
| UUGCUCUGAAUAAGUUCUA | 5107 | UAGAACUUAUUCAGAGCAA | 5108 |
| UGCUCUGAAUAAGUUCUAG | 5109 | CUAGAACUUAUUCAGAGCA | 5110 |
| CUGAAUAAGUUCUAGUGAG | 5111 | CUCACUAGAACUUAUUCAG | 5112 |
| AUAAGUUCUAGUGAGUGAG | 5113 | CUCACUCACUAGAACUUAU | 5114 |
| UUCUAGUGAGUGAGUUAUG | 5115 | CAUAACUCACUCACUAGAA | 5116 |
| UCUAGUGAGUGAGUUAUGG | 5117 | CCAUAACUCACUCACUAGA | 5118 |
| UGAGUUAUGGUGCUGGCUA | 5119 | UAGCCAGCACCAUAACUCA | 5120 |
| GAGUUAUGGUGCUGGCUAU | 5121 | AUAGCCAGCACCAUAACUC | 5122 |
| AGUUAUGGUGCUGGCUAUA | 5123 | UAUAGCCAGCACCAUAACU | 5124 |
| GUUAUGGUGCUGGCUAUAU | 5125 | AUAUAGCCAGCACCAUAAC | 5126 |
| UUAUGGUGCUGGCUAUAUU | 5127 | AAUAUAGCCAGCACCAUAA | 5128 |
| UAUGGUGCUGGCUAUAUUU | 5129 | AAAUAUAGCCAGCACCAUA | 5130 |
| AUGGUGCUGGCUAUAUUUU | 5131 | AAAAUAUAGCCAGCACCAU | 5132 |
| UGGUGCUGGCUAUAUUUUG | 5133 | CAAAAUAUAGCCAGCACCA | 5134 |
| GGUGCUGGCUAUAUUUUGC | 5135 | GCAAAAUAUAGCCAGCACC | 5136 |
| UGCCCUCUCAAAUGUUGCU | 5137 | AGCAACAUUUGAGAGGGCA | 5138 |
| GCCCUCUCAAAUGUUGCUA | 5139 | UAGCAACAUUUGAGAGGGC | 5140 |
| CCCUCUCAAAUGUUGCUAG | 5141 | CUAGCAACAUUUGAGAGGG | 5142 |
| CCUCUCAAAUGUUGCUAGG | 5143 | CCUAGCAACAUUUGAGAGG | 5144 |
| CUCUCAAAUGUUGCUAGGA | 5145 | UCCUAGCAACAUUUGAGAG | 5146 |
| AAAUGUUGCUAGGAAUUCA | 5147 | UGAAUUCCUAGCAACAUUU | 5148 |
| AAUGUUGCUAGGAAUUCAU | 5149 | AUGAAUUCCUAGCAACAUU | 5150 |
| AUGUUGCUAGGAAUUCAUA | 5151 | UAUGAAUUCCUAGCAACAU | 5152 |
| UGUUGCUAGGAAUUCAUAC | 5153 | GUAUGAAUUCCUAGCAACA | 5154 |
| GUUGCUAGGAAUUCAUACU | 5155 | AGUAUGAAUUCCUAGCAAC | 5156 |
| UUGCUAGGAAUUCAUACUG | 5157 | CAGUAUGAAUUCCUAGCAA | 5158 |
| UGCUAGGAAUUCAUACUGC | 5159 | GCAGUAUGAAUUCCUAGCA | 5160 |
| AAAGCAAUGAAUAAGCAUG | 5161 | CAUGCUUAUUCAUUGCUUU | 5162 |
| AAGCAAUGAAUAAGCAUGC | 5163 | GCAUGCUUAUUCAUUGCUU | 5164 |
| AGCAAUGAAUAAGCAUGCC | 5165 | GGCAUGCUUAUUCAUUGCU | 5166 |
| GCAAUGAAUAAGCAUGCCU | 5167 | AGGCAUGCUUAUUCAUUGC | 5168 |
| AAUGAAUAAGCAUGCCUGU | 5169 | ACAGGCAUGCUUAUUCAUU | 5170 |
| AUGAAUAAGCAUGCCUGUU | 5171 | AACAGGCAUGCUUAUUCAU | 5172 |
| UGAAUAAGCAUGCCUGUUU | 5173 | AAACAGGCAUGCUUAUUCA | 5174 |
| GAAUAAGCAUGCCUGUUUU | 5175 | AAAACAGGCAUGCUUAUUC | 5176 |
| AUAAGCAUGCCUGUUUUCC | 5177 | GGAAAACAGGCAUGCUUAU | 5178 |
| AUGCCUGUUUUCCCAUGGC | 5179 | GCCAUGGGAAAACAGGCAU | 5180 |

TABLE 6-continued

| Sense Sequence | SEQ ID NO: | Antisense Sequence | SEQ ID NO: |
|---|---|---|---|
| UGCCUGUUUUCCCAUGGCC | 5181 | GGCCAUGGGAAAACAGGCA | 5182 |
| GCCUGUUUUCCCAUGGCCU | 5183 | AGGCCAUGGGAAAACAGGC | 5184 |
| CCUGUUUUCCCAUGGCCUU | 5185 | AAGGCCAUGGGAAAACAGG | 5186 |
| CUGUUUUCCCAUGGCCUUG | 5187 | CAAGGCCAUGGGAAAACAG | 5188 |
| UUCCCAUGGCCUUGCUUGC | 5189 | GCAAGCAAGGCCAUGGGAA | 5190 |
| GGCCUUGCUUGCCAGAAUU | 5191 | AAUUCUGGCAAGCAAGGCC | 5192 |
| UUGCUUGCCAGAAUUUGAC | 5193 | GUCAAAUUCUGGCAAGCAA | 5194 |
| UGCUUGCCAGAAUUUGACU | 5195 | AGUCAAAUUCUGGCAAGCA | 5196 |
| GCUUGCCAGAAUUUGACUU | 5197 | AAGUCAAAUUCUGGCAAGC | 5198 |
| CUUGCCAGAAUUUGACUUU | 5199 | AAAGUCAAAUUCUGGCAAG | 5200 |
| UUGCCAGAAUUUGACUUUU | 5201 | AAAAGUCAAAUUCUGGCAA | 5202 |
| GAUAUACUACUAUUGCUUG | 5203 | CAAGCAAUAGUAGUAUAUC | 5204 |
| AUAUUGUGGUAUACGGUGU | 5205 | ACACCGUAUACCACAAUAU | 5206 |
| UAUUGUGGUAUACGGUGUC | 5207 | GACACCGUAUACCACAAUA | 5208 |
| AUUGUGGUAUACGGUGUCA | 5209 | UGACACCGUAUACCACAAU | 5210 |
| UUGUGGUAUACGGUGUCAG | 5211 | CUGACACCGUAUACCACAA | 5212 |
| UGUGGUAUACGGUGUCAGG | 5213 | CCUGACACCGUAUACCACA | 5214 |
| GUGGUAUACGGUGUCAGGU | 5215 | ACCUGACACCGUAUACCAC | 5216 |
| UAUACGGUGUCAGGUUUCA | 5217 | UGAAACCUGACACCGUAUA | 5218 |
| AUACGGUGUCAGGUUUCAG | 5219 | CUGAAACCUGACACCGUAU | 5220 |
| UACGGUGUCAGGUUUCAGG | 5221 | CCUGAAACCUGACACCGUA | 5222 |
| UGUCAGGUUUCAGGGUUUU | 5223 | AAAACCCUGAAACCUGACA | 5224 |
| UUCAUUUCAAAUACUCCCU | 5225 | AGGGAGUAUUUGAAAUGAA | 5226 |
| CAUUUCAAAUACUCCCUUU | 5227 | AAAGGGAGUAUUUGAAAUG | 5228 |
| UAGGUAUAACUGUUGAUGA | 5229 | UCAUCAACAGUUAUACCUA | 5230 |
| AGGUAUAACUGUUGAUGAA | 5231 | UUCAUCAACAGUUAUACCU | 5232 |
| UUAUUGUCCAUUUAUACCC | 5233 | GGGUAUAAAUGGACAAUAA | 5234 |
| UAUUGUCCAUUUAUACCCU | 5235 | AGGGUAUAAAUGGACAAUA | 5236 |
| AUUGUCCAUUUAUACCCUG | 5237 | CAGGGUAUAAAUGGACAAU | 5238 |
| UUGUCCAUUUAUACCCUGU | 5239 | ACAGGGUAUAAAUGGACAA | 5240 |
| UGUCCAUUUAUACCCUGUA | 5241 | UACAGGGUAUAAAUGGACA | 5242 |
| GUCCAUUUAUACCCUGUAA | 5243 | UUACAGGGUAUAAAUGGAC | 5244 |
| UAUACCCUGUAAAGCCGUU | 5245 | AACGGCUUUACAGGGUAUA | 5246 |
| AUACCCUGUAAAGCCGUUU | 5247 | AAACGGCUUUACAGGGUAU | 5248 |
| UACCCUGUAAAGCCGUUUU | 5249 | AAAACGGCUUUACAGGGUA | 5250 |
| AGCCGUUUUAGAAUGUAAU | 5251 | AUUACAUUCUAAAACGGCU | 5252 |
| GCCGUUUUAGAAUGUAAUA | 5253 | UAUUACAUUCUAAAACGGC | 5254 |
| AGGUAAUCCAAAAUGUACU | 5255 | AGUACAUUUUGGAUUACCU | 5256 |
| GGUAAUCCAAAAUGUACUA | 5257 | UAGUACAUUUUGGAUUACC | 5258 |

TABLE 6-continued

| Sense Sequence | SEQ ID NO: | Antisense Sequence | SEQ ID NO: |
|---|---|---|---|
| ACAUUUGUAUUGUCUCUUC | 5259 | GAAGAGACAAUACAAAUGU | 5260 |
| CAUUUGUAUUGUCUCUUCU | 5261 | AGAAGAGACAAUACAAAUG | 5262 |
| UUGUAUCGCAAAGCUAUAU | 5263 | AUAUAGCUUUGCGAUACAA | 5264 |
| UGUAUCGCAAAGCUAUAUG | 5265 | CAUAUAGCUUUGCGAUACA | 5266 |
| GUAUCGCAAAGCUAUAUGU | 5267 | ACAUAUAGCUUUGCGAUAC | 5268 |
| UAUCGCAAAGCUAUAUGUG | 5269 | CACAUAUAGCUUUGCGAUA | 5270 |
| AUCGCAAAGCUAUAUGUGC | 5271 | GCACAUAUAGCUUUGCGAU | 5272 |
| UCGCAAAGCUAUAUGUGCA | 5273 | UGCACAUAUAGCUUUGCGA | 5274 |
| UGAUCUAUGCUUUGAGUUU | 5275 | AAACUCAAAGCAUAGAUCA | 5276 |
| GAUCUAUGCUUUGAGUUUG | 5277 | CAAACUCAAAGCAUAGAUC | 5278 |
| AUCUAUGCUUUGAGUUUGC | 5279 | GCAAACUCAAAGCAUAGAU | 5280 |
| UCUAUGCUUUGAGUUUGCU | 5281 | AGCAAACUCAAAGCAUAGA | 5282 |
| CUAUGCUUUGAGUUUGCUU | 5283 | AAGCAAACUCAAAGCAUAG | 5284 |
| UAUGCUUUGAGUUUGCUUU | 5285 | AAAGCAAACUCAAAGCAUA | 5286 |
| AUGCUUUGAGUUUGCUUUC | 5287 | GAAAGCAAACUCAAAGCAU | 5288 |
| AUCUUACCUAAAAGUACUG | 5289 | CAGUACUUUUAGGUAAGAU | 5290 |
| CUUACCUAAAAGUACUGAA | 5291 | UUCAGUACUUUUAGGUAAG | 5292 |

In some embodiments, the antisense nucleic acid molecules targeted to HLA-A comprise or consist of the nucleotide sequences shown in Table 7.

TABLE 7

| Sequence | SEQ ID NO: |
|---|---|
| GUCACUGCUUGCAGCCUGAG | 5293 |
| UGUCACUGCUUGCAGCCUGA | 5294 |
| CUGUCACUGCUUGCAGCCUG | 5295 |
| ACUGUCACUGCUUGCAGCCU | 5296 |
| CACUGUCACUGCUUGCAGCC | 5297 |
| GCACUGUCACUGCUUGCAGC | 5298 |
| GGCACUGUCACUGCUUGCAG | 5299 |

TABLE 7-continued

| Sequence | SEQ ID NO: |
|---|---|
| GGGCACUGUCACUGCUUGCA | 5300 |
| UGGGCACUGUCACUGCUUGC | 5301 |
| UCUCACACUUUACAAGCUGU | 5302 |
| GUCUCACACUUUACAAGCUG | 5303 |
| UGUCUCACACUUUACAAGCU | 5304 |
| CUGUCUCACACUUUACAAGC | 5305 |
| GCUGUCUCACACUUUACAAG | 5306 |
| AGCUGUCUCACACUUUACAA | 5307 |

In some embodiments, the siRNA molecules targeted to HLA-A comprise or consist of the nucleotide sequences (sense and antisense strands) shown in Table 8.

TABLE 8

| Sense Sequence | SEQ ID NO: | Antisense Sequence | SEQ ID NO: |
|---|---|---|---|
| GGCUGCAAGCAGUGACAGU | 5308 | ACUGUCACUGCUUGCAGCC | 5309 |
| GCUGCAAGCAGUGACAGUG | 5310 | CACUGUCACUGCUUGCAGC | 5311 |
| CUGCAAGCAGUGACAGUGC | 5312 | GCACUGUCACUGCUUGCAG | 5313 |
| UGCAAGCAGUGACAGUGCC | 5314 | GGCACUGUCACUGCUUGCA | 5315 |
| GCAAGCAGUGACAGUGCCC | 5316 | GGGCACUGUCACUGCUUGC | 5317 |

TABLE 8-continued

| Sense Sequence | SEQ ID NO: | Antisense Sequence | SEQ ID NO: |
|---|---|---|---|
| CAAGCAGUGACAGUGCCCA | 5318 | UGGGCACUGUCACUGCUUG | 5319 |
| CUCACAGCUUGUAAAGUGU | 5320 | ACACUUUACAAGCUGUGAG | 5321 |

In some embodiments, the antisense nucleic acid molecules targeted to HLA-B comprise or consist of the nucleotide sequences shown in Table 9.

TABLE 9

| Sequence | SEQ ID NO: |
|---|---|
| UGCACGCAGCCUGAGAGUAG | 5322 |
| CUGCACGCAGCCUGAGAGUA | 5323 |

In some embodiments, the siRNA molecules targeted to HLA-B comprise or consist of the nucleotide sequences (sense and antisense strands) shown in Table 10.

TABLE 10

| Sense Sequence | SEQ ID NO: | Antisense Sequence | SEQ ID NO: |
|---|---|---|---|
| CUACUCUCAGGCUGCGUGC | 5324 | GCACGCAGCCUGAGAGUAG | 5325 |
| UACUCUCAGGCUGCGUGCA | 5326 | UGCACGCAGCCUGAGAGUA | 5327 |

In some embodiments, the antisense nucleic acid molecules targeted to HLA-C comprise or consist of the nucleotide sequences shown in Table 11.

TABLE 11

| Sequence | SEQ ID NO: |
|---|---|
| GCUGUCUCAGGCUUUACAAG | 5328 |
| AGCUGUCUCAGGCUUUACAA | 5329 |

In some embodiments, the siRNA molecules targeted to HLA-C comprise or consist of the nucleotide sequences (sense and antisense strands) shown in Table 12.

TABLE 12

| Sense Sequence | SEQ ID NO: | Antisense Sequence | SEQ ID NO: |
|---|---|---|---|
| UGCUCUCAGGCUGCGUGCA | 5330 | UGCACGCAGCCUGAGAGCA | 5331 |

The inhibitory nucleic acid molecules disclosed herein can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules disclosed herein can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:

Sense: mN\*mN\*/i2FN/mN/i2FN/mN/i2FN/mN/i2FN/
mN/i2FN/mN/i2FN/mN/i2FN/mN/i2FN/\*mN\*/
32FN/

Antisense:/52FN/\*/i2FN/\*mN/i2FN/mN/i2FN/mN/
i2FN/mN/i2FN/mN/i2FN/mN/i2FN/mN/i2FN/
mN/i2FN/mN\*N\*N wherein: "N" is the base; "2F" is a 2'-F modification; "m" is a 2'-O-methyl modification, "I" is an internal base; and "\*" is a phosphorothioate backbone linkage.

The present disclosure also provides vectors comprising any one or more of the inhibitory nucleic acid molecules disclosed herein. In some embodiments, the vectors comprise any one or more of the inhibitory nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules disclosed herein. In some embodiments, the composition is a pharmaceutical composition. In some embodiments, the compositions comprise a carrier and/or excipient. Examples of carriers include, but are not limited to, poly (lactic acid) (PLA) microspheres, poly(D,L-lactic-cogly-colic-acid) (PLGA) microspheres, liposomes, micelles, inverse micelles, lipid cochleates, and lipid microtubules. A carrier may comprise a buffered salt solution such as PBS, HBSS, etc.

The present disclosure also provides methods of identifying a subject having an increased risk for developing an MHC-I-opathy and/or an MHC-II-opathy. The methods comprise performing or having performed an assay on a biological sample from the subject to determine whether the subject comprises: i) an MHC-I-opathy-related HLA genotype and/or an MHC-II-opathy-related HLA genotype; and ii) a functional ERAP2 protein or a nucleic acid molecule encoding a functional ERAP2 protein. When the subject has both the MHC-I-opathy-related HLA genotype and/or an MHC-II-opathy-related HLA genotype and the functional ERAP2 protein or the nucleic acid molecule encoding the functional ERAP2 protein, then the subject has an increased risk of developing the MHC-I-opathy and/or an MHC-II-opathy. When the subject lacks the MHC-I-opathy-related HLA genotype and/or an MHC-II-opathy-related HLA genotype, or lacks the functional ERAP2 protein or the nucleic acid molecule encoding the functional ERAP2 protein, or lacks both, then the subject has a decreased risk of developing the MHC-I-opathy and/or an MHC-II-opathy. In some embodiments, the method further comprises determining whether the subject has a single copy of the MHC-I-opathy-related HLA genotype and/or an MHC-II-opathy-related HLA genotype or two copies of the MHC-I-opathy-related HLA genotype and/or an MHC-II-opathy-related HLA genotype. When the subject comprises two copies of the MHC-I-opathy-related HLA genotype and/or an MHC-II-opathy-related HLA genotype, then the subject has an increased risk of developing the MHC-I-opathy and/or an MHC-II-opathy compared to comprising a single copy of the MHC-I-opathy-related HLA genotype and/or an MHC-II-opathy-related HLA genotype.

In some embodiments, the MHC-I-opathy is BSCR. In some embodiments, the subject is HLA-Aw19$^+$. In some embodiments, the subject is or is suspected of being HLA-A*29$^+$, HLA-A*30$^+$, HLA-A*31$^+$, or HLA-A*33$^+$, or any combination thereof. In some embodiments, the subject has a single copy of HLA-Aw19. In some embodiments, the subject has two copies of HLA-Aw19. In some embodiments, the subject is HLA-A*29$^+$/HLA-A*30$^+$. In some embodiments, the subject is HLA-A*29$^+$/HLA-A*31$^+$. In some embodiments, the subject is HLA-A*29$^+$/HLA-A*33$^+$.

In some embodiments, the subject having BSCR is not HLA-A*29$^+$.

In some embodiments, the subject having BSCR has a copy of at least any two of HLA-A*29, HLA-A*30, HLA-A*31, or HLA-A*33. In some embodiments, the subject having BSCR has a copy of at least any three of HLA-A*29, HLA-A*30, HLA-A*31, or HLA-A*33. In some embodiments, the subject having BSCR has a copy of all of HLA-A*29, HLA-A*30, HLA-A*31, or HLA-A*33.

In some embodiments, the subject having BSCR has one copy of each HLA-A*29 and HLA-A*30. In some embodiments, the subject having BSCR has one copy of each HLA-A*29 and HLA-A*31. In some embodiments, the subject having BSCR has one copy of each HLA-A*29 and HLA-A*33. In some embodiments, the subject having BSCR has one copy of each HLA-A*30 and HLA-A*31. In some embodiments, the subject having BSCR has one copy of each HLA-A*30 and HLA-A*33. In some embodiments, the subject having BSCR has one copy of each HLA-A*31 and HLA-A*33.

In some embodiments, the subject having BSCR has one copy of HLA-A*29 and two copies of HLA-A*30. In some embodiments, the subject having BSCR has one copy of HLA-A*29 and two copies of HLA-A*31. In some embodiments, the subject having BSCR has one copy of HLA-A*29 and two copies of HLA-A*33. In some embodiments, the subject having BSCR has one copy of HLA-A*30 and two copies of HLA-A*31. In some embodiments, the subject having BSCR has one copy of HLA-A*30 and two copies HLA-A*33. In some embodiments, the subject having BSCR has one copy of HLA-A*31 and two copies of HLA-A*33.

In some embodiments, the subject having BSCR has two copies of HLA-A*29 and one copy of HLA-A*30. In some embodiments, the subject having BSCR has two copies of HLA-A*29 and one copy of HLA-A*31. In some embodiments, the subject having BSCR has two copies of HLA-A*29 and one copy of HLA-A*33. In some embodiments, the subject having BSCR has two copies of HLA-A*30 and one copy of HLA-A*31. In some embodiments, the subject having BSCR has two copies of HLA-A*30 and one copy of HLA-A*33. In some embodiments, the subject having BSCR has two copies of HLA-A*31 and one copy of HLA-A*33.

In some embodiments, the subject having BSCR or suspected of having BSCR has two copies of HLA-A*29 and two copies of HLA-A*30. In some embodiments, the subject having BSCR or suspected of having BSCR has two copies of HLA-A*29 and two copies of HLA-A*31. In some embodiments, the subject having BSCR or suspected of having BSCR has two copies of HLA-A*29 and two copies of HLA-A*33. In some embodiments, the subject having BSCR or suspected of having BSCR has two copies of HLA-A*30 and two copies of HLA-A*31. In some embodiments, the subject having BSCR or suspected of having BSCR has two copies of HLA-A*30 and two copies of HLA-A*33. In some embodiments, the subject having BSCR or suspected of having BSCR has two copies of HLA-A*31 and two copies of HLA-A*33.

In some embodiments, the method further comprises administering to the subject an HLA-Aw19 inhibitor. In some embodiments, the HLA-Aw19 inhibitor is an antibody. In some embodiments, the antibody is an anti-HLA-A*29 antibody. In some embodiments, the HLA-Aw19 inhibitor comprises a small molecule degrader or an inhibitory nucleic acid molecule. In some embodiments, the inhibitory nucleic acid molecule is an antisense nucleic acid molecule, a small interfering RNA (siRNA), or a short hairpin RNA (shRNA) that hybridizes to an HLA-Aw19. In some embodiments, the HLA-Aw19 is HLA-A*29.

In some embodiments, the MHC-I-opathy is AS. In some embodiments, the subject is or is suspected of being HLA-B*27$^+$ or HLA-B*40$^+$. In some embodiments, the subject has a single copy of HLA-B*27 or HLA-B*40. In some embodiments, the subject has two copies of HLA-B*27 or HLA-B*40. In some embodiments, the method further comprises administering to the subject an HLA-B*27 inhibitor or an HLA-B*40 inhibitor. In some embodiments, the HLA-B*27 inhibitor or HLA-B*40 inhibitor is an antibody. In some embodiments, the antibody is an anti-HLA-B*27 antibody or an anti-HLA-B*40 antibody. In some embodiments, the HLA-B*27 inhibitor or HLA-B*40 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*27 or HLA-B*40.

In some embodiments, the MHC-I-opathy is Behçet's disease. In some embodiments, the subject is or is suspected of being HLA-B*51⁺. In some embodiments, the subject has a single copy of HLA-B*51. In some embodiments, the subject has two copies of HLA-B*51. In some embodiments, the method further comprises administering to the subject an HLA-B*51 inhibitor. In some embodiments, the HLA-B*51 inhibitor is an antibody. In some embodiments, the antibody is an anti-HLA-B*51 antibody. In some embodiments, the HLA-B*51 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*51.

In some embodiments, the MHC-I-opathy is psoriasis. In some embodiments, the subject is or is suspected of being HLA-C*06⁺. In some embodiments, the subject has a single copy of HLA-C*06. In some embodiments, the subject has two copies of HLA-C*06. In some embodiments, the method further comprises administering to the subject an HLA-C*06 inhibitor. In some embodiments, the HLA-C*06 inhibitor is an antibody. In some embodiments, the antibody is an anti-HLA-C*06 antibody. In some embodiments, the HLA-C*06 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-C*06.

In some embodiments, the MHC-I-opathy is JIA. In some embodiments, the subject is or is suspected of being HLA-B*27+ and/or DRB1⁺. In some embodiments, the subject has a single copy of HLA-B*27 and/or DRB1. In some embodiments, the subject has two copies of HLA-B*27 and/or DRB1. In some embodiments, the method further comprises administering to the subject an HLA-B*27 inhibitor and/or a DRB1 inhibitor. In some embodiments, the HLA-B*27 inhibitor and/or DRB1 inhibitor is an antibody. In some embodiments, the antibody is an anti-HLA-B*27 antibody or an anti-DRB1 antibody. In some embodiments, the HLA-B*27 inhibitor and/or DRB1 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B*27 and/or an DRB1.

In some embodiments, the MHC-I-opathy is IBD or CD. In some embodiments, the subject is or is suspected of being HLA-C*07⁺. In some embodiments, the subject has a single copy of HLA-C*07. In some embodiments, the subject has two copies of HLA-C*07. In some embodiments, the method further comprises administering to the subject an HLA-C*07 inhibitor. In some embodiments, the HLA-C*07 inhibitor is an antibody. In some embodiments, the antibody is an anti-HLA-C*07 antibody. In some embodiments, the HLA-C*07 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-C*07.

In any of the embodiments described herein, the methods can further comprise administering to the subject having an increased risk of developing the MHC-I-opathy-related HLA genotype and/or an MHC-II-opathy an ERAP2 inhibitor. In some embodiments, the ERAP2 inhibitor comprises a small molecule degrader, a proteoloysis-targeting chimera, an immunomodulatory drug, or an inhibitory nucleic acid molecule. In some embodiments, the inhibitory nucleic acid molecule is an antisense nucleic acid molecule, an siRNA, or an shRNA that hybridizes to ERAP2 mRNA. In some embodiments, the inhibitory nucleic acid molecule is an antisense nucleic acid molecule that hybridizes to ERAP2 mRNA. In some embodiments, the inhibitory nucleic acid molecule is an siRNA that hybridizes to ERAP2 mRNA. In some embodiments, the inhibitory nucleic acid molecule is an shRNA that hybridizes to ERAP2 mRNA. In some embodiments, the ERAP2 inhibitor comprises an anti-ERAP2 antibody. In some embodiments, the ERAP2 inhibitor comprises a pseudopeptide. In some embodiments, the pseudopeptide is a phosphinic pseudopeptide. In some embodiments, the phosphinic pseudopeptide is DG002 or DG013. In some embodiments, the phosphinic pseudopeptide is DG002. In some embodiments, the phosphinic pseudopeptide is DG013. In some embodiments, the ERAP2 inhibitor comprises a small molecule.

In any of the embodiments described herein, the assay performed or having been performed on the biological sample from the subject can further determine whether the subject comprises a functional ERAP1 protein or a nucleic acid molecule encoding a functional ERAP1 protein. When the subject has the MHC-I-opathy-related HLA genotype and/or MHC-II-opathy-related HLA genotype and lacks the functional ERAP1 protein or the nucleic acid molecule encoding the functional ERAP1 protein, then the subject has an increased risk of developing the MHC-I-opathy (for MHC-I-opathies except AS and psoriasis) and/or MHC-II-opathy. When the subject has the MHC-I-opathy-related HLA genotype and/or MHC-II-opathy-related HLA genotype and has a functional ERAP1 protein or a nucleic acid molecule encoding the functional ERAP1 protein, then the subject has an increased risk of developing the MHC-I-opathy (for AS and psoriasis). When the subject lacks the MHC-I-opathy-related HLA genotype and/or MHC-II-opathy-related HLA genotype, or has the functional ERAP1 protein or the nucleic acid molecule encoding the functional ERAP1 protein, or both, then the subject has a decreased risk of developing the MHC-I-opathy and/or MHC-II-opathy.

In any of the embodiments described herein, the methods can further comprise administering to the subject an ERAP1 agonist or inhibitor, depending upon the MHC-I-opathy. For AS and psoriasis, an ERAP1 inhibitor can be administered. For the remaining MHC-I-opathies, an ERAP1 agonist can be administered.

In some embodiments, the ERAP1 agonist comprises an oligonucleotide. In some embodiments, the oligonucleotide is ODN1826. In some embodiments, the ERAP1 agonist comprises a peptide. In some embodiments, the ERAP1 agonist comprises a lipopeptide. In some embodiments, the lipopeptide is Pam3CSK4 or FSL-1. In some embodiments, the lipopeptide is Pam3CSK4. In some embodiments, the lipopeptide is FSL-1. In some embodiments, the ERAP1 agonist comprises a small molecule. In some embodiments, the ERAP1 agonist can comprise an ERAP1-specific transcriptional activator, an ERAP1 protein stabilizer, an agonist of ERAP1 enzymatic activity, or an activator of ERAP1 secretion. In some embodiments, the ERAP1 agonist can comprise an ERAP1-specific transcriptional activator. In some embodiments, the ERAP1 agonist can comprise an ERAP1 protein stabilizer. In some embodiments, the ERAP1 agonist can comprise an agonist of ERAP1 enzymatic activity. In some embodiments, the ERAP1 agonist can comprise an activator of ERAP1 secretion. Additional examples of ERAP1 agonists are described in, for example, Goto et al., J. Immunol., 2014, 192, 4443-4452.

In some embodiments, the ERAP1 inhibitor comprises a small molecule degrader, a proteoloysis-targeting chimera, an immunomodulatory drug, or an inhibitory nucleic acid molecule. In some embodiments, the inhibitory nucleic acid molecule is an antisense nucleic acid molecule, an siRNA, or an shRNA that hybridizes to ERAP1 mRNA. In some embodiments, the inhibitory nucleic acid molecule is an antisense nucleic acid molecule that hybridizes to ERAP1 mRNA. In some embodiments, the inhibitory nucleic acid molecule is an siRNA that hybridizes to ERAP1 mRNA. In some embodiments, the inhibitory nucleic acid molecule is an shRNA that hybridizes to ERAP1 mRNA. In some embodiments, the ERAP1 inhibitor comprises an anti-ERAP1 antibody.

In some embodiments, the assay for determining whether the subject comprises an MHC-I-opathy-related and/or MHC-II-opathy-related HLA genotype and a functional ERAP2 protein and/or ERAP1 protein, or a nucleic acid molecule encoding a functional ERAP2 protein and/or ERAP1 protein, is a genotyping assay or sequencing assay. In some embodiments, the nucleic acid molecule encoding a functional ERAP2 protein and/or ERAP1 protein comprises genomic DNA, mRNA, or cDNA obtained from mRNA. By comparing the nucleotide or protein sequence of the ERAP2 protein and/or ERAP1 protein in the sample from a subject to the wild type sequence for ERAP2 protein and/or ERAP1 protein or nucleic acid molecule, or to published sequences of variant ERAP2 proteins and/or ERAP1 proteins or nucleic acid molecules having reduced or no activity, a determination can be made whether the subject comprises a functional ERAP2 protein and/or ERAP1 protein, or a nucleic acid molecule encoding a functional ERAP2 protein and/or ERAP1 protein. In addition, although an individual ERAP2 protein and/or ERAP1 protein may have biological activity, the overall function of the ERAP2 protein and/or ERAP1 protein may not be functional due to reduced levels of expression. Thus, as used herein, an ERAP2 protein and/or ERAP1 protein can be determined not to be functional because the ERAP2 protein and/or ERAP1 protein lacks or had reduced biological activity or because the expression level is reduced.

Determining whether a subject has an MHC-I-opathy-related and/or MHC-II-opathy-related HLA genotype and/or a functional ERAP2 protein and/or ERAP1 protein, or a nucleic acid molecule encoding a functional ERAP2 protein and/or ERAP1 protein, in a biological sample from a subject can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a biological sample obtained from the subject.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any particular nucleic acid molecule, preliminary processing designed to isolate or enrich the biological sample for the particular nucleic acid molecule can be employed. A variety of techniques may be used for this purpose. Various methods to detect the presence or level of an mRNA molecule or the presence of a particular genomic DNA locus can be used.

In some embodiments, the biological sample comprises a cell or cell lysate. Such methods can further comprise, for example, obtaining a biological sample from the subject comprising genomic nucleic acid molecules or mRNA molecules, and if mRNA, optionally reverse transcribing the mRNA into cDNA. In some embodiments, the method is an in vitro method. In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

Detecting the presence or absence of any particular HLA allele can be carried out by numerous techniques. Detection of HLA-A alleles on a 2-digit and 4-digit resolution can be carried out. For example, an assay that targets the HLA region in high resolution (all class-I and class-II genes) can be used. In some embodiments, the assay amplifies the full HLA gene (in this case HLA-A) from the 5'UTR to the 3'UTR and provides genetic variants across the full ampli-con (the DNA that is the product of this amplification of the gene). A method can then be used to call the HLA-A alleles with high accuracy (e.g., PHLAT2; Bai et al., Methods Mol. Biol., 2018, 1802, 193-201). The output of PHLAT2 provides the HLA-A 4-digits allele data for each sample, which can be used for the analysis that identified other Aw19 alleles as enriched in Birdshot cases. In addition, commercial sources of HLA typing are available.

Detecting the presence or absence a functional ERAP2 protein and/or ERAP1 protein, or a nucleic acid molecule encoding a functional ERAP2 protein and/or ERAP1 protein, can be carried out by numerous techniques. For example, detection of presence or absence of ERAP2 protein and the relevant nucleotide sequence can be carried out as described in Andres et al., PLoS Genetics, 2010, 6, 1-13. For example, a subject having an ERAP2 intronic variant designated rs2248374-A has a functional ERAP2 protein, or a nucleic acid molecule encoding a functional ERAP2 protein, and has an increased risk of developing the MHC-I-opathy. A subject having an ERAP2 variant designated rs10044354, HapA has a functional ERAP2 protein, or a nucleic acid molecule encoding a functional ERAP2 protein, and has an increased risk of developing the MHC-I-opathy. In addition, a subject having an ERAP1 intronic variant designated rs27432-G does not have a functional ERAP1 protein, or a nucleic acid molecule encoding a functional ERAP1 protein, and has an increased risk of developing the MHC-I-opathy. A subject having an ERAP1 variant designated rs2287987, Hap 10 does not have a functional ERAP1 protein, or a nucleic acid molecule encoding a functional ERAP1 protein, and has an increased risk of developing the MHC-I-opathy. A subject having an ERAP2 splice variant designated rs2248374-G does not have a functional ERAP2 protein, or a nucleic acid molecule encoding a functional ERAP2 protein, and has a decreased risk of developing the MHC-I-opathy.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Methods

Study Subjects and Samples

The genomic DNA samples from 286 patients with BSCR and 108 unrelated healthy local French volunteers that exhibited HLA tissue typing common in the French population were included in this study. The patients were recruited at Hopital Cochin, Paris, France. All patients met the criteria for diagnosis of BSCR as defined both by an international consensus conference held in 2002 and by the Standardization of Uveitis Nomenclature (SUN) Working Group. In brief, all patients had a posterior bilateral uveitis with multifocal cream-colored or yellow-orange, oval or round choroidal lesions ("birdshot spots"). Although the presence of the HLA-A*29 allele was not a requirement for the diagnosis of BSCR according to the international criteria, all patients included in the current study carried the HLA-A*29 allele. The control DNA samples were collected from volunteer donors recruited by the hematopoietic stem cell donor center of Rheims for France Greffe de Moelle Registry, and local control healthy individuals of the Registry. The DNA samples were isolated from peripheral blood samples using a standard salting out method or QlAamp Blood Kit (Qiagen, Chatsworth, CA, USA). Quality and quantity of DNA was determined by UV spectrophotometry and the concentration was adjusted to 100 ng/ml. Signed informed consent documentation was obtained from all participants, and all research adhered to the tenets set forth in the Declaration of Helsinki. All study-related data acquisitions were approved by the Paris Cochin institutional review board.

Genetic Data

A comprehensive approach was taken to both sequence the exomes and genotype all samples, to allow for identification of common and rare variants filtered based on high quality calls. DNA from participants was genotyped on the Illumina Global Screening Array (GSA) and imputed to the HRC reference panel. Prior to imputation, the variants that had a MAF>=0.1%, missingness <1% and HWE p-value >$10^{-15}$ were retained. Imputation using the HRC reference panel yielded 8,385,561 variants with imputation INFO>0.3 and MAF>0.5%.

Exome sequencing was performed to a mean depth of 31X, followed by variant calling and quality control as reported previously (Van Hout et al., Nature, 2020, 586, 749-756), resulting in 238,942 variants. When integrated, this produced an overall dataset with 8,459,907 variants: 65.5% common (MAF>5%), 34.5% low-frequency (0.5%<MAF<5%) and 0.01% rare (MAF<0.5%).

HLA Genotyping

HLA Class I genes (HLA-A, -B, and -C) were amplified in a multiplex PCR reaction with primers encompassing the full genomic loci for each target. The resulting amplicons were enzymatically fragmented to an average size of 250 base pairs and prepared for Illumina sequencing (New England Biolabs, Ipswich, MA). The libraries were sequenced on the Illumina HiSeq 2500 platform on a rapid run flow cell using paired-end 125 base pair reads with dual 10 base pair indexes. Upon completion of sequencing, raw data from each Illumina HiSeq run was gathered in local buffer storage and uploaded to the DNAnexus platform (Reid et al., BMC Bioinformatics, 2014, 15, 30) for automated analysis. The FASTQ-formatted reads were converted from the BCL files and assigned to samples identified by specific barcodes using the bcl2fastq conversion software (Illumina Inc., San Diego, CA). All the reads in sample-specific FASTQ files were subject to HLA typing analysis using an updated version of PHLAT program (Bai et al., BMC Genomics, 2014, 15, 325) with the reference sequences consisting of GRCh38 genomic sequences and HLA type reference sequences in the IPD-IMGT/HLA database v3.30.0 (Robinson et al., Hum. Immunol., 2016, 77, 233-237).

In addition, HLA allele imputation was performed following SNP2HLA (Jia et al., PLoS One, 2013, 8, e64683) with the T1DGC HLA allele reference panel (Rich et al., Ann. N.Y. Acad. Sci., 2006, 1079, 1-8). HRC-imputed genotypes in the extended Major Histocompatibility Complex (MHC) region (chr6:25-35 Mb) were filtered for high INFO score (>0.9) and certainty (maximum GP>0.8 for all genotyped), in order to increase overlap with the T1DGC reference panel, were re-phased along with chromosome 6 array genotypes using SHAPEIT4 (Delaneau et al., Nat. Commun., 2019, 10, 5436), and were imputed using Minimac4 (Das et al., Nat. Genet., 2016, 48, 1284-1287). HLA allele imputation quality was assessed by examining INFO score vs MAF, and imputed vs reference panel MAF.

Genetic Association Analyses

Association analyses in each study were performed using the genome-wide Firth logistic regression test implemented in SAIGE (Mbatchou et al., bioRxiv, 2020, 2020.2006.2019.162354, doi:10.1101/2020.06.19.162354; and Zhou et al., Nat. Genet., 2018, 50, 1335-1341). In this implementation, Firth's approach is applied when the p-value from standard logistic regression score test is below 0.05. The directly genotyped variants with a minor allele frequency (MAF)>1%, <10% missingness, Hardy-Weinberg equilibrium test P-value>$10^{-15}$ and linkage-disequilibrium (LD) pruning (1000 variant windows, 100 variant sliding windows and $r^2$<0.1) were included for GRM for SAIGE. The association model included as covariates sex and the first 10 ancestry-informative principal components (PCs) derived from the GRM dataset. Haplotype analyses were performed using PLINK 1.0 (Purcell et al., Am. J. Hum. Genet., 2007, 81, 559-575)-chap and -hap-assoc and -hap-logistic, and in R. High haplotype imputation and phasing quality was indicated by PLINK-hap-phase maximum likelihood haplotype genotypes' posterior probabilities all equal to one.

HLA-A Allele Association Analyses

Association of HLA-A alleles was performed as follows: for each sample, both HLA-A alleles were typed as described above. Following HLA allele typing, related samples were removed. For the remaining cohort of 282 cases and 106 controls, one HLA-A allele that is not A*29 (the "second" allele) was obtained next. Samples carrying two copies of A*29, were considered having A*29 as the second allele. The cohort was then subjected to a Fisher's exact test, which tested the association of each allele that was identified in three or more BSCR cases, with the case-control status. To answer the question of whether the A19 allele group is also associated with the case-control status, the samples were combined, and tested together in two different ways: carrying all Aw19 alleles (A*29, A*30, A*31, A*32 and A*33). Since A*32 is biologically different than the other Aw19 alleles in its peptide binding domain, a group that is made of samples carrying all Aw19 alleles excluding A*32 was also constructed and tested. The final odds-ratios and p-values are presented in the table in FIG. 1.

Example 2: HLA-Aw19 Broad Antigen Serotype Alleles and BSCR Risk

The HLA-A29-controlled cohort allowed for examination of the HLA region while controlling for the strong association of HLA-A29 with BSCR, and therefore to detect possible additional association signals in the HLA region.

First, it was asked whether rare variants on the HLA-A29 background were enriched in BSCR cases. No significant enrichments of rare single or aggregated variants were identified either within or outside the MHC region.

Second, the question was whether other HLA-A alleles in addition to the HLA-A29 allele increased BSCR risk. An assay to type HLA-A alleles in this cohort (see Methods) was constructed, and tested the second HLA-A allele (other than the known first HLA-A29) was tested for association with BSCR. Additional HLA-A alleles were found to be associated with BSCR, and those with the largest effects belonged to the same HLA-Aw19 broad antigen serotype group: HLA-A29:02, A30:02, A31:01 and A33:01 (FIG. 1). As a group, HLA-Aw19 alleles were significantly enriched in the second allele of BSCR patients (OR=4.44, p=2.2e-03, FIG. 2, blue bars). This result suggests, for example, that individuals carrying two copies of HLA-A29 would be at a greater risk of developing BSCR compared to those carrying one copy. It also suggests that other Aw19 allele may play a role in BSCR co-susceptibility or pathogenesis in concert with A29. The sole exception within the HLA-Aw19 sero-type group is HLA-A32, which has been reported not to share the defining Aw19 binding domain (McKenzie et al., Genes Immun., 1999, 1, 120-129); HLA-A32 appears to be depleted in BSCR cases and thus protective against BSCR (OR=0.28, p=0.1).

The above results presented two issues due to the small numbers of controls in UParis (n=108): 1) The frequency of alleles might not represent the frequency of HLA-A alleles in general EUR population. 2) While the high ORs replicate in several HLA-Aw19 alleles, the numbers are not sufficient to support significant associations. To tackle these concerns, the frequency of HLA-A alleles in three other large European (EUR) ancestry control populations, two cohorts from the Geisinger Health System (GHS cohort #1, n=77,198 and GHS cohort #2, n=59,072) and the UK Biobank (UKB, n=463,315) were examined. In all three datasets, the EUR samples carrying at least one HLA-A29 allele were selected, matching the BSCR cohort: 4,014 A29 carriers from GHS cohort #1 (5.2% of all EUR subjects), 2,829 A29 carriers from GHS cohort #2 (4.8% of all EUR), and 38,543 A29 carriers from UKB (8.3% of all EUR). The frequencies of the second HLA-A alleles in these cohorts were compared to those observed in the BSCR cohort (FIG. 2, FIG. 1). The results support the enrichment of four of the five HLA-Aw19 alleles in BSCR cases, with highest increased risk for HLA-A30:02 (GHS cohort #1 OR=4.31, GHS cohort #2

OR=6.6, UKB OR=4.6) and HLA-A33 (GHS cohort #1 OR=3.4, GHS cohort #2 OR=2.8, UKB OR=4.9). When combining samples carrying the four co-susceptibility alleles A29, A30, A31 and A33, was found a highly significant enrichment in BSCR cases was found a when compared with the larger control cohorts (GHS cohort #1 p-val=1.29E-06, GHS cohort #2 p-val=1.07E-06, UKB p-val=9.62E-07, FIG. 1 top row). This analysis excludes A32 because of its biological difference in the sequence of the peptide binding domain as previously reported. The additional analyses with all Aw19 alleles including A32 showed that the enrichment in cases is reduced when it is included (FIG. 1 bottom row).

In order to test whether these associations are affected by measurable confounders, logistic regression tests were conducted to evaluate the effects of the second HLA-A allele in HLA-A29 carriers, in UParis BSCR cases compared with each control cohort, with covariates included for sex and principal components, calculated based on genetic array data for each analytic set (FIG. 3). The results were consistent with increased risk for the HLA-Aw19 co-susceptibility alleles, A29, A30, A31, and A33.

Example 3: HLA-A32 Exhibits Protection from BSCR in an HLA-A29 Positive Cohort HLA-A32 is underrepresented in BSCR cases (3/286, ~1%) versus A29 carrier controls (4/108, 3.7%), corresponding to a nominally significant protection from risk (OR=0.28, p=0.1; FIG. 1). When compared with the larger control cohorts, the trend protection is maintained with both UKB controls (3.4%, OR=0.3, p=0.02) and GHS controls (cohort #1: 3.8%, OR=0.27, p=0.01; cohort #2: 3.7%, OR=0.27, p=0.02). While nominally significant, this result does not pass the threshold of multiple test correction (p=3.57e-03) and will need to be further validated with additional case cohorts.

Example 4: ERAP1 and ERAP2 are Independently Associated with BSCR

All variants and gene burdens were tested for association with case-control status, while controlling for sex and ten principal components, using a generalized linear mixed model (SAIGE). Due to the fact that both cases and controls were A29 allele carriers, the expected strong HLA-A signal was at least partially controlled, as evidenced by the strongest HLA p-value=8.98E-07, compared with p=6.6e-74 with 125 cases in the previous BSCR report (Kuiper et al., Hum. Mol. Genet., 2014, 23, 6081-6087). Overall, no locus passed the genome wide significance threshold (p<5e-8). Other than the remnant signal at HLA-A, only the ERAP1/ERAP2-LNPEP locus on chromosome 5 showed an association with disease at p<1e-6 (FIG. 2).

The top association within the ERAP1/ERAP2-LNPEP locus is the ERAP1 intronic variant rs27432 (OR (95% CI)=2.58 (1.78-3.76), p=6.6e-7), a strong eQTL associated with decreased ERAP1 expression (Kuiper et al., Hum. Mol. Genet., 2018, 27, 4333-4343; and Paladini et al., Sci. Rep., 2018, 8, 10398), which also tags the risk-increasing common ERAP1 haplotype. A haplotype analysis was further performed to assess ERAP1 haplotype associations with BSCR status in the present data. The results were consistent with three levels of risk differentiated by nonsynonymous ERAP1 variant haplotypes corresponding to Kuiper et al. Haps 1+2 (OR=0.41, Cases AF=0.17, controls AF=0.35, p=6.7e-06), Hap10 (OR=1.78, Cases AF=0.28, controls AF=0.17, p=8.0e-03), and haplotypes 3-8 (OR=1.32, Cases AF=0.55, controls AF=0.48, p=0.11) (FIG. 4).

The previously reported top association for BSCR at this locus tags a common variant near ERAP2/LNPEP, rs10044354. This reported risk allele is in a strong linkage disequilibrium (D'=0.99, R²=0.76), with a strong eQTL increasing ERAP2 expression. The results show a nominal association of rs10044354 with increased risk for Birdshot (OR (95% Cl)=1.55 (1.13-2.11), p=5.8e-3). Furthermore, no significant evidence was found for an interaction of rs10044354 with rs27432-rs2287987 haplotypes (conditional haplotype test p=0.46).

Next, a meta-analysis of the results with the published results from Kuiper et al. was carried out, which yielded genome-wide significant associations for both ERAP1 (rs27432, OR (95% Cl)=2.46 (1.85-3.26), p=4.07e-10) and ERAP2 (r510044354, OR (95% Cl)=1.95 (1.55-2.44), p=6.2e-09) loci with BSCR (FIG. 1). Both previous and current studies showed consistent directionality for both variants, which, separated by over 201,222 bp, show low linkage disequilibrium (LD) in the present cohort (R2=0.18, D'=0.79).

The expression of ERAP2 has been previously reported to be disrupted by a common splice region variant (rs2248374, AF=0.53) that causes mis-splicing of intron 10 and eventual transcript degradation via nonsense-mediated decay (Andres et al., PLoS Genet., 2010, 6, e1001157; and Coulombe-Huntington et al., PLoS Genet., 2009, 5, e1000766), and which is in high LD with rs10044354 (R2=0.8, D'=1). Thus, about 25% of the population of most ancestries (including European, AF=0.53; African, AF=0.57 and South Asian, AF=0.58) is estimated to be lacking an active ERAP2 protein. Both datasets were examined for rs2248374 associations and found that it is protective for BSCR with nominal significance in both datasets (FIG. 5). Furthermore, ERAP2-rs2248374 that disrupts ERAP2 expression is protective (OR 0.56; 95% Cl [0.45-0.70]; p=2.39e-07; FIG. 6). In summary, higher expression of ERAP2 protein increases risk for BSCR and a lower expression is protective.

Figure 7:
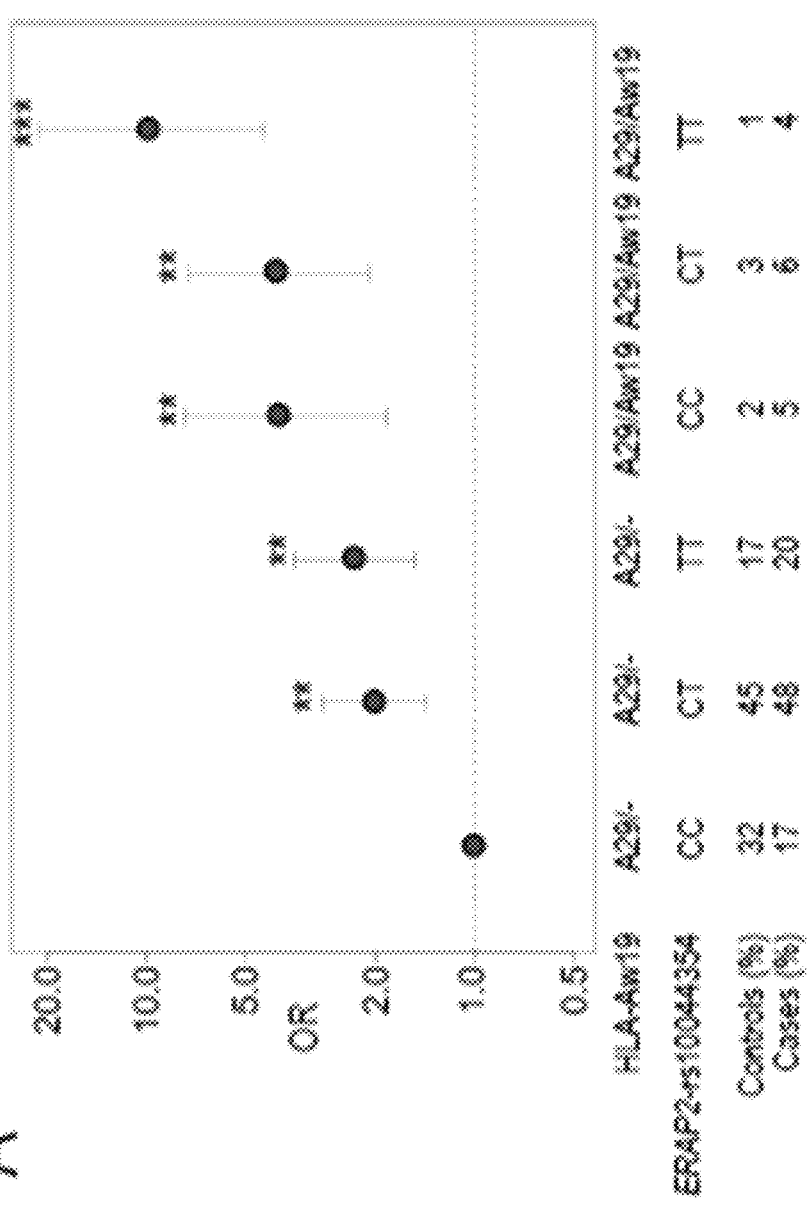
FIG. 7 shows the combined risk of ERAP1, ERAP2 and two copies of Aw19. Utilizing 286 Birdshot cases and 4,014 controls from GHS cohort #1 to calculate additive risk while combining risk factors in ERAP1, ERAP2 and Aw19. Panel A) An additive genotype model of ERAP2 risk signal tagged by rs10044354 and single (A29/-) or double (A29/Aw19) Aw19 copies relative to lowest risk combination of rs10044354-CC and one copy of Aw19 allele (A29). Panel B) An additive genotype model of ERAP1 risk signal tagged by rs27432 and single (A29/-) or double (A29/Aw19) Aw19 copies relative to lowest risk combination of rs27432-AA and one copy of Aw19 allele (A29). Panel C) An additive genotype model of ERAP1 risk signal tagged by rs27432 and ERAP2 signal tagged by rs10044354 relative to lowest risk combination of rs27432-AA and rs10044354-CC. Panel D) An additive genotype model of ERAP1 and ERAP2 risk signals and single (A29/-) or double (A29/Aw19) Aw19 copies relative to lowest risk combination. The genotypes are combined as following: 0=ERAP1 and ERAP2 homozygous for protective allele. 1/[01],[01]/1=either homozygous protective or heterozygous genotypes of both ERAP1 and ERAP2. 2/ . . . /2=homozygous risk allele of either ERAP1 or ERAP2. 2/2=homozygous risk allele of both ERAP1 and ERAP2.
Figure 7:
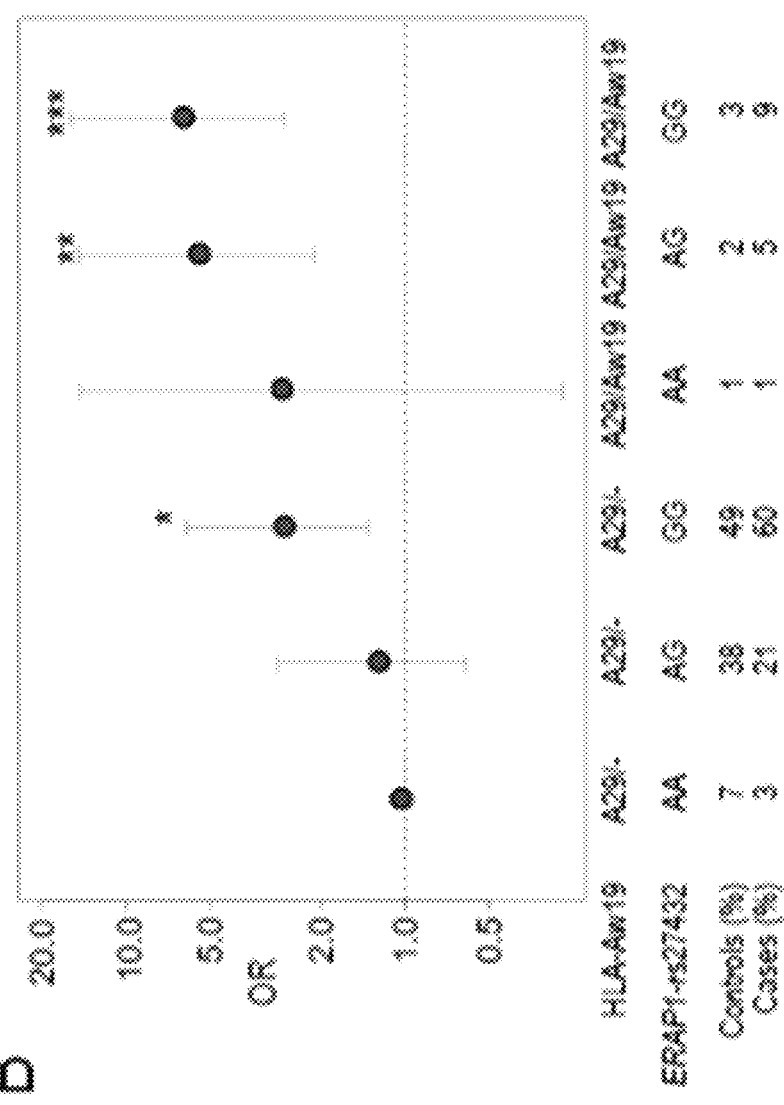
Figure 7:
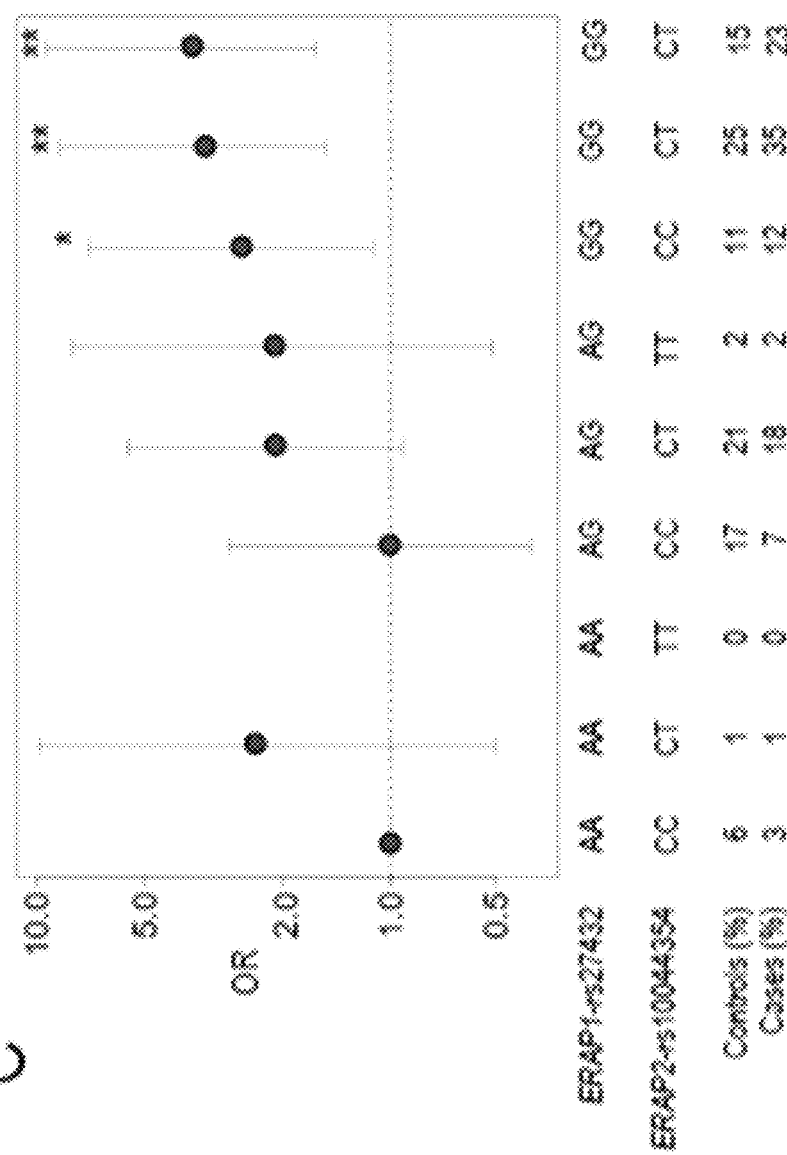
Figure 7:
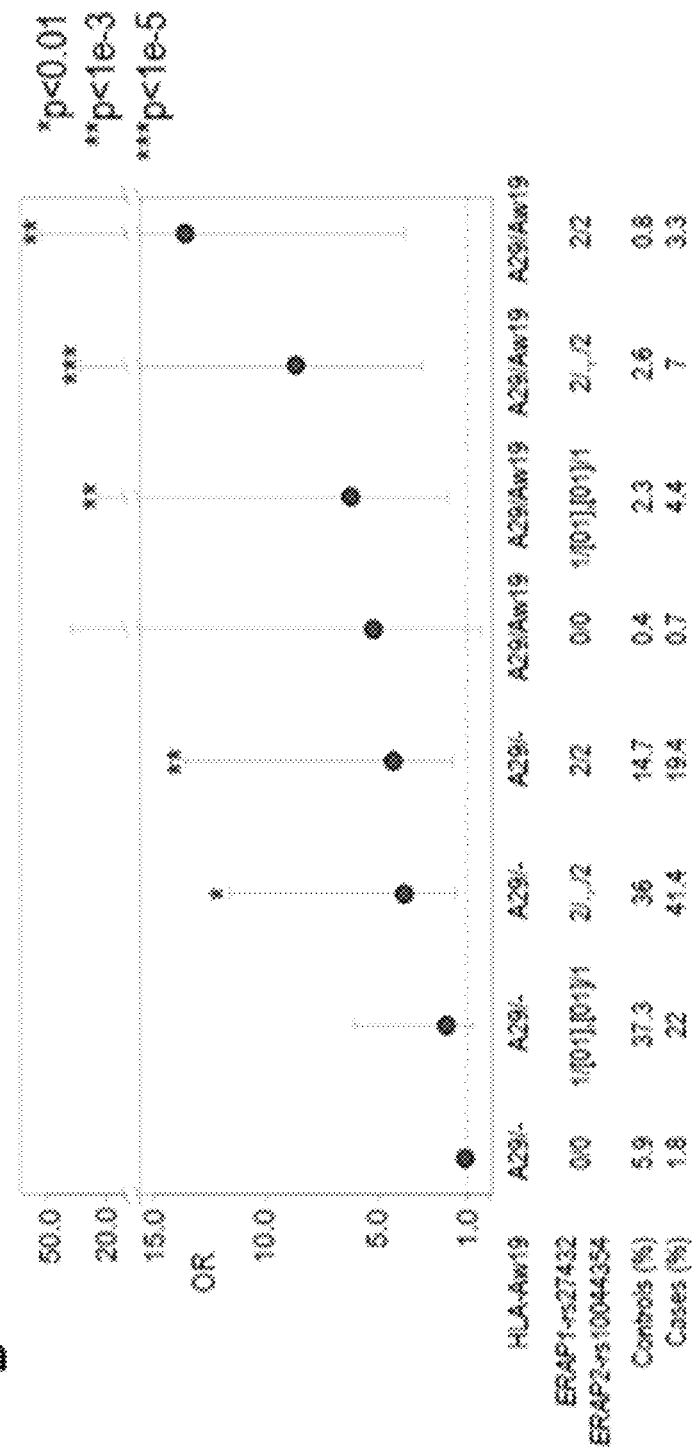

Example 5: Cumulative Effect of HLA-Aw19 Alleles and ERAP1/ERAP2 Haplotypes on BSCR Risk The potential interactions between the ERAP1 and ERAP2 association signals and between HLA-Aw19 and ERAP1/ERAP2 signals was examined by calculating the cumulative effects of HLA-Aw19, ERAP1 and ERAP2 genotypes on BSCR risk using the 286 cases and the 4,014 A29 carriers from the GHS cohort #1. First, an analysis of ERAP2-rs10044354 risk haplotype, the top non-MHC signal in Kuiper et al. was performed, stratified by single (A29/-) versus double (A29/AW19) Aw19 background, which yielded a trend of increased risk with additional ERAP2-rs10044354-T variant alleles, particularly on the double A29/AW19 background (FIG. 7, Panel A). The combination of rs10044354-TT and two copies of Aw19 with 12 cases and 34 controls was found to have the highest risk (OR=9.9 [4.4-21.2], p=1.66e-07, FIG. 8).

A similar analysis of the ERAP1-rs27432 risk haplotype, the top non-MHC association, stratified by single (A29/-) versus double (A29/AW19) Aw19 background, yielded the same trend of increased risk with additional ERAP1-rs27432-G variant alleles, particularly on the double A29/AW19 background (OR=6.2 [2.7-15.51], p=1.54e-06, FIG. 7, Panel B and FIG. 9).

The combined effects of the ERAP1 risk haplotype tagged by rs27432, and the ERAP2 risk haplotype tagged by rs10044354 were calculated next (FIG. 7, Panel C). It was found that the highest risk is conferred by the combination of ERAP1-rs27432-GG and ERAP2-rs10044354-TT (OR=3.6 [1.62-9.45], p=4.03e-04, FIG. 10), and as mentioned above, these data are consistent with additive effects of the variants/haplotypes.

Next, all risk haplotypes were combined to a single risk analysis. Due to the small number of cases, the genotypes of intermediate genotypes were combined into four main groups: 1) homozygous to the protective alleles in both ERAP1 and ERAP2, homozygous in one and 2) heterozygous in the other, 3) homozygous risk allele in either ERAP1 or ERAP2, and 4) homozygous risk allele in both ERAP1 or ERAP2 (FIG. 7, Panel D and FIG. 11). A gradual increase in risk with the addition of each risk allele was observed, with the highest risk presented when carrying homozygous risk alleles in both ERAP1 and ERAP2, on top of two copies of A19 alleles (OR=13.53 [3.79-54.77], p=1.17e-05). These results suggest that both ERAP1 and/or ERAP2 confer greater BSCR risk, which is further increased in the double Aw19 background.

Example 6: Absolute BSCR Risk

The calculation of the absolute risk of BSCR when considering all risk alleles is presented in FIG. 7, Panel D. Since the prevalence of BSCR in general population is estimated at 0.2-1.7:100,000 (Minos et al., Orphanet J. Rare Dis., 2016, 11, 61), 1:100,000 was used as an approximation. The absolute risk was further calculated when carrying one A29 carrier based on the frequency of A29 in UKB EUR population of 8%, and reach an absolute risk of 1:29,000 (FIG. 11). It was observed that the absolute risk climbs with each risk genotype presented in FIG. 7, Panel D, reaching the most prominent risk at 1:2,160 for cases that carry homozygous risk alleles for both ERAP1 and ERAP2, and two copies of Aw19 alleles. Exhibiting a significant increase in absolute risk of disease when carrying all three risk haplotypes.

Example 7: Discussion

The sequencing of a new large BSCR patient cohort and HLA-A*29 controls has confirmed the importance of the ERAP1 and ERAP2 polymorphisms in increasing risk for developing BSCR. ERAP1 and ERAP2 reside back-to-back on chromosome five in opposite orientation and share the regulatory regions, which upregulate one and downregulate the other, and vice versa. The association of both ERAP1 and ERAP2 haplotypes is consistent with a mechanism in which coordinated decreased ERAP1 and increased ERAP2 expression contribute to disease risk. Several studies have reported that the ERAP1 and ERAP2 haplotypes affect their expression as well as the resulting peptidome (Kuiper et al., Hum. Mol. Genet., 2018, 27, 4333-4343; Paladini et al., Sci. Rep., 2018, 8, 10398; and Sanz-Bravo et al., Mol. Cell Proteomics, 2018, 17, 1564-1577).

The present study found that several other HLA-Aw19 family alleles (HLA-A29, A30, A31, A33) contribute additional risk as the second HLA-A allele, in addition to HLA-A29 risk allele. HLA-Aw19 family alleles have a similar antigen-binding sequence and therefore would bind similar peptide motifs. Hence, the enrichment of Aw19 alleles in cases supports the inferred mechanism underlying activation of the immune response in BSCR: having two copies of these alleles may increase the cell-surface presentation of specific types of peptides in BSCR cases compared to HLA-A29 positive controls. Furthermore, it was found that the HLA-A32 allele within the Aw19 family is potentially protective.

These results indicate that a decreased expression of ERAP1 and an increased expression of ERAP2 confer stronger risk for BSCR than each one separately. Furthermore, this effect is increased in the presence of two copies of HLA-Aw19. The combined and additive effect of risk factors associated with peptide processing and presentation is suggestive of a peptide presentation threshold hypothesis as a driving mechanism for the immune response underlying development of BSCR disease. Results from this and other studies suggest that increased ERAP2 along with decreased ERAP1 expression in BSCR cases would lead to higher availability of ERAP2-processed peptides for presentation onto HLA class I proteins. Additional HLA-Aw19 alleles, with similar peptide-binding properties, would increase presentation of similar peptides. Therefore, both the production of a unique peptide pool by dominant ERAP2 activity and the increased expression of HLA-Aw19 risk allele proteins presenting these peptides may increase the likelihood that a putative ocular autoantigen would be processed and presented above a certain threshold to activate an immune response. On the other hand, having lower expression of ERAP2 (and higher expression of ERAP1), along with a single HLA-A*29 allele, lowers the ocular antigenic peptide presentation below the threshold and thus reduces the risk of generating the immunological response leading to BSCR in HLA-A*29 healthy control carriers. This further highlights the importance of the shaping and generation of the available peptide pool by ERAPs to be presented by specific HLA class I proteins in promoting the generation of an immune response or, in the case of autoimmune disease, an aberrant response to a self-antigen.

ERAP1 and ERAP2 polymorphisms and risk haplotypes have also been reported in other HLA class I-associated autoimmune diseases (Babaie et al., Mol. Immunol., 2020, 121, 7-19; and Yao et al., Hum. Immunol., 2019, 80, 325-334). Polymorphisms in ERAP1 increase risk for Ankylosing Spondylitis in HLA-B*27 carriers, for psoriasis vulgaris in HLA-C*06 carriers, and for Behçet's disease in HLA-B*51 carriers, further supporting the combinatorial impact of peptide trimming and HLA class I allele in initiating autoimmune responses (Evans et al., Nat. Genet., 2011, 43, 761-767; Wisniewski et al., Hum. Immunol., 2018, 79, 109-116; Nat. Genet., 2010, 42, 985-990; and Takeuchi et al., Ann. Rheum. Dis., 2016, 75, 2208-2211). Ankylosing Spondylitis and Behçet's disease-associated ERAP1 variants have also been experimentally shown to shape the resulting HLA-B*27 and HLA-B*51 peptidome, respectively (Sanz-Bravo et al., Mol. Cell Proteomics, 2018, 17, 1308-1323; and Guasp et al., J. Biol. Chem., 2017, 292, 9680-9689). Therefore, it is possible that the combination of risk ERAP1/ERAP2 haplotypes and specific risk HLA class I alleles can predispose an individual to develop an HLA class I associated disease in a similar fashion as it is hypothesized for BSCR. This implies that the peptide threshold hypothesis may have broader implications as a disease mechanism in HLA class I associated immunological diseases.

HLA-A32 is the only HLA-Aw19 member that is found at lower rates in BSCR patients compared to controls, suggesting that it could be protective. The HLA-Aw19 serotype was initially identified by antibody binding to related family members; however, this identifies the HLA-A proteins based on structure outside of the peptide-binding groove. Sero-families have since been re-analyzed by overall and peptide binding region sequences (McKenzie et al., Genes Immun. 1999, 1, 120-129). Comparison of the sequences in the peptide binding region reveals that HLA-A32 is more distantly related than the other Aw19 alleles which are identified as novel risk factors in this present study: HLA-A29, A30, A31, A33. When examining the differences in sequence between these Aw19 alleles, two main differences are evident: at position 9, which is part of the peptide binding domain, and a stretch of amino-acids at positions 79-83 that is only found in HLA-A32 and not the other Aw19 alleles (FIG. 12). Theoretically, the peptide pool bound by HLA-A32 would differ from the remaining members of the Aw19 family and would not activate the same subset of responding CD8 T cells. This adds further evidence supporting the hypothesis of the threshold requirement of an increased concentration of the driving autoantigenic peptide pool presented on high-risk HLA-A proteins as a driving component for development of BSCR uveitis.

In summary, the combinatorial impact of ERAP1/2 shaping the immunopeptidome along with differential peptide selection by the key residues in HLA-A29 and HLA-Aw19 family members supports the immunological hypothesis of a peptide pool that is generated by this combination and available for immune cell recognition and activation initiating an inflammatory cascade. Avenues to reduce the expression and recognition of ERAP2-processed and HLA-Aw19-presented peptides in the eye may be beneficial against BSCR disease and/or progression.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

---

SEQUENCE LISTING

The patent contains a lengthy sequence listing. A copy of the sequence listing is available in electronic form from the USPTO web site (https://seqdata.uspto.gov/docdetail?docId=US12662539B2). An electronic copy of the sequence listing will also be available from the USPTO upon request and payment of the fee set forth in 37 CFR 1.19(b)(3).

What is claimed is:

1. A method of treating a subject having Birdshot Chorioretinopathy (BSCR), the method comprising administering to the subject an Endoplasmic Reticulum Aminopeptidase 2 (ERAP2) inhibitor, wherein the ERAP2 inhibitor comprises an ERAP2 siRNA comprising a sense strand having a nucleotide sequence set forth in one of odd-numbered SEQ ID NOs: 859-2748 and a corresponding antisense strand having a nucleotide sequence set forth in even-numbered SEQ ID NOs: 859-2748; and wherein the subject has at least one HLA-Aw19 allele.

2. The method according to claim 1, wherein the ERAP2 inhibitory nucleic acid molecule comprises an ERAP2 small interfering RNA (siRNA).

3. The method according to claim 1, wherein the subject has a plurality of HLA-Aw19 alleles.

4. The method according to claim 1, wherein the at least one HLA-Aw19 allele comprises at least one HLA-A*29 allele, at least one HLA-A*30 allele, at least one HLA-A*31 allele, or at least one HLA-A*33 allele.

5. The method according to claim 1, wherein the at least one HLA-Aw19 allele comprises at least one HLA-A*29 allele.

6. The method according to claim 1, wherein the at least one HLA-Aw19 allele comprises:

i) at least one HLA-A*29 allele and at least one HLA-A*30 allele;

ii) at least one HLA-A*29 allele and at least one HLA-A*31 allele; or iii) at least one HLA-A*29 allele and at least one HLA-A*33 allele.

* * * * *